(12) United States Patent
Labib et al.

(10) Patent No.: US 10,952,961 B2
(45) Date of Patent: Mar. 23, 2021

(54) IMPLANTS AND CONSTRUCTS INCLUDING HOLLOW FIBERS

(71) Applicant: NOVAFLUX, INC, Princeton, NJ (US)

(72) Inventors: Mohamed E. Labib, Yardley, PA (US); Stanislav S. Dukhin, Goldens Bridge, NY (US); Peter Materna, Metuchen, NJ (US); Jeffrey C. Robertson, Rochester, NY (US); Ching-Yue Lai, Pennington, NJ (US); Yacoob Tabani, Basking Ridge, NJ (US)

(73) Assignee: Novaflux, Inc., Princeton, NJ (US)

( * ) Notice: Subject to any disclaimer, the term of this patent is extended or adjusted under 35 U.S.C. 154(b) by 0 days.

(21) Appl. No.: 16/712,365

(22) Filed: Dec. 12, 2019

(65) Prior Publication Data

US 2020/0138708 A1    May 7, 2020

Related U.S. Application Data

(63) Continuation of application No. 15/743,763, filed as application No. PCT/US2016/043585 on Jul. 22, 2016, now abandoned.
(Continued)

(51) Int. Cl.
*A61L 31/04* (2006.01)
*A61L 31/16* (2006.01)
(Continued)

(52) U.S. Cl.
CPC ...... *A61K 9/0092* (2013.01); *A61B 17/06166* (2013.01); *A61C 15/041* (2013.01);
(Continued)

(58) Field of Classification Search
None
See application file for complete search history.

(56) References Cited

U.S. PATENT DOCUMENTS

| 3,875,008 A | 4/1975 | Yashino et al. |
| 3,918,455 A | 11/1975 | Coplan |

(Continued)

FOREIGN PATENT DOCUMENTS

| WO | WO-2016028774 A1 | 2/2016 |
| WO | WO-2017083476 A1 | 5/2017 |

OTHER PUBLICATIONS

Lumen [online] retrieved from: https://www.merriam-webster.com/dictionary/lumen on Jun. 23, 2020; 2 pages.) (Year: 2020).*
(Continued)

*Primary Examiner* — Ernst V Arnold
(74) *Attorney, Agent, or Firm* — Merchant & Gould P.C.

(57) ABSTRACT

Hollow fiber drug delivery devices are described. Device can contain structural or solid fibers. Fabric can be formed by fibers being interwoven or joined to each other. All or some of the fibers can be resorbable. Fibers can be subdivided, by deformations or closure points, into numerous compartments that separately deliver drug. Deformations can be located at points of fiber intersection or joining. Different drug or drug formulation can be provided in different places. Fibers can be given appropriate surface treatments or coatings to achieve desired properties such as wetting of pores and surfaces. Different release characteristics in different directions can be achieved. The hollow fibers can contain solid particles of drug, and can contain gel. Possible applications include hernia meshes, pouches, sutures, catheters, wound dressings, stents, nerve regrowth guides, refillable/drainable devices, and devices that deliver drug to lymphatic flow.

22 Claims, 32 Drawing Sheets

Related U.S. Application Data

(60) Provisional application No. 62/196,289, filed on Jul. 23, 2015, provisional application No. 62/197,814, filed on Jul. 28, 2015, provisional application No. 62/359,102, filed on Jul. 6, 2016.

(51) Int. Cl.
| | | |
|---|---|---|
| *A61M 37/00* | (2006.01) | |
| *A61K 9/00* | (2006.01) | |
| *A61L 17/00* | (2006.01) | |
| *A61B 17/06* | (2006.01) | |
| *A61C 15/04* | (2006.01) | |
| *A61F 2/00* | (2006.01) | |
| *A61F 13/00* | (2006.01) | |
| *A61L 31/14* | (2006.01) | |
| *A61M 27/00* | (2006.01) | |
| *A61B 17/00* | (2006.01) | |

(52) U.S. Cl.
CPC ...... *A61F 2/0063* (2013.01); *A61F 13/00063* (2013.01); *A61L 17/005* (2013.01); *A61L 31/04* (2013.01); *A61L 31/146* (2013.01); *A61L 31/148* (2013.01); *A61L 31/16* (2013.01); *A61M 27/002* (2013.01); *A61B 2017/00893* (2013.01); *A61F 2250/0068* (2013.01); *A61L 2300/406* (2013.01); *A61M 37/00* (2013.01)

(56) References Cited

U.S. PATENT DOCUMENTS

| | | |
|---|---|---|
| 4,175,326 A | 11/1979 | Goodson |
| 4,235,236 A | 11/1980 | Theeuwes |
| 4,801,458 A | 1/1989 | Hidaka et al. |
| 5,024,671 A | 6/1991 | Tu et al. |
| 5,092,884 A | 3/1992 | Devereux et al. |
| 5,100,392 A | 3/1992 | Orth et al. |
| 5,342,348 A | 8/1994 | Kaplan |
| 5,447,724 A | 9/1995 | Helmus et al. |
| 5,458,582 A | 10/1995 | Nakao |
| 5,466,462 A | 11/1995 | Rosenthal et al. |
| 5,516,522 A | 5/1996 | Peyman et al. |
| 5,538,735 A | 7/1996 | Ahn |
| 5,660,854 A | 8/1997 | Haynes et al. |
| 5,700,476 A | 12/1997 | Rosenthal et al. |
| 5,707,385 A | 1/1998 | Williams |
| 5,843,172 A | 12/1998 | Yan |
| 5,891,101 A | 4/1999 | Wilcox et al. |
| 5,919,473 A | 7/1999 | Elkhoury |
| 5,972,027 A | 10/1999 | Johnson |
| 5,997,524 A | 12/1999 | Burbank et al. |
| 6,071,305 A | 6/2000 | Brown et al. |
| 6,235,009 B1 | 5/2001 | Skow |
| 6,273,913 B1 | 8/2001 | Wright et al. |
| 6,287,628 B1 | 8/2001 | Hossainy et al. |
| 6,350,253 B1 | 2/2002 | Deniega et al. |
| 6,485,462 B1 | 11/2002 | Kriesel |
| 6,491,720 B1 | 12/2002 | Vallana et al. |
| 6,551,290 B1 | 4/2003 | Elsberry et al. |
| 6,551,608 B2 | 4/2003 | Yao |
| 6,565,534 B1 | 5/2003 | Winters |
| 6,582,715 B1 | 6/2003 | Barry et al. |
| 6,585,765 B1 | 7/2003 | Hossainy et al. |
| 6,596,296 B1 | 7/2003 | Nelson et al. |
| 6,740,120 B1 | 5/2004 | Grimes |
| 6,753,011 B2 | 6/2004 | Faour |
| 6,852,106 B2 | 2/2005 | Watson et al. |
| 6,942,634 B2 | 11/2005 | Odland |
| 6,989,071 B2 | 1/2006 | Kocur et al. |
| 7,033,603 B2 | 4/2006 | Nelson et al. |
| 7,169,179 B2 | 1/2007 | Shanley et al. |
| 7,181,287 B2 | 2/2007 | Greenberg |
| 7,235,295 B2 | 6/2007 | Laurencin et al. |
| 7,384,660 B2 | 6/2008 | Hossainy et al. |
| 7,465,291 B2 | 12/2008 | Massengale |
| 7,481,826 B2 | 1/2009 | Cichocki, Jr. |
| 7,514,095 B2 | 4/2009 | Nelson et al. |
| 7,737,060 B2 | 6/2010 | Strickler et al. |
| 7,875,055 B2 | 1/2011 | Cichocki, Jr. |
| 7,923,042 B2 | 4/2011 | Cozzolino |
| 8,048,150 B2 | 11/2011 | Weber et al. |
| 8,070,797 B2 | 12/2011 | Flanagan et al. |
| 8,128,656 B2 | 3/2012 | Cichocki |
| 8,167,836 B2 | 5/2012 | Lee et al. |
| 8,216,177 B2 | 7/2012 | Heruth et al. |
| 8,252,044 B1 | 8/2012 | Boyle |
| 8,257,393 B2 | 9/2012 | Cichocki, Jr. |
| 8,263,108 B2 | 9/2012 | Gibson et al. |
| 8,267,905 B2 | 9/2012 | Lobl et al. |
| 8,315,700 B2 | 11/2012 | Citron et al. |
| 8,343,135 B2 | 1/2013 | Porto et al. |
| 8,381,774 B2 | 2/2013 | Mitchell et al. |
| 8,449,602 B2 | 5/2013 | Lye et al. |
| 8,460,745 B2 | 6/2013 | Mitchell et al. |
| 8,480,647 B2 | 7/2013 | Shohat et al. |
| 8,486,143 B2 | 7/2013 | Laurencin et al. |
| 8,529,937 B2 | 9/2013 | Brunner et al. |
| 8,591,531 B2 | 11/2013 | Buevich et al. |
| 8,591,564 B2 | 11/2013 | Dimatteo et al. |
| 8,632,846 B2 | 1/2014 | Avelar et al. |
| 8,815,273 B2 | 8/2014 | Atanasoska et al. |
| 8,828,474 B2 | 9/2014 | Mitchell et al. |
| 8,834,772 B2 | 9/2014 | Schindler et al. |
| 8,840,914 B2 | 9/2014 | Crudden et al. |
| 8,876,864 B2 | 11/2014 | Spedden et al. |
| 8,916,226 B2 | 12/2014 | Mauch et al. |
| 8,933,290 B2 | 1/2015 | Lefranc et al. |
| 8,951,284 B2 | 2/2015 | Graziano |
| 8,961,590 B2 | 2/2015 | Baillargeon et al. |
| 9,080,263 B2 | 7/2015 | Egnelöv |
| 9,080,285 B2 | 7/2015 | Lshimaru |
| 9,119,736 B2 | 9/2015 | Thompson |
| 9,204,982 B2 | 12/2015 | Peterson |
| 9,216,239 B2 | 12/2015 | Rubin |
| 9,237,889 B2 | 1/2016 | Dumanian et al. |
| 9,254,202 B2 | 2/2016 | Diaz et al. |
| 9,278,002 B2 | 3/2016 | Merrell et al. |
| 9,283,305 B2 | 3/2016 | Birdsall et al. |
| 9,402,973 B2 | 8/2016 | Phillips et al. |
| 9,446,226 B2 | 9/2016 | Zilberman |
| 9,486,340 B2 | 11/2016 | Dolan et al. |
| 9,561,351 B2 | 2/2017 | Kleine |
| 9,566,339 B2 | 2/2017 | McGee |
| 9,597,484 B2 | 3/2017 | Dunn |
| 9,603,738 B2 | 3/2017 | Haffner et al. |
| 9,700,404 B2 | 7/2017 | Martin et al. |
| 9,821,141 B2 | 11/2017 | Stice et al. |
| 9,901,687 B2 | 2/2018 | Meng et al. |
| 10,058,688 B2 | 8/2018 | Cima et al. |
| 10,315,019 B2 | 6/2019 | Lee et al. |
| 2001/0004709 A1 | 6/2001 | Dabrul |
| 2002/0055759 A1 | 5/2002 | Shibuya |
| 2003/0003135 A1 | 1/2003 | Leung et al. |
| 2003/0068353 A1 | 4/2003 | Chen et al. |
| 2004/0006382 A1 | 1/2004 | Sohier |
| 2004/0193281 A1 | 9/2004 | Grimes |
| 2005/0171467 A1 | 8/2005 | Landman |
| 2005/0182390 A1 | 8/2005 | Shanley |
| 2007/0041952 A1 | 2/2007 | Guilak et al. |
| 2007/0077268 A1 | 4/2007 | King et al. |
| 2007/0077270 A1 | 4/2007 | Wen |
| 2007/0197970 A1 | 8/2007 | Shen-Gunther |
| 2007/0239206 A1 | 10/2007 | Shelton et al. |
| 2009/0024209 A1 | 1/2009 | Ozdil et al. |
| 2009/0035351 A1 | 2/2009 | Berglund et al. |
| 2009/0143855 A1 | 6/2009 | Weber et al. |
| 2009/0187254 A1 | 7/2009 | Deal et al. |
| 2009/0192593 A1 | 7/2009 | Meyer et al. |
| 2009/0220612 A1 | 9/2009 | Perera |
| 2010/0119604 A1 | 5/2010 | Prescott et al. |
| 2010/0234244 A1 | 9/2010 | Anderson et al. |
| 2010/0291182 A1 | 11/2010 | Palasis et al. |

(56) References Cited

U.S. PATENT DOCUMENTS

| | | |
|---|---|---|
| 2011/0091515 A1 | 4/2011 | Zilberman et al. |
| 2013/0071463 A1 | 3/2013 | Palasis et al. |
| 2013/0209522 A1 | 8/2013 | Brooks et al. |
| 2013/0274687 A1 | 10/2013 | Boyle |
| 2014/0148782 A1 | 5/2014 | Odland et al. |
| 2014/0199364 A1 | 7/2014 | Palasis et al. |
| 2014/0209100 A1 | 7/2014 | Kiser et al. |

OTHER PUBLICATIONS

Stevenson et al., "Hydraulic Permeability of Hollow-Fiber Membranes", J Biomed Mater Res. May 1978;12(3):401-19, May 1978.

Moroni et al., "Polymer hollow fiber three-dimensional matrices with controllable cavity and shell thickness", Biomaterials, 2006, vol. 27, pp. 5918-5926, Dec. 2006.

Pacella et al., "Darcy Permeability of Hollow Fiber Bundles Used in Blood Oxygenation Devices", J Memb Sci. Oct. 15, 2011; 382(1-2): 238-242, Oct. 2011.

International Search Report and Written Opinion for Application No. PCT/US2016/043585 dated Nov. 4, 2016.

European Supplementary Partially Search Report for Application No. 16828615.1 dated Feb. 26, 2018.

European Supplementary Partially Search Report for Application No. 16828615.1 dated Jun. 27, 2019.

\* cited by examiner

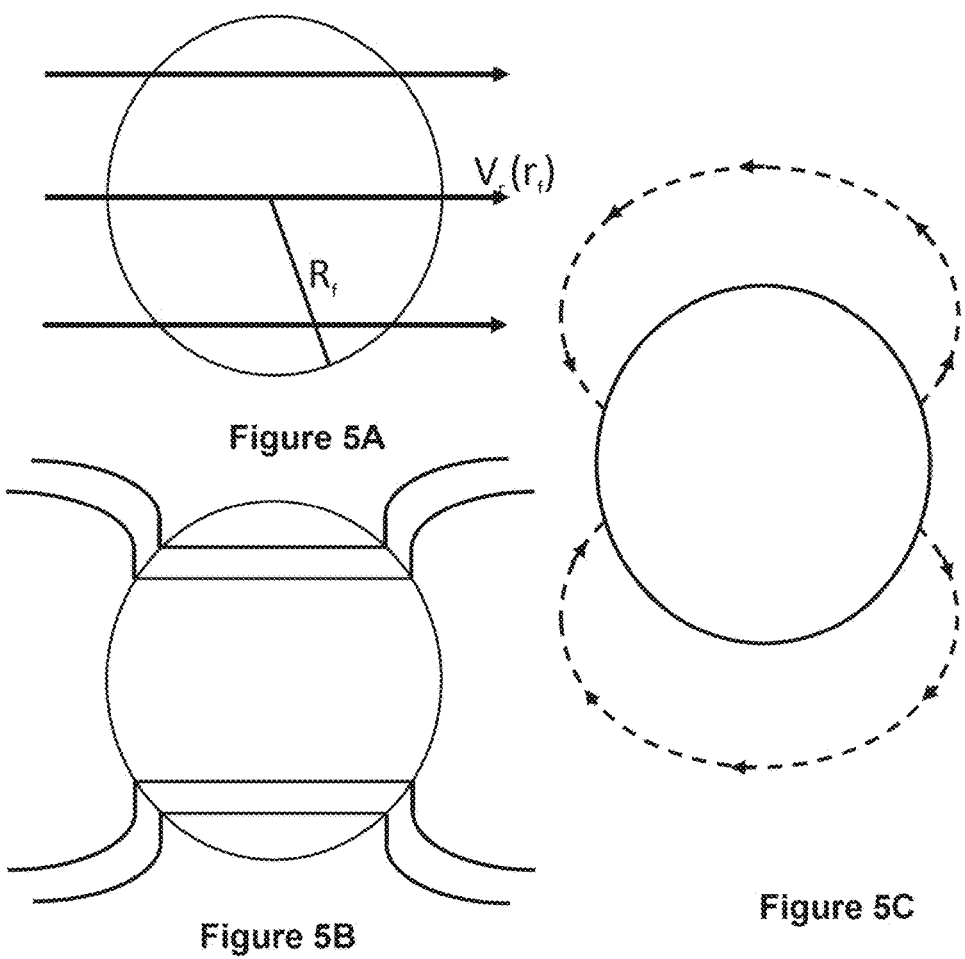
Figure 5A
Figure 5B
Figure 5C
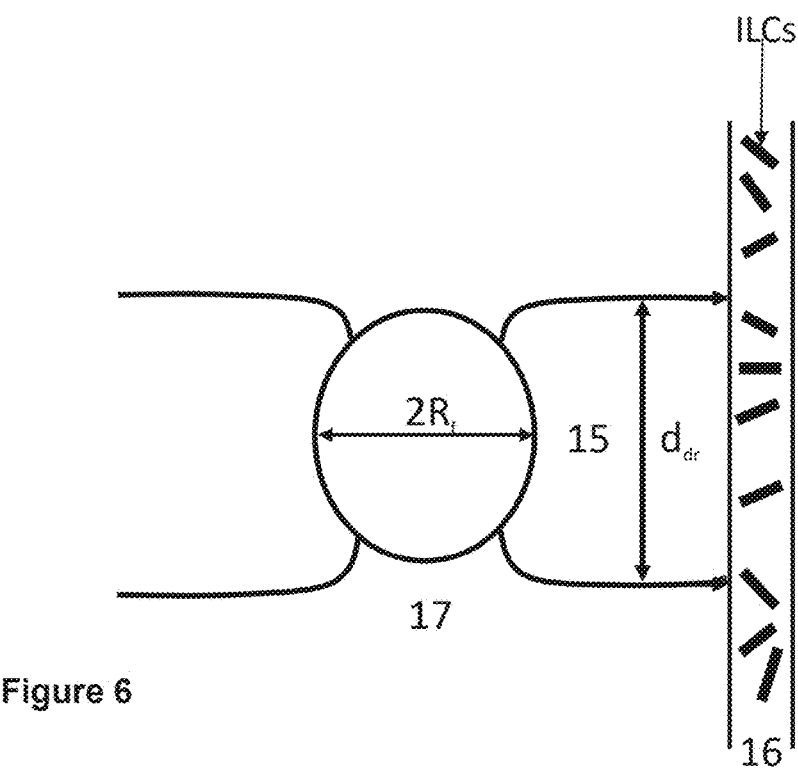
Figure 6

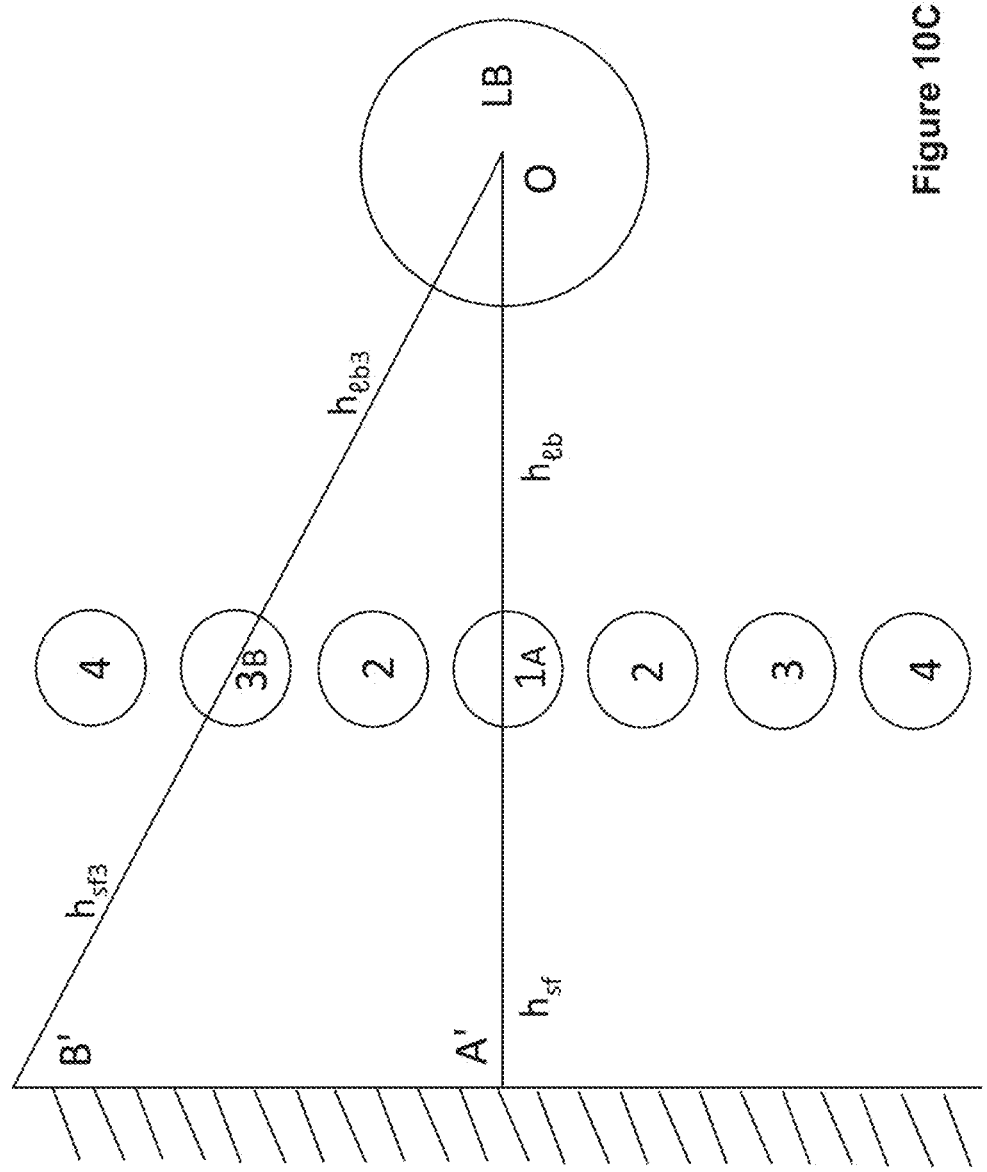

250

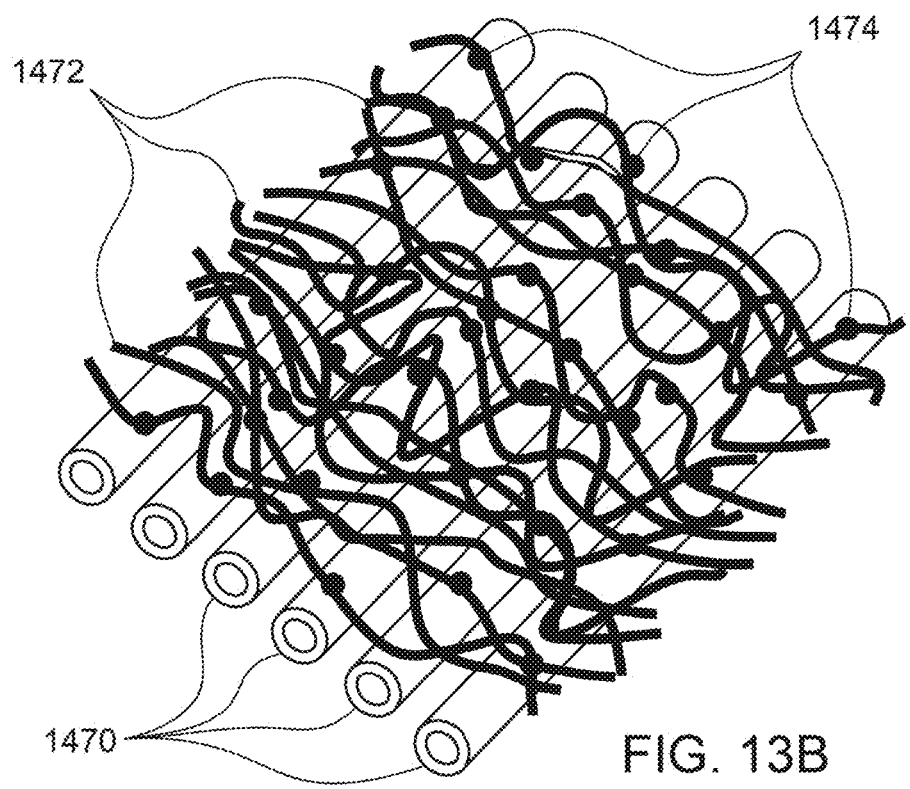
FIG. 13B
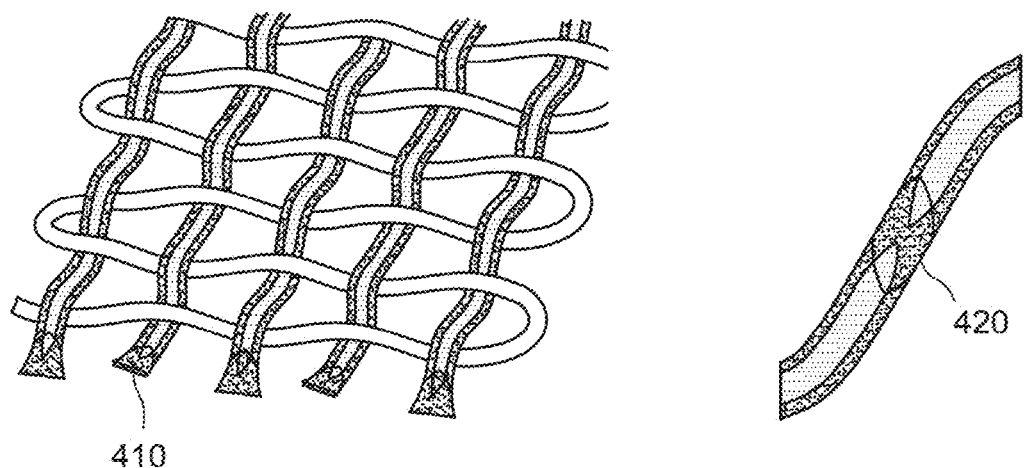
FIG. 14A
FIG. 14B 470  487  FIG. 14I

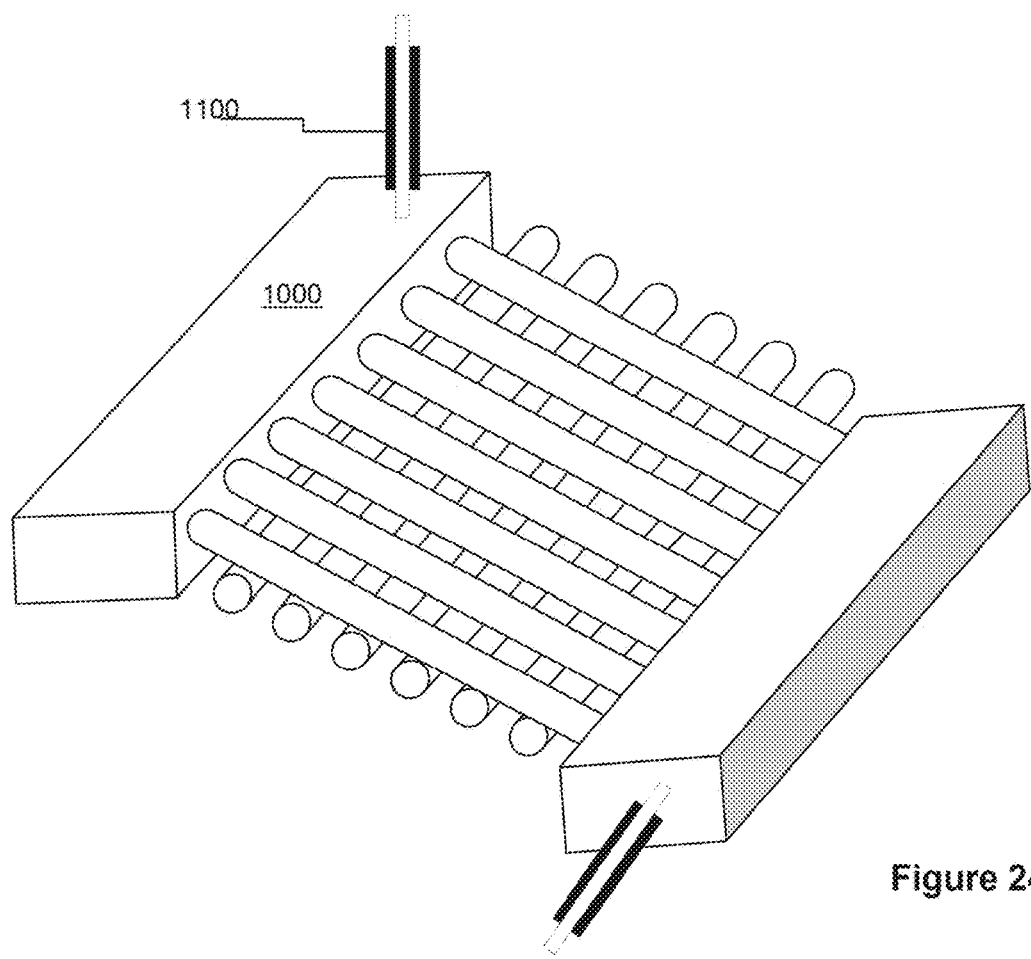
Figure 24C
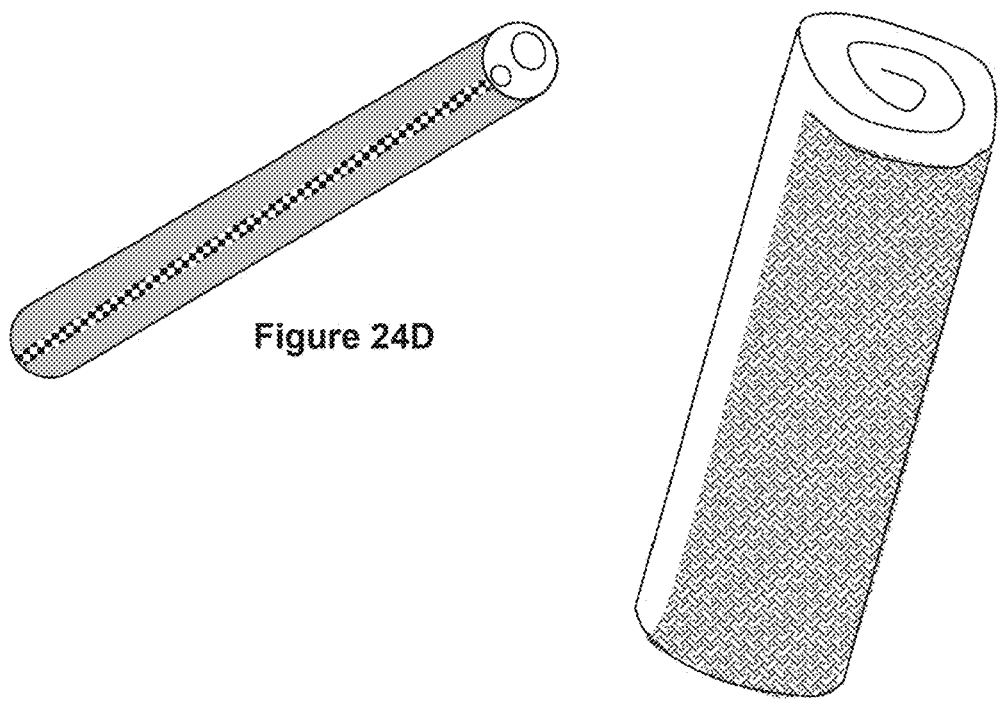
Figure 24D
Figure 24G

Figure 26A  Figure 26B

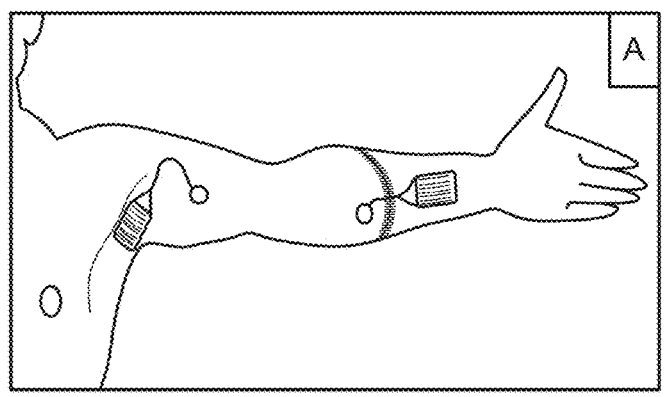 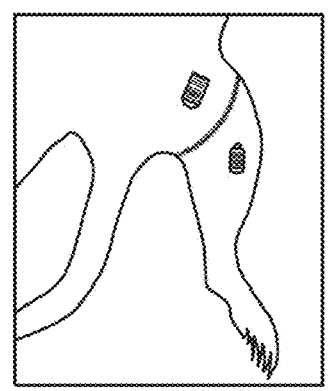
FIG. 30A  FIG. 30B
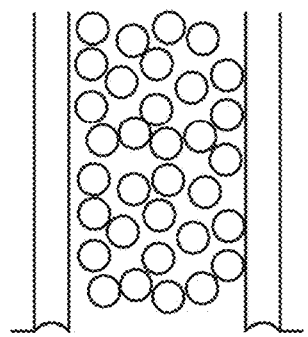 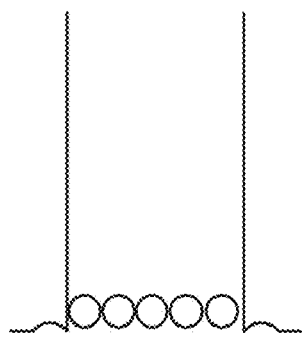 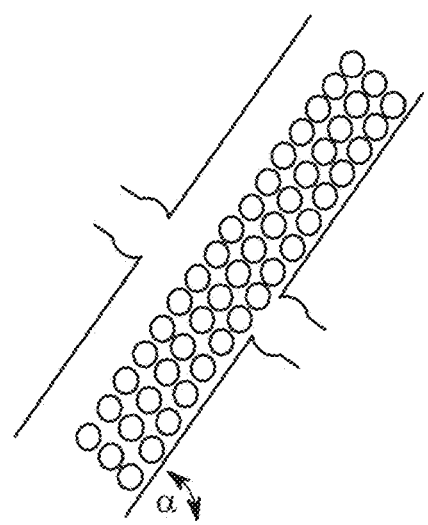
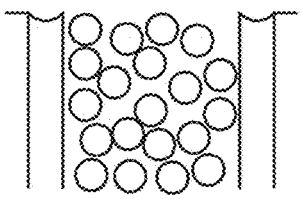
FIG. 31  FIG. 32  FIG. 33
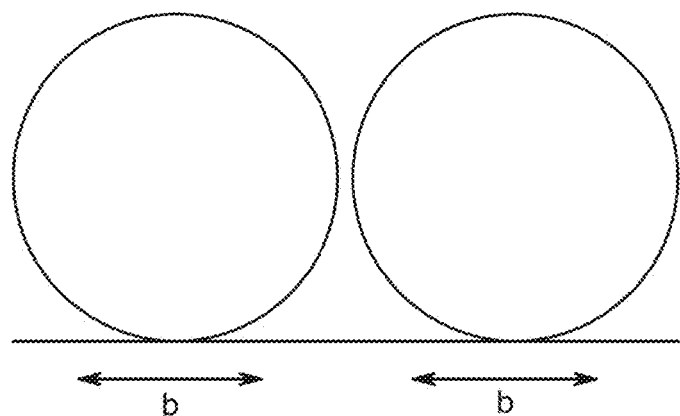
FIG. 34

IMPLANTS AND CONSTRUCTS INCLUDING HOLLOW FIBERS

This application is a continuation of U.S. Ser. No. 15/743,763, filed Jan. 11, 2018, which is a National Phase application of PCT/US2016/043585, filed Jul. 22, 2016, and claims the priority of 62/196,289, filed Jul. 23, 2015; 62/197,814, filed Jul. 28, 2015; and 62/359,102, filed Jul. 6, 2016, the contents of which are incorporated herein in their entirety.

FIELD OF THE INVENTION

Embodiments of the invention pertain to the delivery of drugs to sites in need of such treatment, and pertain to new drug delivery systems, designs, devices and methods comprising hollow fibers, hollow fiber fabrics and meshes, hollow fiber based devices and hollow fiber constructs made therefrom.

BACKGROUND OF THE INVENTION

Various technologies exist for the controlled delivery of drugs to patients. For example, for implanted fabrics or meshes, the solid fibers comprising the fabric or mesh are sometimes coated with small molecular drugs or biologics prior to implantation. However, the type, class and amount of the drug or biologic that can be introduced in this manner is somewhat limited, and can be depleted quickly after implantation. In many applications such drug delivery systems are not suitable for long-term release therapies or some other therapies.

In another approach, drugs can be blended or impregnated into the fibers of a degradable (resorbable) fabric or mesh, such that the drugs would be released over a time, and the material of which the fibers are made is then absorbed into the body. This method works but can be limited to pharmaceuticals or biologics that can tolerate elevated temperatures, or exposure to solvents, and can remain active after harsh processing conditions needed to create the drug delivery device.

Accordingly, it is desirable to have greater ability and flexibility to control the release rate, drug quantity, location, and other parameters of the drug delivery system and implants. It would also be desirable to combine the drug delivery with another function such as structure of the device that incorporates the drug to be delivered. It would also be highly desirable to employ drug delivery systems such that sensitive drugs or biologics can be loaded or incorporated into devices without degrading such drugs during preparation, processing or manufacturing.

In clinical practice, implanted surgical meshes such as hernia repair meshes or other constructs used in reconstruction procedures can become infected with bacteria in the form of biofilm. A major reason that infections associated with prosthetic meshes cannot be resolved using systemic antibiotic chemotherapy, and therefore require removal of the prosthetic mesh or device, is because pathogens form bacterial biofilms directly on the meshes themselves, and biofilm bacteria are highly resistant to antibiotics, requiring therapeutic concentrations thousands of times the minimum biocidal concentration (MBC) as determined by conventional antibiogram. These antibiotic concentrations far exceed those achievable by systemic administration. Weavable and flexible filament that can provide the mechanical strength needed for the implantable device while at the same time eluting antibiotics and antimicrobials to prevent the formation of biofilm, which is extremely desirable for use in patients with high risk of infection. Another important consideration in the design of anti-biofilm surgical meshes and sutures for soft tissue repair is that: 1) they target a wide range of Gram positive and Gram negative bacteria since these types of infections are often polymicrobial, and 2) they have the potential to specifically target biofilm formation. Ideally, such a material would provide prophylactic protection preventing biofilm formation on the device for a period of weeks to months, which appears from the clinical data to be the critical "at-risk" period.

Known implantable drug delivery devices mainly operate using diffusion as the drug release mechanism. This limits the types of therapies to which they are applicable, as determined by the release characteristics that they are able to provide.

SUMMARY OF THE INVENTION

This invention described herein is of medical devices, uses thereof, and method of preparing the same. Various advantages, aspects, and features of the present disclosure, as well as details of illustrated embodiments thereof, will be more fully understood from the following description and drawings. The foregoing summary is not intended, and should not be contemplated, to describe each embodiment or every implementation of the present invention. The Detailed Description and exemplary embodiments therein more particularly exemplify the present invention.

BRIEF DESCRIPTION OF THE ILLUSTRATIONS

Embodiments of the invention are further described but are in no way limited by the following illustrations.

FIG. 1A illustrates the spatial relation of the drug particles, the porous wall of the fiber, and the external tissue for a situation where the wall has low hydrodynamic permeability and the drug release is diffusion-dominated; FIG. 1B illustrates the spatial relation of the drug particles, the porous wall of the fiber, and the external tissue for a situation where the wall has high hydrodynamic permeability and the drug release is hydrodynamically-driven; FIG. 1C shows the geometric relation of fiber wall, lumen, drug particles and tissue; FIG. 1D shows the location of a diffusion layer outside the hollow fiber.

FIG. 2A shows anatomy of the lymphatic system (1. lymphatic venous anastomosis, 2. node blood supply, 3. afferent lymphatic vessels, 4. efferent lymphatic vessels, 5. lymphangion, 6. lymph node); FIG. 2B schematically shows flow of interstitial fluid from interstitium 8 towards an initial lymph capillary (ILC) 7, and thereby into afferent lymphatic vessel 3. Inset (a) shows decreased pressure inside an ILC as it nears an afferent lymphatic vessel, and the axial dependence of pressure. Inset (b) shows interstitial fluid flow towards an initial lymph capillary, where Jr(R,Z) is the flyux density in the dadial direction around the ILC with axial symmetry.

FIG. 3A is a schematic showing in cross-section prenodal lymphatics including branching of passageways, including afferent capillary 3, precollectors 9 and ILCs 3; FIG. 3B shows a schematic for a velocity distribution around a disk-like lymphatic bed of initial lymph capillaries.

FIG. 4A shows an exemplary geometric relation of a fiber and a lymphatic bed (with a cross-section inset); FIG. 4B is similar to FIG. 4A, but includes an epithelial barrier (skin tissue) and definitions of geometric parameters; FIG. 4C shows a positioning of Initial Lymph Capillaries and the skin; FIG. 4D shows a velocity distribution in the vicinity of a lymphatic bed, in side view and cross-section (skin, 11, afferent capillary 3, initial lymph capillaries 7, streaming lines of interstitial fluid 12, 13).

FIG. 5A shows a locally uniform velocity distribution past a fiber if the fiber did not disturb the flow; FIG. 5B shows a schematic for real velocity distribution. The real velocity distribution 5B can be presented as the superposition of 5A and 5C; FIG. 5C shows a velocity distribution of a hydrodynamic dipole.

FIG. 6 shows a schematic illustrating a drug convective strip 15 caused by hydrodynamically-driven drug release from a high hydrodynamic permeability hollow fiber 17, which encounters small portion of a disk-like lymphatic bed (LB) 16.

FIG. 7A is a schematic illustrating disposition of hollow fiber fabric and disk-like lymphatic bed (LB) (At small htb<<$2R_{lb}$, the interstitial flow through the fabric is almost uniform); FIG. 7B is a schematic illustrating drug strip with width, ddr>>$2R_{fi}$ caused by hydrodynamically driven drug release which encounters a small portion of a disk-like lymphatic bed (LB); FIG. 7C is a schematic illustration of the distribution, along fiber (sphere) surface, of the normal component of lumen velocity, $V_r^e(R, \theta)$; Legend as in FIG. 6.

FIGS. 8A and 8B, schematic for angular dependence of diffusion layer thickness δ in case of hydrodynamically impermeable sphere and for a permeable sphere, respectively. The δ extension of $\Theta > \pi/2$ is caused by outward velocity and is not relevant in our analysis, focused on $\Theta > \pi/2$.

FIG. 8B is a schematic for angular dependence for δ when the sphere is hydrodynamically permeable. The hydrodynamic flow opposite to diffusion retards diffusion departure of solute from fiber lumen. This decreases δ thickness at $\Theta \sim \pi/2$ diffusion layer separates from membrane and forms thin coaxial cylinder around hydrodynamic strip originated due to convection through the lumen. As the width of coaxial cylinder is smaller than in the case of impermeable sphere, the diffusion contribution to hydrodynamically driven release is small.

FIG. 9 illustrates a schematic for pressure distribution arising after placement of hollow fiber into interstitial flow generated by lymphatic bed (LB). The fiber axis is parallel to LB surface. 1) Fiber lumen 17A, hollow fiber membrane wall 17B and tissue 21 are indicated. Shown by straight line 31 is the linear pressure distribution $P_{ext}$, that existed before fiber placement; pressure distribution 32 in lumen with small gradient $K_L$; pressure distribution 33 with membrane with higher pressure gradient because $K_m<<K_L$; pressure distribution 34 inside adjacent tissue with high pressure gradient near membrane surface because of $K_{ti}<<K_m$, pressure gradient gradually decreases approaching at large distance to initial pressure gradient; and lumen surface 35.

FIG. 10A is a schematic to mechanism of preventing drug diffusion from lumen into tissue due to opposite liquid flow in a single isolated straight pore (hollow fiber membrane). FIG. 10B is a schematic for angular dependence for radius and tangential V$\Theta$ components of liquid velocity on surface of hollow fiber (represented by circle) which affects drug diffusion from lumen into tissue (drug-release). Large radial velocity and small tangential velocity at $\Theta < \Theta_b$ suppress diffusion. The diffusion becomes noticeable in vicinity of $\Theta = \pi/2$ where normal velocity decreases fast while the tangential velocity is at its maximum.

FIG. 10C shows an arrangement of fibers (17-1A, 17-2, 17-3, 17-3B, 17-4) for analysis of drug release, providing Proof, that $h_{sf3}=h_{lb3}$, when $h_{sf}=h_{lb}$. Triangles ABO and A'B'O' are similar, because they have two equal angles near O and near A or A'. FIG. 10D shows another arrangement of fibers (17-1 through 17-8) for analysis of drug release. FIG. 10E shows a result for a multi-layer fabric. FIG. 10F shows a positioning of skin 11, fabric 22 and lymph node 6.

FIG. 13B shows hollow fibers that are attached to each other by randomly oriented fibers.

FIG. 14A shows a woven fabric comprising hollow fibers and solid fibers, with the ends of the hollow fibers closed.

FIG. 14B shows an individual hollow fiber having a deformation that separates the lumen on one side of the deformation from the lumen on the other side of the deformation.

FIG. 14I shows an implant comprising a nonresorbable hollow fiber this attached to itself by joining structures.

FIG. 24C shows an arrangement of hollow fibers connected to two manifolds, one as an inlet and the other as an outlet.

FIG. 24D shows a catheter that also contains a hollow permeable-walled fiber.

FIG. 24G shows an embodiment of the invention in the form of a rolled-up fabric.

FIG. 26A shows fluorescein release from a hydrophilic polypropylene fiber at 30 seconds after being placed on the filter FIG. 26B shows fluorescein release from a hydrophilic polypropylene fiber at 8 hr after being placed on the filter.

FIG. 30A illustrates the possible placement of devices of an embodiment of the invention, for a possible human limb transplant.

FIG. 30B similarly illustrates possible device placement for a limb transplant in a rat.

FIG. 31 illustrates arrangement of powder particles inside a fiber lumen, showing a thin region near the wall that is not occupied by powder particles, due to dissolution.

FIG. 32 shows rearrangement of the positions of powder particles.

FIG. 33 illustrates a sloped fiber whose powder column that remains in approximately its original configuration as particles shrink due to dissolution.

FIG. 34 illustrates, in cross-section, a parallel array of hollow fibers that forms contact zones with adjacent tissue.

Figure 35:
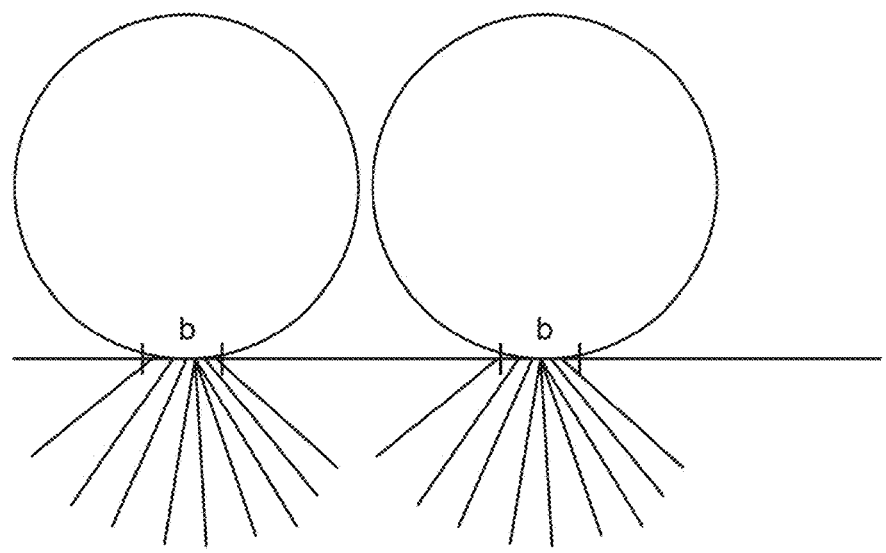

FIG. 35 illustrates diffusion occurring through the contact zone.

Figure 36:
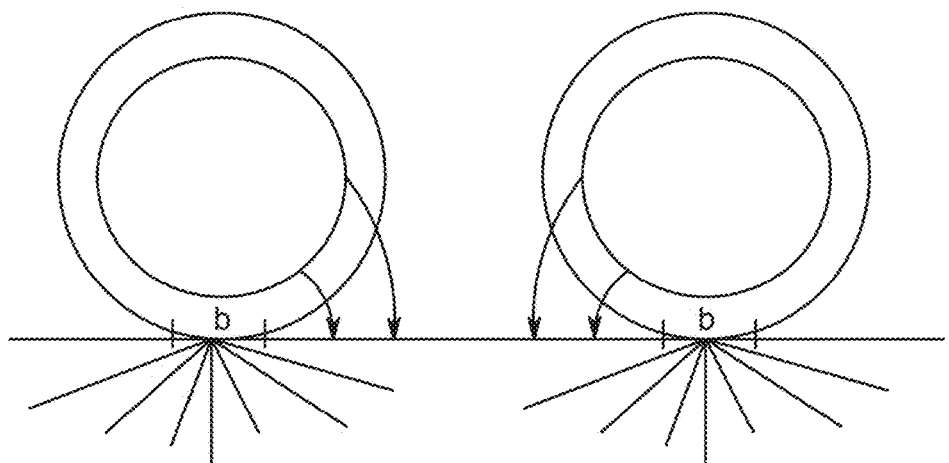

FIG. 36 illustrates diffusion occurring both through the contact zone and through adjacent tissue.

Figure 37A:
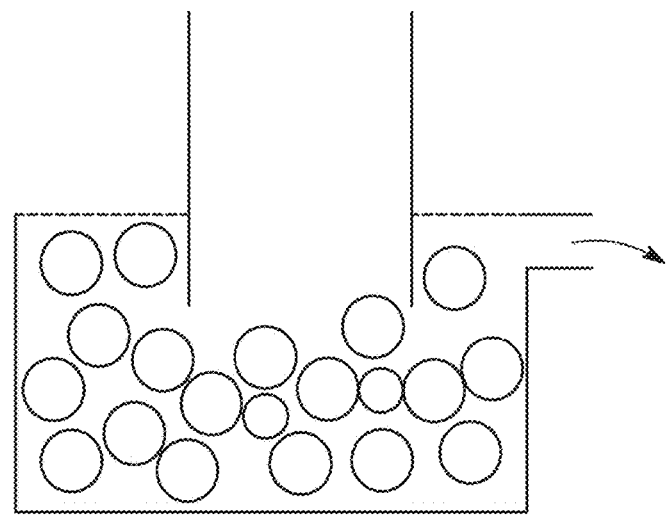

FIG. 37A shows an empty hollow fiber whose end is immersed in a bed of powder particles, with several particles of suspension entering the bed.

Figure 37B:
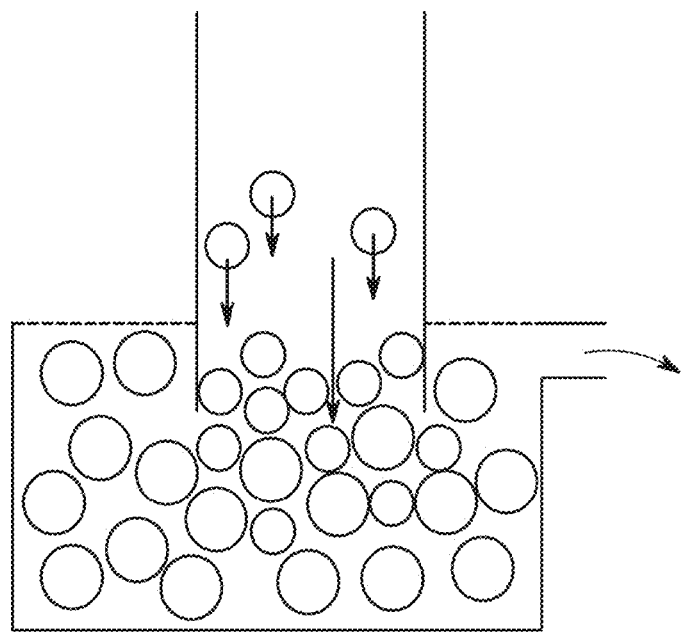

FIG. 37B shows the configuration of FIG. 27A with slightly more suspension particles.

Figure 37C:
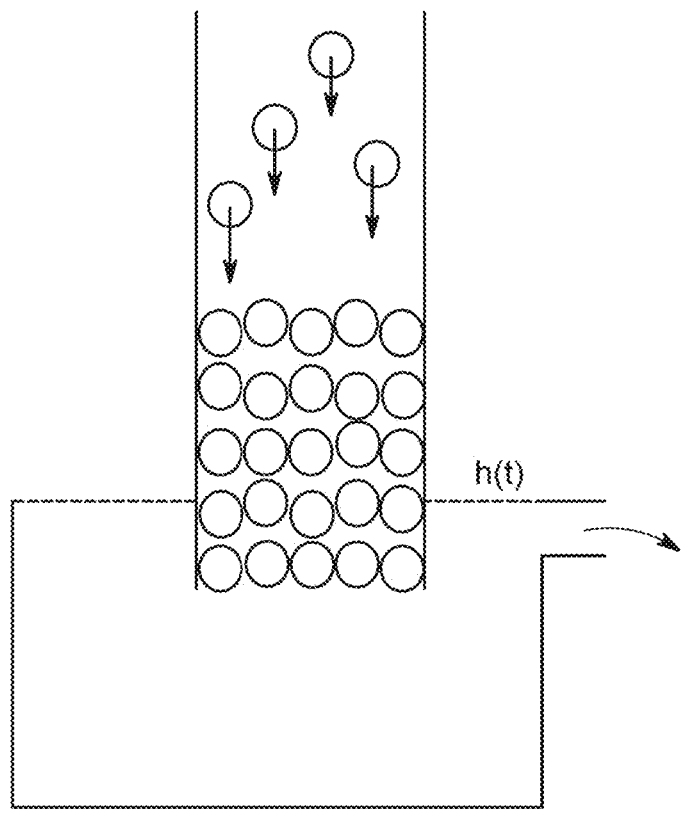

FIG. 37C shows a still larger collection of suspension particles inside the fiber.

Figure 38:
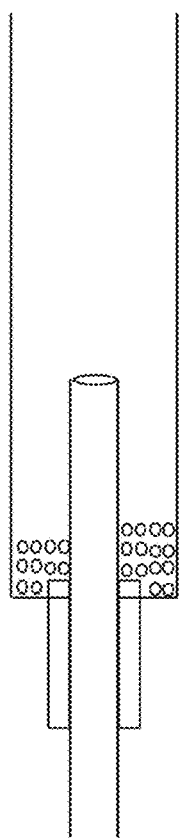

FIG. 38 illustrates an exemplary arrangement for causing flow of suspension into a hollow fiber for purposes of filling the fiber lumen with particles.

Figure 39:
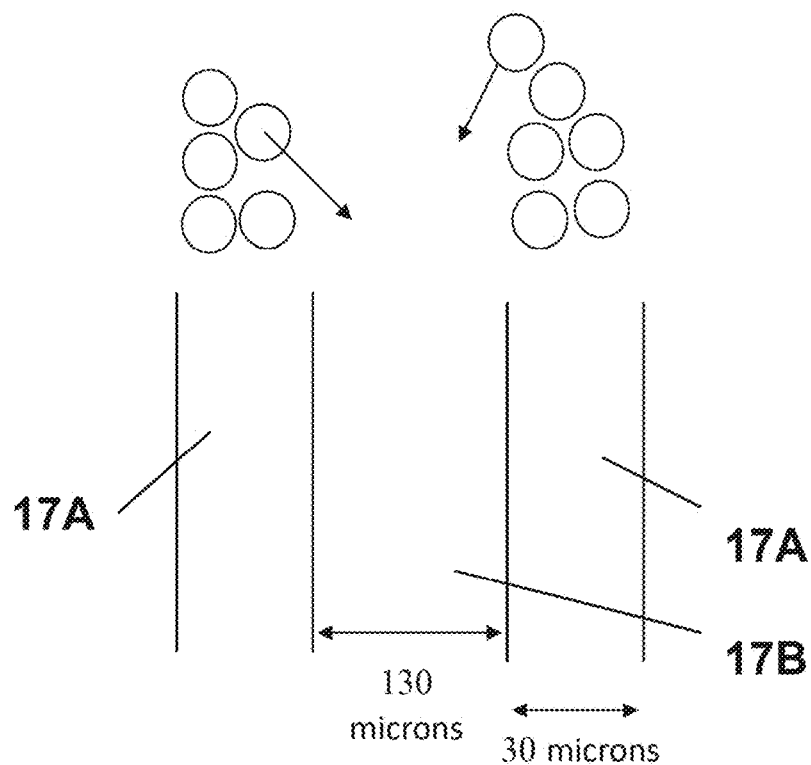

FIG. 39 illustrates a deposition of some powder particles on an edge surface of a wall of a hollow fiber.

Figure 40:
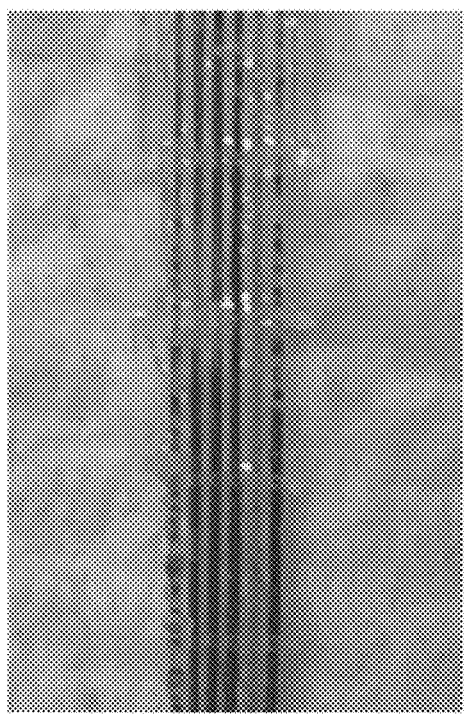

FIG. 40 illustrates an experimental result for the filling of a hollow fiber with particles.

DETAILED DESCRIPTION OF THE INVENTION

In embodiments of the invention, provided is an article having a hollow fiber having walls that are permeable, which can be understood to include any one or more of being semi-permeable, being nanoporous or microporous, or having holes through such walls.

A "deformation" at a selected place along the length of hollow fiber obstructs, including prevents, fluid communication in the fiber interior from one side of the deformation to an opposite side of the deformation.

A "distinct drug composition" is one that utilizes a different drug from the comparative, or uses the same drug but is formulated differently (e.g., different excipients, or different additional drugs).

A "fabric construct" can be for example a woven fabric, a knitted fabric, a nonwoven fabric, a mat, or the like, and can for example form a flexible sheet, a tubular structure, or the like. Fabric constructs can be formed by linking strands of fiber (e.g., bonding or spot welds), or the like. The linking structures can be small amounts of material ("dots") adhered to separate parts of a hollow fiber, or linking parts of a mass of separate fibers. Such linking structures can be resorbable. A fabric construct is a network of one or more fibers and can take any shape.

A "fiber-complex" is a fabric construct or a yarn construct.

A "laminate" is a bonding, fusing, adhesion, or the like between polymer layers, or between polymer and fabric layers, such that in the range of anticipated use the laminate is a unitary structure.

"Linearly cohesive fibers" in un-restrained form provide a string-like flexible fiber or group of fibers where the fibers are connected enough that the pulling on one point of the linearly cohesive fibers draws the fibers in the same way that pulling on a point of a string would. In use, points in the linearly cohesive fibers can be connected say with resorbable connections or fibers such that the overall structure resists such string-like pulling. After the connections degrade, a device with linearly cohesive fibers can be withdrawn for example through a small incision by such string-like pulling.

A "mechanical property" for a fiber will be recognized by those of skill in the art, and can include for example tensile strength, elasticity, elongation at fracture or break, Young's modulus, shear modulus, stiffness, compressive strength; yield stress, flexural strength, flexural modulus, bulk modulus, shear modulus, Poisson's ratio, fracture strength, fracture toughness, creep strength, fatigue strength, ductility, being hollow or being solid. Being "stronger" is a subset of these properties, and indicates greater strength by one of (as applicable to the material) tensile strength, compressive strength, flexural strength, bulk modulus or fracture strength.

A "native permeable wall" pursuant to this invention is one that is permeable by reason of the permeability resulting from the bulk processing or manufacturing process of the wall material, but not including manufacturing steps that create defined channels or holes in predetermined locations. The pores of a native permeable wall are not formed by mechanical or other drilling (e.g. laser), or other processes conducted after the fiber is formed. The pores of a native permeable wall are not formed by molding the fiber shape with intrusions in the mold that will define macroscopic pores or passageways. Stretching the fiber during bulk processing or manufacturing can provide a native permeable wall (with pores elongated in the stretch direction). In embodiments, the average pore diameter in a native-permeable wall is from about 1 nm to about 1 micrometer.

A "non-metallic" fiber can be for example a polymeric fiber or a composite fiber comprising a solid dispersion in polymer. It also could be a ceramic fiber.

The conjunction "or" includes the meaning "and/or" unless the context clearly excludes that meaning.

A "potting material" is a material available in a liquid or moldable form that can be used to mold or form a leak-resistant gasket around a hollow fiber or a group of hollow fibers. In embodiments, the potting material can set (e.g., crosslinked) after molding or forming.

Certain embodiments utilize a "reservoir-providing amount" of a drug, which is an amount that, in its region of interior channel, provides when in use in a subject's body a solution of free drug and drug in a solid formulation. In embodiments, the amount of drug in a solid formulation is effective, when operating in diffusion mode, to provide a reservoir of drug that would extend the period of time over which the device emits a pharmaceutically effective amount of drug over that time without the solid formulation. The solid formulation can be solid (undissolved) drug, a time-release formulation (e.g., encapsulated. compressed with time-release polymers or other components, adsorbed to solids including cyclo-binding entities such as cylcodextrin, and the like).

Molecules are "resistant" to passage through or permeation through a barrier for example large molecules are retained in fiber lumens for the effective life of the medical device, or drugs are prevented from achieving the target concentration on the wrong side of a barrier layer. Absolute prevention of such passage or permeation is included within the concept.

In embodiments with deformations, between deformations there can be areas that are substantially free of drug to provide cut zones. "Substantially free of drug" in such embodiments that the amount of drug present will not have a material effect on drug dosing.

A drug emitting material "substantially surrounds" an area of tissue or an area where tissue growth is sought if it sufficiently surrounds along an axis of the tissue or sought tissue so as to deliver a pharmaceutically effective amount of drug to the peripheries of the tissue or sought tissue along the axis.

A "tissue location" can be a location in a tissue, between tissues, or otherwise in a subject's body.

"Treating" a disease, disorder or condition includes ameliorating the symptoms of the disease, disorder or condition, or delaying or ameliorating the progression or initiation of disease, disorder or condition, including symptoms or complications thereof. Given appropriate drug, any animal can be treated, including mammals such as humans. To treat indications with a therapeutic agent, an "effective amount" of a drug will be recognized by clinicians but includes an amount effective to treat, reduce, alleviate, ameliorate, eliminate or prevent one or more symptoms of the condition sought to be treated, or alternately, the condition sought to be avoided, or to otherwise produce a clinically recognizable favorable change in the condition or its effects.

Drug can be contained within space defined by the hollow fiber, such as in the lumen of the fiber. It is also possible that drug can be contained in the pore space of the fiber wall and possibly also on the outer surface of such fibers. Drug can be defined broadly as any beneficial substance for medical treatment, including small molecular drugs and also including biologics such as peptides, proteins, enzymes, antibodies, DNA, RNA, growth factors or modulators, immunogens, immune-therapeutics or the like, and any substance such as a chemical that can act on a cell, virus, tissue, organ or organism to create a change in the functioning of the cell, virus, organ or organism to achieve a pharmaceutical or therapeutic effect. The lumens of the hollow fibers can contain an appropriate pharmaceutical drug which can be a small molecular drug or a biologic such as proteins and the like. Still other substances such as excipients or drug release enhancers or modulators could also be present in the lumen or in other parts of the fiber or in the drug delivery device or constructs.

A "yarn construct" can be for example a woven yarn, a nonwoven yarn, or the like. Yarn constructs can be formed by linking strands of fiber (e.g., bonding or spot welds), or the like. The linking structures can be small amounts of material ("dots") adhered to separate parts of a hollow fiber, or linking parts of a mass of separate fibers. Such linking structures can be resorbable.

In certain embodiments, a drug is a biological, in that it is extracted from tissue or cell culture, or a substantial portion of its mass (40% or more) is derived from tissue or cell culture.

In certain embodiments, a drug has a molecular weight of 1,000 or higher.

Hollow fiber based drug delivery devices are described. The device can also contain structural or solid fibers. Fabric can be formed by fibers being interwoven or attached to each other. All or some of the fibers can be resorbable.

In some embodiments of the invention, drug-loaded hollow fibers can be subdivided, by deformations or closure points, into numerous compartments that separately deliver drug. Deformations can be located at points of fiber intersection or joining, or can have any of various different patterns or designs. Via such compartments, a different drug or drug formulation can be provided at a given place in the device.

Fibers can be given appropriate surface treatments or coatings to achieve desired properties as far as wetting of pores and surfaces. Surfactant can be included in the formulation. Different release characteristics in different directions can be achieved. The hollow fibers can contain for example solid particles of drug, and can contain gel.

Possible applications include hernia meshes, pouches, sutures, catheters, wound dressings, stents, nerve regrowth guides, devices for use in the female reproductive tract, refillable/drainable devices, and devices that deliver drug to systemic or lymphatic flow.

Embodiments of the present invention pertain to novel means and devices for delivering antimicrobial agents, other drugs or biologics to prevent infections associated with repair sutures and meshes or to treat other diseases. A depot of anti-biofilm agents contained within a novel drug delivery device fashioned as a microporous or semi-permeable hollow fiber mesh will allow for slow but sustained release. Because a clinically significant amount of drug can be loaded into hollow fibers of the meshes or fabrics or constructs, and because the release kinetics from the drug delivery device mesh construct are highly predictable and controllable, it will be possible to achieve effective therapeutic concentrations without the issues associated with conventional systemic delivery.

The drug delivery systems and devices included in embodiments of the present invention are not to be limited to infection treatment or prevention, but can deliver drugs or biologics of all classes to body tissues and organs to treat disease.

In an embodiment of the invention, provided is an implantable medical device, comprising: one or more first fibers, the first fibers having a first mechanical property, the first fibers being hollow fibers comprising a permeable wall that defines an interior, wherein a first drug or a first drug formulation is located in at least some of the interior, wherein the wall and its porosity characteristics at least partially determine a release rate of the drug or the drug formulation; and one or more second fibers having a second mechanical property different from the first mechanical property, wherein the second fibers are interwoven with the first fibers. In embodiments the device generally forms a fabric shape (e.g., flat, but bendable).

In an embodiment of the invention, provided is an implantable medical device, comprising: first fibers, wherein the first fibers are oriented generally in a first direction, wherein the first fibers are hollow fibers and contain an active pharmaceutical ingredient in their lumens; and second fibers, wherein the second fibers are oriented generally in a second direction different from the first direction, wherein the second fibers are solid fibers or are fibers that do not contain an active pharmaceutical ingredient, the first fibers and the second fibers being attached to each other at least some crossing points. In embodiments the second fibers are structurally stronger than the first fibers. In embodiments the device generally forms a fabric shape (e.g., flat, but bendable).

In an embodiment of the invention, provided is an implantable medical device, comprising: fibers, wherein said fibers are oriented generally in a first direction, wherein said fibers are hollow fibers and contain an active pharmaceutical ingredient in their lumens; and joining structures that join one of said fibers to another of said fibers, wherein said joining structures joining structures are located between one of said fibers and its nearest neighbor fiber.

In an embodiment of the invention, provided is an implantable medical device, comprising: first fibers oriented generally in a first direction, wherein the first fibers are hollow fibers and contain an active pharmaceutical ingredient in their lumens; second fibers that are solid fibers or are fibers that do not contain an active pharmaceutical ingredient, wherein the second fibers are oriented generally in a second direction different from the first direction and third fibers that are solid fibers or are fibers that do not contain an active pharmaceutical ingredient, wherein the third fibers are oriented generally in a third direction different from the second direction. In embodiments the second fibers and the third fibers are stronger than the first fibers.

In an embodiment of the invention, provided is an implantable medical device, comprising: first fibers, wherein the first fibers are oriented generally in a first direction, wherein the first fibers are hollow fibers and contain a first drug or a first drug formulation in their lumens; and second fibers, wherein the second fibers are oriented generally in a second direction different from the first direction, wherein the second fibers are hollow fibers and contain a second drug or a second drug formulation, distinct from the first, in their lumens, wherein the first fibers and the second fibers are attached to each other at points where the first fibers and the second fibers cross each other.

In an embodiment of the invention, provided is an implantable medical device, comprising: at least one first fiber, the first fiber being a hollow fiber comprising a permeable wall that defines an interior, wherein a first drug or a first drug formulation is located in at least some of the interior, wherein the wall at least partially determines a release rate of the first drug or the first drug formulation, wherein the first fiber is substantially non-resorbable; and at least one second fiber, wherein the second fiber is resorbable, the second fiber crossing the first fiber in at least some locations.

An embodiment of the invention provides a method of treating a patient, comprising: implanting in the patient a device comprising a non-resorbable fiber or fibers, and a resorbable fiber or component restraining the non-resorbable fiber; allowing the device to remain in the patient for a sufficiently long time so that enough of the resorbable fiber or component is resorbed so that the non-resorbable fiber or fibers become structurally unrestrained; and removing the non-resorbable fibers from the patient by pulling the non-resorbable fibers generally along their length.

In an embodiment of the invention, there provided is an implantable medical device, comprising: first fibers, wherein the first fibers are oriented generally in a first direction, wherein the first fibers are hollow fibers and contain a first drug or a first drug formulation in their lumens; and second fibers, wherein the second fibers are oriented generally in a second direction different from the first direction, wherein the second fibers are hollow fibers and contain a second drug or a second drug formulation in their lumens, wherein the first fibers and the second fibers are interwoven with each other.

In an embodiment of the invention, provided is an implantable medical device, comprising: a first layer comprising one or more first hollow fibers having a first permeable wall that defines a first interior, wherein a first amount of a first drug or a first drug formulation is located in at least some of the first interior, wherein the first wall at least partially determines a first release rate of the first drug, the first hollow fibers having a first release characteristic and a first set of dimensions; a second layer, located near the first layer, comprising one or more hollow fibers having a second permeable wall that defines a second interior, wherein a second amount of a second drug or a second drug formulation is located in at least some of the second interior, wherein the second wall at least partially determines a second release rate of the second drug, the second hollow fibers having a second release characteristic and a second set of dimensions, wherein at least one of the first drug, the first drug formulation, the first amount of the first drug, the first release characteristic and the first set of dimensions differs from a corresponding one of the second drug, the second amount of the second drug, the second drug formulation, the second release characteristic and second set of dimensions.

In an embodiment of the invention, provided is an implantable medical device, comprising: one or more hollow fibers having a permeable wall that defines an interior, wherein a drug is located in at least some of the interior, wherein the wall at least partially determines a release rate of the drug, wherein in different parts of the drug delivery device, one or more hollow fibers contain a drug formulation that is different from a drug formulation found in fibers in another part of the device.

In an embodiment of the invention, provided is an implantable medical device, comprising: a first layer comprising one or more first hollow fibers having a first permeable wall that defines a first interior, wherein a first amount of a first drug or a first drug formulation is located in at least some of the first interior, wherein the first wall at least partially determines a first release rate of the first drug, the first hollow fibers having a first release characteristic and a first set of dimensions; a second layer, located near the first layer, comprising one or more second fibers, the second fibers being stronger than the first fibers.

In an embodiment of the invention, provided is an implantable medical device, comprising: at least one first fiber, the first fiber being hollow having a wall that defines an interior, wherein a first drug or a first drug formulation is located in at least some of the interior, wherein the wall is permeable to the first drug or the first drug formulation, wherein the wall at least partially determines a release rate of the first drug or the first drug formulation, wherein the fiber has one or more deformations at selected place(s) along its length, wherein in the deformation, a first portion of a wall of the fiber deformed toward a second portion of the wall of the fiber that is opposed to the first portion of the wall of the fiber.

In an embodiment of the invention, provided is an implantable medical device, comprising: a first polymeric layer; a second polymeric layer; and junctions between the first layer and the second layer, wherein the junctions define discrete regions enclosing individual volumes between the first layer and the second layer, wherein at least some of the discrete regions contain a first drug or a first drug formulation, wherein the first layer is permeable to the first drug or the first drug formulation. The layers can be attached to each other in either continuous or intermittent fashions or both. Either or both layers can have characteristics to deliver drug in a diffusion-dominated manner, or a hydrodynamically-driven manner, or a combination thereof.

In an embodiment of the invention, provided is an implantable medical device, comprising: one or more hollow fibers having a wall that that defines an interior, the wall being permeable, wherein at least some of the interior contains a drug composition, wherein the wall at least partially determines a release rate of the drug composition, and wherein at least some of the interior further contains an absorbent substance suitable to absorb water when in the presence of aqueous bodily fluids, wherein the drug can pass through the wall and the absorbent has a molecular weight such that the absorbent is unable to pass through the wall.

In an embodiment of the invention, provided is an implantable medical device, comprising: one or more hollow fibers having a wall that that defines an interior, the wall being semi-permeable, wherein at least some of the interior contains a drug composition, wherein the wall at least partially determines a release rate of the drug composition, and wherein at least some of the interior further contains a viscosity-enhancing or gel-forming substance that produces a high viscosity or a gel when in aqueous solution, wherein the viscosity-enhancing or gel-forming substance has a molecular weight such that the viscosity-enhancing or gel-forming substance is unable to pass through the wall.

In an embodiment of the invention, provided is an implantable medical device, comprising: one or more longitudinal hollow fibers having a wall that that defines an interior, the wall being permeable, wherein at least some of the interior contains a drug composition, wherein the wall at least partially determines a release rate of the drug composition, and wherein at least some of the interior further contains at least one surfactant, wherein the surfactant or surfactants are placed having different compositions or different concentrations in different places within the device.

In an embodiment of the invention, provided is an implantable medical device, comprising: one or more hollow fibers having a wall that defines an interior and an exterior, the wall being permeable, wherein a drug is located in at least some of the interior, wherein the wall at least partially determines a release rate of the drug from the interior, wherein the wall comprises a bulk material that is naturally hydrophobic but is treated to render it more hydrophilic than in its untreated condition.

In an embodiment of the invention, provided is an implantable medical device, comprising: one or more hollow fibers having a wall that defines an interior and an exterior, the wall being permeable, wherein a drug is located in at least some of the interior, wherein the wall at least partially determines a release rate of the drug from the interior, wherein, inside solid material of the wall, the wall comprises a first substance that does not contain any oxygen-bearing groups, and at surfaces of the wall or adjoining the pores, comprises a second substance that chemically is chemically similar to the first substance but comprises at least some oxygen-containing groups.

In an embodiment of the invention, provided is an implantable medical device, comprising: one or more hollow fibers having a wall that defines an interior and an exterior, the wall being permeable, wherein a drug is located in at least some of the interior, wherein the wall at least partially determines a release rate of the drug from the interior, wherein the wall comprises a first substance that does not contain any oxygen-bearing groups, and at surfaces of the wall or adjoining the pores, comprises a second substance that chemically is chemically similar to the first substance but comprises at least some polar groups containing nitrogen, sulphur or phosphorus.

In an embodiment of the invention, provided is an implantable medical device, comprising: one or more hollow fibers having a wall that defines an interior and an exterior, the wall having punctures or pores therethrough, wherein a drug is located in at least some of the interior, wherein the wall at least partially determines a release rate of the drug from the interior, wherein the wall comprises a first substance and a second substance, the first substance defining a geometry of the wall and the punctures or the pores, the second substance forming a coating on exposed surfaces of the punctures or pores, the second substance being more hydrophilic than the first substance.

In an embodiment of the invention, provided is an implantable medical device, comprising: one or more hollow fibers having a wall that defines an interior and an exterior, the wall being permeable, wherein a drug is located in at least some of the interior, wherein the wall at least partially determines a release rate of the drug from the interior, wherein the wall comprises a first substance that forms a bulk of the wall and a second substance that is absorbed among molecules of the first substance near exposed surfaces, the second substance being more hydrophilic than the first substance.

In an embodiment of the invention, provided is an implantable medical device, comprising: one or more hollow fibers generally made of a material and having a permeable wall that defines an interior, wherein a drug is located in at least some of the interior, wherein the wall at least partially determines a release rate of the drug, wherein the one or more hollow fibers are arranged into an array, and wherein at least some parts of a surface of the array are treated to be more hydrophilic than the material in its untreated state.

In an embodiment of the invention, provided is an implantable medical device, comprising: one or more hollow fibers having a wall that defines an interior and an exterior, the wall being permeable, wherein a drug is located in at least some of the interior, wherein the wall at least partially determines a release rate of the drug from the interior, wherein the wall comprises a first substance that is hydrophobic commingled with a second substance, the second substance being different from the first substance, wherein the second substance is more hydrophilic than the first substance.

In an embodiment of the invention, provided is an implantable medical device, comprising: one or more hollow fibers having a permeable wall that defines an interior, wherein a drug is located in at least some of the interior, wherein the wall at least partially determines a release rate of the drug, wherein the drug particles are surrounded by liquid having a viscosity greater than 1000 centipoise or are surrounded by a gel.

An embodiment of the invention can comprise a method of depositing drug into a lumen of a delivery device, the method comprising: creating a suspension of particles of the drug in a first liquid, causing the suspension to flow into the lumen through and end of the lumen; retaining the particles in the lumen by causing the first liquid to exit the lumen either through and end of the lumen or through pores or both; replacing the liquid with a substance whose viscosity is temperature-dependent, at a temperature at which the viscosity is relatively small; and changing a temperature to a temperature at which the viscosity is relatively large or at which a gel forms.

An embodiment of the invention can comprise a method of depositing a drug into a lumen of a fiber of a delivery device, the method comprising: embedding a discharge end of the fiber in a bed of larger particles having a larger particle size; creating a suspension of particles of the drug in a first liquid, the drug comprising smaller particles having a smaller particle size; and causing the suspension to flow into the lumen through a supply end of the lumen, whereby the first liquid flows into the bed of the larger particles while the smaller particles are retained inside the lumen.

In an embodiment of the invention, provided is an implantable medical device, comprising: hollow fibers having permeable walls that define interiors, wherein a drug is located in at least some of the interiors, wherein the walls at least partially determine a release rate of the drug; and a manifold that is in fluid communication with lumens of the hollow fibers.

In an embodiment of the invention, provided is an implantable medical device, comprising: hollow fibers having permeable walls that define interiors, wherein a drug is located in at least some of the interiors, the interiors comprising lumens, wherein the walls at least partially determine a release rate of the drug; a first manifold that is in fluid communication with the lumens of the hollow fibers at first ends of the fibers; and a second manifold that is in fluid communication with the lumens of the hollow fibers at first ends of the fibers.

In an embodiment of the invention, provided is an implantable medical device, comprising: one or more hollow fibers having a permeable wall that defines an interior, wherein a drug is located in at least some of the interior, wherein the wall at least partially determines a release rate of the drug, and further comprising a barrier on one side of the fabric, the barrier being either impervious or resistant to passage of the drug therethrough, wherein the device has a generally flat configuration having a perimeter, wherein the one or more hollow fibers are arranged into a form of a fabric, and wherein the barrier adheres or is attached to at least some of the one or more hollow fibers. The barrier can comprise for example a layer of polymer, or a laminate of polymer layers.

In an embodiment of the invention, provided is a suture, the suture comprising: a leading end that is stiff and sharp-pointed; rearward of the leading end, at least one structural fiber, and rearward of the leading end, a plurality of hollow fibers having a permeable wall that defines an interior, wherein a drug is located in the interior; wherein the plurality of hollow fibers and the at least one solid fiber are connected to the leading end.

In an embodiment of the invention, provided is a suture, the suture comprising: a leading end that is sharp-pointed and relatively stiff; and rearward of the leading end, a plurality of hollow fibers having a permeable wall that defines an interior, wherein a drug is located in the interior, wherein the plurality of hollow fibers are braided with each other, wherein the plurality of hollow fibers are connected to the leading end.

In an embodiment of the invention, provided is a guide for promoting tissue growth, comprising: one or more hollow fibers having a permeable wall that defines an interior of the hollow fiber, wherein a drug or biological substance is located in the interior, wherein the wall at least partially determines a release rate of the drug or the biological substance, wherein the one or more hollow fibers are arranged to form a generally tubular construct having a central region; and a sheath that is external to and generally surrounding the tubular construct, the sheath being substantially impermeable to passage therethrough of the drug or the biological substance.

In an embodiment of the invention, provided is an implantable medical device, comprising: one or more hollow fibers having a permeable wall that defines an interior of the hollow fiber, wherein a drug is located in the interior, wherein the wall at least partially determines a release rate of the drug, wherein the hollow fibers are arranged in a configuration of a pouch that is suitable to at least partially surround an implantable medical object.

In an embodiment of the invention, provided is a medical device, comprising: an array of hollow fibers having permeable walls that define interiors, wherein a drug is located in at least some of the interiors, wherein the walls at least partially determine a release rate of the drug, wherein the hollow fibers are arranged in a configuration having a perimeter; a barrier on one side of the mat, the barrier being resistant to passage of liquid therethrough, and the barrier extending in at least one direction beyond a perimeter of the mat; and an adhesive located on at least some portion of the barrier that extends beyond the perimeter.

In an embodiment of the invention, provided is a catheter, comprising: a first lumen defined by an impervious wall; and a second lumen defined by a permeable wall, wherein the second lumen contains a drug.

In an embodiment of the invention, provided is an implantable medical device, comprising: one or more hollow fibers having a permeable wall that defines an interior, wherein a drug is located in the interior, wherein the wall at least partially determines a release rate of the drug, wherein the drug delivery device comprises a swellable material inside the interior, the swellable material increasing its volume upon absorption of bodily fluids, and wherein swelling of the swellable material urges the drug out of the interior.

In an embodiment of the invention, provided is a drug delivery device having a permeable wall that defines an interior, wherein a drug is located in the interior, such that the permeable wall has a permeability that is greater than the permeability of the surrounding tissue in which the device is implanted. In such a device, the average dimension of pores can be larger than the dimension of a molecule of drug contained inside the lumen, or 10 times as large, or 100 times as large, or amounts in between. This can create or provide a specific regime for delivery of the drug. In such a design, lymphatic or interstitial flow can flow through the wall into the interior or lumen, can dissolve drug, and can then flow out through the wall of the device. Such a device can comprise a flat sheet that is a permeable wall. Such a device can comprise a hollow fiber that defines a lumen, wherein the drug exists inside the lumen. In such a device, drug release is responsive mainly to the flowrate of interstitial or lymphatic flow in the vicinity of the device.

The described fiber, or other fibers in the article, can also serve a purpose such as to satisfy a structural or geometric purpose. Drug-containing fibers can be combined with other fibers that do not contain drug. There can be more than one kind of drug-containing fiber. There can be more than one kind of non-drug-containing fiber. It is possible that fibers can be filled with drug at the time of manufacturing and can be closed off. Alternatively, fibers can have a connection to a filling mechanism even while the fiber is implanted or otherwise in use for treating a patient, so that the fiber can be filled or re-filled whenever desired during use. Hollow fibers can be made into or included in fabric, mesh or cloths that can be used to make implants and constructs for use in drug delivery alone or to also satisfy structural functions.

In some embodiments, such fibers can be hollow tubular or different-shaped fibers having nanopores or micro-pores in the tube walls. Such fibers can resemble fibers that are commonly used in dialysis, ultra-filtration or micro-filtration filters. The fibers can be straight, undulated or wavy or can have kinks in them or can have still other shapes. The hollow fibers according to the invention can also be similar to those used in blood oxygenators or in other filters and membranes.

The hollow fibers can contain within them an aggregation of solid particles of drug. After implantation of the device, the drug particles can gradually dissolve into whatever liquid surrounds them. The drug molecules can then be released to the surrounding tissue either by diffusion or by hydrodynamic flow of interstitial fluid or by a combination of these mechanisms.

An assumption in most of the problem formulations herein is that the drug release is assumed to occur inside a closed wound or when the fibers are surrounded by tissues. In such a situation, the environment is essentially water and the drug solution cannot evaporate. If a dry layer were to exist near the external surface of the fiber wall or inside the pores due to water evaporation, a large decrease in drug release rate can occur, because the transport of molecules would be by surface diffusion along a dry surface which would be very slow. So, an underlying assumption is a liquid water-based environment.

It can be appreciated that the process of delivering drug to tissue can involve a series of steps and can be considered to resemble a series of resistances to the passage of substances (mass transfer) therethrough. It is not clear at the outset which steps or which resistances are especially significant or influential on the delivery of drug. Indeed, the relative importance of these steps and resistances can vary from one situation to another, and can depend of the type of therapy or treatment. For this discussion, it can be assumed that at least some of the drug is present in the form of solid particles located inside the lumen. First, within the lumen itself, there can be a process of dissolution of drug particles into the liquid or gel that can occupy the interior space of the lumen surrounding the drug particles. Next, there can be a process of diffusion or motion of drug from one location to another within that liquid or gel within the cross-section of the lumen. This can especially be significant if the contents of the lumen include a gel or high-viscosity liquid. Next, the drug can pass through the pores or intermolecular space or holes of the wall of the hollow fiber. This drug delivery process can involve diffusion or convection or both. In some embodiments of the invention, the drug delivery process can be hydrodynamically driven. The drug delivery process can be influenced by the dimensions of the pores or other features of the drug delivery system including processes that occur in the tissues, organs and systems. If there is an osmotic pump phenomenon present in the device, this could influence the characteristics of drug delivery from the hollow fibers. Next, there can be a process of diffusion of drug into the tissue that surrounds the drug delivery device. The fiber-to-fiber spacing among fibers in the device can play a role in this. Finally, the surrounding tissue can contain a flow or motion of interstitial fluid that can carry away drug or result in drug transport during treatment. Such interstitial fluid flow could "refresh" the surrounding tissue and determine the concentration gradient of the drug near the outside of the fiber. Usually not all of these steps will be of equal importance. One or two of them can be a rate determining factor or can be important or most important in determining the overall rate and amount of drug delivery. Individual situations can determine the relative importance of these steps and processes. As described elsewhere herein, there is also a mode of operation in which liquid enters through the membrane in some places and exits in other places, receiving drug while the liquid is inside the device.

In general, delivery of drug from an implant can involve one or more kinds of interaction between the implant and the surrounding tissue. One mechanism usually present in drug release from an implant is diffusion. Furthermore, the surrounding tissue can have an interstitial flow of liquid in or through it. Such flow can be part of a pattern of lymphatic flow system or can be a more localized flow, and can be either steady or unsteady. Such flow of interstitial fluid can transport drug and can interact with the device. In terms of interaction with the device there is further a range of possibilities. The tissue itself can have an effective permeability for flow, and the wall or the device can have a wall or device permeability. In general, the permeability of the device or of the wall of the device can be either greater than, roughly comparable to, or less than the tissue permeability.

Figure 1A:
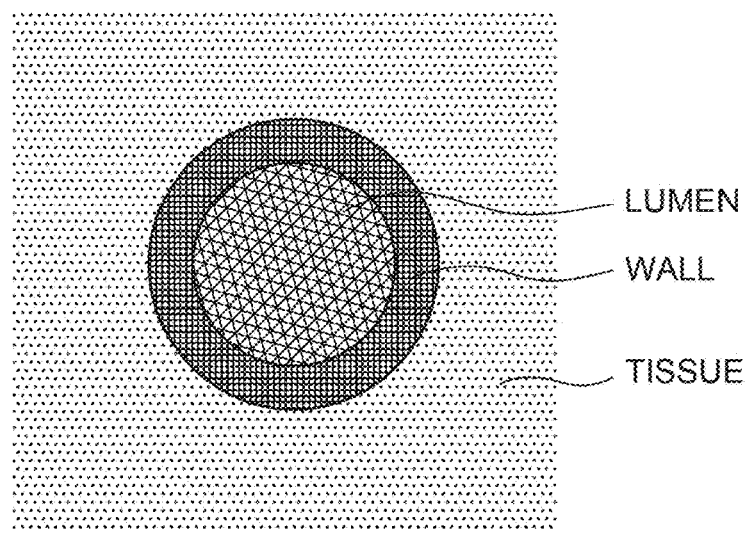
Figure 1B:
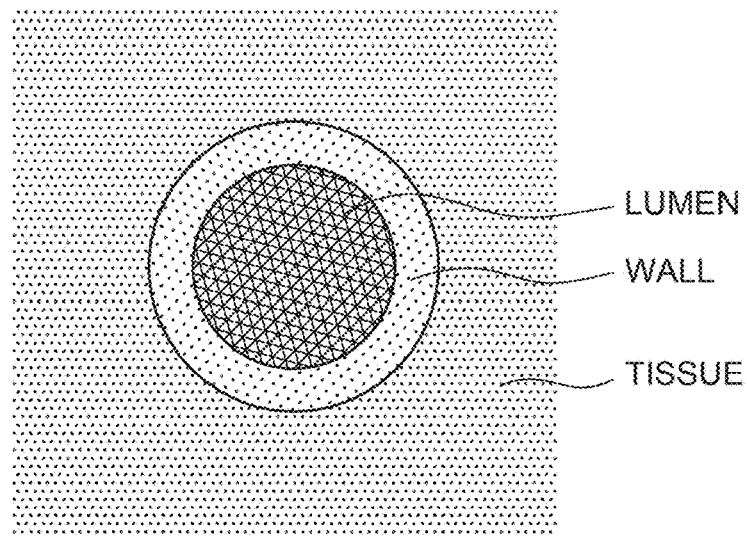

Two situations are shown schematically in FIGS. 1A and 1B, using variations in hatching appearance. In both Figures, the lumen is populated by a filling or aggregate of relatively large particles shown as a coarse hatching. In both Figures, the tissue is shown as having a moderate density of hatching. In FIG. 1A, the wall is shown as having a tight porosity and pore size relative to both the lumen particle aggregate and the surrounding tissue. This represents the diffusion-dominated situation. In FIG. 1B, the wall is shown as having a porosity and pore size that are larger than those of the surrounding tissue (although still the pore size is not as large as that of the aggregate of drug particles inside the lumen).

Drug Release from Hollow Fibers Drug Delivery Device

Figure 1C:
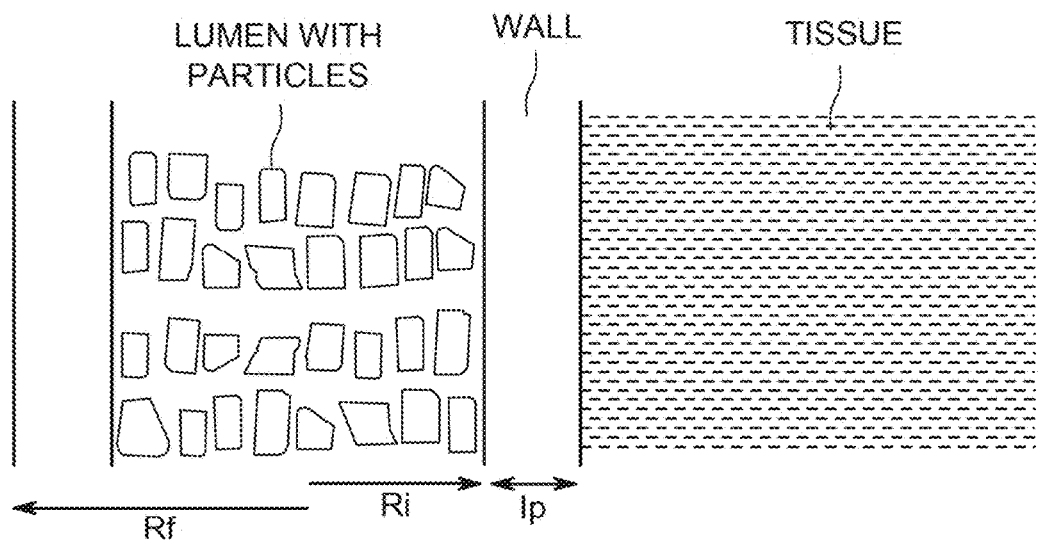
Figure 1D:
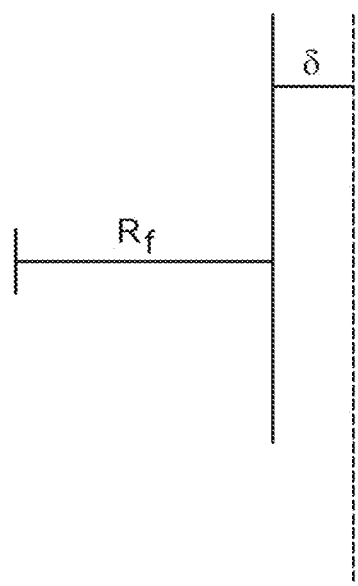

An illustration of the spatial relation of the drug particles, the porous wall of the fiber, and the external tissue is given in FIG. 1C. FIG. 1D illustrates that a diffusion layer of thickness δ exists in the tissue, at the boundary between the fiber and the tissue. If there is lymphatic flow or interstitial fluid, convective transport of drug dominates at some distance from the outer surface of the hollow fiber beyond δ, while diffusion predominates within the diffusion layer of thickness δ.

Drug Release by Diffusion from Hollow Fiber(s) Loaded with Drug Powder

One mode of drug release is that diffusion is one of the dominant processes in the drug release. (A different release mode, hydrodynamically driven drug release, is also discussed in other places herein.)

In this situation, and given the water-based environment, the drug transport basically occurs due to diffusion in water. For purposes of modeling according to embodiments of the invention, compartments can be introduced with essential differences in conditions for drug diffusion. The first compartment is the lumen of the hollow fiber. The second compartment is the porous layer (wall) of hollow fiber. The third compartment is the tissue of the wound. Not wishing to be bound by theory or modeling or specific results, the following description specifies the main processes involved in drug release according to embodiments of the invention.

Diffusion of substances such as drug can be estimated by considering the existence of various compartments (lumen, pores in wall, tissue, as discussed elsewhere herein) each having respective characteristic dimensions. For the pores, the characteristic dimensions of compartments are can be estimated based on (FIG. 1A) $R_i$~120 microns internal radius of lumen, $l_p$ is the thickness of the porous layer, approximately 30 microns. The characteristic time of diffusion $T_p$ strongly depends on the characteristic dimension $l_p$, and can be estimated using equation $$l_p^2 \sim 2 D_p T_p \quad (1)$$

$$T_p \sim l_p^2 / 2 D_p \quad (2)$$

For the lumen, the analogous equation is $$T_l \sim R_i^2 / 2 D_l \quad (3)$$

If the diffusivity within the lumen $D_1$ and the diffusivity within the porous layer $D_p$ are similar in magnitude to each other, which is likely, because the fluids in both locations are essentially the same (essentially water), then $$T_l \sim 10 T_p \text{ because } R_i^2 / l_p^2 \sim 10 \quad (4)$$

While a steady state of diffusion through a porous layer or fiber wall can be achieved after time Tp, this might not occur because the diffusion within the lumen continues. In the case when the lumen is filled with drug solution, a layer with decreased concentration of drug forms near the lumen wall due to decrease of drug concentration in adjacent porous space. The thickness of this layer increases with time, which corresponds to a decrease in drug release rate with time. This undesirable feature can be eliminated if the lumen is filled with drug powder. As soon as the drug concentration near the lumen wall decreases due to diffusion of drug into the porous layer or fiber wall, there is dissolution of drug particles, which restores the drug concentration into the solution adjacent to the drug particle. This allows us to consider the boundary condition as being steady, namely drug concentration C equals $C_s$, which is the saturation concentration, at the boundary between the lumen and the porous layer, i.e. at $r=R_i$ (which is the inner radius of the wall of the hollow fiber)

$$C(R_i) = C_s \quad (5)$$

So, it is appropriate and advantageous to consider drug transport for the situation in which the lumen is filled with particles of drug. The solid particles of drug can serve as a reservoir of drug and can gradually dissolve, which can cause the liquid immediately in contact with the drug particles to become and remain saturated with dissolved drug.

Diffusion in Porous Media

Because detailed information about pores is usually unavailable, diffusion within pores is difficult to characterize, although the diffusion coefficient is known, namely, the diffusivity in water.

The pore dimension, when it exceeds essentially the dimension of the diffusing molecules in the pores, does not affect diffusivity in pores, and, consequently, the transport through the pores. However, the smaller is the total cross-section of pores per unit area of the fiber wall, the smaller is the diffusion flux per unit area, which can be characterized by diffusivity $D_p$ decreased in comparison with diffusivity in water $D_w$. $D_p$ is a function of porosity and approaches $D_w$ when the porosity approaches 1. The geometry of porous space is modeled with spherical or cylindrical particles of a certain volume fraction Ø, that allows one to obtain $D_p$ as a function of Ø or as a function of porosity ε=1-Ø. For example, $D_p \sim 0.3 * D_w$, for ε=0.5.

Diffusion Transport in Tissue

Molecular transport within biological tissue is usually modeled as an analog of transport in porous media. The diffusion occurs within interstitial fluid. Biological cells that are present decrease the cross-section for diffusion, which is accounted for as a decrease in the diffusivity of the tissue. Because the interstitial liquid occupies about half of the tissue volume, $$D_{ti} \sim 0.3 * D_w \quad (6)$$

where $D_{ti}$ is the effective diffusivity in tissue, and $D_w$ is the diffusivity of water.

Coupling Diffusion Through Membrane and Through Adjacent Tissue in Steady State

For a steady state condition, the diffusion fluxes through the porous layer and through the adjacent tissue have to be equal:

$$D_p \frac{C_s - C_m}{l_p} = D_{ti} \frac{C_m}{R_f} \quad (7)$$

where $C_m$ is the unknown concentration at the external surface of the membrane, and $R_f$ is the external radius of the fiber, and $D_p$ is the effective diffusivity within the pores, and $D_{ti}$ is the effective diffusivity in tissue. This equation can be used to determine the unknown $C_m$ as $$C_m = C_s \frac{D_p R_f}{D_{ti}\ell_p + D_p R_f} \quad (8)$$

$$M_r = \frac{D_p C_s}{\ell_p} \frac{1}{1 + \frac{D_p}{D_{ti}}\frac{R_f}{\ell_p}} = \frac{D_{ti} C_s}{R_f} \frac{1}{1 + \frac{D_{ti}\ell_p}{D_p R_f}} \quad (9)$$

The Equation (9) for release rate $M_r$ simplifies in two extreme cases, $$M_r = \frac{D_p C_s}{\ell_p} \quad (10)$$

when $$D_p R_f \ll D_{ti}\ell_p \quad (11)$$

and $$M_r = \frac{D_{ti} C_s}{R_f} \text{ when} \quad (12)$$

when $$D_{ti}\ell_p \ll D_p R_f \quad (13)$$

When condition (11) is true, the diffusion through the porous layer of the fiber wall controls the release rate. When condition (13) is true, the diffusion within the tissue controls the drug release. As $D_p \sim D_{ti}$ and $R_f \gg \ell_p$, conditions (12) and (13) are valid.

The result obtained is that for considering these three locations (inside the fiber lumen, inside the pores, and in the tissue), the diffusion inside the wound tissue is what controls the drug release. Nevertheless the increase in $C_s$ and the decrease in $R_f$ are important to enhance the release rate. It can be noted that this analysis and discussion and conclusion are for the absence of convective motion of fluid in the tissue.

Convection-Dominated or Hydrodynamically Driven Drug Release

It is also appropriate to consider another (contrasting) regime of drug release. In general, it can be considered that the wall of a construct has a permeability or a Darcy constant, and also the tissue itself has a permeability or a Darcy constant. A large Darcy constant corresponds to large permeability. One possibility, in some embodiments, is that the tube wall or membrane or drug delivery device can be more permeable than the surrounding tissue. For example, the permeability of the wall could be more than two times the tissue permeability, or more than five times the tissue permeability, or could be some other numerical ratio. It is furthermore possible that the contents of the lumen can be drug particles having a large enough particle size so that the space within the lumen also is more permeable than the surrounding tissue. In this situation, and if there is a defined flow pattern of interstitial fluid, there can be a flowpath for flow of interstitial fluid such that interstitial fluid flows in through the wall of the hollow fiber, through the cross-section of the array of drug particles, and out through the wall of the hollow fiber. In this situation, it is possible that liquid flowing through the tissue can find the path through the hollow fiber to be an easier path, with less resistance to flow, than the path through a comparable amount of nearby tissue going around the hollow fiber. This can actually cause interstitial fluid to flow preferentially through the cross-section of the hollow fiber, as compared to flowing through nearby tissue.

In such a situation, some interstitial liquid flows in through the wall of the hollow fiber, then spends a certain amount of time inside the lumen of the hollow fiber, and then flows out through the wall of the hollow fiber. It can be expected that the interstitial fluid dissolves some drug from the drug particles that are contained inside the lumen, and carries that dissolved drug with it when it exits from the hollow fiber, and transports that dissolved drug to nearby tissue.

It can also be noted that even with a high-permeability wall, the importance of diffusion depends on what is the convection near the implant. Even with a high-permeability wall, it is still possible that diffusion could be the dominant mechanism in drug release, if there is very little convective motion or velocity of interstitial fluid near the implant.

Yet another situation is also possible. This situation is that there might be a body part in which the overall net interstitial flow is negligible or small, but there might be local oscillatory flow on a small scale. It is contemplated that in such a situation drug transfer by bulk convection would not be important, but there might be an effect similar to increasing the effective diffusivity of the tissue.

Many of the prior art uses of hollow fibers in connection with drug release provide diffusion-dominated drug release, in which the properties of the fiber wall significantly influence the drug release. In contrast, for a convection-dominated drug delivery situation, the wall of the hollow fiber or membrane or drug delivery device might not be the major influence in how much drug is released. In fact, the wall of the hollow fiber or membrane or drug delivery device might have little or no influence on drug release. Instead, the amount of drug released might more significantly depend on how much flow there is of interstitial fluid past and through the device. The amount of interstitial flow might not be known to great accuracy, such as with regard to patient-to-patient variations or variations in the amount of bodily activity of a particular patient. There might be some situations in which it is acceptable for the amount of drug release to vary as a function of the amount of flow of interstitial fluid. For example, in treatment of cancer or prevention of metastatis of cancer, this might be a useful situation. On the other hand, there might be situations in which it might be desired that the amount of drug released not exceed a certain amount. This could be true, for example, if the drug is toxic. So, the desirability of convection-dominated drug release could vary according to particular applications. Of course, it is also possible that, in embodiments, a drug delivery situation could be between these two extremes, and could show influence of both convection and diffusion.

Part 1: Mode of Release at High Permeability of Porous Wall

The pores of typical biological tissue are permeable for proteins and are not permeable for nanoparticles having dimensions about 100 nm. This implies that the tissue has a mean pore diameter of about 30 nm while the pore size distribution can be rather wide.

In an embodiment of the invention, the pores of the membrane that forms the wall of the hollow fiber can be chosen to be larger, perhaps even much larger, than the just-described tissue pores. In addition, the spaces between drug particles, which fill the lumen of the hollow fiber, can be chosen to be much wider than the pores in the membrane. Taken together, this means that hydrodynamic permeability of hollow fiber can be much greater than that of tissue. The interstitial flow through the lymphatic bed arises due to a pressure gradient in a direction perpendicular to axis of the lymphatic bed, causing the liquid to soak into lymph capillaries. The same pressure gradient affects liquid in pores of the membrane of the fiber and liquid in the spaces between drug particles in the packed bed of drug particles that exists inside the lumen. The liquid inside the hollow fiber is even more easily mobilized than the liquid in tissue, when the pore diameter and porosity of the membrane are greater than those parameters within tissue, as shown in FIG. 1B. Interstitial flow enters from tissue into hollow fiber, crosses the fiber wall, flows through the packed bed of particles, crosses the fiber wall again, and re-enters into tissue. Because for certain situations this can be the major mechanism of drug release, we present a brief outline of our theory for interstitial flow around single initial lymph capillary (ILC) [Refs.: de Witte L, Nabatov A, Geijtenbeek T B. Trends Mol Med 2008; 14:12-19; also Ballou B, et al. Bioconjugate Chemistry 2007; 18:389-396].

In an embodiment of the invention, the pores can have an average size that is larger than the molecular dimension of a drug that is contained inside the drug delivery device. In an embodiment of the invention, the pores can have an average size that is at least 10 times as large as the molecular dimension of a drug that is contained inside the drug delivery device. In an embodiment of the invention, the pores can have an average size that is at least 100 times as large as the molecular dimension of a drug that is contained inside the drug delivery device. Of course, the average pore size also can be chosen to be smaller than the particles of drug that are loaded into the lumens of the fibers, in order that the fiber can retain the drug particles inside it. More specifically, the average pore size also can be chosen to be smaller than the particles of drug after they have undergone some amount of dissolution so that the drug particles are still retained inside the lumen even after they have undergone some amount of dissolution. The described pore dimension, or ratio of pore dimension to drug molecule dimension, can exist together with the feature that the hydrodynamic permeability of hollow fiber can be greater than the hydrodynamic permeability of nearby tissue. The hydrodynamic permeability of hollow fiber can be greater than 10 times the hydrodynamic permeability of nearby tissue. The hydrodynamic permeability of hollow fiber can be greater than 100 times the hydrodynamic permeability of nearby tissue.

The described properties can be used in a hollow fiber drug delivery device, or a drug delivery device that comprises material in the form of a sheet or membrane, or generally in any type of drug delivery device.

1. Coupling Between Lymph Hydrodynamics and Hydrodynamics in Interstitium 1.1. Transport Properties Transport properties have been addressed in connection with the composition of the interstitium (collagen, glycosaminoglycan, etc.) in [Aukland K, Reed R K. Physiol Rev 1993; 73:1-78]. The composition of the interstitium affects its hydration, where upon hydration, the calculated pore radius can double with about a three to five times increase in interstitial fluid volume. The concept of the interstitium as a static structure predominates in the description of transport properties, and this would thus influence the modeling, which is primarily based on the Darcy law [Happel J, Brenner K. Low Reynolds Number Hydrodynamics, Prentice Hall; 1966]. Specifically, values that are reported for the hydraulic conductivity of normally hydrated tissue are: $1.5*10^{-9}$ cm$^4$ dyn$^{-1}$ sec$^{-1}$ [Guyton A C, Scheel K, Murphree D. Circ Res 1966; 19:412-419] and $5*10^{-12}$ cm$^4$ dyn$^{-1}$ sec$^{-1}$ [Swabb E A, Wei J, Gullino P M. Cancer Res 1974; 34:2814-2822].

1.2. Pre-Nodal Lymphatics

Figure 2B:
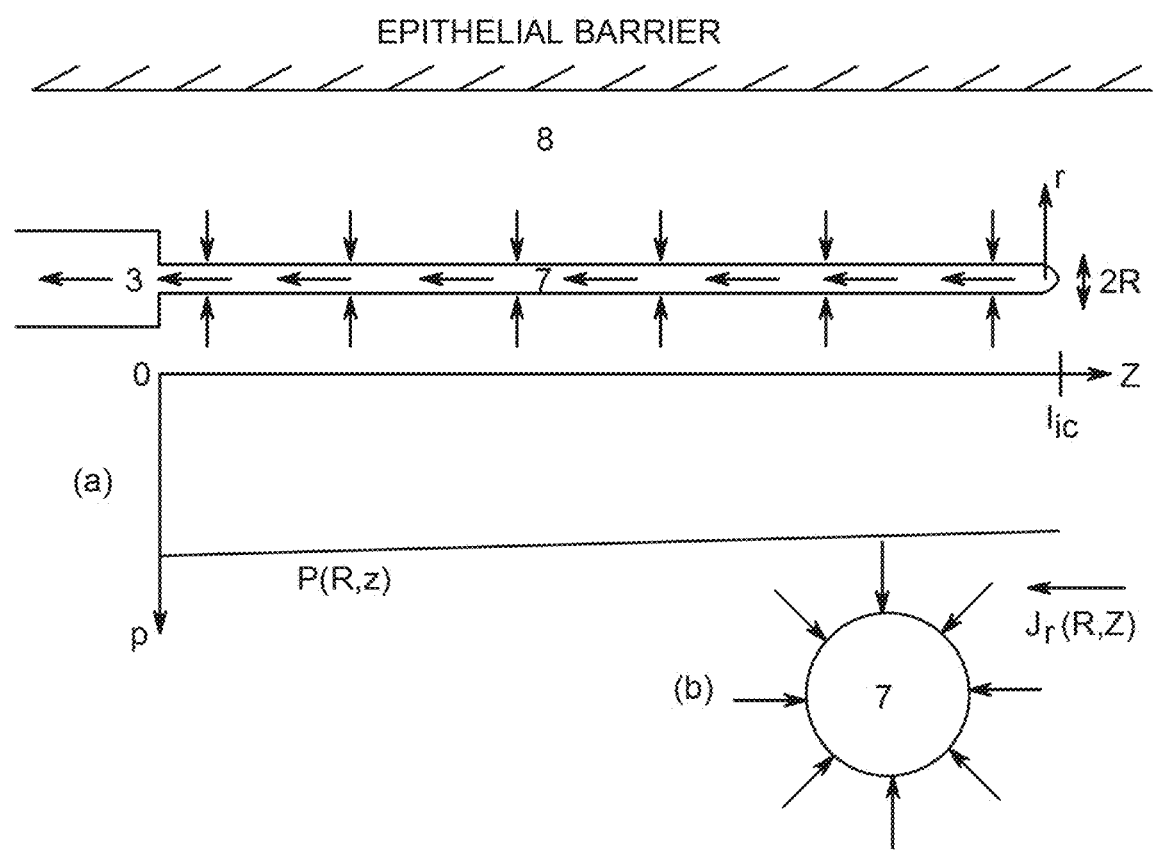
Figure 2A:
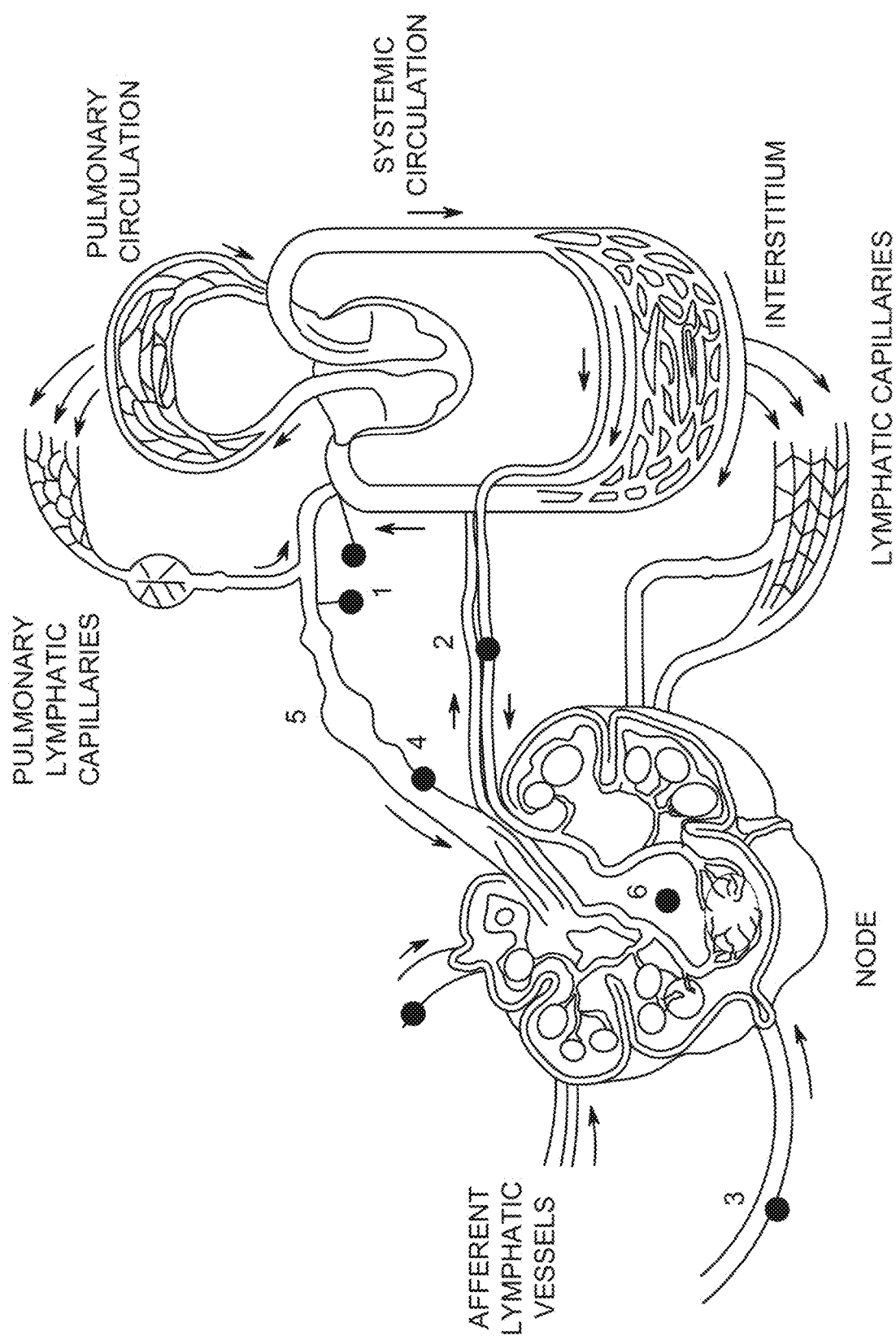
Figure 3A:
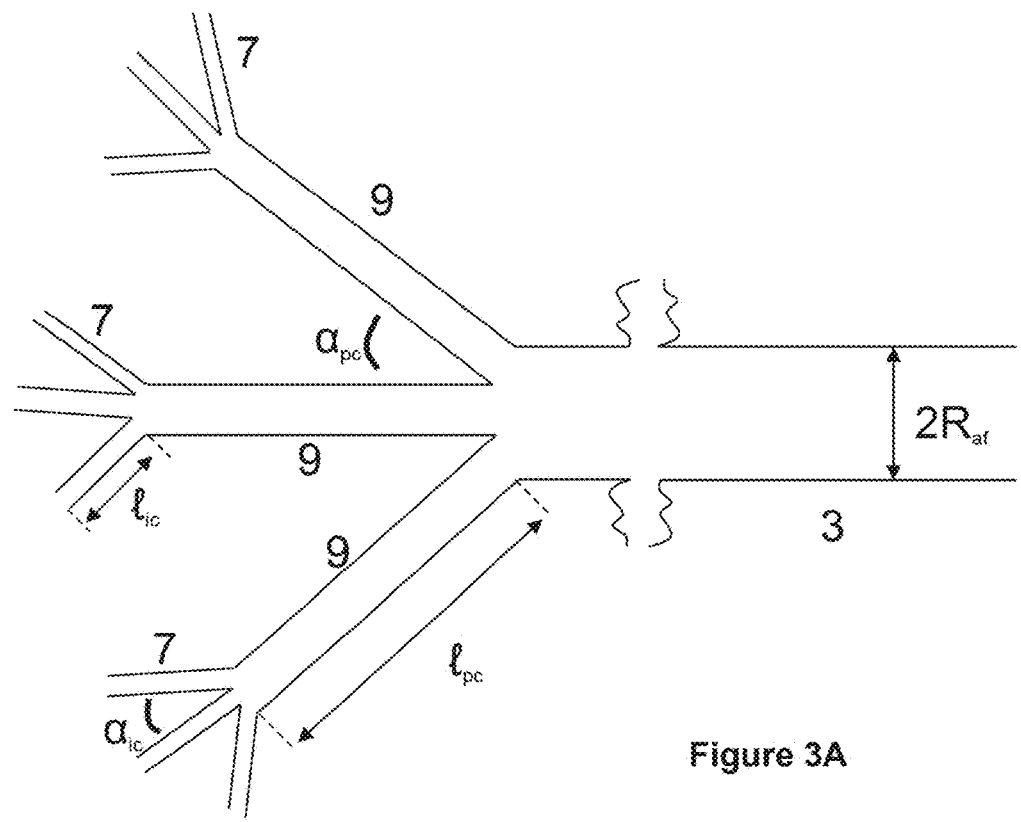
Figure 3B:
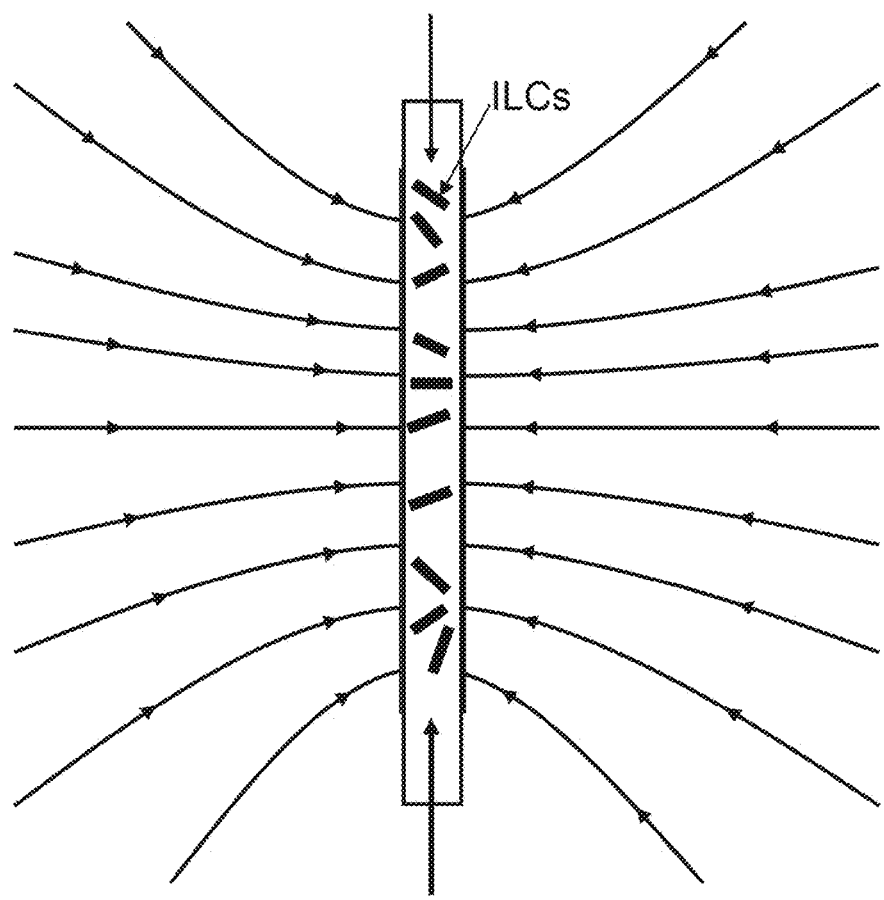
Figure 4A:
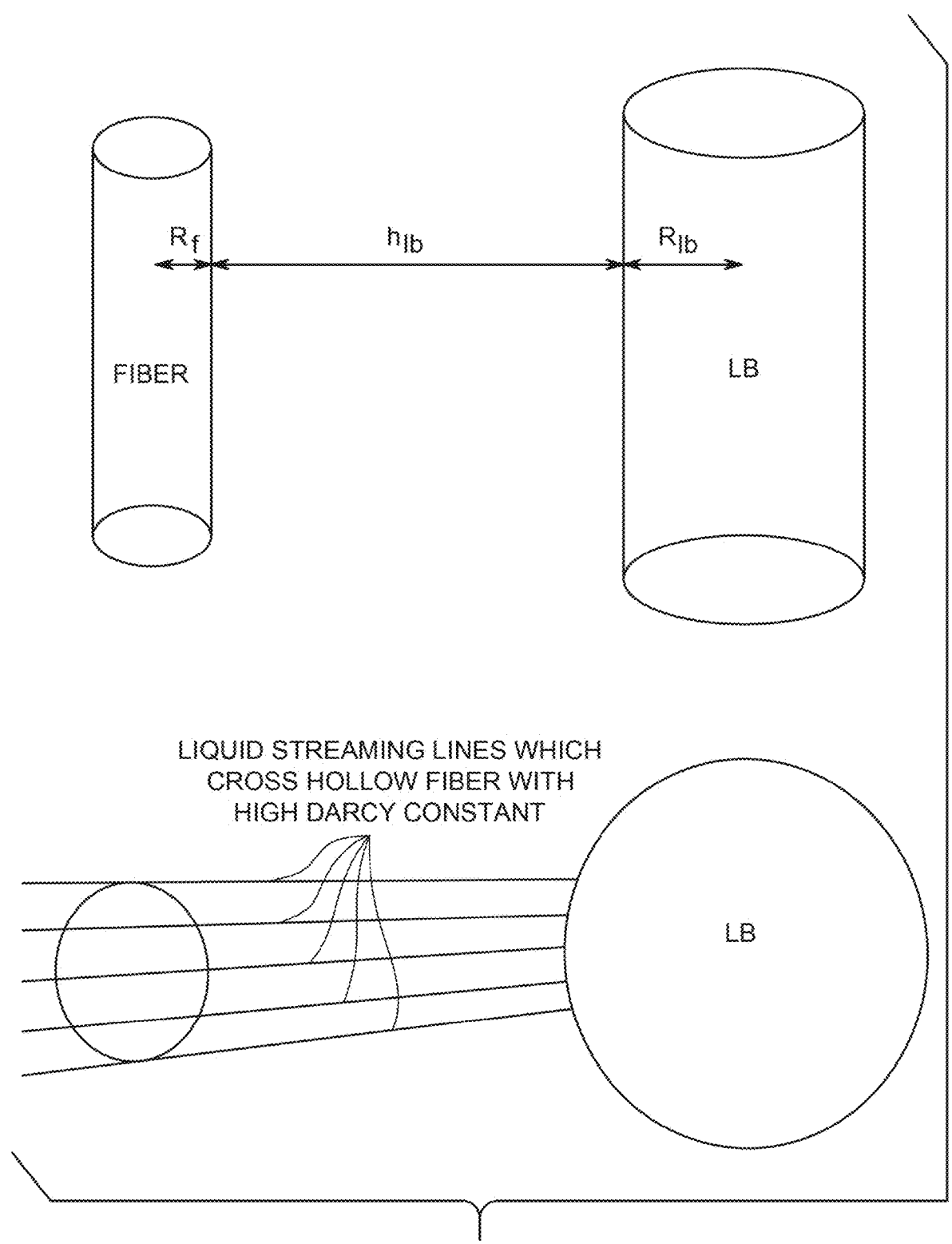
Figure 4B:
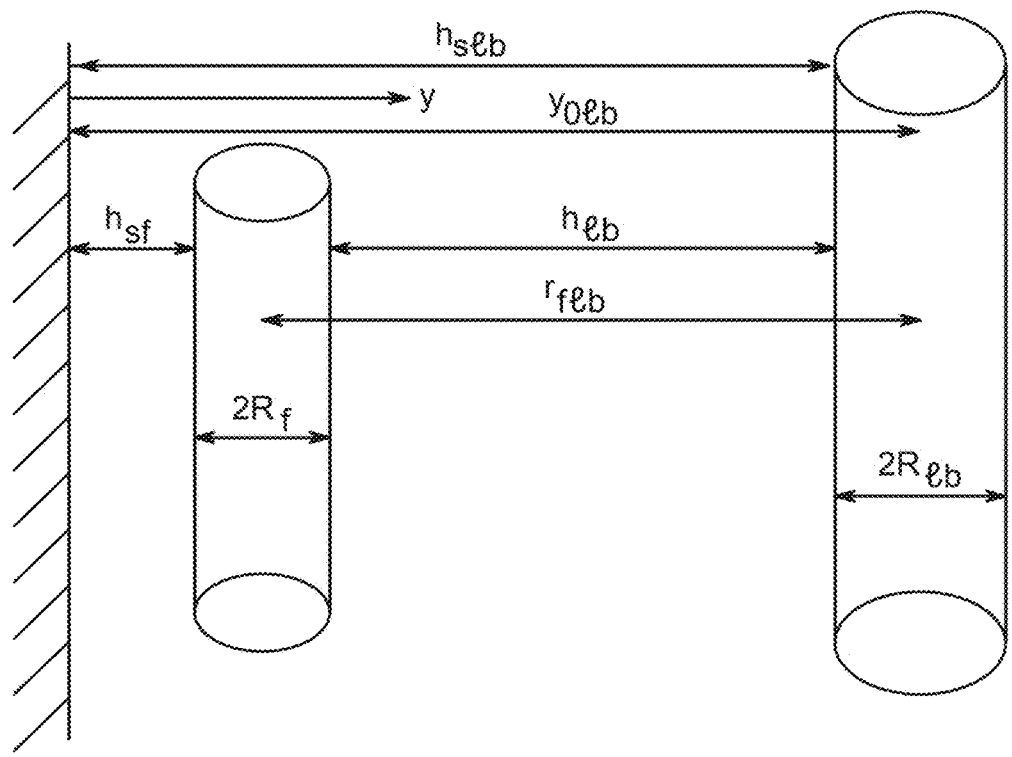
Figure 4C:
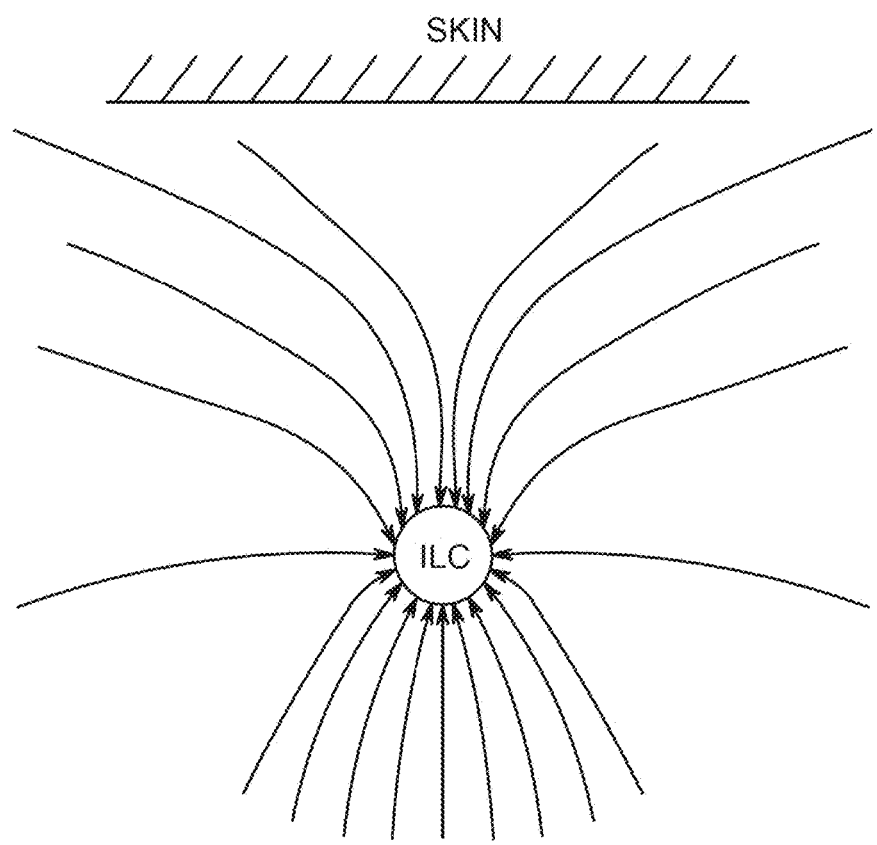
Figure 4D:
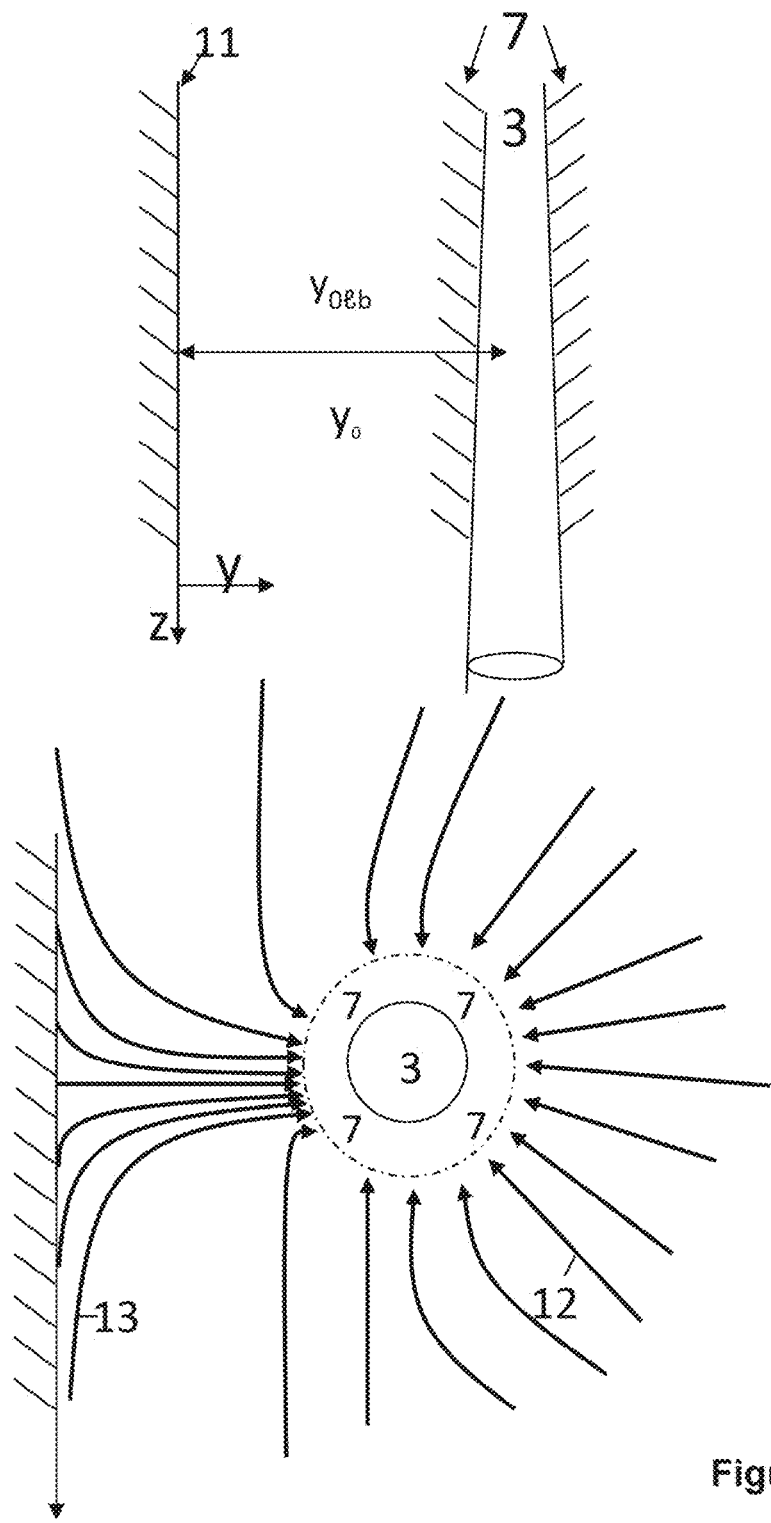

The lymphatic system is composed of a network of vessels, termed lymphatics, which include lymph nodes and lymphoid organs. Pre-nodal lymphatics consist of initial lymphatics, pre-collecting lymphatics and collecting lymphatics. Interstitial fluid enters through the small lymph capillaries (also called initial or terminal lymphatics) that gradually combine to form larger diameter vessels, namely the pre-collectors, or simply collectors. This is illustrated in FIGS. 2A, and 3A and 3B.

1.3. Mechanisms of Interstitial Fluid Mobilization

Interstitial fluid originates when blood plasma leaves the arterioles and flows into tissue, where it becomes tissue fluid, also known as interstitial fluid. When this interstitial liquid enters the initial lymph capillaries, it is called "lymph," and this transition process is called the lymph formation. When the arteriole is distant with respect to the lymph capillary, the influence of the arteriole can be weak or non-existent depending on the distance.

Oncotic pressure caused by the gradient of protein concentration and hydrostatic pressure can contribute to lymph formation. However, there are many unanswered questions regarding the role of oncotic pressure in lymph formation [Zawieja D C, von der Weid P-Y, Gashev A A. Microlymphatic Biology, Chapter 5 in Comprehensive Physiology, American Physiological Society by Wiley-Blackwell; 2011].

The hydrostatic pressure theory of lymph formation relies on the development of hydrostatic pressure differences between the interstitium and the lumen of the initial lymphatic. This theory relies on the contraction/compression and relaxation cycle of either the intrinsic (FIG. 3) or extrinsic lymph pump in initial or collecting lymphatics, and on the function of one-way valves in the initial and collecting lymphatics. These one-way valves allow for the transient entry of fluid into the initial lymphatics during the expansion/relaxation phase and they prevent fluid loss during the contraction/compression phase.

In turn, interstitial flow is connected with lymph formation. One concludes that interstitial flow depends on the contractile activity of lymphangions as well as the action of extrinsic forces.

1.4. Release Process and Release Parameters

While earlier attempts to model the hydrodynamics of interstitial fluid movement were accomplished for understanding the mechanism of edema and are referred to in [Zawieja D C, von der Weid P-Y, Gashev A A. Microlymphatic Biology, Chapter 5 in Comprehensive Physiology, American Physiological Society by Wiley-Blackwell; 2011; also Margaris K N, Black R A. J R Soc Interface 2012; 9(69): 601-612], a recent investigation explored the delivery of protein drugs to lymphatics via subcutaneous injection as the primary delivery route [Reddy S T, Berk D A, Jain R K, Swartz M A. J Appl Physiol 2006; 101:1162-1169]. Since there is no subcutaneous injection in our case, it was shown [de Witte L, Nabatov A, Geijtenbeek TB. Trends Mol Med 2008; 14:12-19; also Ballou B, et al. Bioconjugate Chemistry 2007; 18:389-396] that this will lead to an essential modification of the task when considering both the movement of interstitial liquid and the convective transport of nanoparticles. Nevertheless, the fundamentals in our approach cannot differ from those described in the literature [Reddy S T, Berk D A, Jain R K, Swartz M A. J Appl Physiol 2006; 101:1162-1169]. The bases for our modeling are: i) the conservation laws which govern the transport of interstitial fluid and drug particles, ii) the transport properties of the interstitium, iii) the hydrodynamics of afferent lymphatics, and iv) the equations which interconnect lymph flow and the flow of interstitial liquid, as follows:

i) The conservation law for mass, for incompressible fluids, is:

$$\text{div } v = 0 \quad (1.1)$$

where v is the velocity distribution in space.

The conservation law for momentum is the Darcy law for the interstitium, which is:

$$v = -(K_{in}/\eta)\text{grad } p \quad (1.2)$$

where p is pressure distribution in space, is viscosity of the interstitial fluid and $K_{in}$ is the hydraulic conductivity of the interstitium.

The conservation law for the momentum for propulsion in the initial lymph capillaries is the Navier-Stokes equation.

1.5 Modeling Fluid Flow in Interstitium Around Initial Capillary Initiated by Intrinsic Pump As the distance between the interstitium zone and the nearest ILC (initial lymph capillary) is short, the influence of the intrinsic pump can predominate within this zone. With respect to applications having an axis of cylindrical symmetry, we assume that a single ILC is oriented parallel to the axis of symmetry. As the interstitium around the ILC is considered initially as not confined, the hydrodynamic task attains cylindrical symmetry with the axis which coincides with the ILC axis.

As the initial capillary is blind ended, the axial volumetric velocity Q is small here and gradually increases downstream due to the uptake of the surrounding interstitial fluid up to maximal normal value $Q(z=0)=Q_{af}$ where z=0 corresponds to location of the last lymphangion.

Volumetric Velocity Along ILC

Q(z) is caused by axial dependence of negative pressure inside the ILC. The interconnection between them can be expressed by Poiseuille's law inside the ILC and by Darcy's law outside the ILC. This yields a differential equation (equation 2.14 in [de Witte L, Nabatov A, Geijtenbeek T B. Trends Mol Med 2008; 14:12-19]) the for radial and axial dependence of the pressure distribution in the interstitium around the ILC. Because the ILC length (about 0.5 m) is much larger than its radius (10<R<30 micron), $$\frac{dp}{dr} \gg \frac{dp}{dz} \quad (1.3)$$

and correspondingly, the radial component of interstitial velocity essentially exceeds the tangential component.

$$V_r(r,z) \gg V_z(R,z) \quad (1.4)$$

This allows us to represent $V_r(r,z)$ through $V_r(R, z)$ approximately as:

$$V_r(r, z) = V_r(R, z)\frac{R}{r} \quad (1.5)$$

$$V_r(R, z) \cong V_r(R) = \frac{Q_{af}}{2\pi R l_{ic}} \quad (1.6)$$

The interstitial flow in a lymphatic bed arises due to a pressure gradient in a direction perpendicular to the axis of the LB (lymphatic bed), causing the liquid to soak into lymph capillaries. This same pressure gradient affects liquid in pores of fiber membrane and pores in drug packed bed formed in lumen. The liquid inside hollow fiber is even more easily mobilized than that in tissue when the pore size and the porosity of the membrane exceed those in tissue, as shown in FIG. 1B. Interstitial flow enters from tissue into hollow fiber, crosses the fiber wall, flows through the packed bed of particles, crosses the fiber wall again, and re-enters into tissue.

When liquid flows between drug particles inside the fiber lumen, dissolution of the drug particles causes the flowing liquid to become saturated with drug. Hence, in this case, the drug release rate can be quantified without account for diffusion process, because the drug release rate is controlled by convective transport. Hence, this is a special mode of drug release, which qualitatively differs from the release that is controlled by drug diffusion. Diffusion-dominated drug release occurs when the pore dimension and the porosity of membrane are smaller than that of tissue. Although in the diffusion-dominated case there could be hydrodynamic flow that penetrates the hollow fiber, the convective transport in this case is very weak in comparison with diffusion, which is what controls the drug release rate.

In order to quantify the conditions corresponding to convection controlled and diffusion controlled modes of drug release, the notion of Darcy constant K can be used, namely Darcy constant for tissue $K_{ti}$ and Darcy constant for porous wall of membrane $K_m$.

The Convection Controlled Mode of Drug Release (CCMDR) corresponds to high hydrodynamic permeability of membrane, i.e., to $$K_m \gg K_{ti} \quad (1.7)$$

In the opposite case $$K_m \ll K_{ti} \quad (1.8)$$

the convective transport through the membrane is weak and the Diffusion Controlled Mode of Drug Release (DCMDR) is realized.

Because filling the lumen with a gel/drug suspension mixture has a significant advantage, it is important to clarify whether CCMDR is possible in this case or not. The question arises because gel's hydrodynamic permeability can be lower than that of the membrane. However, simultaneously, the volume fraction of drug particles is rather high. This case can be excluded from consideration because of the very high hydrodynamic resistance and the associated very long time required for filling hollow fiber with gel/drug mixture. A good exemplary candidate for the gel mixing with drug powder is nonfibrillated cellulose (NFC) having a fiber diameter in the range 50 nm<$d_f$<500 nm. In case where the volume fraction of NFC is not very large, its Darcy constant essentially exceeds that of tissue and its $K_m$ value controls the mode of drug release.

In order to derive equations for the drug release rate and for the decrease of drug concentration along its path to the lymph node LN, we consider a single fiber and a single lymphatic bed parallel to each other at a distance between their surfaces $h_{lb}$ (FIG. 4). For the sake of simplicity, initially we consider the situation when $$h_{lb} \gg R_f \quad (1.9)$$

where $R_f$ is the fiber diameter. In the absence of the hollow fiber, there is axial symmetry in the velocity distribution around the lymphatic bed LB. The velocity at any point is directed to fiber axis and depends on distance to axis only, i.e.

$$V_r(r) = V(R_{lb})\frac{R_{lb}}{r} \quad (1.10)$$

where $R_{lb}$ is LB radius (FIG. 4). When the fiber is placed at a large distance from LB according to this condition, this single velocity distribution is preserved within almost the entire space. Naturally, fiber placement distorts the velocity distribution in the immediate vicinity of the fiber. This distortion can be easily quantified when the condition (1.9) is valid. Approximately, the velocity distribution can be considered as uniform and its absolute value is $V_r(r=R_{lb}+h_{lb}+R_f)$ where r equals the distance between the axes of the LB and of the fiber, if in addition to condition (1.9), the condition $$R_f \ll h_{lb} \quad (1.11)$$

is introduced.

In the approximation of locally uniform velocity, the liquid stream is loaded by drug by virtue of flowing through the fiber wall into the fiber lumen, flowing among the drug particles, and flowing through the fiber wall out of the fiber lumen. This liquid stream is simply the product of local velocity and the area of the axial cross-section of the fiber.

$$q_f = 2R_f l_f V_r(r_{fib}) \quad (1.12)$$

where $$V_r(r_{fib}) = V_r(R_{lb}) \cdot \frac{R_{lb}}{r_{fib}} = V_r(R_{lb})\frac{R_{lb}}{R_{lb} + h_{lb} + R_f} \quad (1.13)$$

The drug stream due to convection into the lymphatic bed LB is expressed by the product $$J_f = q_f C_s \quad (1.14)$$

This drug stream mixes within the LB with the liquid stream that does not contain drug, which equals the product of the surface area of the LB (lymphatic bed) and velocity $$Q_{lb} = V_r(R_{lb}) 2\pi R_{lb} l_{lb} \quad (1.15)$$

Dilution of the drug concentration occurs due to this mixing, which can be easily quantified using Eqs. (1.14) and (1.15). One obtains for concentration at the lymph node LN $$C_{ln} = \frac{q_f}{Q_{lb}} C_s = \frac{1}{\pi} \frac{R_f}{R_f + R_{lb} + h_{lb}} \frac{l_f}{l_{lb}} \quad (1.16)$$

where Eq. (1.13) is used.

The decrease of concentration within LN can be smaller in order of magnitude in comparison with $C_s$ because $R_f \sim 150$ micron, $200 < R_{lb} < 500$ micron, $l_f/l_{lb}$ can be about 1 if $h_{lb} < 2R_{lb}$. That further $C_{ln}$ decrease occurs when $h_{lb}$ increases because the larger $h_{lb}$ is, the smaller $V_r(R_f + R_{lb} + h_{lb})$ is, according to Eq. (1.13).

The release duration $T_{rel}$ can be quantified because the drug stream from the hollow fiber j is invariant in time in the approximation used here. The decrease in the amount of drug present in the lumen, dM, during time dt is proportional to j $$dM = -jdt \quad (1.17)$$

Integration of this equation yields $$M_e = jT_{rel} \quad (1.18)$$

where the initial mass of drug $$M_e = \pi R_i^2 l_f \rho W \quad (1.19)$$

where $\rho$ is the drug density, $R_i$ is the internal diameter of fiber and W is drug volume fraction in lumen.

Combining Eqs. (1.11), (1.12) and (1.13), one obtains $$T_{rel} = \frac{M_e}{J} = \frac{\pi R_i^2 l_f \rho r_{fib} W}{2R_f l_f V(R_{lb})R_{lb}} = \frac{\pi}{2} \frac{R_i^2 (R_f + R_{lb} + h_{lb})W}{R_f R_{lb} V_r(R_{lb})} \frac{\rho}{C_s} \quad (1.20)$$

Because direct measurement for $V_r(R_{lb})$ is rather difficult, it is reasonable to express $V_r(R_{lb})$ through the volumetric velocity of afferent capillary $Q_{af}$ for which some data can be found in the literature. It can be understood that liquid stream entering into an ensemble of initial lymph capillary (ILC), i.e., $Q_{lb}$ afterwards enters afferent capillary, i.e.

$$Q_{lb} = Q_{af} \quad (1.21)$$

and that $$Q_{lb} 2\pi R_{lb} l_{lb} V_r(R_{lb}) \quad (1.22)$$

Combining these equations yields $$V_r(R_{lb}) = \frac{Q_{af}}{2\pi R_{lb} l_{lb}} \quad (1.23)$$

Substitution according to Eq. (1.23) into Eq. (1.20) yields $$T_{rel} = \pi^2 \frac{R_f(R_f + R_{lb} + h_{lb})l_{lb} W}{Q_{af}} \frac{\rho}{C_s} \quad (1.24)$$

Figure 17:
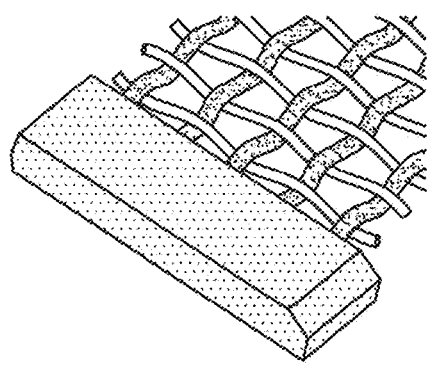
FIG. 17 shows the fibers encapsulated in potting material.

According to FIG. 17 in a Review article [Aukland K, Reed R K. Physiol Rev 1993; 73:1-78], $Q_{af}$ varies in the range from $5*10^{-2}$ to $25*10^{-2}$ cm$^3$/min, i.e., $8*10^{-4}$ to $4*10^{-3}$ cm$^3$/sec. As $l_{lb}$ has to be at least 5 times larger than $l_{ic}$, i.e., 0.5 cm, $l_{lb} \sim 5*0.05$ cm $\sim 0.25$ cm. Substitution of these values and $R_f \sim 1.5*10^{-2}$ cm, $R_{lb} \sim 4*10^{-2}$, $h_{lb} \sim 2R_{lb}$ into Eq. (1.24) yields $$T_{rel} \sim B\frac{\rho}{C_s} \quad (1.25)$$

where B=0.35 W and B=0.07 W for $Q_{af} = 8*10^{-4}$ and $4*10^{-3}$ cm$^3$/sec, respectively. The Table shows values of B for two values of $Q_{af}$ and W. B is a coefficient in the above equation. W is the drug volume fraction in the lumen.

|  | W |  |
| --- | --- | --- |
| $Q_{af}$ (cm$^3$/sec) | 0.3 | 0.1 |
| $8*10^{-4}$ | 0.1 | 0.03 |
| $4*10^{-3}$ | 0.2 | 0.06 |

While B values are not large, the ratio $\rho/C_s$ can be very large. The smaller the drug solubility $C_s$ is, the longer is the drug release time. However, there is a constraint regarding $C_s$ value, expressed by the condition that $$C_{ln} > MIC \qquad (1.26)$$

$$C_{ln} \sim 0.1 C_s \qquad (1.27)$$

where MIC (minimum inhibition concentration) is the minimum concentration required to suppress cancer or to prevent the rejection of an extremity that may have been attached by surgery. More generally, MIC can be understood to represent the Minimum Effective Concentration of a substance required to kill pathogens or to achieve any other desired effect. Combining Eqs. (1.25), (1.26) and (1.27), one concludes that $$C_s > 10 MIC \qquad (1.28)$$

$$T_{rel} \leq B \frac{\rho}{10 MIC} \qquad (1.29)$$

The derived equations were obtained using an approximation of locally uniform hydrodynamic flow, which is illustrated in FIGS. 4 and 5A. The streaming lines are straight, parallel and uniformly spaced, which is valid only when the velocity distribution is uniform. But the velocity distribution cannot be uniform when $K_m$ and $K_{ti}$ differ. There is an apparent trend that the liquid stream is stronger where hydrodynamic resistance is smaller, i.e., K is larger, i.e., inside the fiber (at condition (1.7)). This is shown in FIGS. 4 and 5A-5C, because the distance between parallel portions of streaming lines within fiber is smaller than it is in the approximation of locally uniform distribution. The same stream before and after crossing the fiber has a larger cross-section than that of fiber. This means that the velocity distribution has to be represented as a sum of a uniform distribution and an additional distribution, with the additional distribution being a two-dimensional distribution that describes the transition that occurs at the transition from external uniform to internal uniform flow.

$$V = V_{lu} + V_d \qquad (1.30)$$

where $V_{lu}$ is locally uniform velocity, and $V_d$ is a correction to $V_{lu}$. The exact theory shows that $V_d$ is the velocity distribution of a hydrodynamic dipole. In FIG. 5c, liquid exits the fiber cross-section near the right pole, moves back and return to the fibers on the left side. The remarkable feature of this dipole-like velocity distribution is that it does not contribute to transport at distances essentially larger than $R_f$, i.e., its contribution to transport towards LB is weak. Hence, the theory outlined above based on a model of locally uniform hydrodynamic flow is consistent. However, there is a constraint, characterized by condition (1.11). This condition allows to represent local velocity, as the superposition (1.30). When kb decreases, higher multiplets (triplets, etc.) have to be accounted for. The smaller the $h_{lb}$ is, the larger is the amount of multiplets that are required for describing the velocity distribution.

However, the condition (1.11) does not cause a practical constraint because the placement of fiber at small distance $h_{lb} \sim R_f \sim 150$ μm from LB is very problematic for surgery. The larger $h_{lb}$ is chosen, the easier the fiber placement especially with account that rather long fiber has to be parallel to LB.

Part 2: Influence of Fiber Location Between LB and Skin on Drug Release 2.1 General A drug delivery device (DDD) is relatively easy to implant near and under the skin. In this case the distance between skin and LB plays a large role, namely ha in FIG. 7, as well as distance between fiber and skin $h_{sf}$. The modeling in Part 1 has not accounted for the influence of the skin on the hydrodynamic field around LB. As skin is hydrodynamically impermeable, it affects the hydrodynamic field originated due to lymphatic pump, namely it destroys the axial symmetry of the hydrodynamic field as illustrated in FIG. 1*b*. In particular, both normal $V_y(y=0)$ and tangential $V_x(y=0)$ components of velocity equal zero at the skin surface y=0:

$$V_y(y=0)=0 \tag{2.1}$$

This decreases the velocity within the broad vicinity of the skin, in particular, where the fiber is located. This means that the real velocity is lower than that given by Eq. (1.13). Consequently, the release rate is slower than that given by Eq. (1.14) and specified by Eq. (1.12). The smaller the distance $h_{sf}$ is, the stronger is the influence of the skin and the larger is the correction that is required to be applied to the release rate. As the general approach for estimation of release rate remains valid, it is sufficient to revise only Eqs. (1.13) and (1.14) by means of the influence of the skin on the velocity distribution.

2.2 the Velocity Distribution Between ILC and Skin

The modeling was accomplished in the basic theory for virus transport from the vagina towards regional lymph nodes (LN) [de Witte L, Nabatov A, Geijtenbeek T B. Trends Mol Med 2008; 14:12-19; and Ballou B, et al. Bioconjugate Chemistry 2007; 18:389-396]. The intact vaginal wall can be a barrier not only for virus transport but for interstitial flow as well. As this was assumed in [de Witte L, Nabatov A, Geijtenbeek TB. Trends Mol Med 2008; 14:12-19; and Ballou B, et al. Bioconjugate Chemistry 2007; 18:389-396], the theory proposed in these two references describes the skin influence on interstitial hydrodynamics as well. Regardless of whether the vaginal wall or skin is under consideration, its influence on interstitial hydrodynamics is accounted for by the boundary condition (2.1). The influence of the skin on the velocity distribution is qualitatively illustrated in FIG. 7.

An illustration, similar to FIG. 7?, shows the direction of the local velocity while the information about the absolute value of velocity is not given. The equation characterizes both direction and absolute value of velocity for any point:

$$V_y(x, y)|V_r(R)|\left(\frac{1}{r}\frac{dr}{dy} - \frac{1}{r'}\frac{dr'}{dy}\right) = a\left[\left(\frac{y_0 - y}{r^2}\right) - \left(\frac{y + y_0}{r^2}\right)\right] \tag{2.2}$$

where $a=|V_r(r=R)|R$, $r=\sqrt{(y_0-y)^2+x^2}$ and $r'\sqrt{(y_0+y)^2+x^2}$

The next equation follows from the general equation for the normal component of liquid velocity distribution along the shortest distance between EB and ILC, i.e., for x=0

$$V_y(y, 0) = |V_r(R)|R\left[\frac{1}{(y_0 - y)} - \frac{1}{(y_0 + y)}\right] = |V_r(R)|R\frac{2y}{y_0^2 - y^2} \tag{2.3}$$

As it is seen from Eq. (2.3), $V_y(y=0)=0$ at $y=0$ and linearly increases with increasing y, i.e., drug release linearly increases with increasing $h_{sf}$.

2.3 Hydrodynamic Velocity Distribution Around Lymphatic Bed (LB)

Lymph capillaries collect lymphatic loads from the interstitial areas and gradually join together into bigger lymph vessels, which are the so-called afferent capillary (FIG. 3). The velocity distribution under skin is caused by interstitial flow into an ensemble of ILCs, entering a single afferent capillary. This system is called lymphatic bed (LB). Hence, the drug transport is affected by LB. The determination of velocity is simplified if afferent capillary is parallel to EB and if ILC are distributed more or less uniformly along afferent capillary (FIG. 3). In first approximation, LB can be considered as a body with cylindrical symmetry, characterized by length $l_{lb}$ and radius $R_{lb}$. The analog of $y_0$ in the LB case is the distance between the afferent capillary axis and the mucus/interstitium interface $y_{0lb}$. An afferent capillary begins with a blind ending ($z=l_{ic}$), where $Q_{lb}(z=l_{ic})=0$. $Q_{lb}(z)$ increases with increasing z due to lymph entering from ILCs. There is some information about $Q_{af}$, i.e., maximal. With introduced simplifications, there is a large similarity between this hydrodynamic problem and the problem that is described in Section 2.2. Due to this similarity, Eq. (2.3) can be modified into an equation for describing the distribution around LB for they component of superficial velocity. It is sufficient to replace R with $R_{lb}$, $y_0$ with $y_{0lb}$, and $V_r(r=R_{lb})$ can be expressed through $Q_{af}$ $$V_r(R_{lb}) = \frac{Q_{af}}{2\pi R_{lb} l_{lb}} \quad (2.4)$$

Taking all this into account, one obtains $$V_y(y, x) = \frac{Q_{af}}{2\pi l_{lb}} \left[ \frac{(y_{0lb} - y)}{r_{lb}^2} - \frac{(y_{0lb} + y)}{r'^2_{lb}} \right] \quad (2.5)$$

where $r_{lb} = \sqrt{(y_{0lb} - y)^2 + x^2}$, $r'_{lb} = \sqrt{(y_{0lb} + y)^2 + x^2}$ $$V_y(0, y) = \frac{Q_{af} y}{\pi l_{lb}(y_{0lb}^2 - y^2)} \quad (2.6)$$

A scheme for velocity distribution around LB is given in FIG. 6.

2.4 Release Rate with Account for Skin Influence on Velocity Distribution

It is sufficient to replace $V_r(r_{fib})$ according to Eq. (1.13) by $V_r(r_{fib})$ according to Eq. (2.3) in Eq. (1.12) to reveal decrease in release rate due to skin presence. As the multiplier $V_r(R_{lb})$ is present in both equations, the difference is characterized by difference between $$\frac{1}{r_{fib}} \text{ and } \frac{2y}{y_0^2 - y^2} = \frac{2y}{(r_{fib} + h_{sf} + R_f)^2 - y^2} \quad (2.7)$$

The placement of small $y=h_{sf}+R_f$ leads to a strong decrease in velocity and consequently, in release rate. On the other hand, either small $h_{sf}$ or small $h_{lb}$ are difficult for surgery $$h_{sf} \approx h_{ilb} \quad (2.8)$$

is easiest for implantation. In this case, the decrease in release rate, caused by the presence of skin is characterized by the ratio $$z(R_f, R_{lb}, y_{lb}, y_{ls}) = \frac{2(h_{sf} + R_f)(h_{lb} + R_{lb} + R_f)}{3(h_{lb} + h_{fs} + R_{lb} + 2R_f)^2 - (h_{sf} + R_f)^2} \bigg|_{y(h_{sf} = h_{sf})} =$$

$$\frac{2h_{lb}^2 + 2h_{lb}(R_{lb} + 2R_f) + R_f(R_{lb} + R_f)}{3h_{lb}^2 + 2h_{lb}(2R_{lb} + 3R_f) + R_{lb}^2 + 4R_{lb}R_f + 3R_f^2}$$

There is not very essential difference between numerator and denominator, which shows that the ratio is not significantly different from 1. Taking into account that $h_{lb} > R_{lb} > R_f$, it can be shown that $Z<1$, for example, $Z=67/91$ for $R_{lb}=2R_f$, $h_{lb}=2R_{lb}$. The more detailed calculations are excessive because at $y_{sf}=y_{lb}$, the condition (1.9) is poorly satisfied. One concludes that the decrease in release rate is not very essential for practically important condition (1.9).

Part 3: Modeling for Drug Release Caused by Hollow Fiber Fabrics

It can be appreciated that the time of drug release decreases with increasing release rate. However, for successful treatment both high release rate and long release time are required. Therefore, development in this direction is useful.

3.1 Perfection of Drug Release and its Duration with Proper Choice of $R_f$ Dimension and $H_{lb}$ Dimension, i.e., Choice of LB, Suitable for LN Treatment.

Inspection of the derived equations for $C_{ilb}$, i.e., Eq. (1.16) and for release time, i.e., Eq. (1.24), shows that increasing $R_f$ is favorable. It can be noted that the influence of $R_f$ in the denominator of Eq. (1.16) is weak and can be neglected because $R_{lb}$ and $h_{lb}$ are much larger than $R_f$. Although it is possible to choose a hollow fiber with as large a diameter as possible, there is a constraint and consequently, whether this direction is realistic is not clear. As the distance between LB and skin is rather small ($h_{slb}$ in FIG. 4B), there are practical limits to how large $R_f$ can become. The smaller is the difference between $2R_f$ and $h_{slb}$, the more difficult is placement procedure. The larger $h_{slb}$ is, the larger $2R_f$ can be chosen.

For LN (lymph node) feeding with drug solution, different LB (lymphatic bed) can be used, if some LBs collect interstitial liquid which downstream enters a LN. These different LBs can be located at different locations. There is a certain LB with maximal $h_{slb}$. The selection of LB with maximal $h_{slb}$ makes it possible to achieve a large increase in release time, which can be seen from Eq. (1.24). First, larger $h_{slb}$ makes it possible to implant fibers with larger $R_f$. Second, $T_{rel}$ is proportional to the product $R_f^* h_{slb}$, which is seen from Eq. 1.20). As both $R_f$ and $h_{slb}$ can be increased, it is possible to achieve a fairly large $T_{rel}$. However, it can be appreciated that this situation does not always exist.

Description of Hydrodynamically Driven Drug Release and Release Parameters

Axial lymph flow inside initial lymph capillary (ILC) caused by primary and secondary valves of lymphatics initiates flow of interstitial fluid towards external surface of ILS (FIG. 1). Because the diameter of the ILC is very small (about 20 micron), this axially symmetrical flow can decrease in order of magnitude in distance from ILC $h_{ilcf}$ about fiber radius ($R_f$ about 150 micron). This may not happen because many ILCs of lymphatic bed (LB) contribute to interstitial flow at long distance (at small distance to a certain capillary predominates its contribution). Meantime, the interstitial velocity at long distance is of interest with respect to drug release from hollow fiber because its placement at small distance to ILC is problematic for surgery. Hence, the distribution of interstitial velocity at long distance from LB is of interest respective to drug release from a hollow fiber. According to well-known review [Schmid-Schonbein G W. Microlymphatics and lymph flow. Physiological Reviews 1990 October 70(4):987-1028.], the microanatomy of pre-nodal lymphatics is organ specific in contrast to mechanism of lymph formation and mobilization (valves, primary and secondary, etc.). Initial lymphatics, pre-collecting lymphatics and collecting lymphatics are main portions of pre-nodal lymphatics. The interstitial fluid enters through small initial capillaries of 20 micron diameter that gradually combine to form larger diameter vessels, namely the pre-collectors (150 micro diameters) and collectors (500 micron diameters). There are data in literature [Freitas Jr. R A. *Nanomedicine, Volume IIA: Biocompatibility* 2003, Landes Bioscience, Georgetown, Tex.] about characteristic length for initial capillaries (500 micron), pre-collectors (1000 micron) and collectors (3000 micron). The authoritative reviews [Schmid-Schonbein G W. Microlymphatics and lymph flow. Physiological Reviews 1990 October 70(4):987-1028.; Margaris K N, Black R A. Modelling the lymphatic system: challenges and opportunities. J R Soc Interface 2016 Jun. 5; doi:10.1098/rsif.2011.0751] do not present more detailed information, in particular, about the amount of pre-collectors per one collector and amount of initial capillaries per one pre-collection. Both these amounts are not large, according to brief remarks in literature. Even schematic illustration for very complex three-dimensional structure of pre-nodal lymphatics is very poor, for example, FIG. 1 in [Margaris K N, Black R A. Modelling the lymphatic system: challenges and opportunities. J R Soc Interface 2016 Jun. 5; doi:10.1098/rsif.2011.0751] (FIG. 2) for cardiovascular lymphatics. To make the modelling of drug release more clear, we illustrate spatial structure of pre-nodal lymphatic with an example (FIG. 3). The illustration assumes rather regular structure with respect to angles $2\pi/n_e^{-2}$ and $2\pi/n_{pc}^{-2}$ of rotation around collector axis axis and pre-collector axis, respectively. Then the sequence of rotation around axis of collector and pre-collector makes it possible to characterize the structure of pre-nodal lymphatics in three dimensions. With respect to transformation of interstitial fluid into lymph, the fundamental difference between ILCs and pre-collecting and collecting lymphatics is that this occurs only within ILC wall, while there is no liquid flow through walls of pre-collecting and collecting lymphatics. Hence, being interested in lymphatic flow, we can restrict our interest to ILC ensembles, which will be called lymphatic bed (LB). On another side, the linear dimension for pre-collector and collector allow to estimate the radius of LB $R_{lb}$ from below. It is seen that $R_{lb}$ is about some millimeters exceeds that in order of magnitude the thickness of LB which is about the length of ILC, i.e., about 0.5 mm. This makes it possible to model the shape as a thin disk with radius $R_{lb}$. Unfortunately, there is a large uncertainty regarding $R_{lb}$ value, which can only be evaluated from below and from above, using information about capillary length and radii.

$$R_{lb} = R_c + l_{pc} \sin \alpha_{pc} + l_{ic} \sin \alpha_{ic} \tag{D1}$$

where $l_{pc}$ and $l_{ic}$ are lengths of the pre-collector and the collector, respectively, $\alpha_{pc}$ and $\alpha_{ic}$ are angles between collector and pre-collector axis and between axis of ILS and axis of pre-collector, respectively. The absence of information about $\alpha_{pc}$ and $\alpha_{ic}$ causes an uncertainty. The estimates from below and from above follows when $\alpha_{pc} = \alpha_{ic} = 0$ or $\alpha_{pc} = \alpha_{ic} = \pi/2$.

$$R_c < R_{lb} < R_c + l_{pc} + l_{ic} \tag{D2}$$

or 250 micron<$R_{lb}$<(250+1000+500) micron
250 micron<$R_{lb}$<1750 micron
If $\alpha_{pc} = \alpha_{ic} = \pi/6$, $R_{lb} \sim 1000$ micron. However, the disk is not thin in this case because $2R_{lb} = 2000$ micron exceeds $l_{ic} = 500$ micron only by a factor of 4 times.

Axial lymph flow inside initial lymph capillary (ILC) caused by primary and secondary valves of lymphatics initiates flow of interstitial fluid towards external surface of ILS (FIG. 1). As the diameter of the ILC is very small (about 20 microns), this axially symmetrical flow can decrease in order of magnitude in distance from ILC $h_{ilcf}$ about fiber radius ($R_f$ about 150 micron). This may not happen because many ILCs of lymphatic bed (LB) contribute to interstitial flow at long distance (at small distance to a certain capillary predominates its contribution). Meantime, the interstitial velocity at long distance is of interest with regard to to drug release from hollow fiber because its placement at small distance to ILC is problematic for surgery. Hence, the distribution of interstitial velocity at long distance from LB is of interest respective to drug release from a hollow fiber. According to a well-known review article [Schmid-Schonbein G W. Microlymphatics and lymph flow. Physiological Reviews 1990 October 70(4):987-1028], the microanatomy of pre-nodal lymphatics is organ specific in contrast to mechanism of lymph formation and mobilization (valves, primary and secondary, etc.). Initial lymphatics, pre-collecting lymphatics and collecting lymphatics are main portions of pre-nodal lymphatics. The interstitial fluid enters through small initial capillaries of 20 micron diameter that gradually combine to form larger diameter vessels, namely the pre-collectors (150 micro diameters) and collectors (500 micron diameters). There are data in literature [Freitas Jr. R A. *Nanomedicine, Volume IIA: Biocompatibility* 2003, Landes Bioscience, Georgetown, Tex.] about characteristic length for initial capillaries (500 micron), pre-collectors (1000 micron) and collectors (3000 micron). The authorative reviews [Schmid-Schonbein G W. Microlymphatics and lymph flow. Physiological Reviews 1990 October 70(4):987-1028; Margaris K N, Black R A. Modelling the lymphatic system: challenges and opportunities. J R Soc Interface 2016 Jun. 5; doi:10.1098/rsif.2011.0751] do not present more detailed information, in particular, about the number of pre-collectors per one collector or about the number of initial capillaries per one pre-collection. Both these numbers are probably fairly small, according to brief remarks in the literature. Even the schematic illustration for very complex three-dimensional structure of pre-nodal lymphatics is very poor, for example, FIG. 1 in [Margaris K N, Black R A. Modelling the lymphatic system: challenges and opportunities. J R Soc Interface 2016 Jun. 5; doi:10.1098/rsif.2011.0751] (FIG. 2) for cardiovascular lymphatics. To make the modeling of drug release more clear, we illustrate spatial structure of pre-nodal lymphatic with an example. FIG. 3A shows flow collecting in the various levels of vessels. FIG. 3B shows flow collecting in the Initial Lymph Capillary (ILC). FIGS. 4A-4D show various additional geometric properties of the system. The illustrations assume rather regular structure with respect to angles $2\pi/n_e^{-2}$ and $2\pi/n_{pc}^{-2}$ of rotation around the collector axis and the pre-collector axis, respectively. Then the sequence of rotation around axis of collector and pre-collector makes it possible to characterize the structure of pre-nodal lymphatics in three dimensions. With respect to transformation of interstitial fluid into lymph, the fundamental difference between ILCs and pre-collecting and collecting lymphatics is that this occurs only within ILC wall, while there is no liquid flow through walls of pre-collecting and collecting lymphatics. Hence, being interested in lymphatic flow, we can restrict our interest to ILC ensembles, which will be called the lymphatic bed (LB). On another side, the linear dimension for pre-collector and collector allow to estimate the radius of LB $R_{lb}$ from below. It is seen that $R_{lb}$ is about some millimeters exceeds in order of magnitude the thickness of LB which is about the length of ILC, i.e., about 0.5 mm. This makes it possible to model the shape of the LB as a thin disk with radius $R_{lb}$. Unfortunately, there is a large uncertainty regarding the value of $R_{lb}$, which can only be evaluated from below and from above, using information about capillary length and radii.

$$R_{lb}=R_c+l_{pc} \sin \alpha + l_{ic} \sin \alpha_{ic} \qquad (D1)$$

where $l_{pc}$ and are the lengths of the pre-collector and the collector, respectively, and $\alpha_{pc}$ and $\alpha_{ic}$ are angles between collector and pre-collector axis and between axis of ILS and axis of pre-collector, respectively. The absence of information about $\alpha_{pc}$ and $\alpha_{ic}$ causes an uncertainty. The estimates from below and from above follow when $\alpha_{pc}=\alpha_{ic}=0$ or $\alpha_{pc}=\alpha_{ic}=\pi/2$.

$$R_c<R_{lb}<R_c+l_{pc}+l_{ic} \qquad (D2)$$

or 250 micron$<R_{lb}<$(250+1000+500) micron
250 micron$<R_{lb}<$1750 micron

If $\alpha_{pc}=\alpha_{ic}=\pi/6$, $R_{lb}\sim$1000 micron. However, the disk is not thin in this case because $2R_{lb}$=2000 micron exceeds $l_{ic}$=500 micron only 4 times.

In our earlier work [Dukhin S S, Labib M E. Convective diffusion of nanoparticles from the epithelial barrier toward regional lymph nodes. Advances in Colloid and Interface Science 2013 199-200:23-43], it was shown that the pressure drop in interstitium exceeds essentially the pressure drop along ILC. This means that the pressure change along LB surface is very small and consequently, the tangential velocity is very small in comparison with the normal component $V_n(S_{lb})$, where $S_{lb}$ is LB surface. $V_n(S_{lb})$ is almost invariant and equal for two flat surfaces of disk. The larger distance to flat surface is, the larger is the variation of $V_n(S_{lb})$ between the axis and the edge of the disk. This is illustrated in the schematic illustration of interstitial velocity distribution around thin disk. When the distance h to flat surface of disk like LB is small in comparison with $R_{lb}$, namely h$<R_{lb}$, the velocity distribution is uniform and approximately equal to $V_n(LB)$.

A hollow fiber whose hydrodynamic permeability exceeds that of the nearby tissue can be called a hollow fiber of high hydrodynamic permeability (HFHHP). In this situation, interstitial flow penetrates HFHHP. Moreover, interstitial flow actually concentrates within HFHHP as is shown in FIG. 5, because the interstitial flow meets smaller resistance in tissue space occupied by the fiber. It is known that interstitial flow is very slow and consequently, liquid flow through the lumen also is very slow. This means that the residence time of liquid crossing the lumen is rather long. It can be estimated as $2R_{fi}/V_l$, where $R_{fi}$ is internal radius of fiber, $V_l$ is the velocity in the lumen, whose difference from interstitial velocity before fiber implantation is not large. As liquid entering lumen is free of drug, drug dissolution into slow liquid flow occurs within the lumen. As the residence time is rather high, the interstitial flow crossing lumen almost achieves the saturation with drug. Hence, a portion of interstitial flow which penetrates through hollow fiber becomes saturated with drug. If the volumetric velocity of this portion is denoted as $q_f$, the amount of drug released from a single fiber per unit of time, i.e., drug release rate is $Jc=q_fC_s$, where $q_s=2R_{fi}l_fV_l$, $2R_{fi}l_f$ is area of axial cross-section of fiber of length $l_f$. Hence, the release rate in this case can be quantified without accounting for diffusion process because the release rate is controlled by convective transport. Hence, this is a special mode of drug release, which qualitatively differs from the release in a release mode that is controlled by drug diffusion. The diffusion-controlled release mode would occur when pore dimension and porosity of membrane are smaller than that of the nearby tissue. Although even in this diffusion-controlled case hydrodynamic flow might penetrate hollow fiber, the convective transport in this case would be very weak in comparison with diffusion, which would be what controls the drug release rate. This qualitatively different mode of drug release can be called hydrodynamically driven drug release because it occurs due to penetration of interstitial flow inside hollow fiber, which causes drug dissolution and formation of a strip within interstitial flow that is almost saturated with drug. The required conditions for onset of this mode of drug release are the existence of a pressure gradient within tissue with associated interstitial flow and hydrodynamic permeability of the fiber being higher than that of the tissue. While the second condition is easy to satisfy, the first condition leads to a constraint, because a sufficiently large pressure gradient in tissue and a sufficiently large velocity of interstitial flow exist only around LB and venules and at reasonably close distance from them. However, tissues with lymphatics and venules predominate and consequently, hydrodynamically driven release may occur in a majority of tissues. This is important in practice, because it will be shown below that the hydrodynamically driven drug release greatly exceeds the release rate in a diffusion-controlled situation. In turn, maximal possible release rate is practically important to achieve a therapeutic result, which requires the achievement $C_{ln}>$MIC. Only a portion of this flow, which is affected by fiber and its release is loaded by drug, while major portion is not affected by drug release, i.e., does not contain drug (FIG. 6). When these two portions of radial interfacial flow enter the lymphatic bed, they are mixed in with lymph flow. Hence, there is dilution of the drug stream, produced by fiber drug release in interstitial flow after it is entering in lymphatics. As a result, the drug concentration in different capillary and in lymph node (LN) $C_{ln}$ can be much lower than that in the initial stream of drug. This dilution, i.e., decrease in $C_{ln}$, is not helpful because it is still desired that $C_{ln}$, exceed the minimum inhibition concentration (MIC).

A hollow fiber whose hydrodynamic permeability exceeds that of tissue can be called a hollow fiber of high hydrodynamic permeability (HFHHP). Interstitial flow penetrates a HFHHP. Even further, interstitial flow actually concentrates within HFHHP as is shown in FIG. 4A-5C because flow meets smaller resistance in that portion of the tissue space that is occupied by fiber. It is well known that interstitial flow is very slow and consequently, liquid flow through the lumen is very slow. This means that the residence time of liquid crossing the lumen is rather long. The transit or residence time can be estimated as $2R_{fi}/V_l$, where $R_{fi}$ is internal radius of fiber, $V_l$ is velocity in lumen, whose difference from interstitial velocity before fiber implantation is not large. As liquid entering lumen is free of drug, dissolution of drug into slow liquid flow occurs. As the residence time is rather long, the interstitial flow crossing lumen almost achieves saturation with drug. Hence, a portion of interstitial flow which penetrates through hollow fiber becomes saturated with drug. If the volumetric velocity of this portion is denoted as $q_f$, the amount of drug released from single fiber per unit of time, i.e., drug release rate, is $J_f = q_f C_s$, where $q_f = 2R_{fi} l_f V_I$, $2R_f l_f$ is the area of an axial cross-section of fiber of length $l_f$. Hence, the release rate in this case can be quantified without accounting for the diffusion process because the drug release rate is controlled by convective transport. Hence, this is a special mode of drug release, which qualitatively differs from the release controlled by drug diffusion. Diffusion-controlled release occurs when the pore dimension and the porosity of membrane are smaller than those of tissue. Although hydrodynamic flow penetrates hollow fiber in this diffusion-controlled case as well, the convective transport in this case is very weak in comparison with diffusion, which is what controls the drug release rate. This qualitatively different mode of drug release can be called hydrodynamically driven drug release because it occurs due to penetration of interstitial flow inside hollow fiber that causes drug dissolution and formation of strip within interstitial flow almost saturated with drug. The required conditions for onset of this mode of drug release are the existence of pressure gradient within tissue with concomitant interstitial flow and hydrodynamic permeability of fiber higher than that of tissue. While the second condition is easy to satisfy, the first condition leads to a constraint because sufficient pressure gradient in tissue and sufficient velocity of interstitial flow exist only around LB and venules and at not too long distance from them. However, tissues with lymphatics and venules predominate and consequently, hydrodynamically driven release may be arranged in majority of tissues. This is of practically importance because below it will be shown that the hydrodynamically driven drug release greatly exceeds the release rate in a diffusion-controlled situation. In turn maximal possible release rate is practically important to achieve a therapeutic result, which requires the achievement of $C_{In}$>MIC.

The undesirable dilution of drug concentration can be counteracted if a fabric or an array of hollow fibers is implanted instead of single fiber. The total release rate caused by numerous fibers of fabric can exceed that caused by single fiber by as much as an order of magnitude or more. This leads to an increase of $C_{In}$ in order of magnitude, and is favorable for achieving the desired condition $C_{In}$>MIC.

It can be assumed that a fabric is placed parallel to flat surface of disk-like LB at distance $h_{lb}^{fab}$. As $R_{lb}$ is rather large, the condition $h_{lb}$<<$2R_{lb}$ can be satisfied. This means that liquid velocity on this distance before fabric placement is uniform and approximately equal to $V_n(LB)$. The placement of fabric with fibers of lower hydrodynamic permeability than that of tissue, would decrease the $V_n(h_{lb})$ to values that are essentially lower than $V_n(LB)$. As we are interested in hydrodynamically driven release, the opposite case of HFHHP is of interest. In this case, $V_n(h_{lb}^{fab})<V_n$ (LB). This value of velocity is valid for only fiber of fabric. Using the result described in two paragraphs preceding, one obtains for release rate from any fiber: $q_f = 2R_f l_f V_n(h_{lb}) C_s$.

For a fabric of fibers that can be assumed to be square, it is reasonable to choose the length of a square as equal to $2R_{lb}$. this will provide uniform drug flux over entire flat surface of the LB. This choice specifies the above-written equations for $q_f$ as $q_f = 4R_f R_{lb} V_n (h_{lb}) C_s$ It is further assumed that the stream saturated with drug through one flat surface of LB and an equal stream of drug-free liquid through the opposite flat surface of LB are mixed. Hence, the dilution is rather small (about 50%) in the case of fabric, in contrast to an unacceptably high dilution that occurred in the case of a single fiber embedded in tissue. The volumetric velocity of the entire interstitial flow which enters both flat surfaces of LB is $2\pi R_{lb}^2 V_n(R_{lb})$, where $V_n(R_{lb})$ is difficult to measure. This interstitial flow transforms into lymph flow in the collector, with volumetric velocity about $Q_{af}=\pi R_{af}^2 V_{af}$. Some relevant information exists in the literature. Hence, the unknown $V_n(R_{lb})$ can be calculated as $Q_{af}/2\pi R_{lb}^2$, that yields $$V_n(R_{lb}) = \frac{V_{af}}{2}\left(\frac{R_{af}}{R_{lb}}\right)^2.$$

This equation makes it possible to eliminate the unknown $V_n(R_{lb})$ from the equation for release rate: $q_f=2V_{af}C_s R_f R_{af}^2 R_{lb}^{-1}$. The release rate for fabric can be obtained as product $q_f$ and $N_{fab}$ (fiber amount in fabric) because there is no essential difference in release rate for fibers. In turn, $N_{af}$ can be expressed through fiber dimension $2R_{lb}$ and $(2R_f+h_f)$, where $h_f$ is mean distance between adjacent fibers in fabric: $Q_{fab}=4V_{af}R_{af}^2 C_s R_f(2R_f+h_f)^{-1}$ The large release rate is required to achieve $C_{ln}$>>MIC in spite of dilution by the predominating (in single fiber case) stream $Q_{lb}$ of interstitial fluid. And simultaneously, a release time as long as possible is required for prolonged treatment inside LN and outside it and outside the efferent capillary. Meantime, the release duration decreases with increasing release rate, because a larger portion of drug stored in drug delivery device leaves it due to increasing release rate. This poses a fundamental difficulty for perfecting implanting therapy. If the distance between skin in LB $h_{lb}$ is large, increasing the fiber diameter allows to increase the stored amount of drug proportional to $h_{if}^2$. This approach fails, however, if $h_{if}$ is not sufficiently long. A fabric formed from hollow fiber makes it possible to increase the release rate and simultaneously to also achieve a longer duration of release. The release of drug from an individual hollow fiber is not affected by release of drug from adjacent fibers. Hence, the release time $T_f$ for a single fiber determines the total release time $T_{fab}$ of entire fabric: $T_{fab}=T_f$. The amount of drug lost by a single fiber per unit time equals $J_f$. This drug loss is invariant in time before the release abruptly stops. Hence, the release terminates at time $T_f$, when the total released amount of drug $J_f T_f$ equals to the amount of drug stored in fiber $M=\pi R_{if}^2 \mu l_f$, where $R_{if}$ is the internal fiber radius, ρ is density of solid drug. Using this equality and equation for $J_f$ $$T_{fab} = T_f = \frac{\pi}{2}\frac{R_{if}^2}{R_f V_n(LB)}\frac{\rho}{C_s}$$

where $C_s$ is the saturated drug concentration in solution, by weight.

At first glance, it might appear that the use of fabric might not extend the release duration. However, actually the use of a fabric is helpful. It is questionable, whether a release rate providing $C_{ln}$>>MIC is actually required, because the side effects increase when $C_{ln}$ increases substantially above MIC. We assume that therapeutic release rate provides $C_{ln}$>MIC, but $C_{ln}$ exceeding MIC is not essential. On the other hand, in the case of a single fiber when a lot of dilution occurs, $C_s$ has to substantially exceed MIC because $C_{ln}$ eventually decreases in comparison with $C_s$ because of dilution by the predominating stream of drug-free interstitial fluid. When there is a fabric, in contrast to the case of a single fiber, $C_s$ can be chosen only slightly above MIC because the only a slight amount of dilution occurs. This is useful, taking into account that the longer the release time for a fiber is, the smaller $C_s$ is (because release rate decreases with decreasing $C_s$). As soon as for single fiber the release time increases, it increases for fabric. The number of fibers in the fabric equals $2R_{lb}/(2R_f+h_f)$, i.e., $4<N_{fab}<7$.

It can be concluded that the drug delivery device (DDD) in the form of fabric offers an additional degree of freedom (N), which makes it possible to solve the central problem in drug release, because the use of a fabric makes it possible to increase simultaneously the release rate and the release duration. This can be a premise for the development of new technique in implanting therapy, i.e., long-term implanting therapy.

The larger the distance between skin and LB $h_{slb}$, the larger is the amount of drug that can be stored in the DDD and the longer is the duration of drug release that can be achieved. In particular, two or three layers of fibers can be implanted parallel to LB with only a small distance between the layers. The numbering of the mesh implanted at largest distance from LB is 1. Interstitial fluid without drug enters the first fabric and exits being saturated with drug. Hence, as long as the release from fabric 1 takes place, the interstitial fluid entering the next fabrics (2, 3, . . . ) is almost saturated with drug. As long as the release from fabric 1 continues, the release from more-downstream fabrics is low. After the release from fabric 1 terminates, drug-free interstitial fluid enters fabric 2, which causes the release from fabric 2, while the release from fabric 3 is weak. Hence, multiple fabrics provide sequential release from fabric 1, 2, 3 without a pause between them. Thus, there can be a phenomenon of a traveling wave that progressively moves through the layers of the fabric. The release time for multiple fabrics is proportional approximately to their amount $N_{fab}$. Denoting the release time in case of $N_{fab}$ $T_{rel}^{N_f}$, one obtains $T_{rel}^{N_f}\sim N_{fab}T_{rel}^{1}$.

Even though $T_{rel}$ is already rather long due to fabric, increasing it by a further factor of 2 or 3 times can be very useful. It can be appreciated that multiple fabrics or layers of fabric can be implanted as single implant. The fabrics have to be densely packed with each other to increase entire width of the fabric package.

As the package of fabrics has the width $N_{fab}(2R_f+h_{fab})$, where $h_{fab}$ is the distance between adjacent fabrics, single fabric consisting of thicker fibers, with diameter $2R_{fl}$ equals to width $N_{fab}(2R_f+h_{fab})$ can be used. As the DDD width is the same and other dimensions can be chosen the same, there is no difference for implantation. But simple calculation shows that the volume fraction for drug stored in DDD can be larger in the case of a single fabric of fibers of larger diameter $2R_{fl}$. The volume fraction depends on the ratios $h_f/R_f$ and $h_{fl}/R_{fl}$, where $h_f$ and $h_{fl}$ are distances between fiber in fabrics for small $R_f$ and larger $R_{fl}$, respectively. The calculation shows that the drug volume fraction is always larger in case of larger fiber diameter, if $h_f/R_f=h_{fl}/R_{fl}$, and can be increased by a factor of about 4/3 to 5/3 for reasonable values of the ratios. In spite this advantage of fibers of large diameter, use of such fibers has to take into account that hollow fibers having diameter about 300 micron are commercially available, while the use of fibers with diameter several times larger would require additional design and fabrication effort.

The local velocity distribution changes after fiber implantation. At first glance this change has to contribute interstitial flow through fiber and consequently, the accomplished theoretical analysis has shown that the velocity distribution can be represented as a binomial. Its first term is described in approximation of local uniform velocity. The second term is velocity distribution, originated from hydrodynamical dipole (FIG. 5A-5C). The first decay of such a dipole velocity distribution as a function of distance away from the dipole is well known. Hence, the dipole term does not contribute to drug release, when the condition $h_{lb}>>R_f$ is valid. The approximation of locally uniform velocity distribution essentially simplifies the quantification of hydrodynamically driven release.

Considering membranes with decreasing hydrodynamic permeability, the transition occurs from mode of hydrodynamically driven release to mode of diffusion controlled release. The maximal possible diffusion flux is $D/t_m$, where $D_m$ and $t_m$ are diffusivity within the membrane and its thickness, respectively. Its comparison with release rate that is controlled by hydrodynamics, namely $J_c=C_sV_l$, where $V_l$ is velocity in lumen, reveals an increase of release rate due to transition to strong penetration of lumen of hydrodynamic flow $J_c/J_D\sim V_l l_m/D$. Naturally, this ratio can essentially decrease if hydrodynamic permeability of membrane $K_m$ decreases in comparison with $K_{ti}$ with concomitant decrease of $V_l$. However, the comparison of maximal possible values for hydrodynamically driven release and diffusion driven release is of practical importance.

Maximal release rates for both mechanisms are achieved, when pores dimension and porosity are sufficiently large. At these conditions $K_m>>K_{ti}$. It means the comparison is of interest for proposed HFHHM, with respect to hydrodynamically driven release. The maximal diffusion driven release occurs in the case of HEHHP too, because diffusivity achieves its maximal value with increasing diameter of membrane pores, no matter what is molecular weight of molecules.

Assuming that the pore diameter essentially exceeds the molecule dimension, which is necessary for drug release to occur in any of the modes of drug release, $D_m$ can be presented as product of three multipliers: diffusivity in water D, membrane porosity ε and tortuosity $t_0$; $D_m=D\varepsilon t_0^{-1}$. The maximal porosity is about 0.5. Taking into account the tortuosity $t_0=2$, $D_m\sim 0.25D$. $V_l$ has to be replaced by local interstitial velocity $V_{int}$. In turn, $V_{int}$ can be specified as $V_n(LB)$, when the condition $2R_{lb}>>R_f$ is valid and the fabric is placed at a small distance from LB. Hence, $J_c/J_D\sim 4V_n(LB)l_m/D$ in case of HEHHP. As to $l_m$, having its value be small is desirable for the diffusion-dominated case.

Decreasing $l_m$ below 30 micron can worsen the mechanical properties of the hollow fiber. The unknown parameter $V_n(LB)$ can be expressed through the characteristics of the afferent channel using the result from several paragraphs previous. This yields $$J_c/J_D\sim 2V_{af}\left(\frac{R_{af}}{R_{lb}}\right)^2\frac{l_m}{D}$$

The ratio $$E=\frac{V_n(LB)l_m}{D_m}\sim V_{af}\left(\frac{R_{af}}{R_{lb}}\right)^2\frac{l_m}{D}$$

can be called the index of coefficient of hydrodynamically driven release. This equation underestimated E because the diffusion flux $D_m(C_D-C_m)/l_m$ is over-estimated when the concentration on the boundary between the fiber membrane and the tissue $C_m$ is replaced by zero. This is the well-known sink approximation, which is valid when the concentrations drop between $C_m$ and zero concentration in liquid stream, when it equals zero is neglected. But zero concentration in interstitial flow is achieved at some distance δ, which is called the diffusion layer thickness δ. The diffusion flux through the tissue adjacent to the fiber surface is equal to the diffusion flux through membrane, when steady transport is under consideration. This dictates a certain value for $C_m$. An equation for $C_m$ follows from the condition that locally the flux through the membrane equals the flux through the tissue. Such rather simple approach is valid when diffusion layer is thin: $δ<<R_m$. In turn, this condition is valid if so called Peclet number Pe=Vl/D is large. The physical meaning of the Peclet number is that it characterizes ratio of convection flux to diffusion flux. A large Peclet number means strong predominance of convection over diffusion. When dissolution of solid spherical particles is under consideration in the classical Leveque-Levich theory, both normal and tangential components of velocity equal zero at the solid surface. Hence, the diffusion predominates near surface due to hydrodynamic stagnation. But convection starts to predominate with increasing distance to surface, because velocity increases. Meantime, along liquid trajectories within pure convective transport, the concentration does not change. As a result, the concentration drop within tissue is located within thin diffusion layer δ. Correspondingly, diffusion flux can be expressed as $$J_D = -D_{ti}\frac{C_m}{\delta}.$$

The diffusion through tissue can be slower when $D_{ti}<<D_m$, which is our case when the pores in the membrane are much wider than the pores in the tissue. According to general pattern in kinetics, the slower stage determines the flux in a two-stage process, namely the stage of diffusion through membrane and stage of diffusion through tissue. A second general pattern is that the larger portion of total concentration drop ($C_s$ in our case) occurs at the step where the process is slower (in tissue, in the present case). Hence, $C_m>>(C_s-C_m)$. This makes it possible to replace $C_m$ by $C_s$ in equation for $$J_D^{ti} = -D_{ti}\frac{C_s}{\delta}.$$

The condition for this approximation is that $D_{ti}/\delta >> D_m/l_m$. This condition will be considered a posteriori. The replacement of larger $D_m l_m$ by smaller $D_{ti}/\delta$ in the equation for efficiency index, leads to its larger value:

$$E = \frac{V_n(LB)\delta}{D_{ti}}$$

To our knowledge, the theory of diffusion layer forming around spherical particle in uniform liquid stream is developed only for the traditional task, when the liquid stream does not penetrate into particle. In our case, the manifestation of diffusion has to be much weaker because there is no hydrodynamic stagnation near surface. Hence, using the Levich equation for $\delta = R_f/Pe^{0.5}$, we strongly over-estimate diffusion flux and consequently, underestimate E. The equation arising with the use the Levich equation is:

$$E = \frac{V_n(LB)}{D_{ti}}\frac{R_f}{Pe^{0.5}}$$

This yields, $E=Pe^{0.5}$. This equation estimate E from below, i.e., the real E is essentially larger. A larger Pe means a larger role of convection in comparison with diffusion. Hence, it is clear even without quantification that increase in Pe leads to larger role of convection than diffusion in drug release. But the derived equation quantifies this observation.

The diffusivity D depends on the water viscosity η and on the macromolecule radius r. This dependence is described by the Stokes-Einstein equation:

$$D = \frac{kT}{6\pi\eta r}$$

where k is the Boltzman constant, T is absolute temperature. r increases with molecular weight (MW) and 100<MW<500 g/mole. This is not true for proteins and larger molecules.

| Drug | MW (g/mol) | D (cm$^2$/s) Aqueous | $D_m$ = 0.25 D |
|---|---|---|---|
| Caffeine | 194.2 | 4.9 × 10$^{-6}$ | 1.5 × 10$^{-6}$ |
| Insulin | 41,000 | 8.3 × 10$^{-7}$ | 2.5 × 10$^{-7}$ |

With respect to broad pores of membrane in case of HFHHP, $D_m \cong \varepsilon t_0^{-1} D \sim 0.25 D$.

As tissue pores are rather narrow, an additional factor decreases $D_{ti}$ in comparison with $D_m$ at the same drug molecule dimension. With approach $d_{dr}$ to $d_p$, i.e., with increasing ratio $d_{dr}/d_p$, $D_{ti}$ decreases in comparison with diffusivity when pores are broad. Hence, a multiplier $Z(d_{dr}/d_p)$ has to be introduced in equation to interconnect diffusivity in narrow pores with diffusivity in broad pores: $D_{ti}=D_m Z(d_{dr}/d_p)$ Although detailed information about $Z(d_{dr}/d_p)$ is unavailable, it can be appreciated qualitatively that $Z\to 0$ when $d_{dr}/d_p \to 1$ and $Z\to 1$ when $d_{dr}/d_p$ exceeds unity essentially. In fact, $Z(d_{dr}/d_p)$ has to be accounted for in the denominator of the previously presented equation for E. This will lead to a further increase of the Peclet number:

$$Pe = \frac{V_{af}}{2}\left(\frac{R_f}{R_{lb}}\right)^2 \frac{R_f}{D_m Z(d_{dr}/d_p)}$$

$D_{ti}$ are measured for the drugs tenofovir and tacrolimus. On other hand, it is also possible to calculate $D_m$ for those drugs because their known molecular weight makes it possible to determine their hydrodynamic radiuses r according to equation derived in $$r = \left[\frac{3(MW)}{4\pi N\rho}\right]^{1/3}$$

where N is Avogadro's number, and ρ is approximately 1 g/cm³.

$$Z = \frac{D_{ti}^{exp}}{0.25D(r)}$$

Afterwards, substitution of r into the Stokes-Einstein equation yields:

$$D = \frac{KT}{6\pi\eta\left[\frac{3(MW)}{4\pi N\rho}\right]^{1/3}}$$

While the linear velocity inside ILC has been measured by many research groups, the data about velocity along afferent capillary is scarce. There is consensus about velocity along ILC $10 < V_{ic} < 50$ mm/sec. Hence, there is a value given in one reference, namely 0.02 micron/sec, which is three orders of magnitude smaller than the results reported by many other research groups, and so might be a misprint. Indeed, if it is assumed that the units are mm/sec instead of the printed units of micron/sec, this would yield for ILC a reasonable value $V_{ic}=0.2$ mm/sec which is 20 micron/sec, instead of the seemingly erroneous 0.02 micron/sec. Then, the seemingly erroneous value for afferent vessel $V_{af}=0.2$ micron/sec has to be replaced by $V_{af}=0.2$ mm/sec=200 micron/sec.

The substitution $R_f=0.03$ cm and $V_{af}=0.02$ cm in the general equation for $Pe_{ti}$ yields $$Pe_{ti} = \frac{3 \times 10^{-4}}{D_m Z}\left(\frac{R_f}{R_{lb}}\right)^2$$

The estimates for Pe and E for two values of ($R_f/R_{lb}$) and for diffusivities of caffeine and insulin, as example molecules, are given in Table.

| | $D_{ti}$ (cm²/sec) | | | |
|---|---|---|---|---|
| | $1.5 \times 10^{-6} Z^{-1}$ | | $2.5 \times 10^{-7} Z^{-1}$ | |
| $R_f/R_{lb}$ | Pe | $Pe^{0.5}$ | Pe | $Pe^{0.5}$ |
| 1/4 | 12.5 | 3.8 | 75 $Z^{-1}$ | 8.7 $Z^{-0.5}$ |
| 1/7 | 4 | 2 | 24 $Z^{-1}$ | 4.9 $Z^{-0.5}$ |

The caffeine molecule is very small in comparison with the broad pores of the membrane. In the case of caffeine, we omitted Z, whose value can differ only slightly from 1. As Pe is not sufficiently small in the case of caffeine, because the diffusivity of that rather small molecule is high even in narrow pores of tissue, this asymptotic estimate from below is not appropriate. This does not mean that the statement about predominantly hydrodynamically driven drug release is not valid in case of small drug molecule. The real diffusion flux is much lower than that calculated using the Levich equation. Below it will be explained that even in case of a small molecule, hydrodynamically driven release can predominate. Even with this overestimation of diffusion flux Pe is large in the case of the smaller diffusivity of insulin molecule. Pe can be even larger, because for this large molecule, $d_{dr}/d_p$ may not be very small in comparison with unity (in contrast to the case of caffeine) and small Z may contribute to Pe increase. In spite of strong overestimation of diffusion, the hydrodynamically driven release rate exceeds that when diffusion controls release almost by an order of magnitude. With a more consistent theory, the advantage of hydrodynamically release can occur to be even much higher: $E=J_c/J_D$, i.e., enhancement of release rate due to hydrodynamically driven mechanism.

In case of a hydrodynamically impermeable particle, the convection enhances diffusion transport, that manifests itself in the thinning of diffusion layer with increasing Pe. In case of hydrodynamically permeable particle (in particular hollow fiber of high permeability) the convection growth suppresses the diffusion. With increasing velocity, the hydrodynamically driven release rate increases, diffusion driven release rate decreases. However, the quantitative theory of convective diffusion transport in case of a hydrodynamically permeable particle is unavailable, and its elaboration is a serious mathematical problem. In this situation, we can consider the mechanism of influence of hydrodynamic flow through fiber on diffusion rate and show qualitatively that the convection (the growth of Pe) suppresses the diffusion. For this purpose, we needed a quantitative theory of hydrodynamic flow through permeable hollow fiber, which was unavailable.

The local velocity in porous media is proportional to local gradient of pressure, gradp. The coefficient of proportionality is called the Darcy constant K. A relatively large value of the Darcy constant corresponds to a relatively large permeability of a porous medium. As the lumen is filled with powder, this is a porous medium as well with large pores and large Darcy constant $K_l$. It is known that the pressure distribution in porous media p(r, θ) satisfies the Laplace equation. A spherical coordinate system is appropriate because for flow perpendicular to a cylinder, the Laplace equation has to be solved in a cylindrical coordinate system (hollow fiber axes) and two boundary conditions for pressure and pressure gradient on porous cylinder surface. However, a mathematically easier task is the corresponding task for a hydrodynamically permeable sphere. Meantime, the patterns of hydrodynamically driven and diffusion driven release are generally the same for spherical and cylindrical geometries. As our task is to satisfy a mechanism leading to unusual decrease of diffusion driven release, we will analyze this mechanism in the spherical geometry. The second simplification is addressed to the complication that we need to interconnect hydrodynamic transport in the three compartments: tissue, membrane of hollow fiber, and lumen. Accordingly, three values of Darcy constant have to be accounted for: $K_{ti}$, $K_m$ and $K_l$. The general mechanism of convection influence on diffusion transport will not change, if we focus on situation:

$$K_m = K_{ti} = K_{mti}, K_l >> K_{mti}$$

At first glance, it might seem that we violate the main condition for strong hydrodynamically driven release, namely, $K_m >> K_{ti}$. However, at this condition, the velocity within the lumen is almost the same as the given external velocity. This makes it possible to clarify qualitatively, how strongly penetration of external flow inside a porous body affects diffusion transport, which is our purpose.

If we replace a three-compartment drug release system with a two-compartment system, the pressure distributions inside lumen and outside it become:

$$p_{mti}(r, \theta) = |gradp_{ext}|\left(r + \frac{K_{mti} - K_l}{2K_{mti} + K_l}\frac{R^3}{r^2}\right)\cos\theta$$

$$p_e(r, \theta) = |gradp_{ext}|\frac{3K_{mti}}{2K_{mti} + K_l}r\cos\theta$$

using the analogy with electrostatics. Indeed, the electric potential has to satisfy the Laplace equation, the differential Ohm law I=Kgrad φ, where I is the electric current, K is local conductivity which is an analogy of the Darcy law, when p(r,θ) is analog to φ(r,θ) and the Darcy constant is an analog to electric conductivity. The problem of the electric potential distribution around a conducting cylindrical wire in a given transverse uniform electric field (current) was solved for elaboration of the electrophoresis theory when the conducting cylindrical particle is oriented perpendicular to the electric field. We apply locally uniform velocity (pressure) distribution, i.e., we ignore weak variation of external pressure (velocity) distribution around fiber (sphere) and we consider external pressure (velocity) distribution as uniform in vicinity of sphere (fiber). The local external velocity is $V(h_{lb}) = -K_l gradp_{ext}$. It is possible to examine that pressure distribution such that it satisfies two boundary conditions: $p_{mti}(R,\theta) = p_e(R,\theta)$ and $$K_{mti}\frac{\partial p_{mti}}{\partial n}(R, \theta) = K_l\frac{\partial p_l}{\partial r}(R, \theta).$$

The product $r\cos\theta = y_f$ where $y_f$ is the projection of vector $\vec{r}$ with its origin on the center of the sphere (fiber axis) on the coordinate axis $yh_{lb}$. Differentiation with respect to $y_f$ yields the velocity inside sphere (fiber lumen), which occurs uniform $$V = K_l\frac{dp_l}{dy} = \frac{3K_lK_{mti}}{2K_{mti} + K_l}gradp_{ext} = \frac{3K_lK_{mti}}{K_l + 2K_{mti}}V_{mti}(h_{lb}) \cong \frac{3K_lK_{mti}}{K_l + 2K_{mti}}V(LB)$$

In HHPHF case, i.e., at $K_l \gg K_{mti}$ $$V_l = 3V(LB)$$

Figure 7A:
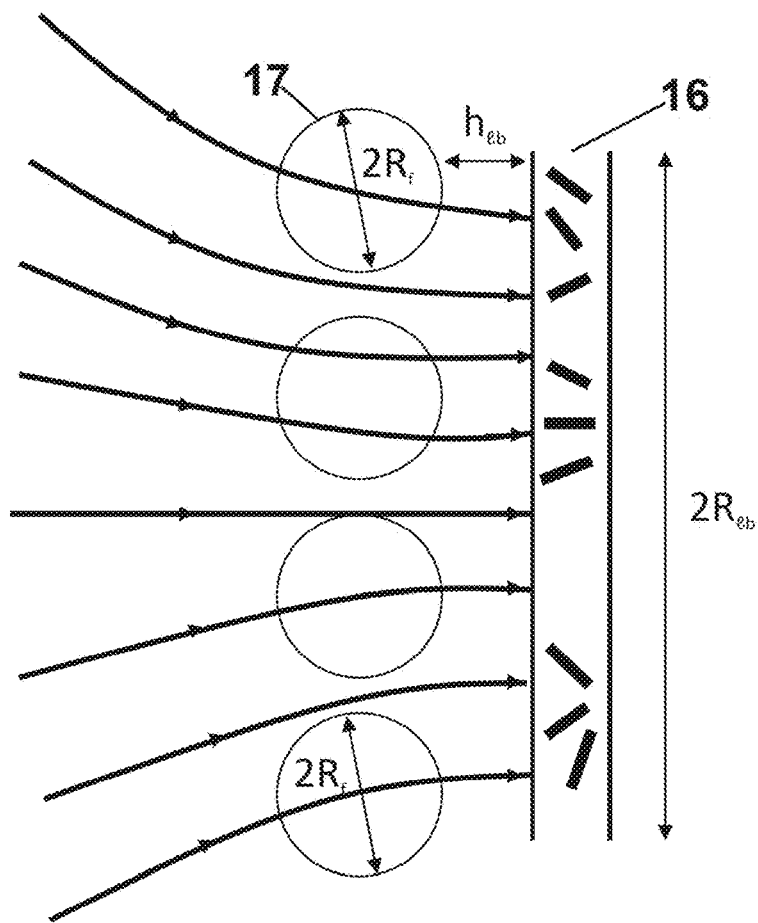
Figure 7B:
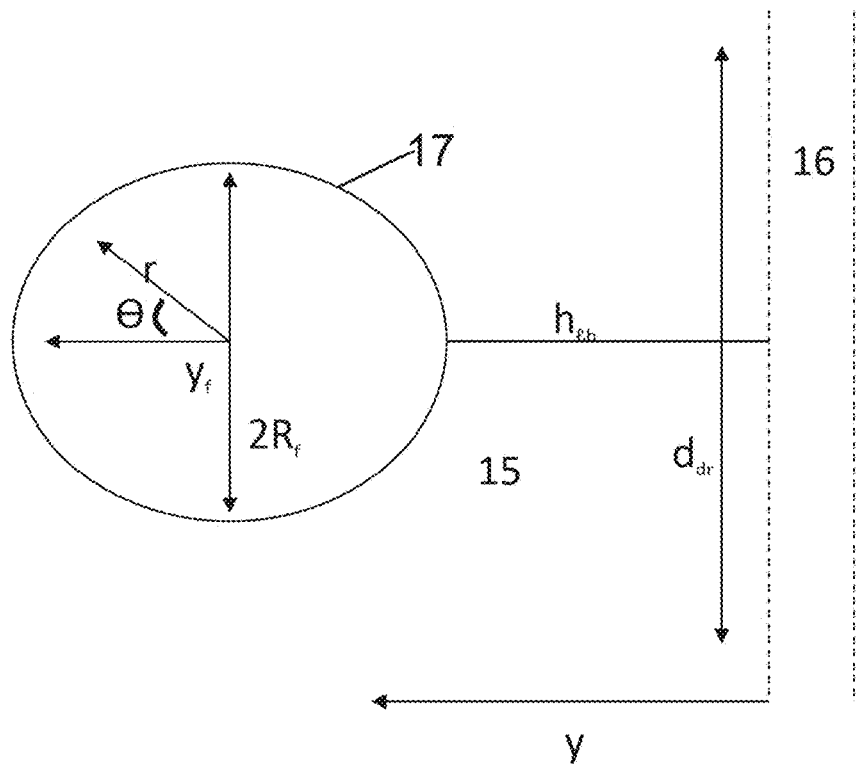
Figure 7C:
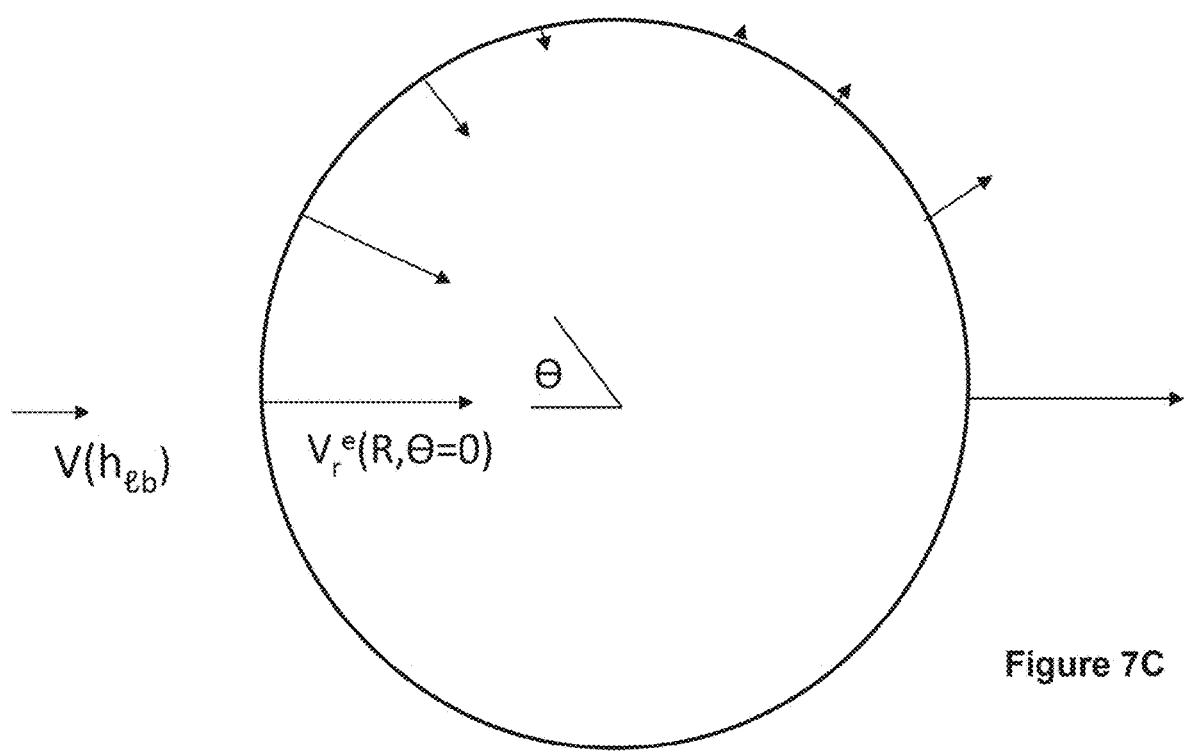

As interstitial flow concentrates within hollow fiber (sphere), the velocity within the lumen can essentially exceed the local interstitial velocity that existed before placement of the fiber. Meantime, the hydrodynamically driven release was quantified with the simplified assumption that $V_l$ equals to $V_n(h_{lb})$. The substitution $V_l$ instead of V(LB) derived from the equation for hydrodynamically driven release will increase its estimate from below. This will be done when the derivation leading to derived equation for $V_l$ will be modified for cylindrical case. The velocity distribution along surface of sphere (fiber) is required for understanding the influence of convection through the lumen on diffusion $$V_r(R, \theta) = -K_l\frac{\partial p_l}{\partial r}(r = R, \theta) \cong 3V(LB)\cos\theta$$

which is illustrated schematically in FIG. 7A-7C.

Figure 8A:
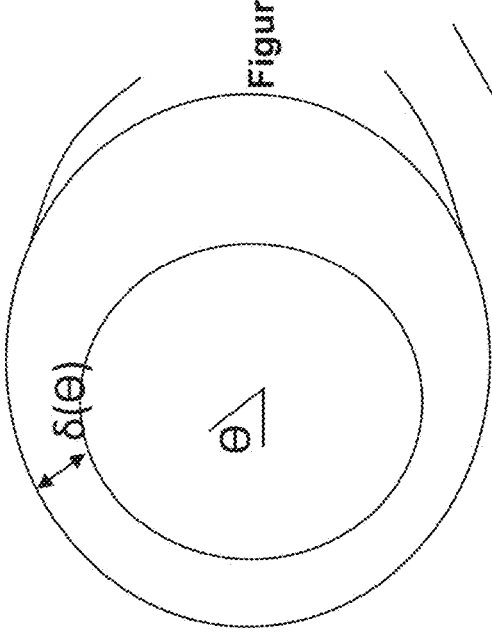
Figure 8B:
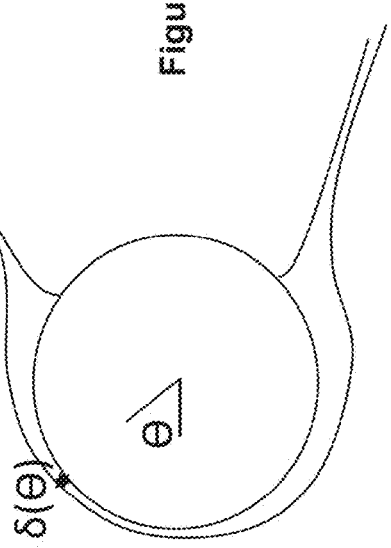
Figure 10A:
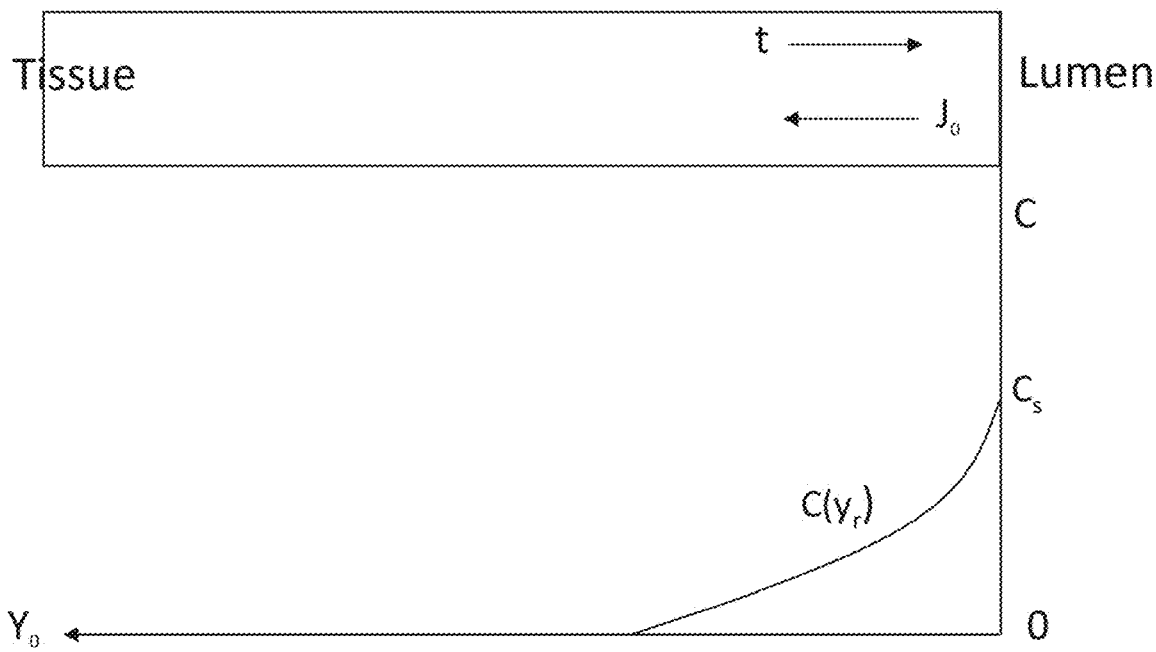
Figure 10B:
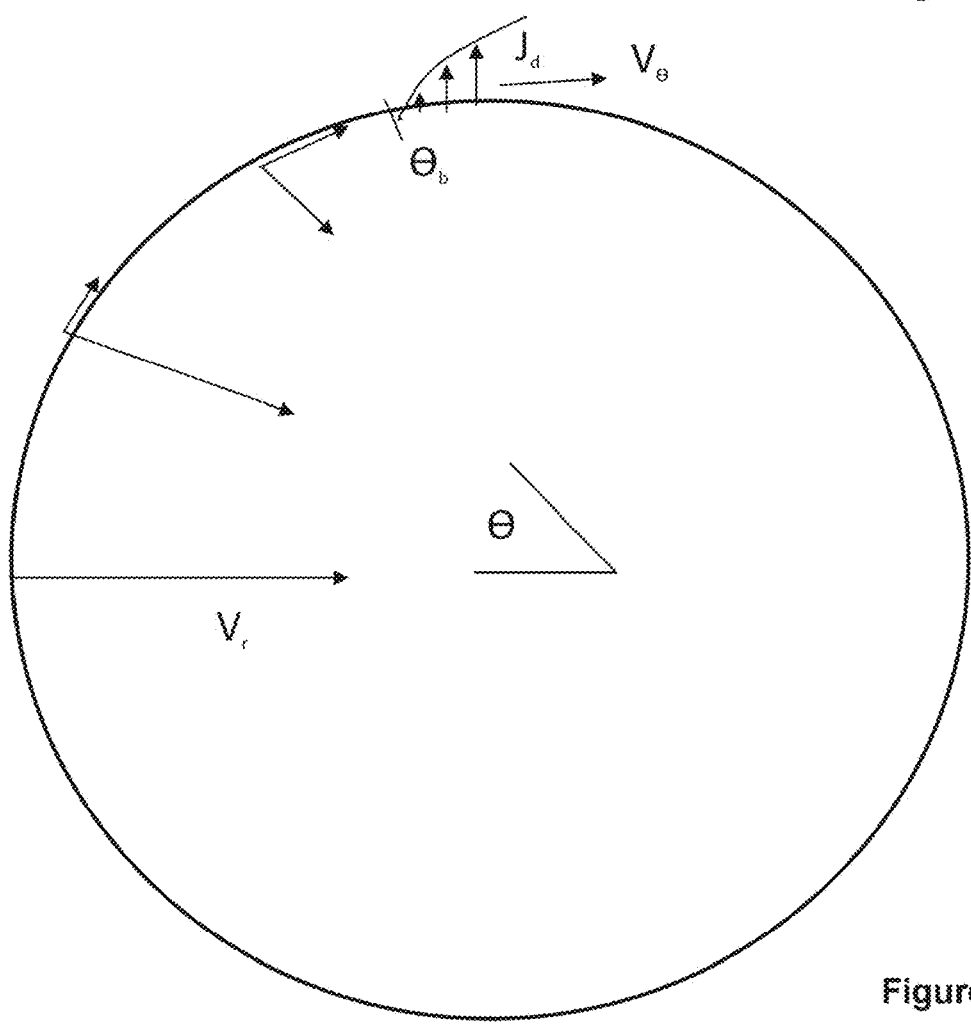

The width of the drug strip (FIG. 7B) characterizes the rate of hydrodynamically driven release for HHPHF. The contribution of diffusion manifests itself as the increase in the strip width. This has to occur because not only the lumen but the membrane as well is filled with saturated solution in the HHPHF case. The drug diffuses from solution into interstitial flow which flows around the fiber (modeled as a sphere) and forms the diffusion layer which is involved in tangential movement of liquid which broadens downstream and unites to form the hydrodynamic drug strip, caused by convective outflow of saturated solution out of lumen (FIG. 8A-8B). The outflow of saturated solution from lumen takes place within angle range π/2<θ<π, where there is outward direction of velocity vector on surface. Hence, the contribution of diffusion occurs at an angle range 0<θ<π/2. Meanwhile, the diffusion within membrane in this angle range occurs opposite to liquid flow. Although diffusion opposite to hydrodynamic flow is possible, the latter suppresses formation of a steady diffusion layer. The larger the normal component of velocity is, the more narrow is the diffusion layer that arises in comparison with that which occurs in case of dissolution from impermeable surfaces of a sphere. While the solution of the relevant problem of convective diffusion is not easy, an unexpected implication occurs when pores of membrane are isolated each other. This is well-known for a nucleopore membrane. As to this case, when pores in the membrane are interconnected, a qualitative analysis is illustrated in FIG. 10A-10B.

In order to explain why suppression of diffusion transport in the condition of hydrodynamically driven release enhances in case of nucleopore, i.e., in case of isolated membrane, we need refuse from preceding simplified two-compartment model which assumes $K_{ti}=K_m$, i.e., we need to consider the realistic case, when $K_m \gg K_{ti}$. This can be done without the use of complicated 3 compartment model $K_l \neq K_m \neq K_{ti}$, taking into account that the pores between powder particles in lumen are much larger than that in membrane even at condition $K_m \gg K_{ti}$. This means $K_l \gg K_m$. As it is so, even a small pressure drop is sufficient to drive liquid across lumen. This pressure drop can be neglected. Approximately uniform pressure in lumen can be identified with locally uniform pressure before fiber implantation, i.e., pressure in cross-section θ=π/2. The schematic of pressure distribution within three compartments is presented in FIG. 9. There are two boundary conditions on interface between tissue and membrane as it was in the preceding two-compartment model between the external compartment and the lumen. The pressure drop across the membrane is larger than that through the lumen, but much smaller than across a comparable distance of tissue. In addition, the membrane thickness is rather small. This makes it possible to consider linear dependence on r within the membrane. As dependencies on r and θ for this model in tissue and in the preceding model for $t_{if}$ compartment are the same, and as these dependencies are the same for the lumen in the preceding model and for the membrane in this model, and as boundary condition are the same, the following linear algebraic equations for coefficients are the same. This means that the equations from the preceding paragraph can be used with a proper change in indexes:

$$p^{ti} = |gradp_{lb}|\left(r + \frac{K_{ti} - K_m}{2K_{ti} + K_m}\frac{R^3}{r^2}\right)\cos\theta$$

$$p^m = |gradp_{lb}|\frac{3K_{ti}}{2K_{ti} + K_m}(r - R_{mi})\cos\theta$$

where $R_{mi}$ is the lumen radius (internal radius of fiber). The formation of diffusion layer on fiber surface is affected by the tangential and normal components of velocity on external surface of fiber, i.e., at $r=R_f$ $$V_n^m(R_f, \theta) = -K^m \frac{\partial p^m}{\partial r}(R_f, \cos\theta) = -\frac{3K_{ti}K_m}{2K_{ti}+K_m}\frac{\partial p^{lb}}{\partial r}(R, \cos\theta)$$

where $p^{lb}(r,\theta)$ is the pressure distribution caused by LB before placement of the fiber, i.e., uniform velocity perpendicular to disk-like disk with absolute value $$|V_{lb}| = \frac{1}{2}\left(\frac{R_f}{R_{lb}}\right)^2$$

The vector $V_{lb}$ can be formally characterized by $\theta$ and $r$ component.

$$V^{lb} = -K_n \operatorname{grad} p^{lb}, p^{lb}(r,\theta) = |\operatorname{grad} p^{lb}|r \cos\theta$$

Combining equations for $V_n^m$ and $V^{lb}$ yields $$V_n^m(R_f, \theta) = \frac{3K_m}{2K_{ti}+K_m}|V^{lb}|\cos\theta$$

where $|V^{lb}|\cos\theta$ is $V_n^{lb}$. A similar procedure yields for $V_\theta^m$ $$V_\theta^m(R_f, \theta) = -K^m \frac{1}{R_f}\frac{\partial p^m}{\partial \theta}(R_f, \theta) =$$

$$\frac{R_f - R_{fl}}{R_f}\frac{3K_m}{2K_{ti}+K_m}K^{ti}\frac{\partial p^{lb}}{\partial \theta} = \frac{3K_m}{2K_{ti}+K_m}\frac{l_m}{R_f}|V^{lb}|\sin\theta$$

It is noteworthy that a rather small multiplier $l_m/R_f$ appeared in expression for tangential velocity. The physical reason is smaller angular dependencies of pressure in the lumen and in the membrane. This is caused by large $K_t$ and small $l_m V_\theta(R_f,\theta)$ and $V_r(R_f,\theta)$, which are also present in the Levich equation for convective diffusion of hydrodynamically impermeable sphere. Their angular dependencies are $\cos\theta$ and $\sin\theta$, respectively, also. However, the amplitudes of the velocity component in the Levich case are almost the same, i.e., $V_\theta(\theta=\pi/4) \sim V_r(\theta=\pi/4)$. In contrast, strong hydrodynamic permeability of the sphere (fiber) leads to two fundamental differences in velocity components. The permeability leads to a decrease by $R_f/l_m$ times of the tangential velocity in comparison with the external velocity $V_{lb}$. Meantime, the larger is $V_\theta(R_f,\theta)$, the stronger is influence of convection on diffusion, the thinner is $\delta$ and the stronger is the diffusion. A decrease by a factor of 10 in $V_\theta(R_f,\theta)$ ($l_m=15$ micron) leads to a decrease by a factor of 10 in Pe and leads to an increase in $\delta$ by a factor of $Pe^{0.5}=10^{0.5} \sim 3.16$.

The velocity distribution thus obtained makes it possible to correct some equations proposed earlier.
$J_n = 3V^{lb}$ where it is taken into account that $K_m \gg K_{ti}$. Accordingly, $J_c$ increases 3 times. $J_c = 3V^{lb}C_s$. The equation for $Pe_{ti}$ takes into account decrease in $V_\theta^m(R_f,\Theta)$ is $$Pe(V_\theta^m) = 3\frac{l_m}{R_f}|V^{lb}|\frac{R_f}{D_{ti}} = \frac{3l_m|V^{lb}|}{D_{ti}}$$

-continued $$Pe[V_\theta^m(R_f, \theta)] = 3\frac{l_m}{R_f}Pe$$

where Pe as given previously was $$\frac{V^{lb}R_f}{D_{ti}}$$

This modifies the equation for E, which was estimated earlier, as $$E = \frac{J_c}{J_D} = \frac{3V^{lb}R_f}{D_{ti}Pe^{0.5}(V_\theta^m)} = \frac{R_m}{l_m}Pe^{0.5}(V_\theta^m)$$

New values for the corrected $Pe(V_\theta^m)$ and E are presented in the following Table. The Peclet number decreased by a factor of approximately 3 times for $R_f/l_m=10$, corresponding to $l_m=15$ micron. The appearance of multiplier $R_f/l_m=10$ in the corrected equation for E leads to E an increase in E by a factor of 3.16 times, because $Pe^{0.5}(V_\theta^m)$ decreased:

|  | $D_{ti}$ (cm$^2$/sec) | | | |
| --- | --- | --- | --- | --- |
|  | $1.5 \times 10^{-6} Z^{-1}$ | | $2.5 \times 10^{-7} Z^{-1}$ | |
| $R_f/R_{lb}$ | $Pe(V_\theta^m)$ | E | $Pe(V_\theta^m)$ | E |
| 1/4 | 3.75 | >6 | 22 $Z^{-1}$ | 27 $Z^{-0.5}$ |
| 1/7 | 1.20 | 6 | 7.2 $Z^{-1}$ | 36 $Z^{-0.5}$ |

As the Peclet number decreased, the Levich theory for $\delta$, used in derivation for E, is valid only for Pe=22. For Pe=1.2 in Table, convection influence on diffusion is weak.

This means that the multiplier $Pe^{0.5}$ can be replaced by 1 in equation for E, which equals to 6 for this case. To our knowledge, the equation for $\delta$, when Pe is not sufficiently large, is unknown. This causes uncertainty in the estimate of E for Pe=3.75 and 7.2. However, the estimate from below appears feasible. In case of Pe=3.8, the comparison with E=6 leads to conclusion that for Pe=3.8, E>6. Indeed, with velocity increase the convective flux increases linearly, diffusion flux increases less-than-linearly. As the difference between cases Pe=1.2 and Pe=7.2 in estimation of E is only due to difference in $D_{ti}$ value only, E for case Pe=7.2 can be estimated by multiplication of E=6 on diffusivities ratio. This yields E=36, while E has to be less than 27. 27 was obtained for a higher convection than in case of E=36. An error of about 25% is not surprising, because these are estimates. Even the Levich theory, perhaps, may cause this error, because 22 may be not sufficiently high.

The accounting for an increase by a factor of 3 times in V, and an associated increase in convective flux, and smaller $V_\theta$ and associated decrease in enhancement of diffusion flux due to tangential convection, reveal the small contribution of diffusion flux in conditions of hydrodynamic driven drug release.

Figure 9:
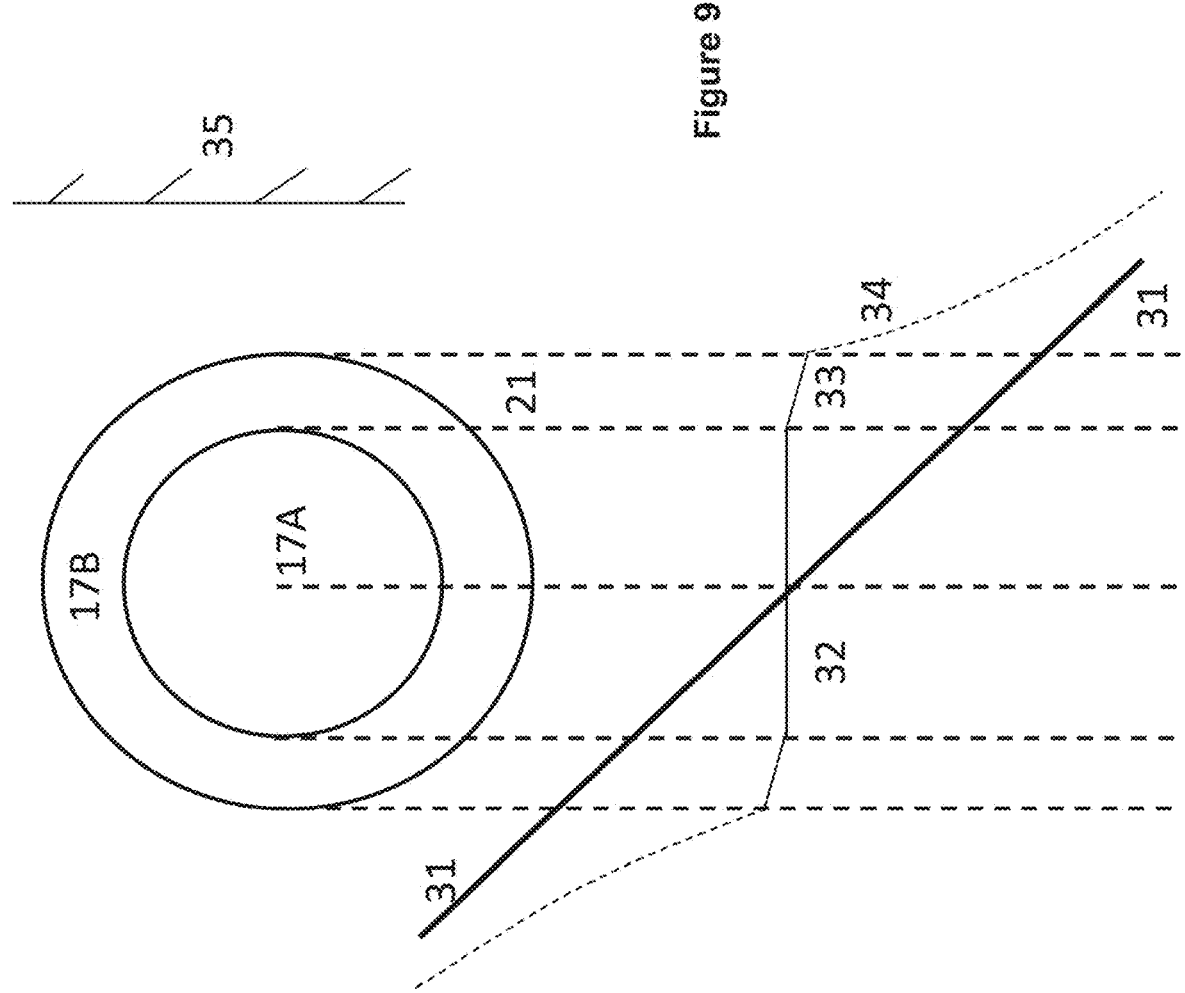

While the Table in the preceding paragraph shows that the diffusion contribution to hydrodynamically driven release (HDR) is very small, it can be even much smaller due to the normal component of velocity directed opposite to diffusion flux. A straight pore of a nucleopore membrane is shown in FIG. 9.

Referring now to FIGS. 10A-10B, with coordinate $y_p$, while $y(0)$ corresponds to the internal surface of the membrane wall, where the concentration equals approximately $C_s$. Within a straight pore, liquid moves with velocity $$V_p = 3\frac{V_{af}}{\varepsilon}\left(\frac{1}{2}\frac{R_f^2}{R_{lb}^2}\right)\cos\theta$$

towards the lumen, while the diffusion proceeds in the opposite direction. After the first onset of steady state, the velocity profile is determined by the condition that the diffusion flux in any cross-section equals the convective flux.

$$-D\frac{dc}{dy_p} - C(y_p)V_p = 0$$

whose solution shows an exponential decay in the direction toward the tissue.

$$n_p(y) - C_p(y) = C_s\exp\left(-\frac{V_p}{D}y_p\right)$$

The characteristic length l of drug penetration into pore opposite to the direction of convection is $$l = D\left[\frac{3V_{af}}{2\varepsilon}\left(\frac{R_f}{R_{lb}}\right)^2\cos\theta\right]^{-1}$$

when $l(\theta_i)=l_f$
there is no release from pores located on fiber at $\theta<0$. This occurs because for smaller $\theta$ (smaller than $\theta_i$, the convective flow prevents diffusional penetration through the entire length of membrane. There is exponentially small drug penetration outside membrane. This small amount of drug is involved in tangential flow that causes exponentially small contribution to diffusional drug release. As $C(R_f,\theta)$ is not zero, there is a penetration of drug in tangential flow around surface. It means that the flux I along pore has to be accounted for in differential equation. One boundary condition $(C_p(y_p=0)=C_s$ is not sufficient to determine I and concentration distribution. Meantime, the formulation of bound condition for $y_p=h_f$ is problematic. When I is small, its account in differential equation leads to a small correction. The condition for possibly disregarding I in the equation follows from accomplished consideration without account for I. At small angle, the velocity can be sufficiently high to decrease $C(R_f,\theta)$ to values much smaller than $C_s$. With increasing θ, the velocity decreases, which leads to onset of concentration $C(R_f,\theta_l)=C_se^{-1}$. I may not be sufficiently small and may affect the derivation of equation for 0i. Nevertheless, the introduction of $\theta_l$ is useful for clarification of the mechanism of suppression of diffusion driven release, when hydrodynamic driven release is strong.

When the difference between $\theta_l$ and π/2 is rather small, the portion of surface area in vicinity of θ=π/2, where the diffusion release is not retarded essentially by liquid inflow into lumen is rather small. This is sufficient condition to disregard diffusion contribution to hydrodynamically driven release. Naturally, there is a matter of convection in choice for $\theta_l$ value. The accomplished primitive quantification allows to formulate a quantitative criterion describing when the diffusion contribution to hydrodynamically driven release can be disregarded because drug diffusion penetration from lumen into tangential interstitial flow around membrane surface occurs within narrow vicinity of θ=π/2.

$$\frac{2D\varepsilon}{3l_f V_{af}}\left(\frac{R_{lb}}{R_{af}}\right)^2 < 1$$

For example, this criterion with $\theta_l$=75° is not satisfied for conditions when in Table of the preceding paragraph, $Pe(V_\theta^m)$=3.75. However, it is satisfied when either D is 30% smaller or $V_{af}$ is 30% larger.

Drug release parameters and features from constructs having multiple fibers or layers of fibers Permeability of Tissues and Construct/Device Membrane As detailed elsewhere herein, embodiments of the invention describe two modes of drug release modes to be employed in different treatments and therapies as required, namely: (i) diffusion-driven release (DDR) and (ii) hydrodynamically-driven release (HDR). Devices that operate according to the DDR, in most cases, are favorably operated when the permeability of the membrane (e.g., fiber wall) used to make the device is lower than that of the target tissue, site or organ. HDR-based devices favorably operate when the permeability of the membrane used is higher than that of the target tissue, site or organ. In other cases, there can be a need to employ devices that provide both DDR and HDR release mode in order to provide effective therapy or treatment. To satisfy the above requirements and to make or select a suitable membrane for making the device/construct, it is necessary to specify the permeability, thickness and pore size of both the membrane and of the target tissue. Membrane material, pore size, porosity, pore shape, pore structure, membrane thickness, hydrophobicity, hydrophilicity and wetting properties are the main parameters that determine the permeability of the membrane and hence can to be considered when making or selecting the hollow fiber or flat sheet membrane for manufacturing the devices and constructs according to the present invention. As described above, the relative permeability values of the membrane and target tissue are favorably factored into making DDR or HDR devices, helping to satisfy the release rate for achieving effective therapy. In this section of the disclosure we provide description the basic design parameters and present some typical values of permeability of the membranes and tissues.

The typical units for membrane (or other porous medium including tissue) permeability Lp are (m/s)/bar, with the permeability defined as: Lp=V/ΔP The units of pressure can be written as Pascals, where 1 Pa=1 Nt/m^2. This would give the units of permeability as m^3/(Nt s). The Darcy permeability, denoted by K, can be thought of as permeability per unit membrane thickness, which for a uniform membrane becomes:

$$K=Lp*h$$

which would have units of m^4/(Nt s). Value h here denotes membrane thickness. This quantity is not typically used for asymmetric membranes because it is difficult to estimate the thickness of the membrane skin layer (which is the region of the membrane that actually provides the key resistance to flow); skin layer is also known as the active membrane layer. However, K is more of an intrinsic property of the membrane because Lp changes with the thickness of the membrane (the thicker the membrane the smaller the value of Lp), but K is a material property of the membrane material.

The permeability values for a series of ultrafiltration membranes are included in the Table below. In this case, the permeability was defined by the first equation but with V in units of LMH (L/m^2/hr), where 1 LMH=2.78×10^-7 m/s. It is easy to convert those into units of m^3/(Nt s), with the 50 kDa membrane having a permeability of:

$Lp = 470$ LMH/bar$= 1.3 \times 10^{-9}$ $m^3/(Nt\ s)$

The Darcy permeability can then be evaluated using either the skin thickness (probably around 0.5 microns) for asymmetric membranes or the total membrane thickness (which can be around 150 microns). If you use the skin thickness for an asymmetric membrane, we get Darcy permeability K as follows:

$K = 6.5 \times 10^{-16}$ $m^4/(Nt\ s)$

The calculations for the other membranes where the entire thickness is the active membrane are straightforward. In the Tables below, we summarize the typical permeability values of polyethersulfone membranes as well as the conversion to different units. The preferred Darcy permeability units for the purpose of the invention is m4/Ns according to this invention.

TABLE

UF Membrane pore sizes and properties as provided by cited reference*

| Nominal MW Cutoff (kd) | Permeability (LMH/bar) | Pore Radius (nm) |
|---|---|---|
| 50 | 470 | 2.6 |
| 100 | 2100 | 5.3 |
| 300 | 2400 | 5.7 |
| 1,000 | 6900 | 9.8 |

*Filtron polyethersulfone membranes, Robertson et al., J Coli Interf Sci 134: 563 (1990)

TABLE

| h | Permeability (LMH/bar) | Darcy Permeability ($m^4/N \cdot s$) | | | Pore Radius |
|---|---|---|---|---|---|
| | | 0.5 micron (skin thickness) | 30 micron (membrane thickness) | 150 micron (membrane thickness) | |
| 50 kD | 470 | $6.5 \times 10^{-16}$ | $3.9 \times 10^{-14}$ | $2.0 \times 10^{-13}$ | 2.6 nm |
| 100 kD | 2100 | $2.9 \times 10^{-15}$ | $1.7 \times 10^{-13}$ | $8.5 \times 10^{-13}$ | 5.3 nm |
| 300 kD | 2400 | $3.3 \times 10^{-15}$ | $2.0 \times 10^{-13}$ | $1.0 \times 10^{-12}$ | 5.7 nm |
| 1000 kD | 6900 | $9.5 \times 10^{-15}$ | $5.7 \times 10^{-13}$ | $2.9 \times 10^{-12}$ | 9.8 nm |

TABLE

Calculations $1\ \text{bar} = 10^5\ \text{Pa} = 10^5\ \text{N/m}^2$ $$L_p = \frac{m}{\sec \cdot \text{bar}} = \frac{m}{\sec} \frac{m^2}{N} = \frac{m^3}{N \cdot \sec}$$

$$1 \frac{L}{m^2 \cdot hr} = \frac{1000\ cm^3}{(10000)\ cm^2 hr} =$$

$$\frac{1}{10 \times 3600} \frac{m}{\sec} = \frac{1}{1000 \times 3600} \frac{m}{\sec} = 2.78 \times 10^{-7}\ \text{m/sec}$$

$470\ LMH/bar =$ $$\frac{470(2.78 \times 10^{-7})}{10^5\ N/m^2} \frac{m}{\sec} = \frac{1.3056 \times 10^{-4}\ m/sec}{10^5\ N/m^2} = 1.3056 \times 10^{-9} \frac{m^3}{N \cdot \sec}$$

Assume skin thickness h = 0.5 micron = $0.5 \times 10^{-6}$ m $$K = L_p \cdot h = 1.3056 \times 10^{-9} * 0.5 \times 10^{-6} = 6.5 \times 10^{-16} \frac{m^4}{N \cdot \sec}$$

The above data include examples of ultrafiltration membranes, which are characterized by small pore size and high porosity. It is important to note that the present invention can use membranes with large pore size (30 nm to 100 nm or higher for example), namely microfiltration membranes. However, in general, membranes with any pore size could be used in embodiments of the invention. Membranes with larger pore size and higher Darcy permeability are useful to make HDR devices as described elsewhere herein. The following Table provides one example for polycarbonate membrane; however, there are many other membrane materials to select from, both permanent and resorbable, to make the devices and constructs of the invention. It is clear from this description that the permeability of the membrane can be adjusted by selecting key parameters, including pore size, thickness, porosity and material. It clear according to this invention that the desired "effective" permeability can be achieved by the proper selection of the parameters and the invention should not be limited to the examples provided herein. "Effective permeability" means the permeability property needed to satisfy the conditions needed to make DDR or HDR as defined elsewhere herein. This is important to define these quantities without confusion in units or conversions. It should be noted here that the Tables show example calculations for different membranes at the same hydraulic permeability in LMH/bar units. According to such calculations Darcy permeability provided in the Tables represent different membranes. In other words Darcy permeability is a material property, a Darcy constant, for a given membrane material having a given porosity and pore size. It means that a membrane with known Darcy permeability (Darcy constant) should have different hydraulic permeabilities (LMH/bar) at different membrane thicknesses as defined by the above equations.

TABLE

| Pore Radius (nm) | Flow Rate (ml/min · cm²) | (LMH) | Lp ($m^3/N \cdot$ sec) | (LMH/Bar) | Lp * h ($m^4/N \cdot s$) | | |
|---|---|---|---|---|---|---|---|
| | | | | | h = 0.5 micron | h = 30 micron | h = 150 micron |
| 30 | 0.2 | 120.1 | 4.9E−10 | 176.7 | 2.5E−16 | 1.5E−14 | 7.4E−14 |
| 50 | 0.4 | 240.3 | 9.8E−10 | 353.4 | 4.9E−16 | 2.9E−14 | 1.5E−13 |
| 100 | 2.5 | 1501.8 | 6.1E−09 | 2208.5 | 3.1E−15 | 1.8E−13 | 9.2E−13 |

TABLE

Notes about conversion factors and calculations:

1 bar = $10^5$ Pa = $10^5$ N/m$^2$
Δp = 10 psi = 0.68 bar

TABLE

Calculations on Flow Rate; Flow Rate/Pressure; Permeability

Flow Rate:
1 ml/min · cm$^2$ = 1.67 × $10^{-4}$ m/s = 6 × $10^2$ LMH $$1\ LMH = 1\frac{L}{m^2 \cdot hr} =$$

$$\frac{1000\ cm^3}{(10000)\ cm^2 hr} = \frac{1}{10 \times 3600}\frac{cm}{sec} = \frac{1}{1000 \times 3600}\frac{m}{sec} = 2.78 \times 10^{-7}\ m/sec$$

Flow Rate/Pressure:

$$L_p = \frac{m}{sec \cdot bar} = \frac{m}{sec}\frac{m^2}{N} = \frac{m^3}{N \cdot sec}$$

$$1\ LMH/bar = \frac{(2.78 \times 10^{-7})}{10^5\ N/m^2}\frac{m}{sec} = 2.78 \times 10^{-12}\frac{m^3}{N \cdot sec}$$

Permeability:
K = $L_p$ * h
where h = membrane thickness

In order to design the devices and constructs of the invention and define the drug release mode, DDR or HDR, it is useful to know the Darcy permeability of the target tissues as disclosed elsewhere herein. However, permeability values of a tissue depend on the type of the tissue under consideration, and these values may vary by order of magnitude from one tissue type to another. For example the Darcy permeability of human meniscal tissue is very low, about 2.5×10E−16 m4/Ns. Bovine meniscal tissue permeability is slightly low at about 8.1×10E−16 m4/Ns. In regard to porosity, the porosity of most tissues is normally high and is approximately 0.75 or 75%. These values are documented in: "Biomaterial Properties", editors J. Black and G. Hastings, page 51, Chapman and Hall (1998).

According to above reference, the Darcy permeability of loose scar tissue is between 0.3 to 7.8×E−11 m4/Ns, and these values can vary by a factor of 10E5 and can range from 10E−15 to 10E−10 m4/Ns. The Darcy permeability of bone is very low and can range from 10E−20 to 10E−17 m4/Ns. Cartilage permeability is about 10E−14 m4/Ns. Nerve permeability is 1.2 10E−17 m4/Ns.

The permeability of collagen gels is in the range of 0.1 to 1 10E−12 m4/Ns. The permeability of other gels that form tissue scaffolds such as polyacrylamide is between 0.4 to 1.3 10E−11 m4/Ns. These values are reported in: O'Brien et al. "epublication of the Royal College of Surgeons in Ireland". 2007.

The permeability of a solid tumor is reported to be in the range of 10E−13 m4/Ns according Falhgren et al, "Acta of Bioengineering and Biomechanics", volume 14, 47-51 (2012). According to this reference, normal tissue permeability is between 1.6 to 5 10E−11 m4/N-s, which is much higher than that of tumor tissue. It can be appreciated that these permeability values should be taken into consideration for designing the drug delivery devices for treating the tumor or for preventing metastasis via delivery to lymphatics according the present invention.

According to the above description, the permeability values of tissues cover a wide range of values and the target tissue should be considered in designing devices and constructs according to the invention. The membranes can be selected or tailored so that they can satisfy the requirements of the selected drug release mode, DDR or HDR as defined in the present invention. It is clear from the description that membranes, whether hollow fibers, flat sheets or other shapes, can be selected to make the either DDR or HDR as needed for the therapy according to the invention. The membrane material and parameters can be selected or made to obtain the desired permeability as described above. The membrane material can be either permanent or resorbable as needed based on the application or therapy according to the invention.

For cases $K_m$ (for wall)>$K_{ti}$ and $K_m$~$K_{ti}$, the following Table is a useful guide:

| Conditions | Mode of Drug Release |
| --- | --- |
| MW > $10^3$ and $V_{int} > 0.1\frac{micron}{sec}$ | HDR Predominates |
| $V_{int} = 0$ or $V_{int} < 0.1\frac{micron}{sec}$ | DDR Plays a Role |
| MW < $10^3$ | Contributions of HDR and DDR in drug release are comparable |

For cases $K_m$<$K_{ti}$, the following Table is a useful guide:

| Conditions | Mode of Drug Release |
| --- | --- |
| MW > $10^3$ and $V_{int} > 0.1\frac{micron}{sec}$ | HDR and DDR comparable |
| $V_{int} = 0$ or $V_{int} < 0.1\frac{micron}{sec}$ | DDR predominates |
| MW < $10^3$ | DDR predominates |

An example for a low permeability membrane is cellulose acetate which is known to have low molecular weight cutoff, normally from 200 to 500 Daltons. The permeability data provided in the literature can vary by two orders of magnitude as presented in the following two Tables. Difference in permeability can be due to the method of manufacturing in the cited papers. According to the Darcy permeability values provided in the Table, K can vary from 10E−17 m$^4$/Ns to 10E−19 m$^4$/Ns. These values can be used as guidelines for Darcy permeability values for determining where diffusion-driven release (DDR) mode would predominate. Darcy permeability above the values is required to provide sufficient permeability to provide HDR mode, and this of course would depend of the permeability of the tissue to be treated according embodiments of the invention.

3.2 A Universal Approach to Achieve Simultaneously Higher Release Rate and Longer Release is the Application of Hollow Fiber Mesh.

Figure 10F:
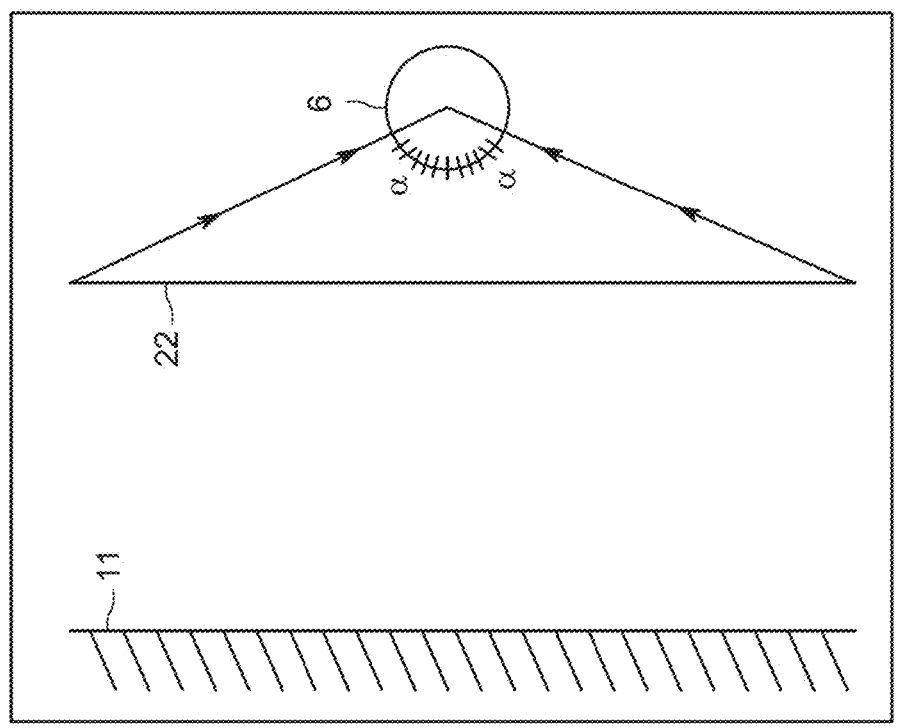
Figure 10D:
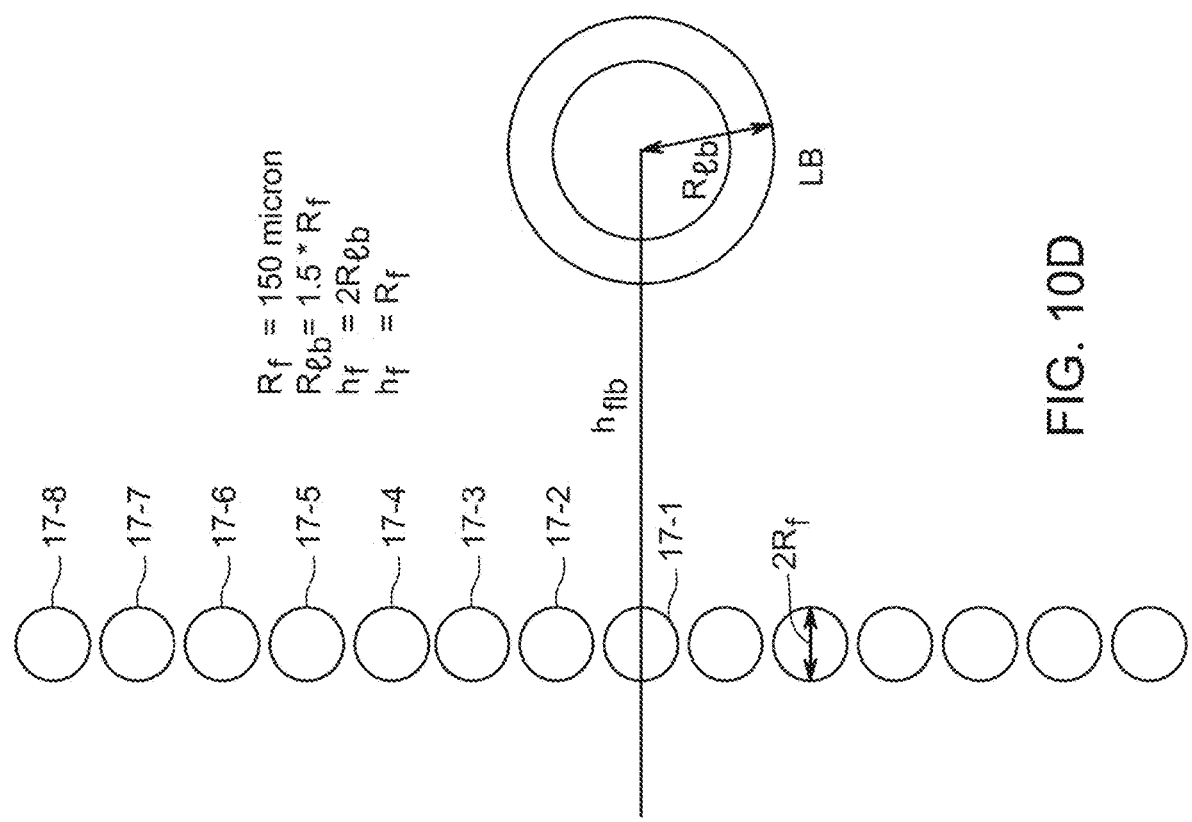
Figure 10E:
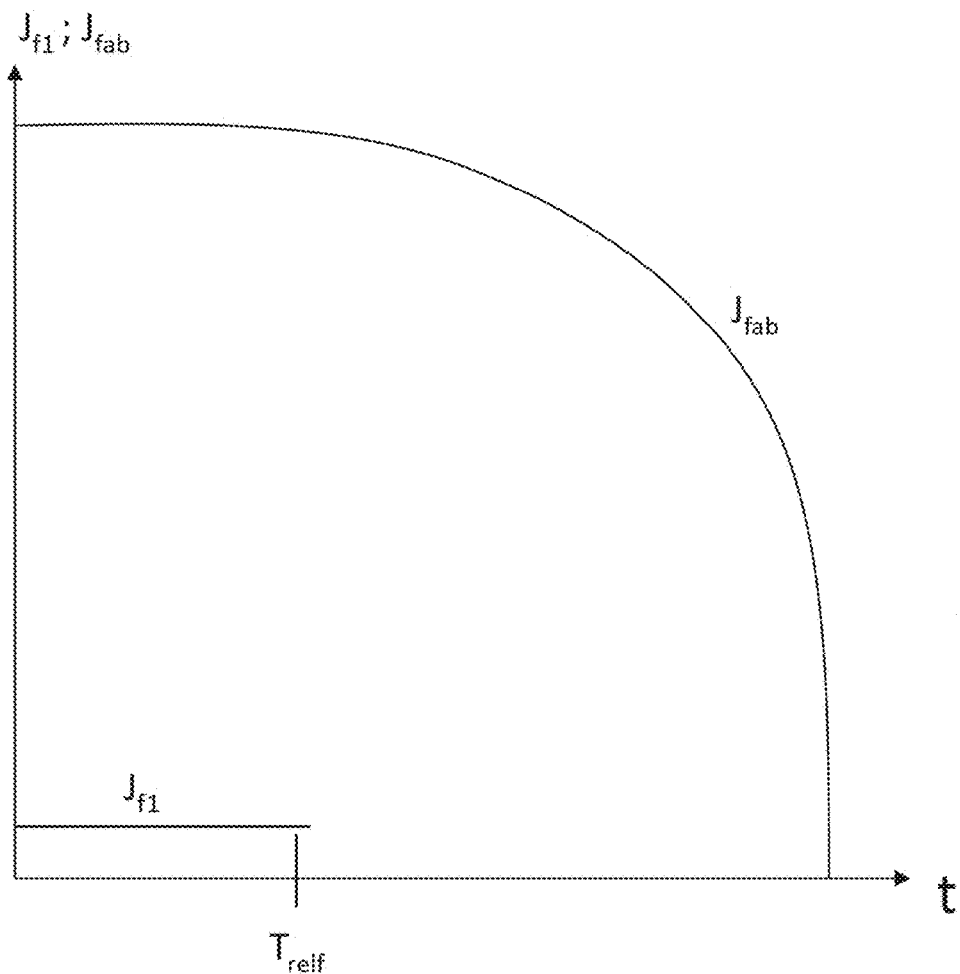

Referring now to FIGS. 10C-10D, for this situation, a mesh has to be established with hollow fibers parallel to both LB and skin. The fiber with the shortest distance to LB is numbered 1. The larger the fiber distance to LB is, the higher is fiber number, i=2, 3, 4 .... The mesh distance to skin $h_{sf}$ and to LB $h_{lb}$ are chosen to be equal, i.e., $h_{sf}$=$h_{lb}$. A favorable consequence is that for any fiber at this condition, the distances to LB and to skin (along the radius) are the same also. This follows from a known geometrical theorem about similar triangles. In our case, similar triangles are OAB and OA'B'. This leads to the conclusion that for any fiber i $$h_{sfi} = h_{lbi} \tag{3.1}$$

It was shown elsewhere herein at this condition that the skin influence on velocity distribution around a fiber (any fiber in the case of a mesh) can be accounted with a multiplier $Z(R_f, R_{lb}, h_{sfi}, h_{lbi})$, which approximately equals ⅔. With the use of this multiplier, we can represent velocity for any fiber using an approximation of local uniformity, i.e., by Eq. (1.13), specified for i-th fiber $$V_{ri}(r_{fbi}) = V_r(R_{lb}) \frac{R_{lb}}{r_{fbi}} \frac{2}{3} \approx V_r(R_{lb}) \frac{R_{lb}}{(R_{lb} + R_f + h_{lbi})} \frac{2}{3} \tag{3.2}$$

Then the analog of Eq. (1.12) for liquid stream loaded by drug of ith fiber is $$q_{si} = 2R_f J_f V_{ri}(r_{fbi}) \tag{3.3}$$

and the analog of Eq. (1.14) for drug stream due to convection through i-th fiber $$J_{fi} = q_{fi} C_s \tag{3.4}$$

The sum of $J_{fi}$ yields the total rate of release when hollow fiber fabric is used $$J_{fab} = \sum_{i=1}^{K} J_{fi} = J_{f1} + 2\sum_{i=2}^{K} J_{fi} = C_s \left[ q_{f1} + \sum_{i=2}^{N} q_{fi} \right] = \tag{3.5}$$

$$\frac{2}{3} C_s V_r(R_{lb}) R_{lb} \left[ \frac{1}{(R_{lb} + R_f + h_{lb})} + 2\sum_{i=2}^{N} \frac{1}{(R_{lb} + R_f + h_{lbi})} \right]$$

Any $h_{lbi}$ can be represented using the Pythagorean equation $$r_{fbi} = \sqrt{(R_{lb} + R_f + h_{lb})^2 + i^2 (R_f + h_f)^2} \tag{3.6}$$

where $h_f$ is the distance between adjacent fibers.

For convenience, Eq. (3.6) can be transformed to $$r_{fbi} = (R_f + h_f)\sqrt{a^2 + i^2} \tag{3.7}$$

$$a^2 = \frac{(R_{lb} + R_f + h_{lb})^2}{(R_f + h_f)^2} \tag{3.8}$$

where

Taking into account these equations, the sum in Eq. (3.5) is transformed to $$\sum_{i=2}^{N} \frac{1}{(R_{lb} + R_f + h_{lbi})} = \frac{1}{(R_f + h_f)} \sum_{i=1}^{N} \frac{1}{\sqrt{a^2 + i^2}} \tag{3.9}$$

This sum can be approximated by the integral $$\sum_{i=1}^{N} \frac{1}{\sqrt{a^2 + i^2}} \sim \int_{1}^{N} \frac{dx}{\sqrt{a^2 + x^2}} \tag{3.10}$$

This transformation assumes that $$\frac{1}{\sqrt{a^2 + i^2}} \cong \int_{1}^{i+1} \frac{dx}{\sqrt{a^2 + x^2}}$$

If to be exact $$\frac{1}{\sqrt{a^2 + i^2}} > \int_{1}^{i+1} \frac{dx}{\sqrt{a^2 + x^2}}$$

because at i<x<(i+1), $\sqrt{a^2+x^2} > \sqrt{a^2+i^2}$

However, the difference between $1/\sqrt{a^2+i^2}$ and corresponding portion of $i^2$ the integral is relatively small. At i<<a, the difference is small because the contribution of $i^2$ into $a^2+i^2$ and into $\sqrt{a^2+x^2}$ are small. At large i, i.e., i>>a, the relative variation of x in range i<x<i+1 is small. Hence, we can use the integral representation for the sum $$\sum_{i=1}^{N} \frac{1}{\sqrt{a^2 + i^2}} \cong \ln(x + \sqrt{a^2 + x^2})\Big|_{1}^{N} = \tag{3.11}$$

$$\ln\left(\frac{N + \sqrt{a^2 + N^2}}{1 + \sqrt{a^2 + 1}}\right) = \ln\left(\frac{N}{a} + \sqrt{1 + \frac{N^2}{a^2}}\right)$$

Asymptotics are $$\ln\left(\frac{N}{a} + \sqrt{1 + \frac{N^2}{a^2}}\right) \sim \begin{cases} N/a & N/a << 1 \\ \ln 2N/a & N/a > 1 \end{cases} \tag{3.12}$$

At small ratio N/a', $N^2/a^2$ the quantity under the square-root can be neglected and the general equation for logarithm reduces to $$\ln\left(1 + \frac{N}{a}\right) \cong N/a$$

At large ratio, 1 under the square-root can be neglected and the general equation for logarithm reduces to ln(2N/a)

The derived asymptotics have a simple physical sense. When N is small, the distances $r_{fbi}$, are approximately the same as $r_{fb1}$ (FIG. 9). This means that the contributions of all fiber for N<<a are the same and consequently, their joint contribution is proportional to their amount N. When N>a, the distance $r_{fbi}$ (i>a) is much larger than $r_{fb}$, i.e., $1/r_{fbi}$<<1/$r_{fb}$. Hence, the contribution of any fiber at N>a is much smaller than at N<<a. Let us show that this manifests itself in asymptotics $$\ln 2 \frac{N}{a} (N > a).$$

Let us obtain the contribution from single fiber from this asymptotics $$\ln 2\frac{(N+1)}{a} - \ln 2\frac{N}{a} = \ln\frac{(N+1)}{N} = \ln\left(1+\frac{1}{N}\right) \cong \frac{1}{N} \quad (3.13)$$

The contribution from a single fiber of fabric is $$\sum_{i=1}^{N} \frac{1/r_{fibi}}{N} \begin{cases} \frac{1}{a} & (N<<a) \\ \frac{1}{N} << \frac{1}{a} & (N>>a) \end{cases} \quad (3.14)$$

Meantime, $$\frac{1}{N} << \frac{1}{a};$$

when N>>a, a question arises whether N>>a has to be selected or not. As the contribution of a single fiber to the release decreases up to order of magnitude, it appears that the use of large fabric with N>>a does not offer much benefit, especially because the difficulty of fabric placement increases with increasing N.

The analysis represented by Eq. (3.14) can be generalized $$\sum_{i=1}^{N} \frac{1/r_{fibi}}{N} \begin{cases} \frac{1}{a} & (N<<a) \\ \frac{\ln\left(\frac{N}{a}\right) + \sqrt{\left(1+\frac{N}{a}\right)^2}}{N} & (N\sim a) \\ \frac{1}{N} << \frac{1}{a} & (N>>a) \end{cases} \quad (3.15)$$

It is remarkable that at N~a $$\frac{\ln\left(\frac{N}{a} + \sqrt{\left(1+\frac{N}{a}\right)^2}\right)}{N} \sim \frac{\ln(2.4)}{N} \sim \frac{1}{a} \quad (3.16)$$

Hence, the contribution from a single fiber does not decrease essentially, not only for N<<a but even for N~a. This also means that N~a can be recommended. In this case half width of fabric is $$N(R_f + h_f) = (R_f + h_f)\left(\frac{h_{lb} + R_f + R_{lb}}{R_f + h_f}\right) = h_{lb} + R_f + R_{lb} \quad (3.17)$$

where Eq. (3.8) is used
Example: $R_{lb}=1.5*10^{-2}$ cm, $R_{lb}=2R_f$, $h_{lb}=2R_{lb}$. $R_f+R_{lb}+h_{lb}=7R_f$, $h_f=R_f$ $$N = \frac{h_{lb} + R_{lb} + R_f}{R_f + h_f} \sim \frac{7}{2}$$

and accordingly, a=N~3
FIG. 10F illustrates a recommended mesh dimension and its placement according to the example at the same large magnification for all characteristics. The Table below shows that an essential and possibly unacceptable increase in mesh width, characterized by N value, leads only to small increase in release rate.

TABLE

| Increase of fabric release $J_{fab}$ with increasing amount of fibers N in fabric. | | | | |
|---|---|---|---|---|
| N | 1 | 3 | 6 | 7 |
| $J_{fab}$ | $J_f$ | 7 $J_f$ | 13 $J_f$ | 15 $J_f$ |

$J_f$ release by single fiber dependence is presented in units of $J_f$. An increase in N from 1 to 3 leads to $J_{fab}$ increasing 7 times, while an increase of the next 6 fibers yield an additional increase of 6$J_f$.

3.3 Drug Release Time for Hollow Fiber Mesh.

As streams of drug from adjacent hollow fibers do not overlap, the release rate from any fiber is not affected by increase from adjacent fibers. This means that time of release for any fiber of mesh is described by equation derived earlier. With a single fiber specification, $h_{lb}$ is different for different fibers, i.e., $h_{lbi}$ has to be shown in the equation $$T_{reli} = \frac{\pi^2}{2} \frac{R_{if}^2(R_{lb} + R_f + h_{lbi})l_{lb}}{R_f Q_{af}} \frac{\rho W_f}{C_s} \quad (3.18)$$

$T_{reli}$ increases with increasing $h_{lbi}$. The shortest release occurs for fiber i=1, because $$h_{lb1} < h_{lbi}(i \neq 1) \quad (3.19)$$

The longest release occurs for fiber N, because $$h_{lbN} > h_{lbi}(i \neq N) \quad (3.20)$$

As the difference between $h_{lb1}$ and $h_{lbN}$ is about a factor of 2 to 3, the difference between maximal and minimal release time is even smaller.

In distinction from release rate for single fiber, which is almost invariant in time, the release from a mesh decreases in time, essentially being at a maximum initially and being at its minimum before the end of the release. All fibers contribute to the initial release. Close to the end of the release, only two fibers, namely i=±N release drug. The release rate decreases in time approximately by a factor of 2(2N+1) times. The factor (2N+1) in this estimate arises because the number of fibers contributing to the release is (2N+1) at the beginning of release and it is one fiber near the end of the release. The factor of 2 arises because $h_{lbN}$ exceeds $h_{lb1}$ by about a factor of 2.

3.4 Decrease Drug Concentration within LN. Comparison with Initial Concentration G, when Hollow Fiber Fabric is Used The generalization of Eq. (1.16) is $$\frac{C_{ln}}{C_s} \sim \frac{q_{f1} + 2\sum_{i=1}^{N} q_{fi}}{Q_{af} - \left(q_{f1} + 2\sum_{i=1}^{N} q_{fi}\right)} = \frac{1}{1-\alpha} \quad (3.21)$$

where $$\alpha = \frac{q_{fi} + 2\sum_{i=1}^{N} q_{fi}}{Q_{af}} = (1 + 2N)\frac{q_f}{Q_{af}} \quad (3.22)$$

Because the liquid stream saturated with drug increased many times (as shown in the Table in Part 3) in the case of a fabric as compared to the single fiber case, this leads to a decrease of clean interstitial liquid stream into LB. This is accounted for in the denominator of Eq. (3.21). As $$q_f = 2R_f l_{lb} V_r(R_{lb}) \frac{R_{lb}}{r_{fib}} \frac{2}{3}, \quad (3.23)$$

$$Q_{af} = 2\pi R_{lb} l_{lb} V_r(R_{lb})$$

$$\frac{q_f}{Q_{af}} = \frac{2R_f}{3\pi(R_f + R_{lb} + h_{lb})}$$

This ratio is about 0.03 for $(R_f+R_{lb}+h_{lb})=7R_f$. Substitution (2N+1)~15 from Table specifies α as follows:

α~(15*0.03)=0.45.

Substitution of this value into Eq. (3.21) yields an estimate $$\frac{C_{In}}{C_s} \sim \frac{0.45}{0.55} \sim 0.8 \quad (3.24)$$

The results for a single fiber and for a fabric having N=15, $h_f=R_f$ are given in the following Table:

|  | Single fiber | Fabric |
| --- | --- | --- |
| $C_{In}/C_s$ | 0.03 | 0.8 |
| J | $J_f$ | 15 $J_f$ |

It is noteworthy that estimated value α~0.45 does not contradict the constraint on the value of $\alpha_{max}=0.5$. The area of α is illustrated (shadowed) in FIG. 10. It can be appreciated that the shadowed portion of surface (α) cannot exceed 0.5. The figure shows well that the width of fabric has to exceed LB diameter many times to achieve value α~0.45. Perhaps, the value of a and correspondingly, data for fabric in the above Table are overestimated. Nevertheless, the advantage of fabric is clear. The values for $C_{In}/C_s$ given in the above Table, are time invariant, which is seen from Eqs. (3.21) and (3.22). The release rate J is invariant during approximately the first half of the release time. After that, it diminishes quickly (FIG. 9).

3.5 Selection of $C_s$ Value in Condition of Release from Fiber and from Fabric

The constraint on selection of $C_s$ value is different in case of fiber and fabric, because $C_s$ value has to be chosen to provide the required value for $C_{In}$. Meantime, the interconnection between $C_{In}$ and $C_s$ is different in case of fiber and of fabric $$\frac{C_{In}^f}{C_s} = 0.03 \quad (3.27)$$

$$\frac{C_{In}^{fab}}{C_s} = 0.8 \quad (3.38)$$

Minimum inhibition concentration, i.e., minimum drug concentration required to suppress cancer or suppress immune system exists for any drug. Similarly, for purposes such as killing pathogens or generally to achieve any desired effect, there can be thought of a Minimum Effective Concentration. Regardless of whether a single fiber or a fabric is used, the requirement is MIC, $$C_{ln}^f = MIC \quad (3.29)$$

$$C_{ln}^{fab} = MIC \quad (3.30)$$

Combining Eqs. (3.27), (3.28) with Eqs. (3.29), (3.30) yields $$C_s^f = \frac{MIC}{0.03} \quad (3.31)$$

$$C_s^{fab} = \frac{MIC}{0.8} \quad (3.32)$$

In fact, the same release rate is required to provide $C_{ln}=C_{MIC}$, regardless of whether a single fiber is used or fabric. As the drug is released from many fibers in the case of fabric, the release rate per fiber can be much lower in the case of fabric. This leads to much smaller $C_s$, required for use of a fabric, as can be is seen from comparison of Eqs. (3.31) and (3.32).

3.6. Large Increase in Release Time at Fabric Application

The release rate of different fibers in fabric is different because $h_{lbi}$ is different. $h_{lbi}$ is larger for larger i. Correspondingly, release rate is smaller for larger i. This leads to a longer release time, when i is larger. Meantime, the release rate is approximately the same for $1\leq i\leq3$. We focus on release time for this group of fibers. It equals to $T_{rel}$ in case of a single fiber with distance to LB $h_{lb}$, and it is described by Eq. (3.18), specified for $h_{lbi}=h_{lb}$. This equation can be written as $$T_{rel} = \frac{A}{C_s} \quad (3.33)$$

where A is easily determined by comparison of Eqs. (3.18) and (3.33). This equation can be applied in cases of single fiber that will give $T_{rel}^1$ and to fabric, that will give $T_{rel}^N$ (but only for N fibers). The equations for $T_{rel}^1$ and $T_{rel}^{fab}$ follows from Eq. (3.33) by substituting $C_s^f$ and $C_s^{fab}$, respectively.

$$T_{rel}^1 = \frac{0.03A}{MIC} \quad (3.34)$$

$$T_{rel}^{fab} = \frac{0.8A}{MIC} \quad (3.35)$$

Comparison of these equations shows that the fabric application leads to an increase in release time by a factor of approximately 27 times (while providing release rate sufficient to achieve $C_{ln}$=MIC).

The substitution of A according to Eq. (3.18) into Eq. (3.33) yields $$T_{rel}^1 = 0.44 \frac{R_{if}^2 (R_{lb} + R_f + h_b) W}{R_f Q_{af}} \frac{\rho}{MIC}$$

The fabric release cannot be characterized with a single time because $h_{lbi}$ are different. However, the difference in $h_{lbi}$ is small for $1 \leq i \leq 7$.

The substitution according to Eq. (3.18) into Eq. (3.34) characterizes release times for different fibers of fabric $$T_{rel}^{fab} = \begin{cases} 12 \frac{R_{if}^2 (R_{lb} + R_f + h_b) W}{R_f Q_{af}} \frac{\rho}{MIC} & 1 \leq i \leq 7 \\ 12 \frac{R_{if}^2 (R_{lb} + R_f + h_{lbi}) W}{R_f Q_{af}} \frac{\rho}{MIC} & i > 7 \end{cases}$$

As a summary: Modeling for drug release from fabrics:

1. Fabric placement: Fabric is oriented parallel to the skin at the half distance between skin and LB (FIG. 7).

2. Fabric release rate: The release rate from any fiber does not depend on any other fiber's release, i.e., it is independent. Consequently, the fabric release rate is a sum of release rates of fibers, but these rates are different because the distances fiber/LB $h_{lbi}$ are different. The release rate decreases with increasing $h_{lbi}$. Approximately 15 fibers are proposed for mesh because the additional contribution of more than this number of fibers (larger i) would be small. The sum of 15 terms is difficult to quantify. An analytical equation is obtained for the representation of the sum. The fabric release rate decreases in time, which is in contrast to the release characteristic of a single fiber. Initially, there is release from all (2N+1) fibers, i.e., maximal release rate. Because the release rate from fibers with i≤7 is faster, they are exhausted earlier. Afterwards, remaining (2N+1-7) fibers release and this amount of releasing fibers gradually decreases to zero. This causes the first stage of constant release rate at a maximum release rate, followed by a second stage of gradually decreasing release rate (FIG. 8).

3. Concentration in LN: $C_{ln}$ is smaller than the initial saturation concentration $C_s$. The decrease from $C_s$ to $C_{ln}$ occurs because the dilution of saturated stream from fiber $q_f$ with larger stream of pure liquid in LB, i.e., $Q_{lb}$ and dilution is high (35 times). As saturated stream increases about 15 times in fabric case, the dilution becomes weak, almost not essential. Because dilution is almost eliminated in the fabric case, $C_{ln}/C_s$ does not differ much from 1, and the concentration in LN (the lymph node) increases 20 to 30 times in the case of fabric.

4. Selection of proper $C_s$ value for single fiber release and fabric release: the minimal inhibition concentration (MIC) in LN is sufficient $C_{ln}$=MIC. However, $C_s$ has to be larger than MIC because $C_{ln}$ is smaller than $C_s$ due to dilution. In a single fiber case, $C_s$ has to be larger than MIC by a factor of about 30 times. In contrast, in a fabric case, $C_s$ can be selected to be almost equal to MIC because the dilution is weak. This is a significant advantage of fabric, in that it allows $C_s$ to be about 25 times smaller than in a single fiber case.

5. The fabric application allows to extend release duration by a factor of about 25 times, in comparison with single fiber: The elimination of $C_{ln}$ decrease in comparison with $C_s$ in fabric case allows to achieve $C_{ln}$ MIC with $C_s$ about 25 times smaller than in single fiber case. In turn, this decrease in release rate makes it possible to extend the release time by a factor of about 25 times in fabric case, which is extremely significant for therapy.

Fibers can comprise membranes having a Molecular Weight CutOff (MWCO). The MWCO can range anywhere from 18 Daltons (which represents water) to greater than 1 million Daltons. The membrane can be an ultrafiltration membrane, a microfiltration membrane, a nanofiltration membrane, or a reverse osmosis membrane. The membrane can allow passage of small molecular weight drug molecules, or depending on the properties of the membrane, the membrane can also deliver biologics. The membrane can retain other molecules such as osmogens or hydrating molecules that can be useful for continuous drug delivery. The size and shape of the pores can be chosen in conjunction with the molecular size and shape of the drug that is to be delivered. Macroscopic holes within the walls of fibers are also possible.

Pores through the wall of the membrane can be generally round, or generally elongated. It is possible to make pores that are highly elongated, such as by stretching the fiber during manufacturing to tailor the shape of the pores as in the case of making fibers for blood oxygenators. The pore structure of the fiber walls can be interconnected or can behave as a porous medium.

The fraction of the fiber surface or fiber wall that is occupied by pores can be anywhere from approximately 0.001% to approximately 50% or more. A typical fraction can be 45%. This can be considered to be the pore fraction of the outside surface of the fiber, or the pore fraction of the inside surface of the fiber. A membrane can be either symmetric (smooth on both inside and outside) or asymmetric (smooth on one surface, rough on the other surface). If there is a smooth surface of the wall or membrane, the smoothness can be either on the inside of the fiber or the outside of the fiber.

A drug that is included in the device can protect against bacteria or other pathogens including viruses, yeast, prions and fungi. The drug can also prevent biofilm from growing on or near the fiber and in the surrounding environment which can comprise tissue or organ. The drug substance could be a growth factor that promotes the growth of certain types of cells or tissue where this can be desirable for the purpose of healing or in making tissue repair more effective, for example after hernia repair or constructive surgery. The drug substance could be a substance that discourages adhesions of tissue or can, if desired, promote scarring. The drug can be either a small-molecule drug or a biologic. The drug can be a growth factor, a substance to suppress fibrosis, a chemotherapeutic substance that kills tumors or cancer cells or prevents cancer metastasis or both. The drug can be an immune modulator or have special functions to deliver drug to lymphatics including lymph nodes or lymph organs. The drug can be a muscle or tissue relaxant to promote the relaxing or stretching of tissue. The drug does not have to be just for purpose of infection control. The drug could be an antimicrobial; an antibiotic, an anti-biofilm drug; a chemotherapeutic drug; a growth factor, a substance to suppress fibrosis; an anesthetic; an analgesic; an anti-inflammatory; an immunosuppressant, an immune modulator; a chemotherapeutic agent; an anti-coagulant; an anti-adhesion drug; a muscle or tissue relaxant; a biologic; or any of various other categories of drugs.

The drug as it exists inside the lumens of the hollow fibers could be a solution of drug in water, a solution of drug in some other solvent or solvent mixture, drug dissolved in a gel or drug particles suspended in a gel, a suspension of drug in an ordinary liquid of any viscosity, a solid powder, foam, or any other state. The drug loaded in lumen of the fibers of any device or construct can be any combination of drugs for treatment or management of any disease. The lumen can contain a drug formulation, which can be any combination of one or more drugs, excipients, additives and other substances as discussed elsewhere herein.

The dimensions of the hollow fibers can be similar to the dimensions of hollow fibers used in cartridges for hemodialysis or blood oxygenators or the like. For example, the outside diameter of the fiber can be up to several hundred microns such as from 50 to 500 microns in outside diameter. The internal dimension of the lumen of hollow fibers can be about from 50 to 450 microns inside diameter or more. Fiber wall thickness can be from about 15 to 50 microns, and can be adjusted to impart mechanical strength or to control release of drugs. The ratio of the inside diameter of the fiber to the outside diameter of the fiber can be in the range of 70% to 90%, for example. The pore fraction in the wall of the fiber can be 0.001% to 45% based on intended applications or desired release rates and duration. The pore size can be selected in the approximate range of from 1 to 1000 nanometers. The pore size can be chosen based on the size of the molecules of drug that is intended to be released, on the form of the drug formulation in the fiber lumen, and on the desired release mode, which can range from diffusion-dominated to hydrodynamically-driven or a combination thereof. A larger pore size would be suitable for a larger-molecule drug, for example. The pore shape and the pore size distribution can also be appropriately chosen to further control the release rate and duration of release.

The lumen can contain a variety of components or substances within it, and there can be certain relationships between the pore sizes of the pores in the fiber wall and the properties of various components. First of all, of course, the pores can be large enough so that water can pass through the pores. Also, the pores can be large enough so that molecules of the drug can pass through the pores. Within the lumen there could be still other substances whose passage out of the lumen is not desired. The molecule size and shape of the molecules of such substances, relative to the pore size and shape, could be such that such substances cannot pass through the pores.

The drug or other substances within the lumen can be in the form of particles of different shapes. The particles can contain one drug or more than one drug, or there could be various kinds of particles each containing a different drug or other substance. Still other substances, either soluble or insoluble, could also be present in the form of particles in the lumen. Any of these particles can be large enough so that they cannot pass through the pores. More particularly, the particles can be larger than the pores by a significant factor such as at least a factor of 5, so that even when the particles have been reduced in size due to gradual dissolution, they still will not be able to pass through the pores until they have shrunk to a small fraction of their original size. At the same time, the particles can be selected so that their diameter or characteristic dimension is less than about one-fifth of the inside diameter of lumen. This can be helpful in regard to the process of filling the lumen with the particles or placing the particles in the lumen. The particle size is also influential, as discussed elsewhere herein, in determining how stable a suspension is, such as how long it will remain a suspension without particles settling out due to gravity, because a suspension is one vehicle for introducing particles into the lumen. The lumen can also contain, and this is especially true if the device is provided in a dry condition, a substance that absorbs liquid such as water. This will help in achieving a liquid or moist state inside the lumen by bringing water in through the pores in the wall at or after the time of implantation or use of the device. The water absorbing substances can be selected from known cross-linked acrylics or cellulosics and can be provided as molecular form or as microspheres or nanoparticles or other forms or shapes.

If the lumen contains liquid, the liquid can be formulated such that it has favorable properties as a suspension at least during the time when the suspension is being caused to flow into the lumen for purposes of bringing the particles into the lumen. The liquid can contain additives to increase its viscosity or even to cause it to form a gel. The liquid can also contain anti-flocculating agents as described elsewhere herein. The liquid can also contain a surfactant as described elsewhere herein. If the device is supplied in a dry condition, the lumen can contain the dried or solid form of any one or more of these additives.

In an embodiment of the invention, provided is a drug that is in solution in water or in a liquid that has properties similar to those of water. In an embodiment of the invention, provided is a drug that is in solution or in a gel. In an embodiment of the invention, provided is a drug that is in the form of particles that are surrounded by or suspended in water or a liquid that has properties similar to those of water. In an embodiment of the invention, provided is a drug that in the form of particles that are suspended in a gel. In any of these combinations, a high viscosity liquid can also be used instead of a gel.

In order to understand embodiments of the invention, it can be helpful to consider drug release in the described geometry as including a series of steps that must occur, and a series of mass transfer resistances through which drug must pass in order to go from its origin to its destination.

If drug exists as a solid, in order to be released, it must first dissolve in a liquid or a gel. Then, there can be some distance within the lumen through which the drug must pass by diffusion, so there can be a diffusion process within the lumen space to transport the drug a distance that is less than or comparable to the radius of the lumen. Then, the drug must pass through the pores or holes in the wall of the fiber, or through the spaces between molecules in the case of a semi-permeable membrane. Then, the drug must disperse in the adjacent tissue. This dispersal in the tissue can occur by simple diffusion, or it can be assisted by convective motion of interstitial liquid within tissue of the body near the drug delivery device; it can also be hydrodynamically driven, as discussed elsewhere herein. In general, it is possible for one or more of these processes to be a significant resistance or resistances that can be rate-controlling for the overall process of drug delivery. It is also possible that one or more of these resistances can be negligible or insignificant in the overall process of drug delivery. Analysis of some of these resistances is discussed elsewhere herein.

In the human body overall, the majority of transport of substances occurs through the flow of blood, but a smaller amount of transport occurs through the movement of interstitial fluid outside the blood stream, which also includes lymphatic flow or circulation. The placement of the implant of embodiments of the invention can be done taking into account the expected direction and magnitude of systemic and lymphatic flow or circulation. This can be done so that for example the implant can be placed upstream of the intended region of delivery, with respect to the lymphatic circulation and motion of interstitial fluid. This can be done, for example, in regard to preventing metastasis of cancer, or for immunotherapy or for targeting a tumor. As discussed elsewhere herein, it is believed that, in at least some situations, the lymphatic circulation provides more mass transport than does diffusion through bodily tissues especially with respect to cancer treatment or treatment involving lymph flow or circulation.

Figure 11A:
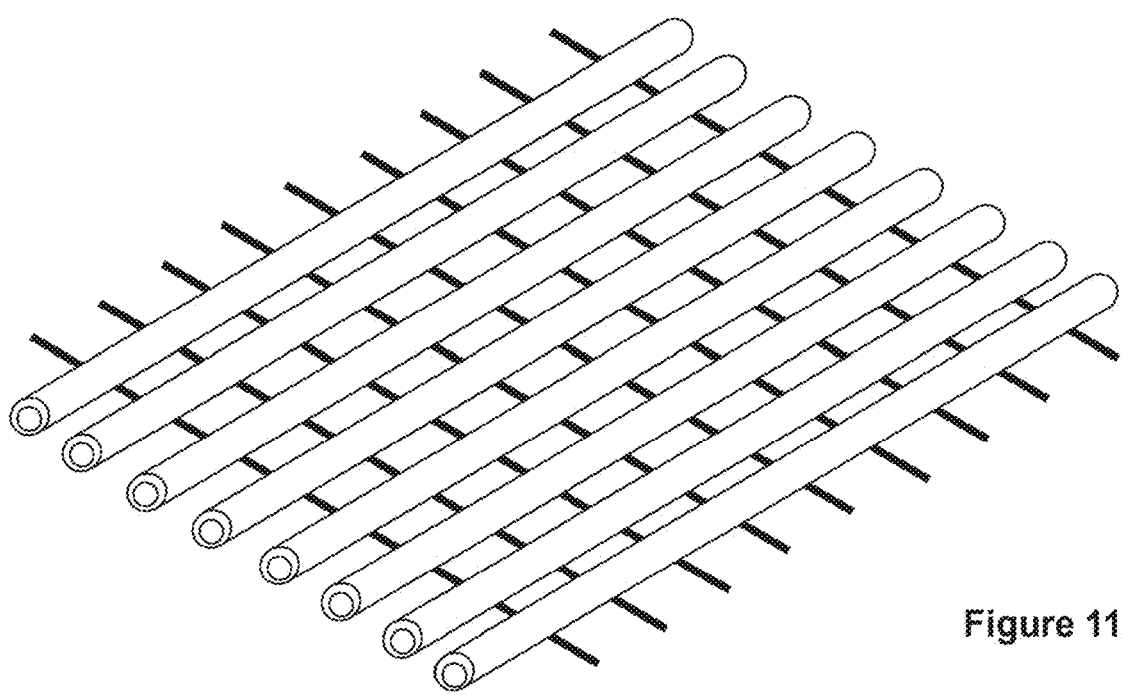
FIG. 11A illustrates a device that contains hollow fibers (prior art in unfilled state) and traverse solid fibers.

Referring now to FIG. 11A, there is illustrated a known commercial product in which porous-walled hollow fibers extend in one direction, with the lumens of the hollow fibers being empty. Transverse to the porous-walled hollow fibers are solid fibers, which are mechanically weaker than the porous-walled hollow fibers. The solid fibers are attached to the hollow fibers. Such a product is commercially available from Celgard (Concord, N.C.), which is a division of Membrana (Germany), which is a division of 3M (St. Paul, Minn.).

Details about Fibers

Materials

In general, the fiber can be made of or can comprise any biocompatible polymer. The fiber material does not have to be hemocompatible.

At least for some applications, the fibers could be made of non-resorbable polymers, such as any of the materials that are conventionally used in making hollow fibers for hemodialysis or hemofiltration cartridges.

Alternatively, the fibers can be made of a material that is resorbable in the human body. For example, resorbable substances include poly lactic acid (PLA), poly glycolic acid (PGA), and poly lactic co-glycolic acid (PLGA). Another resorbable polymer can be based on functional groups such as esters, orthoesters, amides, anhydrides, polycaprolactones or other biodegradable materials as is known in the art. The rates of resorption of these substances can be adjusted by the details of their copolymerization, the molecular weight, chemical nature, resorption mechanism and other details. Materials are also discussed later herein.

Embodiments in the Form of Fabric

In some embodiments of the invention, the fibers can be arranged or woven in the form of a fabric. Braiding of fibers is also possible. Many variations are can be use; for example, one layer could deliver one drug another layer could deliver another drug. It is not necessary that drug be present in every layer or in every fiber within a particular layer. There could also be some fibers that could be structural, i.e., made of a material that is relatively strong, and such fibers could possibly have a solid cross-section. The term "strong" can be understood to refer generically to any one or more of various mechanical properties such as ultimate tensile strength, yield strength, Young's Modulus, stiffness in bending or any other mode, and similar properties.

In embodiments of the invention, it is possible to lay up various layers of fibers. Fibers in layers can be woven or straight or other configuration or combination of configurations. It is possible to use as many layers as desired for structural strength, drug delivery or other design objective. Orientation of fibers relative to each other or to the device as a whole can be isotropic, anisotropic, unidirectional, random, or other orientation as desired. Fibers could be placed in a designed pattern, or could be placed in random orientation. Fibers could be chopped and placed in random orientations. It is possible to attach layers or fibers to each other with a biocompatible glue so that the layers stay in place, or layers or fibers could be bonded to each other by heat-sealing or by other methods.

It can be appreciated that in general, several possible kinds of administration of drug can provide different geometries of drug release. Conventional injection of a drug by a hypodermic needle deposits drug essentially at a point, and drug can spread from that point in all three directions by diffusion or by other means such as convection. However, for some clinical applications, depositing drug essentially at a point can be less than ideally suited for providing drug to a region or organ or local site.

It is also possible that drug can be contained in and released from a structure, such as a fiber, that is long in one direction and small in its other directions. If such a structure is completely surrounded by a medium, such a structure can provide drug release that spreads from its source in two directions.

In some embodiments of the invention, the drug can be contained in hollow fibers that are assembled into the geometry of a fabric or a planar structure, which is essentially a two-dimensional object. If drug is released from such a device, it can spread in the adjacent tissue in substantially a one-dimensional manner. A two-dimensional device such as a piece of fabric can be better suited to delivering drug to a region of desired shape, in comparison to a point delivery by a small object or a line delivery such as can be delivered by a fiber that extends lengthwise in one direction.

In many situations, it would be highly desirable to have biologics or pharmaceuticals such as antibiotics, or growth hormones applied to the wound site during the healing process. In embodiments of the invention, biologics or pharmaceuticals can be incorporated into the fibers of a degradable fabric, such that the biologics or pharmaceuticals are released over a substantial time, before or while the fabric is absorbed into the body. This would be applicable to biologics or pharmaceuticals that would not be seriously degraded or destroyed by the processes used to manufacture the fibers.

In embodiments of the invention, for the sustained delivery of biologics or pharmaceuticals, provided is a fabric with fibers of the type commonly used in dialysis or ultrafiltration filters, with those fibers being hollow tubular fibers having nano-pores or micro-pores in the tube walls, then filling the hollow fibers with an appropriate biologic or pharmaceutical. When the fabric is applied as a dressing, or applied or implanted as a structural support across an incision, or as a support platform for tissue re-growth, the encapsulated biologics or pharmaceuticals would slowly leach through the porous structure or wall, providing an effective local or locoregional dosage of the biologic or pharmaceutical for a significant period of time.

Figure 11B:
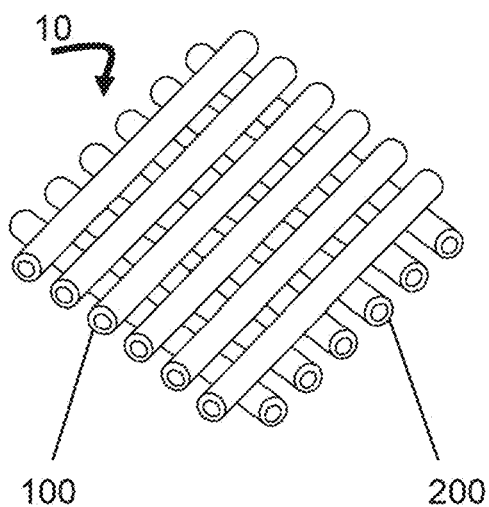
FIG. 11B illustrates hollow fibers in one direction, containing a first drug, and other hollow fibers in a second direction, containing a second drug.

Referring now to FIG. 11B, in an embodiment of the invention, provided is an assembly 10 of fibers, in which there are first hollow fibers 100 in one direction, containing a first drug or drug formulation, and second hollow fibers 200 in a second direction, containing a second drug or drug formulation. Of course, the two drugs or drug formulations could be either the same or different. Although in FIG. 11B the fibers 100, 200 are illustrated as simply crossing each other, alternatively the fibers 100, 200 could instead be woven among each other.

A simple fabric is commonly manufactured by interweaving a first set of fibers oriented in a first direction with a second set of fibers oriented in a second direction, said second direction generally perpendicular to said first direction. When the weaving is done on a loom, the fibers oriented in the long direction of the fabric are referred to as the warp, and the fibers oriented in the crosswise direction are referred to as the weft.

Other fabrics can be made overlaying a first set of spaced fibers oriented in a first direction with a second set of spaced fibers oriented in a second direction, and bonding said first fibers to said second fibers where they contact one another.

Figure 11C:
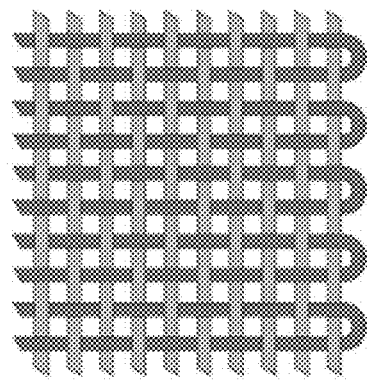
FIG. 11C illustrates fibers interwoven with each other, with fibers in one of the directions having turn-around at their ends.
Figure 11D:
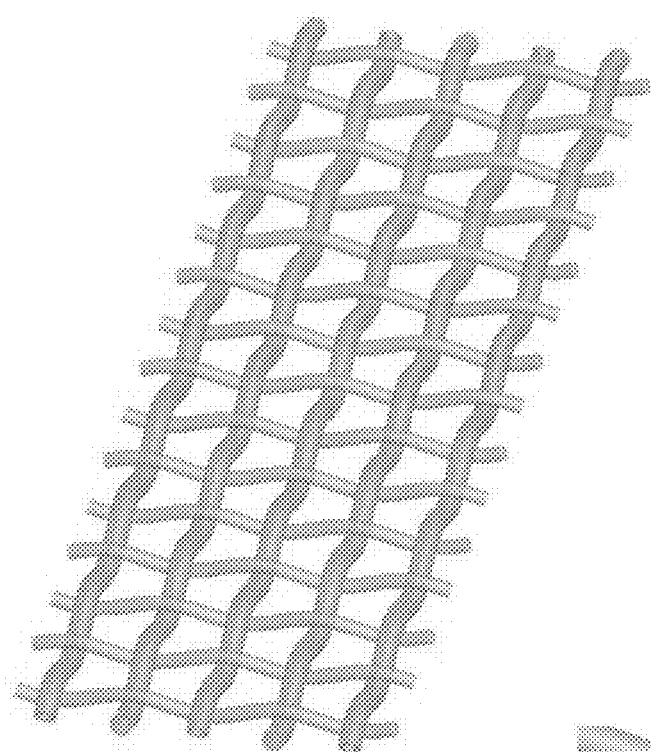
FIG. 11D shows a pattern of weaving with one of the types of fibers being hollow.
Figure 12A:
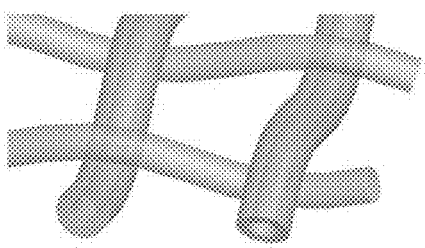
FIG. 12A shows a close-up view of woven fibers of FIG. 11D in which one direction of fiber is hollow fiber and the other direction of fiber is solid fiber.
Figure 12B:
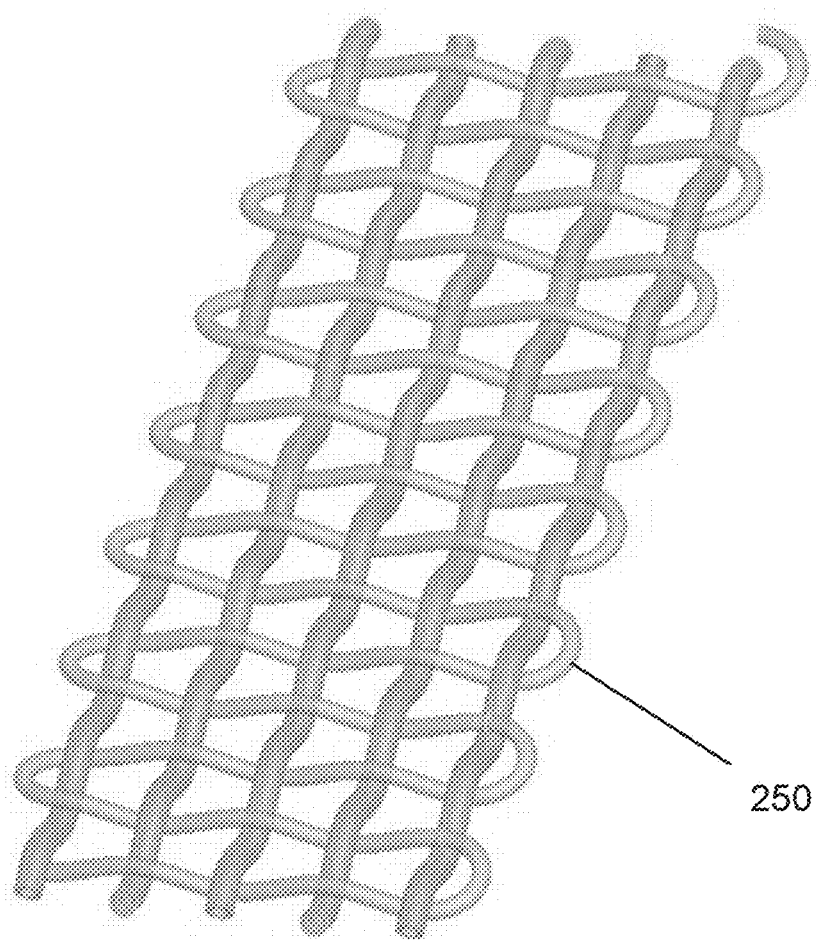
FIG. 12B shows a woven fabric in which one of the fibers turns around repeatedly at edges of the fabric.

FIGS. 11C and 11D depict a woven fabric in which one fiber is used as the warp fiber and another fiber is used as the weft fiber. It is possible that a hollow fiber with a permeable wall, is utilized as the warp fibers, and a non-hollow fiber is utilized as the weft fibers. Alternatively, the opposite is can also be used, wherein a non-hollow fiber is used as the warp fiber and a hollow fiber, with a permeable wall, is utilized as the weft fiber. FIG. 11D shows the interweaving of the various fibers. FIG. 12 is a close-up view of FIG. 11D. The warp and weft fiber spacings can be varied as appropriate for the intended usage. In general, either kind of fiber could be the warp fiber and either kind of fiber could be the weft fiber.

One possibility is that for structural applications, the weft fibers can be solid fibers and can be woven back and forth, to provide selvedge edges 250, as in FIG. 13. Such edges could be sutured across a longitudinal incision to hold the incision closed during the healing process.

Of course, in embodiments of the invention, the warp and the weft could be interchanged from what is illustrated in FIG. 13. For example, if desired, the hollow fiber could be the weft fiber which can be woven back and forth, thereby providing selvedge edges of the hollow fiber. The warp fiber could be a solid fiber, if desired.

In an embodiment of the invention, provided is a product resembling FIG. 11A, but containing a drug or a drug formulation in the lumens of the hollow fibers. The solid fibers can be either weaker than or stronger than the hollow fibers. The solid fibers can be either attached to or woven among the hollow fibers.

In embodiments of the invention, provided is a mat or assembly comprising a first type of fiber in one direction, and a second type of fiber in another direction. The fibers in the first direction can be hollow fibers having walls that are permeable, which can be considered to mean porous (microporous, nanoporous) or semipermeable or having holes therethrough. The second type of fiber can be solid fibers although they do not have to be. The second fibers can be attached to the first fibers and can serve to maintain the first fibers in a desired spacing and pattern. In embodiments of the invention, the first fibers can contain drug inside their lumens. In the embodiment of the invention, the second fibers can be mechanically stronger than the first fibers. Such a device can serve a purpose in which mechanical loads must be carried by the device, at least along the direction of the second fibers. More generally, the non-hollow fiber(s) could have any strength relation to the hollow fiber(s).

In embodiments of the invention, a fabric can be manufactured by interweaving a first set of fibers oriented in a first direction with a second set of fibers oriented in a second direction, the second direction being generally perpendicular to the first direction. Although in FIGS. 11B-13A various fibers are illustrated as being perpendicular to each other, more generally they could be at any angle relative to each other. Fibers can be oriented parallel to each other, perpendicular to each other, 45 degrees with respect to each other, or in general any orientation. Random orientation is also possible.

It is possible to provide different fibers in different places or layers. For example, one layer of fibers could contain one drug while another layer of fibers could contain another drug. It is possible to use two different drugs, with the different drugs being in different fibers or groups of fibers. One of the groups of fibers could be longitudinally oriented containing one drug, and another group of fibers could be transversely oriented, containing another drug, perhaps using a geometry as illustrated in FIG. 11B. Any combination is possible to provide structural or release properties according to the application and purpose of the drug delivery device under consideration. One layer can be structural, another layer non-structural. Some cases such as hernia repair may require both structural and drug delivery functions. Other applications can only require drug delivery only without structural requirements. In embodiments of the invention the combination can include any such combination or permutations, and algorithms to determine the requirements can be developed based on both structural and drug release properties.

Within a given layer, not all fibers have to be identical in every respect. Within a given direction of fibers, not all fibers have to be identical in every respect. Within a given layer, fibers in one direction can be one kind of fiber and fibers in a different direction can be different kind of fibers. Difference among fibers or fiber groups can be in the drug contained therein, the formulation of the drug, the amount of the drug, the material composition of the fiber, the pore size or related characteristics, the surface properties of the fiber surfaces, the surface properties of the pore surface or pore structure, the surface treatment, the mechanical strength, or any other characteristics. Surface properties can refer to surface hydrophibicity, hydrophilicity, contact angle with water, contact angle with organic solvents, organic functional groups, reactivity of surface or bulk functional groups, swellability, or any related properties that can affect or control release of drugs to be delivered from the drug delivery device, as discussed elsewhere herein. The content within the lumens of different fibers could be different. The composition of solids could be different, or the composition of liquid could be different, or both.

Figure 13A:
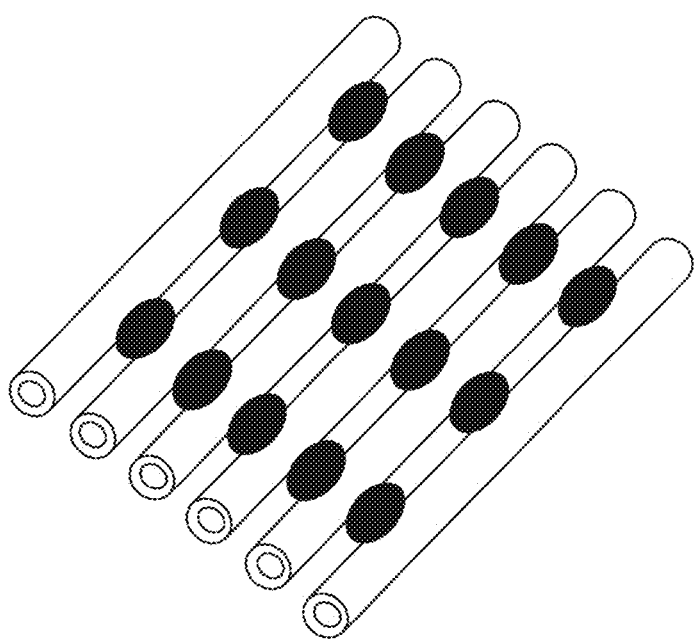
FIG. 13A shows hollow fibers that are attached to each other by joining structures.

Hollow fibers can be made to occupy a U-configuration, such that all of the open ends are located on a common edge of the device. Hollow fibers can occupy a zig-zag pattern, such that there are only a relatively small number of connection points to the lumens of the hollow fibers, as illustrated in FIG. 13A.

Another example is that drug-containing fibers can be parallel to each other or mostly parallel to each other, while fibers that cross the drug-containing fibers can be non-drug-containing fibers. The non-drug-containing fibers can be woven among the drug-containing fibers, or can be merely attached or adhered to the drug-containing fibers such as with biocompatible glues and adhesives.

Other fabrics can be made overlaying a first set of spaced fibers oriented in a first direction with a second set of spaced fibers oriented in a second direction, and bonding said first fibers to said second fibers where they contact one another.

In an embodiment of the invention, provided is first fibers oriented generally in a first direction, wherein the first fibers are hollow fibers and contain an active pharmaceutical ingredient in their lumens. In addition, provided is second fibers that are solid fibers or are fibers that do not contain an active pharmaceutical ingredient, oriented generally in a second direction different from the first direction. The second fibers can be structurally stronger than the first fibers. The first fibers and the second fibers can be interwoven with each other to form a fabric. Either or both of the first fibers and second fibers can be woven in a back-and-forth manner. Alternatively, either or both of the first fibers and the second fibers can be woven as individual fibers that do not have a back-and-forth pattern. Alternatively, the first fibers and the second fibers can be attached to each other at some or all of the places at which they cross each other. Such a configuration can provide a device that has structural strength in at least one direction, while also providing drug delivery. In an embodiment of the invention, provided is first fibers oriented generally in a first direction, wherein the first fibers are hollow fibers and contain an active pharmaceutical ingredient in their lumens. In addition, provided is second fibers that are solid fibers or are fibers that do not contain an active pharmaceutical ingredient, oriented generally in a second direction different from the first direction. In addition, provided is third fibers that are solid fibers or are fibers that do not contain an active pharmaceutical ingredient, oriented generally in a third direction different from the second direction. The third direction could coincide with the first direction, although it does not have to. This described configuration can provide a device that has structural strength in various different directions, while also providing drug delivery. It is possible that a non-drug-containing fiber and a drug-containing fiber could be woven together with each other, with both types of fibers passing together through the same passageways or interstices between other fibers. Alternatively, a drug-containing fiber could be substituted for a non-drug-containing fiber in some places. Similarly, a non-drug-containing fiber could be substituted for a drug-containing fiber in some places.

It is not necessary for the entire construct to be made of hollow fibers. Some layers or some fibers could be drug-eluting while other layers are not drug-eluting. It is further possible to have multiple layers and to have an overlay such that one layer can be an array of solid fibers or mesh and another layer can be or can contain hollow fibers. In embodiments of the invention, such drug delivery devices can be considered as hybrid devices which combine conventional meshes or fibers and hollow fiber-based drug delivery elements as disclosed herein.

In still other embodiments of the invention, some fibers could be solid fibers made of material that is a polymer combined with a drug as described in other commonly assigned patents and patent applications such as U.S. Pat. No. 8,747,883.

Referring now to FIG. 13B, in an embodiment of the invention, provided is an implantable medical device, comprising fibers, wherein the fibers are oriented generally in a first direction, wherein the fibers are hollow fibers and contain an active pharmaceutical ingredient in their lumens. There can further be provided joining structures that maintain the fibers in at least approximately a desired position relative to each other. The joining structures might have a maximum dimension that is similar to a spacing between one of the fibers and its nearest neighbor fiber. For example, the maximum dimension of the joining structure might be less than twice the fiber-to-fiber spacing. For example, the joining structure might remain entirely between one fiber and its nearest-neighbor fiber, without crossing over from one side to the opposite side of a particular fiber. The joining structures could be distinct and separate from each other. The joining structures can be "dots" of a substance such as an adhesive, or any other similar structure or substance. The joining structures can be in-line with each other, as illustrated in FIG. 13B, or they can be staggered, or can be deposited in any other desired pattern.

Assemblage of Fibers Having a Mixture of Patterned and Random Orientations

In an embodiment of the invention, there could in one direction be a pattern of fibers such that the fibers are parallel to each other, and adjacent to this pattern of fibers there could be fibers in a more random orientation. At least some of these randomly oriented fibers could be attached to the first fibers. At least some of these more randomly oriented fibers could help to maintain the parallel fibers in a chosen position relative to each other.

FIG. 13B shows an illustrative such an assemblage. The hollow fibers 1470 with drug in their lumens are shown in a parallel array. Other fibers 1472, which can be randomly oriented, are shown in random orientation and are attached to the hollow fibers 1470 at certain places (joints 1474) where the random fibers 1472 cross the hollow fibers 1470. For purposes of illustration, the joints 1474 are represented by dots. Some of the joints 1474 are shown as occurring at places where one fiber 1472 crosses the hollow fiber 1470. Others of the joints 1474 are shown as occurring at places where two fibers 1472, or even more than two fibers 1472, cross each other and also cross the hollow fiber 1470. Any of these combinations or others can be utilized.

End Closures and Segmentation or Compartmentalization of Fibers

In embodiments of the invention, the fiber can have an open end or ends. Alternatively, in embodiments of the invention, the fiber can have a closed end or ends. The closed end can be closed after drug has been placed inside the lumen of the hollow fiber. If the fibers are provided in a form such that the ends are closed or sealed, it is still possible that the surgeon could cut the fabric or the fiber to size for a specific application. Alternatively, the product could be provided in appropriate or various different sizes so that surgeon does not have to cut the product at the time of use.

Any form of ligation of the cut ends can be performed as part of the process of cutting the fabric or an embodiment of the invention to a desired size and shape. Alternatively, the cut ends could be sealed by a solvent, or by ultrasonic sealing or welding, by heat sealing, or could be sealed by a biocompatible adhesive or sealant or by laser such as a carbon dioxide laser. A possibility is that if a surgeon cuts the device to size near the time of use, the surgeon could perform the cutting by cauterizing the ends of the fibers, so as to heat-seal the ends closed while the cutting is taking place.

Referring now to FIG. 14A, it is illustrated that an end of a fiber can be closed at a closure point 410 such as by crimping or heat-sealing. Both ends of a particular fiber can be so closed, if desired.

In embodiments of the invention, it is further possible, referring now to FIG. 14B, that a deformation 420 such as a crimping or sealing can be created somewhere along the length of a fiber away from the ends of the fiber, without actually cutting or breaking the fiber into separate fibers. Such a configuration would establish, within a given fiber, individual regions of lumen that are not in fluid communication with each other. It is also possible that such a deformation 420 might merely restrict fluid communication across the deformation 420 without actually completely eliminating such fluid communication.

In an embodiment of the invention, if a fabric is manufactured to have deformations 420, one way of manufacturing the device is to fill a fiber or fibers when the fiber(s) is long and unobstructed, and then to subdivide the fiber into compartments by heat-sealing. For example, the fiber could be pressed on in appropriate places by a heated element that can heat or soften the polymer of the fiber enough to cause it to adhere to another part of itself. For example, an interior surface of the lumen could adhere to an opposed interior surface of the same lumen. This can be performed by heat fusing the fiber so as to form periodic fiber segments where each segment contains a small amount of drug or drug formulation. With still other techniques, such segmentation can be effected by solvent embossing, fusion by a high-power laser, ultrasound welding, or like methods and which might not involve a direct heating technique. In any such process, the heat and pressure and duration of sealing and other parameters could be regulated so as deform the fiber or join the fiber wall to its opposite wall, but not to completely sever the fiber. If fibers are arranged in the form of a woven fabric, the heat-sealing could be done either before or after weaving into the form of the fabric. Joints of one fiber to another, and deformations 420, could be located at crossing points at which the hollow fiber crosses other fibers.

In more detail, still referring to FIG. 14B, there could be a pattern of a fiber having a plurality of small closed regions of a fiber, such that fibers are segmented into a large number of individual closed regions, and individual regions contain a fairly small quantity of drug. It is further possible that a fabric could be made of such fibers. For example, there could be a criss-crossing pattern of fibers with short intervals in both directions. That way, a surgeon or user could cut the fabric or fiber to size at the time of use and not very much of the drug would leak out through cut ends of fibers, because not very much drug would be contained in any one compartment or segment.

It is possible that there can be multiple deformations 420 along a length of a fiber. A deformation 420 can be a complete closure, or it could be a narrowing that is less-than-complete closure, which would still have usefulness. At the time of use a surgeon can cut the fiber or mesh as desired. Even if the cut ends of the fibers remain open after the surgeon cuts them, which might allow some drug to exit through the cut ends, it can be understood that the amount of drug that will exit at a particular cut end would be limited to what is inside the fiber between the cut end and the nearest deformation 420. It can be understood that such drug release might not always occur, especially if the fiber or mesh is cut by cauterization. Drug that is contained in regions that do not comprise a cut end would be subject to drug release according to the ordinary design of the fiber and the device.

Deformations 420 or closure points can be distributed in a regular pattern such as equidistantly from each other. Alternatively, deformations 420 or closure points can be distributed in any other desired pattern. Such pattern can be coordinated with an intended shape or dimensions of the device, as can for example relate to a particular location within a patient's body.

It is possible that the deformation 420 can cause a transition from a lumen of generally circular cross-section to a region that has a cross-section that is flatter than circular. It is possible that the undeformed wall can have a cross-section that is generally circular, and the deformation 420 can have a cross-section that is flatter than the generally circular cross-section.

It is possible that the deformation 420 can completely separate the contents on one side of the deformation 420 from contents on an opposite side of the deformation 420. In this situation it is possible that a portion of the interior on one side of the deformation 420 is not in fluid communication with a portion of the interior on an opposite side of the deformation 420. In this case, it is possible that a first portion of the wall and a second portion of the wall opposite the first portion of the wall can be attached to each other. In this situation it is even possible that at or near the deformation 420, some particles of a drug can be embedded in the deformed wall at the joint. For example, it is possible that the process of deforming especially if it includes joining, can involve partial melting or softening of the wall, and squeezing opposite sides of the wall toward each other. The deformation 420 can be introduced by at least one method of: heat sealing, exposing to a laser; ultrasonic welding, and exposure to a solvent. In this situation, it is possible that particles of drug can be trapped between or within the walls.

Alternatively, it is not essential that there be complete separation from one side of a deformation 420 to the opposite side; it is possible that the deformation 420 might only partially separate contents on one side of the deformation 420 from contents on an opposite side of the deformation 420. Even if there is some small fluid communication from one side of the deformation 420 to the other, the deformation 420 can still serve a purpose similar to the purpose it would serve if there were complete separation.

One specific design possibility is that the device can comprise transverse fibers that cross the hollow fiber (either by weaving or joining), and at least some of the deformations 420 can coincide with locations where the transverse fibers cross the hollow fibers. The transverse fibers can be attached to the hollow fiber at such locations, although they do not have to be so attached.

In embodiments of the invention, the deformations 420 can be spaced from each other at substantially equal intervals along the fiber. For example, there can be such deformations at at least three places along a length of the fiber, or at at least 10 deformations along its length. For example, a lumen volume contained between deformations 420 that are nearest each other might be no more than 10% of a total internal volume contained inside the lumen of the fiber.

It is further possible that the fiber can have a closure 410 at one or both of its ends. The end closure 410 can be similar to or different from the deformations 420 elsewhere along the fiber. The closure 410 could be made by any of the methods for making deformations 420, or additionally could be made by adhesive. A fiber can have a first end closure and a second end closure and can have deformations located between the first end closure and the second end closure. Alternatively, ends of the fiber can simply be open, such as if the fiber is cut to length by a blade. In a region between a deformation and a cut end, there can be drug, or alternatively the region can be substantially empty.

If a fiber contains deformations, it is further possible that release characteristics could be different among different regions of a fiber, as bounded by deformations. For example, one region containing certain compartments could have a first drug release characteristic, and another region could containing certain compartments could have a second drug release characteristic that is different from the first drug release characteristic.

One consideration is that if a surgeon cuts the fabric to a desired size or shape using a cutting method that does not cauterize the cut ends of the fabric, there can remain open ends of fibers, and the open ends can release drug through the open end of the fiber. Such release from open ends can be a more immediate release of drug than would occur if passage through the wall of the fiber were the only release mechanism. The amount of drug that could potentially be released from one cut fiber depends on the location of the cut relative to the nearest closure point in the remaining fabric. Such distance is unpredictable but could be approximated by an estimated value that is half of the spacing between neighboring closure points. The amount of such quick drug release can be related to the number of fibers that are cut and to the spacing between closure points. As a result, if deformations 420 or closure points are relatively numerous and close together, the amount of drug that could be released due to cutting of fibers is smaller than would be the case if cutting is performed in a situation where closure points are less-numerous and are more spaced apart from each other.

As a numerical example of segmentation, for the repair of a ventral hernia, using an implant whose length might be approximately 20 centimeters, a desirable number of segmentations might be more than 10 segmentations of a fiber as it spans across the overall dimension of the implant. As another quantification, a possible segmentation length could be less than 1 centimeter, and more preferably 0.25 centimeter. As another quantification, the linear length of a segmentation compared to lumen diameter could be in the range of from 5 to 50 times the lumen diameter, for example approximately 10 times the lumen diameter. There is no limit as to how many segments could be used along the length of a fiber. The number of segmentations could also depend on the potency of drug; for example, if the drug is especially potent or toxic, it might be desirable for the segments to be smaller and more numerous.

Another criterion can also be contemplated relating to the distance between deformations 420 or closure points, or the size of subcompartments. This criterion relates to the filling of the lumen by particles of solid such as powder, and particularly if the orientation of the fiber when implanted in the patient is such that the lengthwise direction of the fiber is vertical or sloped with some vertical component. It can be assumed that the particles are at least somewhat free to move within the lumen. Even if the lumen is initially filled with particles to a fairly dense packing fraction, it can be expected that as drug release occurs along with dissolution of drug from the individual particles, the particles will become smaller and some can disappear before others disappear. Any of these events can render the particles free to rearrange their position within the lumen especially under the influence of gravity. Again, for a vertical or partly-vertical orientation of the lumen, it is possible that particles can settle in a downward direction due to gravity so that the bottom of the stack of particles is supported by the closure point that defines the bottom of that compartment of the lumen. Such settling can correspondingly create a void space near the upper portion of the same compartment of the lumen. The upper portion can be deficient in supplying drug to nearby tissue, because of the inability to replenish drug by dissolution. Accordingly, at this small dimensional scale, local regions of tissue that are adjacent to empty portion of the lumen may receive no drug or less drug than intended. This undesirable effect can be minimized by providing deformations 420 or closure points that are relatively numerous and close-together. As a result of compartmentalization, the drug-deficient regions of tissue will be relatively small and localized, which can make it easier for the local deficiency of drug to be remedied by effects such as lymphatic circulation.

It is possible that the lumen space is less than completely filled with particles, such as the situation that can occur if particles have partially dissolved and have shrunk, and therefore the particles as they remain have the opportunity to settle due to gravity into a smaller amount of space. In such a situation, the orientation of the fiber can make a difference, and the distance between closure points can make a difference. If the fiber is vertically oriented and the particles settle, that can be expected to leave an empty space in the upper region. In this situation, continued drug release will occur only at the lower portion of the region, and would not occur at the upper portion. The importance of this situation can depend on the size of the region, with the expectation that if the regions are small (which can be achieved by having a relatively large number of closure points), this effect can be less important. Further, it can be realized that if a fiber is horizontally oriented and settling occurs, such settling will only involve a fraction of the diameter of the lumen, which is a very small dimension and is likely not important. It can further be realized that if drug-containing fibers are provided in both vertical and horizontal orientations, or mutually perpendicular orientations, within a single construct, there is an improved chance that at least one of the sets of fibers will be insensitive to this redistribution of particles due to the settling process. This can be achieved using drug-containing fibers in two different directions within a single layer, or by using two different layers in which the drug-containing fibers are differently oriented such as perpendicular to each other.

Dish-Shaped Compartments

Figure 14C:
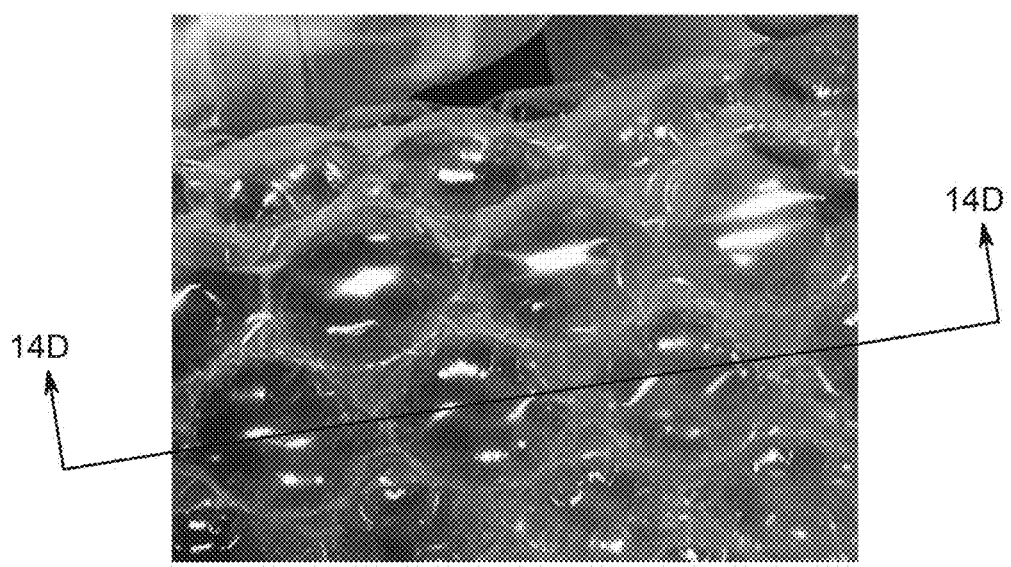
FIG. 14C shows a drug delivery device of an embodiment of the invention, in which two layers of polymeric material are appropriately attached to each other to form a plurality of discrete bubble-like regions.
Figure 14D:
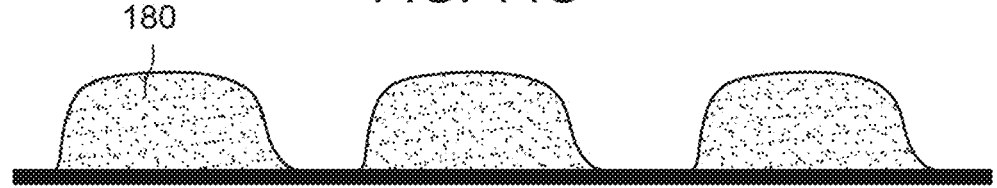
FIG. 14D is a cross-section of FIG. 14C

In an embodiment of the invention, referring now to FIGS. 14C and 14D, provided is a device that comprises a first layer and a second layer. The first layer and the second layer can be attached to each other at joined places in such a way that the joined material surrounds and defines compartments 480 that contain drug or a drug formulation.

For example, it is possible that at least one of the first polymeric layer and the second polymeric layer can have compartments that are dish-shaped. The drug can be contained in the dish-shaped region 480. It is possible that one of the first polymeric layer and the second polymeric layer can be flat. It is possible that the dish-shaped regions 480 can have perimeters that are circular, or alternatively that the joined places between the two layers could be approximately linear in configuration, and the dish-shaped regions could be at least somewhat polygonal.

One of the layers could be permeable to the passage of drug therethrough. It is possible that the other layer could have the same properties as the first layer. Alternatively, it is possible that the other layer could be impermeable or less permeable to the passage of drug therethrough than the first layer. This latter situation could provide a preferred direction of drug release from the device.

Although the device has been described such that the compartments 480 are completely isolated from each other, it is also possible that the compartments 480 could have some extent of fluid communication with each other.

Any one of the layers could have any desired permeability, which could have any desired permeability in relation to the permeability of nearby tissue. It is possible that the layer permeability could be smaller than the tissue permeability and the drug release could be diffusion-dominated, It is possible that the layer permeability could be greater than the tissue permeability and the drug release could be hydrodynamically driven. If the permeability is such as to provide hydrodynamically driven drug release, lymphatic flow could enter through one layer, pick up drug by dissolution, and exit through the other layer, The just-described device comprising dish-shaped compartments 480 could further be used in combination with a layer of interwoven fibers, or with a layer of fibers that are attached to each other, or generally with any of the embodiments described herein.

It would also be possible to make a device from flat membranes such that the device has sub-regions that are long in one direction and narrow in another direction that is at least approximately perpendicular to the long direction. The sub-regions could be generally straight in the long direction. The sub-regions could be located side-by-side with respect to each other. The sub-regions could be parallel to each other. Alternatively, the sub-regions could have some other shape, such as curved. The sub-regions could be separated from adjacent sub-regions, or could be defined, by seams that join one membrane to another membrane or to another part of the same membrane.

Device Placement in Regard to Lymphatic Flow and Cancer Treatment

Still other or additional embodiments of the invention can be useful in particular ways for treatment of cancer. In the treatment of cancer using chemotherapeutic drugs, part of the strategy can be to deliver such drugs at or near the primary site of a tumor. However, another part of the strategy can be to prevent cancer cell transport to other organs or sites or to stop metastases from the primary site of the cancer. This can involve knowledge of the patterns of flow of lymph within the body. For example, in the treatment of breast cancer, the possibility of metastasis is the reason why nodes in the lymph node basin in the underarm region or other draining nodes are sometimes removed as part of surgical treatment of breast cancer. In embodiments of the invention, a device of an embodiment of the invention can be implanted in a patient in an appropriate location or more than one location either before, during or after primary surgical treatment. The location can be chosen such that with respect to the expected direction of lymph flow, the device will be upstream of the lymph node basin. The location at which the device is implanted can be chosen such that with respect to the expected direction of lymph flow, the device will be upstream of the tumor, which would deliver drug to the tumor via the lymphatic flow. Alternatively, the location at which the device is implanted can be chosen such that with respect to the expected direction of lymph flow, the device will be downstream of the tumor, which would prevent metastases from spreading.

Figure 14E:
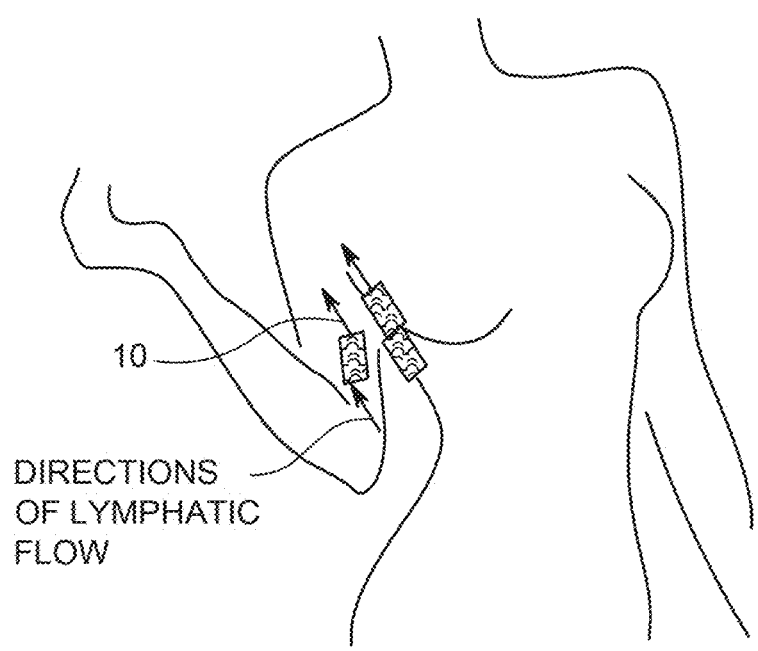
FIG. 14E is an illustration of the human body showing directions of lymphatic flow and showing possible placement of embodiments of the invention.

Referring now to FIG. 14E, there is shown a schematic of the human body illustrating the fact that in the arms there is an overall lymphatic flow from the extremity toward the armpit. The arrows in FIG. 14E illustrate the direction of lymphatic flow. For purposes of combating metastasis, it can be desirable to place a drug delivery device 10 of an embodiment of the invention in the arm in such a location as to intercept and deliver chemotherapeutic or immunogenic drug to lymphatic flow flowing toward the lymph node basin. Another possible location can be in the torso where lymphatic flow approaches the lymph node basin, such as between the breast and the lymph node basin. These or related strategies can be employed to deliver drugs or immunogens to the cancer tumor as desired.

Such a device can contain drug or a drug formulation within it. The amount of such drug or drug formulation can be suitable for a desired length of treatment, such as a month. Alternatively or in addition, such a device can be refilled from a source outside the patient's body. Such refilling, such as with a catheter or manifold, is discussed elsewhere herein. Such a device can have a customized shape that is adapted to a particular implantation site or lymphatic flow characteristics for a particular treatment, and can have release characteristics that are similarly adapted.

Device Features in Regard to Removability

In embodiments of the invention, it can be desirable to remove a drug delivery device after it has completed certain functions. Such removal could apply to the just-described delivery device for chemotherapeutic drugs, or to any other device or form of treatment. Assuming that the device is not totally resorbable or biodegradable by the nature of its materials of construction, a surgical procedure would be required for its removal, and it is always desirable to minimize the impact of such a surgical procedure.

In an embodiment of the invention, referring now to FIGS. 14F-14I, provided is an assembly of fibers in which some fibers are resorbable and other fibers are non-resorbable. The assembly could be in the form of a generally flat mat. For example, there can be a hollow fiber that can be non-resorbable, with the hollow fiber containing drug. In the same device, there can be other fibers that can be resorbable. For example, the non-resorbable hollow fiber and the resorbable fibers can be generally transverse to the each other. The non-resorbable hollow fiber and the resorbable fiber(s) can be interwoven with each other. Alternatively, the non-resorbable hollow fiber and the resorbable fiber(s) could be attached to each other. The resorbable fiber can in general be non-drug-containing, but if desired, it could comprise a blend of polymer and drug or be coated with a drug or contain a drug in any other configuration. This drug, or its formulation, could be either the same as or different from the drug or the drug formulation that is contained in the lumen of the hollow fiber.

In a specific embodiment, the hollow fiber can be such that as it approaches an edge of the device, it turns around and proceeds back into the interior of the device. In this configuration, the device can be made of a single hollow fiber having suitable length. (Of course, it is also possible to have other configurations and other numbers of hollow fibers, such as a small number of hollow fibers.) With such an arrangement, the device can be, at the time of implantation, am assembly that maintains its coherence enough to be easy to handle and manipulate around the time of implantation into the patient. The device would also maintain its coherence for a period of time inside the patient's body after implantation. Nevertheless, as time progresses, the resorbable fiber(s) can be expected to resorb and to lose their strength or integrity or completely disappear. When this happens, the non-resorbable fiber or fibers can become less physically constrained in their position with respect to from each other or to nearby passes of the same fiber, and to become more mobile.

This situation offers the possibility of relatively easy removal of the non-resorbable fiber(s) at an appropriate time, compared to what is possible with the device in its as-implanted configuration. For example, when an implantable device is used in connection with chemotherapy or prevention of metastasis of cancer or for any other treatment or therapy, as is discussed elsewhere herein, the device can be present in the body for a defined amount of time. It might be desirable that after the defined amount of time, the non-resorbed part of the device be removed from the patient's body. It further can be desirable that the removal be done with as little impact on the patient as possible.

Figure 14F:
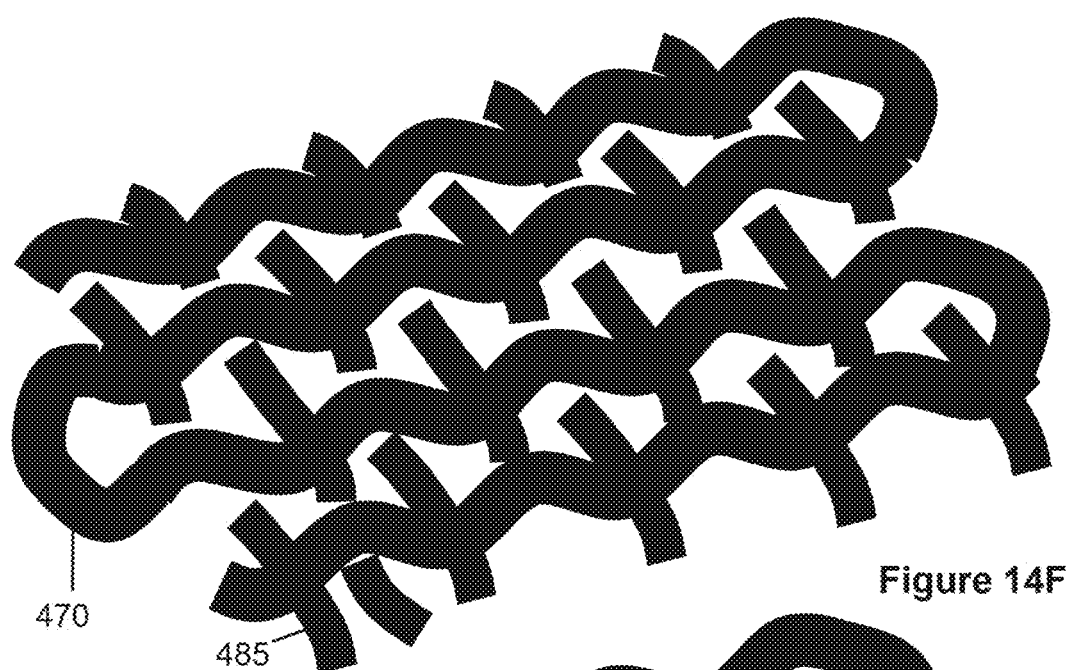
FIG. 14F shows a woven fabric comprising a nonresorbable hollow fiber and also resorbable fibers interwoven among the hollow fiber.
Figure 14G:
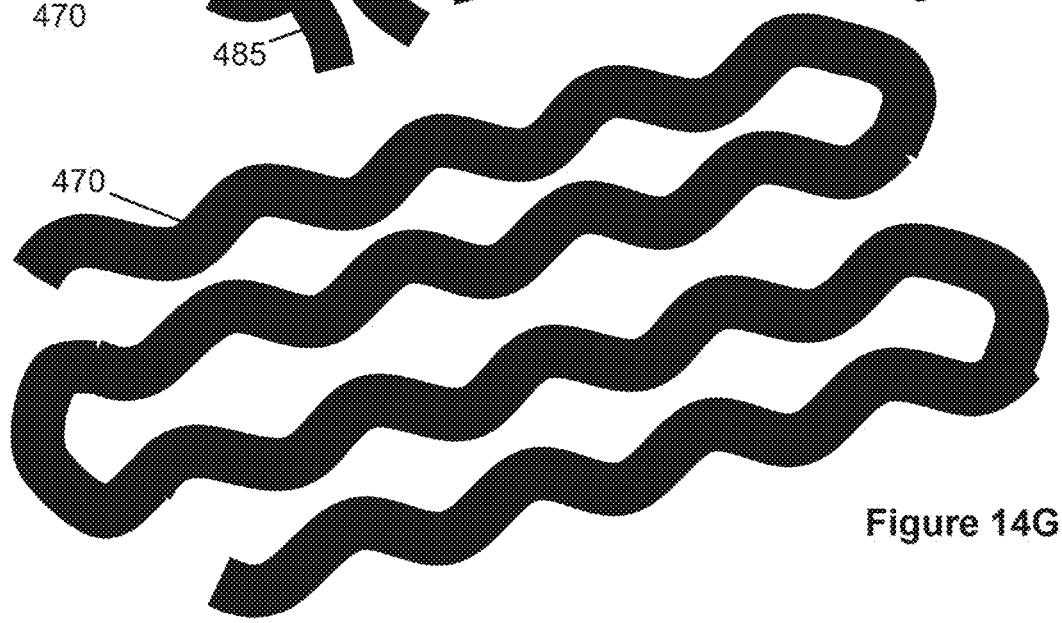
FIG. 14G shows the fabric of FIG. 14F with the resorbable fibers no longer present.
Figure 14H:
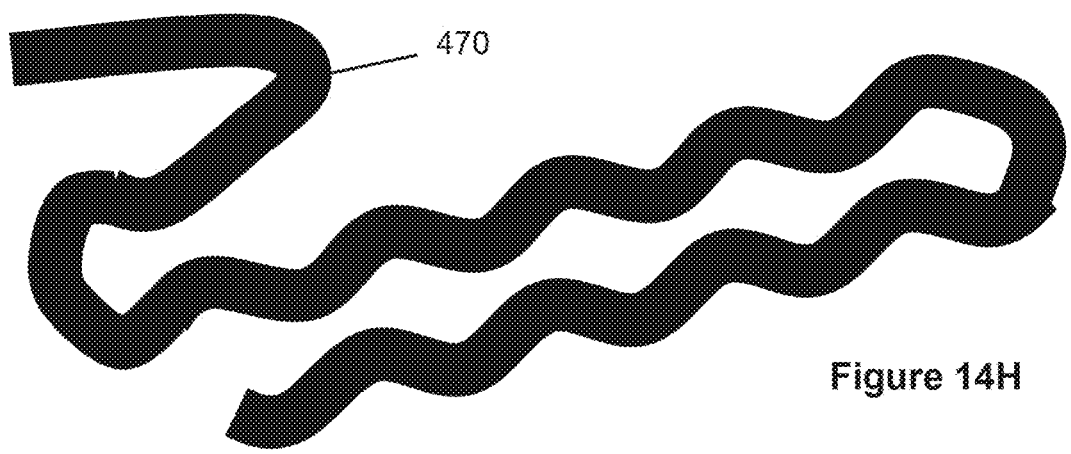
FIG. 14H shows the fiber of FIG. 14G partially pulled out of the implantation site.

With the described configuration, after the resorbable transverse fibers have been completely or at least partially resorbed, what remains can be a back-and-forth path of a non-resorbable fiber. The non-resorbable fiber can be removed from the patient's body essentially by pulling on it, which could be done through a small puncture-like incision. This would contrast with removal procedure for a patch or mat or fabric made of non-resorbable materials, for which such a patch or mat or fabric might require a linear incision of some length. A small incision, such as in this case a puncture-like incision, can be advantageous and preferable in comparison to a linear incision. FIG. 14F illustrates a device of an embodiment of the invention as implanted, in which fiber 470, which is hollow, is non-resorbable and fiber or element 480 is resorbable. FIG. 14G shows what remains of the device after the resorbable fibers 485 or resorbable elements 487 have disappeared. FIG. 14H shows what remains of such a device after some of the length of non-resorbable fiber 470 has been pulled away from the device. Such pulling could continue until the entire fiber 470 is removed from the patient's body. The fiber could be twisted as it is pulled out. A similar design principle could be used for a device that comprises several such fibers. Applying a rotating motion during the removal process can be employed to make the device curl on itself in the form of a cylinder that can be easily removed through a small incision or a puncture without getting stuck within surrounding tissues or anatomical structures.

Referring now to FIG. 14I, there could be provided nonresorbable hollow fiber 470, which can be in a generally back-and-forth arrangement, and nonresorbable hollow fiber 470 can be attached to itself in certain places by a joining structure similarly as was shown in FIG. 13B. The joining structures could be resorbable. After the joining structures have resorbed, the fiber 470 could be pulled out of the implantation site similarly as was done in FIG. 4H.

In yet another possible form of removal, an implanted fabric could be essentially grasped on one of its edges by a rod-like grasping device, and could be rolled up to form substantially a spiral, and that spiral could then be pulled out of the implantation site.

Directional Delivery of Drug

If the hollow fibers are arranged as part of a fabric, it can be desirable for drug to be released to only one side of the fabric, or preferentially to one side of the fabric rather than to the opposite side of the fabric. This can be useful in implantable devices where one side of the implant is more in need of the drug than the other side. This can also be useful in an external topical application such as a bandage or for burn treatment, in which there is a preferred side for release of drug. In some applications it can be undesirable to deliver the drug to one side for some physiological reasons.

Accordingly, it is possible that the fabric or the article can comprise a barrier. The barrier can be either impervious or resistant to the passage of the drug therethrough and thereby can direct released drug in a direction away from the barrier.

Absent an actual barrier, a preferred direction of drug release can be imposed by treating some parts or surfaces of an implant so that some parts or surfaces are more hydrophobic than other parts or surfaces. In other cases, a coating barrier or treatment can be applied to one of the two sides.

An embodiment of the invention can provide local delivery of a desired substance and further can provide a desired spatial distribution of the delivered substance. In connection with an implantable device, in regard to preventing metastasis, it is possible to know the general direction of flow in the local lymphatic and to place embodiments of the invention so as to intercept cells that are traveling to metastasize other sites or organs. An interception screen can be provided to prevent or intercept metastasis of cancer cells or cancerous tissue material that do not involve lymphatic flow or when such cancer cells are transported by some other mechanisms or routes.

Unequal Release on Two Opposite Sides of Fabric

Figure 14J:
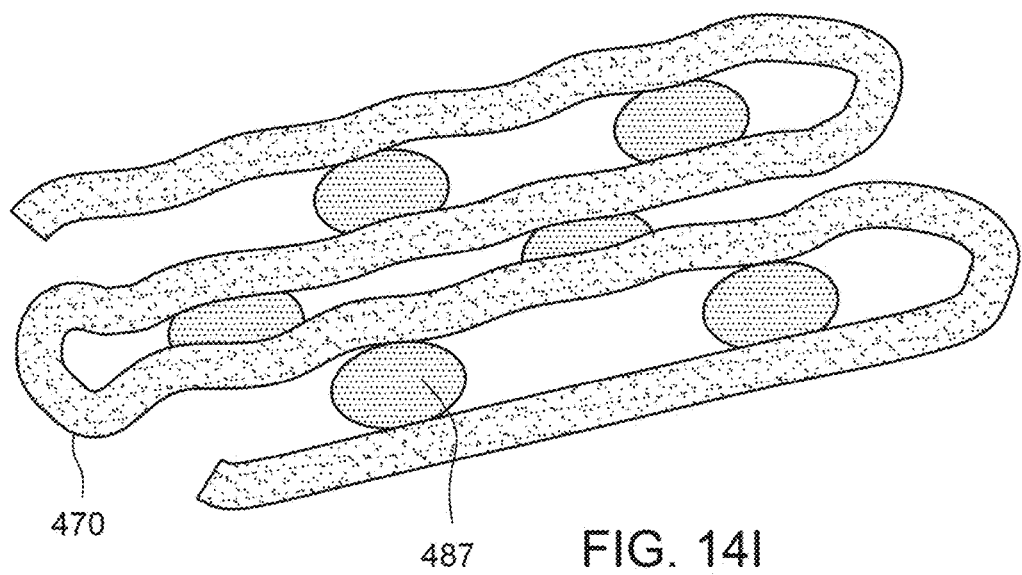
FIG. 14J illustrates a multi-layer construct that has an impervious layer next to the mesh on one side of the mesh, thereby resulting in one-directional release of drug.
Figure 14J:
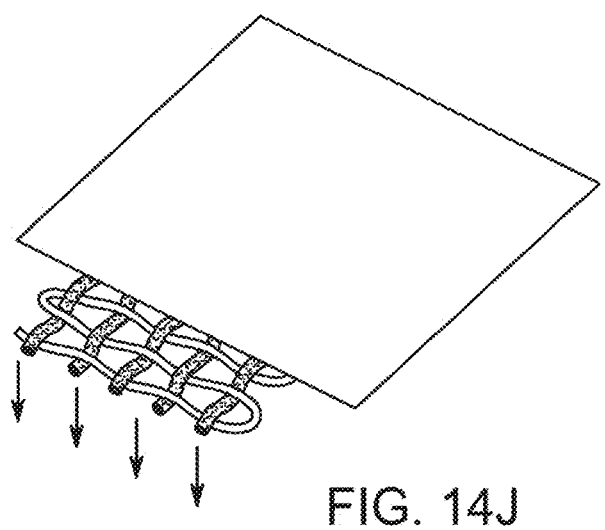
Figure 14K:
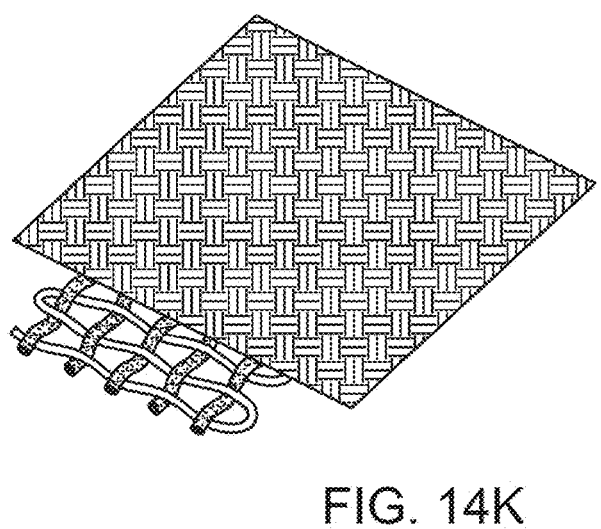
FIG. 14K illustrates a multi-layer construct that has a two different layers resulting in different drug release properties on different sides of the device.

In an embodiment of the invention, referring now to FIG. 14J-14K, provided is a device that has two different layers whose constructions differ in a way that affects drug release.

For example, fibers in one layer can contain a first drug and fibers in a second layer can contain a second drug that is different from the first drug.

Or, for example, fibers in one layer can have a first porosity characteristic, and fibers in a second layer have a second porosity characteristic that is different from the first porosity characteristic. Porosity characteristic could refer to pore size, pore size distribution, pore shape, pore wetting, pore hydrophobicity or any other parameter that affects the passage of drug through pores. In general, the fibers having the larger pore size might release drug faster, for example. Pores that are more hydrophilic can also deliver drug at higher rates compared to less hydrophilic pores.

Another possibility is one layer could have a first set of dimensions or parameters and the second layer could have a second set of dimensions or parameters. Dimensions or parameters could refer to the weave or spacing of the fibers, or dimensions of the fibers themselves such as diameter, number of layers or any other dimension of the fibers. As illustrated, one of the layers has a relatively open weave and the other layer has a relatively tight weave.

It can be expected that the drug release from the upper visible surface as illustrated will be governed more by the characteristics of the upper layer, and drug the release from the lower surface as illustrated will be governed more by the characteristics of the lower layer. Any of these characteristics can be varied by design so as to make the release on the upper side different from the release on the lower side as desired. In some embodiments a separation film or barrier can be placed between the layers to further control the drug release on each side of the device. An example of this can be a special construct for ventral hernia repair, where adhesion should to avoided on the visceral side.

Procedure and Features for Filling and Connection

Figure 15:
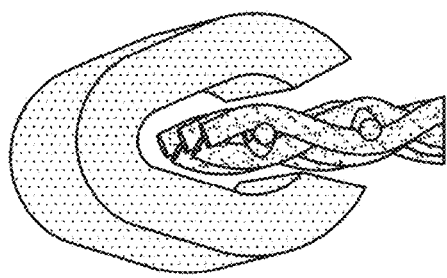
FIG. 15 shows a molding form enclosing ends of one of the directions of hollow fibers that form a fabric, with the molding form in an open position.

To fill the hollow fibers with a biologic or a pharmaceutical drug, it is possible to create a temporary manifold. An appropriate edge of the fabric would be connected to a flexible manifold, made from a silicone rubber or similar material, as shown in FIG. 15. The manifold would be closed on the fabric (FIG. 16), and the biologic or pharmaceutical would be pumped into the manifold cavity, and thus through the hollow fibers. Filling would continue, until the filler material was observed at the opposite edge of the fabric. Filling methods can include but not limited to using pressure, vacuum, capillary forces due to surface tension, displacement with other fluids including gas, other methods or their combinations. Once filled, the fabric would be removed from the filling station, and the ends of the hollow fibers would be closed, or segmented by heat sealing, as depicted in FIG. 14A, or by other means as described elsewhere herein.

Figure 16:
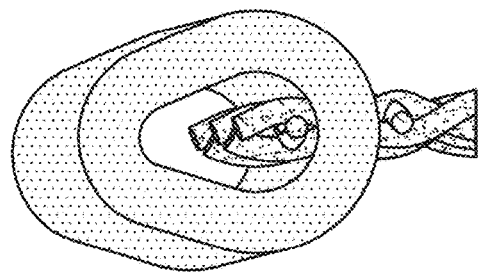
FIG. 16 shows the molding form of FIG. 15, with the molding form in a closed position.
Figure 18:
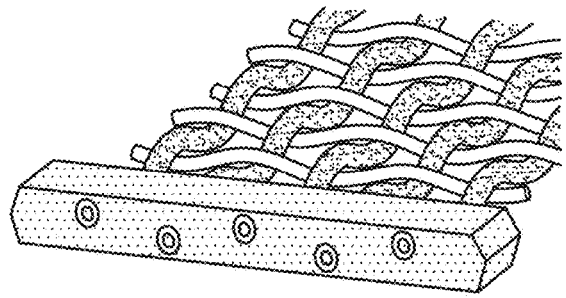
FIG. 18 shows the encapsulation of FIG. 17 with some of the potting material removed to expose the lumens of the hollow fibers.

If the fabric weave is too dense, or the filler material too viscous to fill in the manner shown in FIGS. 15-16, an alternative method would be to pot the fabric edge in a urethane material, wherein the edge of the woven material is immersed in a liquid urethane, which coats the fiber ends, and then cures into a solid mass (FIG. 17). The solidified urethane potting material is then partially cut away, re-exposing the fiber lumens, as shown in FIG. 18. The rigidized fabric edge would then be clamped to an appropriate filling manifold, and sufficient pressure applied to the filling material so as to cause it to flow through the fiber lumens.

After filling, the urethane encapsulated edge of the fabric can be cut away and discarded, and fiber ends can be sealed as in FIG. 16 and FIG. 14A. This can have similarity to the manner in which ends of hollow fibers in hemodialyzers and ultrafilters are potted and are cut and polished after potting. The rigidized fabric edge can then be clamped to an appropriate filling manifold, and sufficient pressure applied to a material such as a liquid, gel, suspension or other forms of drug-containing material so as to cause it to flow into or through the fiber lumens.

Alternatively, it is possible that the fiber ends can be left in the potting and the device can be used in that manner, which would permit refilling during the time that the device is implanted in the patient as is discussed elsewhere herein.

Spatial Non-Uniformity of Drug

It is possible that a hollow fiber could be filled along some of its length with a first drug-containing liquid or a drug at a first concentration, and could be filled somewhere else along its length with a second drug-containing liquid that is different from the first drug-containing liquid, or with the drug at a second concentration that is different from the first concentration. As a result, the substance or amount of substance that is delivered to tissues at different locations could be different. Drug can refer to pharmaceutical, or biologic, or other effective or beneficial substance.

Depositing a Suspension into the Fiber Lumen

It would be possible to cause a suspension to flow into the lumens of the fibers and thereby deposit particles of a drug or other substance in the lumens of the fibers.

When the lumen is being loaded with drug, the drug particles can flow into the lumen along its flowpath as a suspension. The suspension can comprise the drug particles, and water or other solvents, and any of various other additives as mentioned elsewhere herein. The downstream end of the fiber can contain a retention filter such as a sponge or other form of porous medium such as a bed of solid particles, which is suitable to allow liquid or the suspending medium to pass through the retention filter but retains drug particles such that they would accumulate in and fill the lumens of hollow fibers. The retention filter can have pores that are sufficiently small to retain the particles, but the pores in the retention filter do not need to be as small as the pores in the wall of the hollow fiber. The suspension, at the time of flowing into the lumens of the hollow fibers, can be a fairly dilute suspension so that it flows easily without clogging until it reaches the retention filter. In this way, flow of the suspension can still be generally along the direction of the hollow fiber. As particles are retained at or upstream of the retention filter, a deposit of particles can build up starting at the retention filter and progressing upstream in the lumens of the hollow fibers. This deposit of particles can have flow resistance properties that are dependent upon the particle size and other geometric properties, as can be described by the literature of flow through a porous medium. If the flow resistance of the deposited particles for flow of liquid through the retention filter and the deposited particles becomes excessive, it is possible that liquid can instead exit through the pores in the wall of the hollow fiber. This has been described in the sense that flow is directed into the lumen by a pump or mechanism that causes a defined flow.

In an embodiment of the invention, introducing a suspension into the lumen can be performed at least partially using capillary action, in the sense that comprises orienting the hollow fiber in an orientation that is at least partially sloping having a lower end that is an open end, followed by submerging the open end below a surface of the solution so that the solution rises into said lumen by capillary action. The surface tension of the liquid and the lumen diameter of the hollow fibers can be selected to facilitate filling by capillary action.

It is still further possible that if the drug is not very soluble in water or in solvents of interest, then the drug could be introduced into the fiber lumens as a dilute suspension, and the suspension could flow through the length of the lumen while some of the suspending medium exits through the pores. In so doing, particles of suspension can be carried into the pores and, although the carrier liquid can escape through the pores, the suspension particles can be retained in the pores. In embodiments, suspension particles can be deposited in or can occupy the fiber lumens.

For representative conditions the velocity of settling of the particle can be estimated by Stokes' Law, as discussed elsewhere herein, based on the assumption that the particle is spherical and is unaffected by the presence of any nearby particles. The appropriate parameters can be chosen so that the settling velocity, in combination with a typical device dimension, gives a settling time of at least many minutes.

The liquid can also contain an anti-flocculating additive that discourages the formation of clumps of particles. An anti-flocculating additive can comprise surfactants of all types, poly electrolytes, hydrating agents such as polyvinyl alcohol and organic liquids or solvents. The use of an anti-flocculating agent can, for example help to maintain the suspension in a flowable condition prior to and while it is flowing into the hollow fibers to fill the hollow fibers. Further discussion of methods of loading drug into fiber lumens using suspensions is given in Examples herein.

Depositing Drug into the Fiber Through the Use of Alcohol and Other Solvents

Some drugs of practical interest are not very soluble in water. However, sometimes such drugs are soluble in other solvents such as organic solvents. Some drugs are far more soluble in alcohol or other organic solvents than they are in water. It is possible that a fiber can store drug inside it in the form of a solution of the drug in an organic solvent that is benign to the human body. Examples of such solvents include ethanol and certain other alcohols. Of course, it would be necessary to choose a solvent such that the hollow fiber itself is not significantly soluble in the solvent, while the drug is soluble in the solvent. It is possible that a solution of the drug in the solvent is introduced into the fiber lumen and is left in the finished product as a solution. Alternatively, it is possible that a solution of the drug in the solvent enters the fiber lumen, and then the solvent is allowed or caused to evaporate, thereby leaving a deposit of the drug inside the fiber. It is possible that this process could be performed more than once on the same fiber if desired, using either the same solvent or a different solvent, and using either the same drug or a different drug, in various repetitions of the process. In such a way, perhaps a greater amount of drug could be loaded or deposited into the fiber lumen than would be possible with just one filling. Drug can be deposited in the lumen of the fiber, in the pores within the wall of the fiber, or any combination thereof. This process has an advantage that the only form of matter that is transported into the lumen is a liquid, which can reach small and tortuous places more easily than a suspension could. The solid is formed by precipitation only after the liquid has reached the desired locations.

It is further known that, as with most substances, the solubility of drugs in solvents is temperature-dependent. For example, rifampicin is soluble in methanol at room temperature to a concentration of at least 50 milligrams/milliliter. However, the same solution, when cooled to a temperature of −20 C, is subject to the drug precipitating out from solution. This effect can be used beneficially in the sense that a solution can be made to flow into and fill the lumens as a true solution at a first temperature, and then the construct can be chilled to a second lower temperature at which some of the drug will precipitate out of solution and be deposited. The remaining liquid can then be removed by flushing or flashing, or could be evaporated as described elsewhere herein. A freeze-drying process (lyophilization) could be performed. The process could be repeated any number of times to deposit more and more of the drug. Drug can be deposited in the lumen of the fiber, in the pores within the wall of the fiber, or any combination thereof. This process has an advantage that the only form of matter that is transported into the lumen is a liquid, which can reach small and tortuous places more easily than a suspension could. The solid is formed by precipitation only after the liquid has reached the desired locations.

Yet another process that could be used for depositing drug involves the use of a solvent at conditions that are supercritical or near-critical. A common solvent used for such purposes is carbon dioxide with or without co-solvents, although other solvents are also possible. It is known that in such processes, the ability of the solvent to dissolve solute varies strongly with conditions such as pressure and with the nature of the co-solvent used. At a relatively high pressure that is in the supercritical or near-critical regime, the ability to dissolve solutes can be quite large. At lower pressures, the ability to dissolve solutes is reduced considerably. It is possible to perform the process without actual separation of phases into liquid and gas; in fact, the process can be viewed as approximately the use of a liquid solvent whose dissolving ability varies strongly as a function of pressure. In addition to the supercritical state, it is also possible to operate at parameters that are somewhat below the critical point yet near the critical point, and in such conditions it is still possible to obtain high solubility and a strong variation of solubility as a function of pressure.

In an embodiment of the invention, provided is a method of depositing solid material inside the lumen of the hollow fiber, which includes passing such material in through the pores of the fiber while the material is in solution in a liquid.

One such method starts with potting the ends of fibers so that the lumens of the fibers are open to manifolds, and the exteriors of the fibers are exposed to an environment that is separate from the manifolds. Then, the exteriors of the fibers can be exposed to or immersed in a solution containing the desired solute. The liquid solution can be caused to flow from the outside of the fiber, through the permeable wall of the fiber, into the lumen of the fiber. This flow can be caused by capillary action, by the action of a pressure difference from the exterior to the interior, or any other suitable method. Such flow can continue for a suitable duration of time so that most air bubbles or pockets that might be present within or near the fibers could be flushed out. Then, the fibers could be treated such that some or all of the dissolved solute comes out of solution in the form of a solid. Examples of such treatments include ordinary drying or evaporation and freeze drying (lyophilization). It is also possible that the solution of the solute in the solvent could have a significant temperature dependence, as is discussed elsewhere herein. Most commonly, solubility decreases with decreasing temperature. If this is the case, the temperature of the fibers with the solution inside them could be decreased so as to cause some of the solute to come out of solution. This could be followed by either removing the remaining liquid or by performing any form of drying.

Yet another method that could be used to deposit drug is dissolving the drug in a solvent that is at supercritical or near-critical conditions, with an example solvent being carbon dioxide, as is discussed elsewhere herein. Such solution could be caused to flow from the fiber exterior, through the permeable wall of the fiber, and into the lumen of the fiber. Deposition of the solute could then occur due to reduction of pressure. It is possible that this could be performed without potting of the ends of the fibers.

Yet another method could involve the use of reduced pressure such as near-vacuum. Such a method could allow the outside-in filling of fibers while not requiring the ends of the fibers to be potted. In this method, a desired solution could be created inside a chamber. When the hollow fibers are inside the chamber but not yet immersed in the solution, the pressure of gas inside the chamber could be reduced such as by a vacuum pump. For example, the pressure inside the chamber might be reduced to the vapor pressure of the solvent making up the solution, or to a value that is slightly above such vapor pressure. In such a situation, very little air would remain. Then, the hollow fibers could be immersed in the solution. Then, the pressure inside the chamber could be increased to atmospheric pressure, or even higher. This would cause any bubbles or pockets of air that might remain inside the fiber lumens or inside pores to shrink drastically, and be replaced by solution. Then, the liquid could be removed by any method such as evaporation, or freeze-drying (lyophilization).

Any of these methods could be performed more than once. Such repetition would progressively increase the amount of solute deposited inside the lumen of the fiber. This might help to overcome limitations on how much of a particular solute can be dissolved in a solvent.

In these described methods, the solid that comes out of solution and is deposited within the lumen might be deposited in an irregular form of solid, i.e., not necessarily in the shape of spherical particles. Nevertheless, it can still be expected that the solid can dissolve as needed during the residence time of the device in a patient's body.

Depositing Drug Using Thermo-Reversible Gels

Yet another type of substance that can be used in connection with filling lumens of fibers is thermoreversible substances of the family of triblock copolymers. Such substances are commercially available under names such as Poloxamer and Pluronic® and Lutrol® (available from BASF, Mt. Olive, N.J.). They have the chemical structure polyoxyethylene-polyoxypropylene-polyoxyethylene. Such substances have the unusual property that their aqueous solutions have a viscosity that increases with increasing temperature, which is the opposite of experience with most solutions of most ordinary substances. Thus, a solution of these polymers can be processed cold and can flow relatively easily. When the solution of such a substance warms up to room temperature or body temperature, it becomes more viscous or even becomes a gel. If such a solution were made containing a drug in solution, or even containing particles of a drug in suspension, such a solution could be caused to flow into the interiors of the fiber lumens under cold conditions. Then, upon warming to room temperature or body temperature, the drug would be kept in position inside the fiber lumens even more effectively than was the case during flowing of the formulation into the lumen. For example, such a drug might not leak out of the ends of the fibers even if the fiber ends were left open. It is possible that a simple solution of a drug can be made comprising a thermoreversible gel. It is also possible that a thermoreversible gel substance can be used with particles of drug, which would help in maintaining the particles in the form of a suspension.

Fluid Communication and Control of Drug Release by Tailoring the Hydrophobicity or Hydrophilicy of Fiber and of Pore Surfaces Present within the Hollow Fiber Wall In embodiments of the invention, there are various parameters related to the hydrophobicity or hydrophilicy or wetting properties of the pore surface and hollow fiber surfaces (internal and external) that can affect the drug delivery characteristics of the device. It is also useful to consider the properties of liquid that can contact parts of the device or can contain dissolved drug.

In order for a drug to diffuse or to be transported out from the lumen of the hollow fiber, it is desirable that there be some form of liquid communication between the drug molecules present in the lumen and the fiber external environment such as the interstitial fluids of the tissues. This path for this fluid communication can be through the pore structure present within the wall of the hollow fiber.

It can further be appreciated that in many instances, at least some portions of the device will be supplied in a dry condition at the time of use. For example, it is possible although not necessary that the drug contained in the fiber lumens can be in a dry condition. Regardless of whether or not the content of the lumens is in a dry condition, it is possible that the interiors of the pores will be dry. Thus, it can be desirable to establish, at or around the time of implantation, the wetting of various surfaces by bodily fluids that are present at the surgical site, or by other fluids as may be appropriate. More particularly, it can be desirable to establish the liquid path through the pores, connecting bodily fluids external to the device with liquid in the pores and with liquid, if present, in the lumens of the hollow fibers.

To achieve such fluid communication, wetting of pores and of fiber surfaces with a liquid can be necessary for the hollow fiber-drug combinations to allow for drug diffusion and drug release from the lumen to the external environment. Accordingly, surface properties of the fiber surface and pore surface can, in embodiments, be adjusted or modified or tailored to allow fluid communication in order to permit drug release from the device. In embodiments of the invention the surface properties of the fiber surface and of the pore surfaces present in fiber wall can adjusted to control drug release characteristics from the hollow fibers. Properties of liquids, such as surface tension and surface wetting, are also relevant.

One example of the influence of surface properties on wetting and related phenomena is found in the hollow fibers that are used in blood oxygenation. This is an example that is actually the opposite in many respects in comparison to embodiments of the present invention. In a blood oxygenator, it is desired to create effective oxygen transfer from oxygen gas flowing inside the lumens of hollow fibers to blood circulating outside the hollow fiber. This is used during critical surgeries such as in heart bypass surgery. In this case one side of the fiber comprises pure oxygen gas (lumen) while the exterior side of the fiber comprises circulating blood which is mostly water. Inherently, two different phases (liquid and gas) are present, and in this case communication between the two fluids takes place via the pores present in the wall of hollow fiber. However, in this example, the two fluid phases involved should remain separated from each other to better achieve effective oxygen transfer to blood. During this process, pore wetting is not desirable because once the pores become wetted with blood plasma or water, oxygen transfer rates decrease dramatically due to loss of the defined interface between oxygen and blood. This wetting of pores phenomenon is known as "weeping." In order to prevent weeping, polypropylene is the preferred material for making blood oxygenators and similar membrane contactors. The pores of polypropylene hollow fibers are naturally hydrophobic and narrow, and this prevents the pores from becoming wetted with blood plasma during oxygenation.

For drug delivery systems according to the present invention fluid communication via the pores and pore structure is needed to permit drug diffusion, transport and mass transfer from the fiber lumen to an environment outside of the fibers. It is desirable to establish some form of fluid communication between drug formulation and external environment. There can be two liquids, one on each side of fiber wall, and there can be liquid bridging or pore wetting to allow such fluid communication. In cases where the hollow fiber is made from a hydrophobic polymer such as polypropylene or similar polymers, the surface of the pores or surfaces comprising the pore structure can be made hydrophilic or somewhat hydrophilic to allow fluid communication between the two compartments, one compartment being the lumen and the other being the external environment. If this is not done, air might remain lodged in the pores and pore wetting might not be achieved, and this in turn might not permit drug release from fiber lumens to the external environment. An embodiment of present invention can comprise surface modification of pore surface properties of hollow fibers in order to adjust or control wetting properties and to facilitate drug release and transport from hollow fiber-based drug-releasing devices and constructs. Anticipated surface modification of pore surfaces can involve making them more hydrophilic in some cases or can involve making them somewhat hydrophobic depending on the drug and the nature of the fiber materials used.

Drug release characteristics can be influenced by the surface energy or other surface characteristics of the wall or of the pores within the wall. In an extreme case, if the liquid is not able to wet the surface of the wall, or is not able to wet the interior surfaces of pores, it is possible that air might remain inside the pores and liquid might never be able to establish a liquid path of communication through the pores, connecting the interior with the exterior of the hollow fiber. Such a situation would be conducive to the retention of air pockets within pores and to condition of unwetting, which would limit or prevent establishment of a liquid path of communication through the pores. In such a situation, drug might not be released at all. However, the teachings herein allow for this circumstance to be avoided.

In general, it can be appreciated that a hydrocarbon chain is relatively hydrophobic, and a polymer that contains hydroxy (—OH) groups or carboxylic groups (—COOH) or other functional groups is relatively hydrophilic. Even the presence of a small number of such groups in a molecule that is otherwise hydrocarbon or nonpolar can render the overall surface more hydrophilic.

In an embodiment of the invention, the material of which the wall is made could be a blend of more than one polymer. The first polymer could be a polymer, such as a hydrophobic polymer, which might make up a majority of the material. Such a polymer could, for example, have properties in regard to structural strength as might be desirable. The second polymer could be a polymer that is more hydrophilic than the first polymer. The second polymer could be chosen so as to make the polymer blend have overall properties that are appropriately hydrophilic. As an example in another medical technology, a polymer combination that is sometimes used for hollow fibers in kidney dialysis cartridges is polyethersulfone (PES) in combination with polyvinylpyrrolidone (PVP) or with polyethylene glycol. In embodiments of the invention, the first polymer could be polypropylene or some other hydrophobic polymer such as polysulfone. The second polymer could be any of various materials such as alcohols, polyvinyl alcohol, polyethyleneoxide, polyvinylpyrrolidone, polyethylene glycol (PEG) and others. The proportions of the two polymers could be chosen such as to avoid unduly weakening the overall material, avoid causing cracking, etc., while still giving the desired properties such as hydrophilicity of the surface. The proportion of the polymers used can depend on whether the fibers is intended to be used for structural application or for drug delivery purpose only.

Within the category of blends of a first polymer and a second polymer, the two polymers could be chosen and manufactured such that they are substantially uniformly mixed. Alternatively, they could be chosen, such that the second polymer tends to migrate to the surfaces of an object, leaving the bulk of the object with a higher concentration of the first polymer.

In embodiments of the invention, it is desired that the liquid, such as bodily fluids, should wet the pores (which is the opposite of the situation in a blood oxygenator). If it is desired to make use of a material such as polypropylene, which has a well-established manufacturing base and experience, the exposed surface of the material as well as the pore surfaces present in fiber walls can be modified.

One method to modify the surface properties of the hydrophobic pores or pore structure is to treat the fibers with a hydrophilic solvent that does not dissolve the fiber itself or cause collapse or closure of the pores. This process is similar in some ways to plasticization. In this sense the treatment can only address the surface of the pores without causing polymer dissolution or change in the pore size or pore size distribution or alter membrane properties such as permeability or sieving characteristics. Treatment of polypropylene hollow fibers or fiber meshes with alcohols including ethanol, n-propanol, isopropanol, n-butanol, isobutanols and other higher alcohols was found to render the pore surfaces more hydrophilic. This treatment or surface modification was found to enhance drug release from polypropylene hollow fibers and meshes. This was tested using sodium fluorescein as a model hydrophilic water-soluble drug and also using other drugs with different hydrophobicity including rifampicin and vancomycin. Treating fiber meshes made from polypropylene with alcohols for 30 minutes to 24 hours by immersion or spray methods followed by drying the meshes was found to significantly facilitate the release of sodium fluorescein and other drugs from polypropylene hollow fibers and meshes, compared to fibers and meshes without treatment.

We have discovered that treating polypropylene hollow fibers and meshes with alcohols, with the purpose of facilitating drug release from fiber lumens, has an effectiveness that depends on the molecular weight and chemical structure of the alcohol. Higher molecular weight alcohols were found to produce better surface treatment of polypropylene hollow fibers and meshes. For example, higher drug diffusion was found when treating the fibers or meshes with isopropanol compared to ethanol. Although not wishing to be bound by explanation, it is believed that low molecular weight alcohols may not stay in the surface layer of the polymer long enough and may be lost by evaporation during drying. According to embodiments of the invention, the organic solvents used in surface modification of the pore structure of hollow fibers produces a lasting effect or more permanent surface treatment and should not be lost or eroded beyond usefulness during processing or during periods of drug release or treatment.

The organic molecules that can be used to achieve surface modifications or some form of surface plasticization of hollow fibers and meshes are not be limited to alcohols, but rather further can include ketones, aldehydes, acids, esters, amines, amides. pyrrolidones or other organic chemistry classes. The modifying compounds can also include one or more functional groups, can be aliphatic or aromatic, and can be employed either as pure substances or as mixtures.

The selection of compounds can provide surface properties for facilitating drug release from fiber lumens to external environment without substantially altering pore size or pore size distribution. The effectiveness of surface treatment of fibers or meshes surface can be tested by measuring the contact angle of water on the surface of the polymer. In the case of polypropylene the contact angle before treatment is about 102 degrees. After treatment the contact angle can be in the range of 50-60 degrees, and preferably even 20-40 degrees. Another method for testing the effectiveness of the treatment is to measure drug release rate and duration with model hydrophilic and hydrophobic drugs using simple hollow fiber constructs with known surface area and known drug loading. In this case a normalized release rate per unit surface can be calculated and used to design the drug delivery device.

In embodiments of the invention, surface treatment of the hollow fibers, meshes or entire device or construct can be made by chemical treatment that changes the chemical structure of the material, at least near the exposed surfaces. A known surface treatment of hydrophobic polymers such as polyethylene or polypropylene comprises exposure to reactive gases such as ozone, hypochlorite, chlorine dioxide or peroxy compounds such as hydrogen peroxide, peracetic acid or nitrogen oxides. To achieve such a treatment, the fibers or meshes can be for example placed in a container with reactive oxidizing gases or liquid flowing over the surface of the fibers or meshes. Alternatively, such gases or liquids can be made to flow from the fiber lumens to external environment or from the outer surface to the lumen under pressure or vacuum. The latter flow can be made in the form of cross flow or dead-end flow as it well known in membrane technology. Reaction with reactive or oxidizing gases can produce hydroxyl, carobxyl, or peroxy acid functional groups, and the presence of such groups make the surface hydrophilic. The degree of hydrophilicity or wetting with water can be adjusted according to the time of treatment, the concentration of reactive species and the temperature and time of the process. The reactive species can also be made with the aid of irradiation including but not limited to ultraviolet, x-ray, electron beam or Gamma irradiation or alternatively with the use of plasmas. The gases can pass through a reaction zone before coming into contact with fibers or meshes, or the gases can be applied directly in the treatment chamber where the fibers or meshes are placed while gases are being circulated around or inside such fibers or meshes.

In still other embodiments of the invention, the hollow fibers and meshes can be treated with oxidizing liquids such as but not limited to nitric or chromic acid, nitric acid or other oxidizing agents that are known to produce hydrophilic functional groups on polymer surfaces or other similar organic surfaces. Hydroxyl, carboxyl, peroxy or other polar functions groups that can include nitrogen, sulphur or phosphorous can also be utilized. According to the embodiments of the invention, it is not wished to be limited to any specific organic groups, because the main purpose of surface modification is to promote wetting of the pores and to effect fluid communication between the lumen and external environment during drug release.

Some drugs are more hydrophilic while others are more hydrophobic, which can be characterized by the parameter log(10) P. P is the partition coefficient describing the relative concentration of a substance dissolved in water and the same substance dissolved in an organic solvent. Typically the organic solvent is octanol. P=[Organic]/[Aqueous], where the brackets indicate concentration. Log P=1 means a 10:1 ratio of Organic:Aqueous, which indicates a hydrophobic situation. Log P=0 means a 1:1 ratio of Organic:Aqueous. Log P=−1 means a 1:10 ratio of Organic:Aqueous, which is a hydropohilic situation. It is possible that drugs that are not very soluble in water can be more soluble in other solvents. Examples of such other solvents include alcohols, esters, amines and amides. Alcohols, depending on the chain length, can also have some miscibility with water. Alcohol is an example of a solubilizer or compatibilizer substance. Accordingly, it is possible that inside the lumen provided is a solubilizer or compatibilizer substance along with a drug to modulate its hydrophobicity or partition properties. Those of skill will recognize other attributes that can influence drug delivery properties.

It is believed that parameters that control release kinetics of an agent, and duration of release, include: a) amount of drug loaded in the mesh; b) hydrophobicity and solubility of the agent in water; c) agent molecular size; d) composition of the fiber material and its porosity; and e) dimensions of the device including surface area.

In embodiments of the invention, the wall can comprise a large portion of polypropylene or a similar polymer. Polypropylene has an extensive history in regard to its manufacturing and use. Polypropylene also is known to have good mechanical strength. Available manufacturing technology for polypropylene provides the ability to control parameters and dimensions such as strength, wall thickness, pore size, pore size distribution, and pore shape.

In embodiments of the invention, the pore size, the pore size distribution, and the pore shape can influence what drug molecules are able to pass through pores and what drug molecules are not able to pass through pores. These parameters also can influence the rate at which a drug passes through the pores. The pore size, the pore size distribution, and the pore shape can be chosen so as to result in a desired release characteristic for a particular drug.

It is also possible that drug release characteristics can be influenced by the surface tension of the liquid intended to pass through the wall. In embodiments of the invention, the liquid that comprises the drug solution or suspension can be formulated so as to have a desired value of surface tension. The desired value of surface tension can be less than the surface tension of pure water. The formulation of the liquid can include a surfactant or similar substance into the solution or formulation. The surfactant can be selected from the group consisting of anionic surfactants, cationic surfactants, nonionic surfactants, and zwitterionic surfactants. Examples of suitable surfactants include sodium dodecyl sulfate (SDS), pluronics, tetronics, glucosides, and others that can be safely implanted in the human body. It is further possible that some amount of ethanol or some other alcohol or other solvents can be included in an aqueous formulation, with an effect similar to that of a surfactant with respect to decreasing surface tension.

In embodiments of the invention, there are various possible surface treatment processes that could be performed on an object to make it more hydrophilic. Such treatment could be performed after initial manufacturing of the object, but before loading of drug into the object. Alternatively, the surface treatment or modification of the hollow fiber drug delivery device of construct can be made immediately before implantation into the body. An example of this was found with polypropylene fibers and meshes pre-loaded with drug. Treatment with alcohol prior to implantation in an animal model was found to be necessary for the drug to be released from the hollow fiber constructs.

In an embodiment of the invention, it is possible that the wall could be manufactured out of a bulk material and then could be subjected to a treatment that deposits an additional substance into the bulk material, possibly depositing the additional substance preferentially near exposed surfaces. Such additional substance could be deposited by absorption into the bulk material of the wall. For example, such additional substance could be an alcohol, or an aldehyde, or more generally an organic solvent or plasticizer. The additional substance could be chosen such that it does not evaporate quickly and has a tendency to remain absorbed within the bulk material for a sufficiently long time to last for the intended duration of the device. For example, the additional material could be chosen such that it has an appropriate vapor pressure such that it does not evaporate from the wall especially when the constructs are used for topical treatments. Examples of an additional material include isopropanol, isobutanol and other short to medium chain length alcohols. It is possible that absorption of the additional material could cause the bulk material to swell slightly.

In an embodiment of the invention, it is possible that the object could be manufactured out of a bulk material and then could be subjected to a surface treatment process that chemically changes some of the molecules of the material. Such embodiments can involve some form of introducing oxygen into the molecules of the material. As mentioned elsewhere herein, molecules that have functional groups such as hydroxyl or carboxyl functional groups are believed to be generally more hydrophilic than molecules lacking such groups. An example of such a process involves exposing the material to ozone ($O_3$) or other similar reactive species. Ozone has a tendency to separate into a molecule of diatomic oxygen, which is stable, and a monoatomic or free radical oxygen, which tends to react with whatever it comes into contact with. Such a monoatomic or free radical oxygen can insert itself into molecules of the material, and can thereby create groups such as hydroxyl groups, carboxyl groups or others, which can increase the hydrophilicity of the surface. A similar effect can be achieved by exposing the object to oxygen plasma, argon plasma or similar treatment involving the use of a plasma source.

In another embodiment of the invention, an oxidative surface process could be performed not involving a gas or a gas-like plasma state, but rather involving a liquid. The object could be exposed to an aqueous acid such as nitric acid ($HNO_3$). Another such acid is hydrofluoric acid (HF). Exposure to an acid could accomplish similar modification of the chemical composition of molecules of the bulk material near exposed surfaces. For example, the object could be immersed in a desired liquid to tailor the hydrophilic or the hydrophobic properties of the material.

In any of these processes, the liquid or gas could be supplied under pressure to a certain region of the hollow fiber or hollow fiber fabric such as the interior, and could be caused to flow through the pores to another region such as the exterior.

In yet another embodiment, the object could be exposed to gamma radiation or electron beam radiation in such a way as to increase the hydrophilicity of exposed surfaces.

The surface tension of the liquid can be adjusted if desired by incorporation of a surfactant or similar substance into the solution or formulation. Even the incorporation of a small fraction of a simple additive such as ethanol can significantly change the surface tension of a fluid.

Additionally, the material and other parameters of the hollow fiber can be selected so as to provide desired characteristics for the passage of liquid therethrough. For example, two materials that are common in the production of hollow fibers for dialysis cartridges are polyethersulfone (PES) and polyvinylpyrrolidone (PVP). Polyethersulfone (PES) is used as the major material for construction of the fibers, and polyvinylpyrrolidone (PVP) is used as an additive related to the formation of pores. Polyethersulfone (PES) is the more hydrophobic of the two materials, whereas polyvinylpyrrolidone (PVP) is a hydrophilic material. Accordingly, the relative proportions of PES and PVP can be adjusted so as to provide a desired degree of hydrophobicity or hydrophilicity of the material of the hollow fiber. Additionally, surface treatments can also influence this property. For example, it is believed that if the fiber is immersed in isopropanol for a period of time, its surface will become more hydrophilic. This can be due to absorption or plasticization of the alcohol into the surface of the polymer. For polypropylene fiber material, the alcohol soaks into the polymer and swells or plasticizers the polymer and makes the polymer hydrophilic. It is believed that isopropanol, isobutanol and other short to medium chain length alcohols are suitable for use in such treatment of polymers.

It is believed that making the surface of pore hydrophilic or somewhat hydrophobic or intermediate between hydrophobic and hydrophilic achieves better release of the drug from the hollow fibers to surrounding tissues and organs. The level of the hydrophobic-hydrophilic balance required can depend in part on the nature of the drug to be delivered and in part on the tissue or organ intended to be treated. Fatty tissues can present more hydrophobic character compare to muscle tissue which require more hydrophilic character. In most cases, it would desirable to retain some level of hydrophilicity in order to establish and maintain fluid communication between drug or drug formulation present in fiber lumens and interstitial fluid present in the tissues. The level of desired hydrophilic-hydrophobic balance of pore surfaces, pore openings, or external surface of the fiber itself can be determined by measuring the contact angle or other attributes of surface wetting as it is known in the field surface science. Other means of assessing the hydrophilic-hydrophobic balance can be assessed by measuring surface tension using liquid mixtures with known log p or with surfactants with know HLB or with known surface tension or with known other wetting property. One example of such methods can include capillary rising in the hollow fibers or similar methods. An alternative method of assessing this balance can depend on measuring filtration rate or permeability of the hollow fiber using solvent mixture with known properties under pressure. In this respect wetted pores will be permit higher filtration rates or higher permeability at low pressures in contrast with hydrophobic pores which will require high pressure to permit permeability. The latter methods are known in membrane science, e.g., bubble point or the like. Hydrophilic-hydrophobic which sometimes referred to as hydrophilic-lipophilic can be quantified by comparing it to log p as well-known in pharmaceutics to control drug delivery kinetics or to HLB (hydrophilic-lipophilic balance as used in the surfactants field to control wetting. Other scales including acid-base or donor-acceptor properties of surfaces as known in the art and can be adopted to control the surface properties of the pore and fibers in order to control drug delivery rates and duration of the devices and constructs according to embodiments of present invention.

The construct could be made with a surface that is more hydrophilic in places or directions where drug release is desired, and more hydrophobic in places where drug release is not so much desired. In connection with this, a drug formulation could be either an aqueous formulation or a non-aqueous drug formulation or between, as desired. This range of formulations could contain the same or different surfactants or other excipients.

Different parts of a construct can be given different treatments in this respect, so that different parts of a construct can have different degrees of hydrophobicity or hydrophilicity. Alternatively or in addition, the drug formulation, even if it is the same drug in different places, could have different formulations in regard to surface tension of the drug formulation or to its wetting properties, such as by the use of different solvents or combination of solvents in different places, or the presence or absence of surfactants in different places.

The release rate and duration of release of the drug can further be influenced or controlled by the intrinsic porosity of the fiber wall, and by the formulation, and by total surface area of the fibers in the device or construct.

In some embodiments, the pharmaceutical or biologic substance can pass through the walls of the hollow fiber by diffusion, driven by the difference in concentration of the pharmaceutical or biological substance between the exterior and the interior of the hollow fiber.

In some embodiment of the invention, the pharmaceutical drug or biologic substance can be delivered more by convection as it is the case with osmotic pumps or by adjusting the formulation such as by inclusion of osmotic agents, osmogens or super-absorbents. In other embodiments drug delivery from the hollow fibers of the present invention can comprise both diffusion and convection. The contribution of diffusion or convection can be higher or lower during the implantation time of the device in the body. For example there can be more contribution of convection to drug delivery rate early after implantation and less after some time depending on the device and treatment.

In related embodiments of the invention, the contribution of convection or diffusion to drug delivery rates can be controlled or adjusted by periodically filling the constructs with desired drug formulations during implantation. Devices and constructs based on hollow fibers which can be loaded with drugs or drug formulations during therapy period are described elsewhere herein.

Drug Delivery Rates and Durations

One simple way that a drug can be stored in the lumen of a hollow fiber is in the form of a solution, in which the drug is dissolved in a liquid solvent such as water or alcohol or other organic solvents or solvent blends. Similarly, an aqueous solution of a drug could also contain thickening agents or other agents that cause the aqueous solution to have properties of a gel or a high-viscosity fluid at body temperature. However, many drugs of practical interest have fairly small solubility in water. Accordingly, the amount of drug that is capable of being stored in solution form in the lumens of the hollow fibers can be smaller than is desired for clinical or therapeutic reasons. Drug solutions loaded in the hollow fibers can, in some embodiments, only be suitable for short duration therapies and can last for hours or days as described elsewhere herein.

A way to store larger amounts of drug is to provide solid particles of drug in the lumens of the hollow fibers. In this way, the solid particles can serve as reservoirs of the drug. As drug molecules exit from the lumens by diffusion or by convection of liquid, additional drug will be able to dissolve from the solid particles. This drug can enter the liquid that remains inside the lumens or that enters the lumens to replace any liquid that has left the lumens. Thus, solid particles of drug could maintain a substantial concentration of the drug in liquid, up to its solubility limit, that exists in the pores of the hollow fibers, and could provide a substantially long duration of administering the drug to the patient. Loading the drug as solid particles or power at volume fraction between about 3% to about 50% can be very desirable since many therapies require prolonged treatments possibly days or months. High drug loading levels cannot be provided by other drug delivery methods such surface coating. According to embodiments of the inventions the hollow fibers can be filled with solid drug particles at desired volume fraction to achieve drug delivery rates at therapeutic levels for long durations used for different therapies.

Applications

Use External to the Body Such as Wound Dressings and Burn Management

In medical applications, such fabrics, meshes and constructs according to the invention can be used as dressings to cover wounds or sores caused accidentally, or as a result of surgical procedures or disease, or as the result of burns.

In embodiments of the invention, such fabrics, meshes, constructs or devices can be implanted in patients, possibly to provide structural support across an incision, or to provide a support for tissue re-growth or treat or prevent infections. Such implants can be permanent or temporary, or, when the fabric is comprised of a bio-degradable material, can eventually be absorbed by the body. In related embodiments, such devices or constructs can be designed so that they can be removed for the body with ease without invasive surgery as described elsewhere herein.

In many situations, it would be highly desirable to have low molecular weight pharmaceutical drugs or biologics which can include antimicrobial agents, antiseptic agents, antibiotics, anti-inflammatory agents, analgesics, chemo-therapeutics, immuno-therapeutics, pain medications, growth hormones or other drugs that treat or control disease applied to the wound or surgical site during the healing process.

When the fabric or construct is applied as a dressing, or is applied or implanted as a structural support across an incision, or as a support platform for tissue re-growth, the encapsulated drugs can, of example, slowly leach or diffuse through the porous tubular wall of the fibers, providing an effective local or loco-regional dosage of the pharmaceutical or biologic for a desired period of time. The driving force for drug release can be made possible by manipulating concentration gradients between the drug and surrounding tissues, inclusion of osmotic agents or osmogens in the drug formulation, dissolution vehicles, swelling agents, other excipients, direct mechanical pressure as with the catheter, with an osmotic pump and or combinations as desired. In embodiments of the inventions the driving force for drug release can not be limited to one of the above methods or their combinations. Other means known in the art of drug delivery can be employed to achieve drug delivery For surface wounds as it pertains to topical applications or treatment, these fabrics or constructs including the hollow fibers can be applied periodically, whenever the wound dressing is changed or can be devised so that it would provide sustained long-term release based on the type of wound or preferred treatment or therapy. In some embodiments the hollow fiber constructs according to the invention can be equipped with a filling port so that they can be periodically loaded with drugs as described elsewhere herein.

In embodiments of the invention, provided is an article, containing drug-containing hollow fibers or hollow fiber fabric or hollow fiber based mesh, that fits around or is intended for use on the exterior of the body. Fibers of embodiments of the invention can be used in the form of a garment or a sleeve that touches or surrounds appropriate parts of the body. For example, such an article could be a sleeve that can be cylindrical or other appropriate shape such as wrap-around construct. For example, such an article could be a sleeve for diabetic sores on toes or can be used over an entire limb such as an arm or a leg.

Also such an article could be a simple patch that is intended to be placed in contact with external skin of a patient. An example of such application can be patch that includes cytotoxic cancer drug for long-term treatment of melanoma or skin cancer or for preventing metastases from a lesion. Such patch can itself be adhesive to skin, or can be provided in combination with other components that adhere to skin. Similarly, an embodiment of the invention could comprise a bandage can be used for transdermal drug delivery such as nicotine, pain medications or other drugs that treat addiction or other diseases It can be noted that a use external to the body, such as a bandage, presents a somewhat different situation from a use internal to the body like implants. In an internal use, it is possible or even likely that the implant will be entirely surrounded by liquid bodily or interstitial fluids, and it is possible that no air or gas may be in contact with any part of the implant. In contrast, for a use external to the body, such as a bandage, there might be some part of the device that is in contact with air or gas, while other parts of the device are wetted by bodily or interstitial fluids, or can be purposely irrigated with liquids. It is believed that such a situation might increase the importance of providing hydrophilic characteristics for the surfaces of the fibers and of the pores. An external or topical device such as a bandage might be in contact with tissue in which there is little or no local lymphatic flow or motion of interstitial fluid. Accordingly, the role of interstitial or lymphatic or interstitial fluid motion in spreading drug through the tissue might be limited. Accordingly, in this situation, it might be more important that the drug-containing fibers be close together, and possibly also of narrow diameter, and minimize evaporation as much as possible. A bandage or patch type of device could, for example, be intended for use in treating burns. Such a device might comprise a layer of gel or superabsorbent material, fibers or polymer facing the wound, so as to lessen the likelihood of the device becoming attached to or to adhere to the wound. For similar reasons, such a device could have a layer of resorbable material or polymer facing the wound. Such a device might contain both drug (e.g., antibiotic), and also analgesic, pain management agents, adhesion preventing agents and anesthetic.

In the situation of a bandage or when treating topical sites, the drug delivery portion of the device could be made to a defined external shape, which might have entirely closed ends with no open ends. There further might be provided an adhesive for attachment to skin. Devices made for topical treatment can deliver drugs in one direction to diseased surface by having a film on the other direction facing the outside as described elsewhere herein. It can also be desirable to make the film overlay to have holes in order to ventilate the site and to prevent anaerobic growth as it is known in the art of wound healing.

Adhesion Barrier

In some surgery, especially abdominal surgery such as in ventral hernia repair, it is useful to leave behind a barrier that separates certain organs or tissues from each other and thereby discourages them from improperly adhering to the fabric or mesh used for repair. Such a barrier can take the form of a fabric, a sheet, a coating, or still other forms. If the adhesion barrier takes the form of a fabric, the fabric can comprise hollow fibers loaded with adhesion prevention agent or drug of an embodiment of the invention. In this way, the barrier can deliver desired medical, biological or anesthetic substances to the site in a controlled manner and prevent adhesion of the device to internal organs as in the case ventral hernias. Special coatings or layers of resorbable material can be a part of the hollow fiber devices and constructs so that to prevent adhesion as required for achieving effective therapy.

Hernia Mesh and Mesh for Other Surgery

It is known that in the treatment of hernias, conventional meshes sometimes become infected with very high incidents about 25% in some cases. This recurrence has required additional corrective surgeries which is usually associated with high morbidity and cost. It happens that the mesh becomes infected due to growth of biofilm. Similarly, mesh pouches are sometimes placed around pacemakers, defibrillators and similar implanted devices. When such devices are implanted similar problems of infection can arise because of contamination and biofilm growth inside and around the implant site. Meshes are also sometimes used in various types of surgical repair or reconstruction. Vaginal or pelvic meshes have also had problems and this has been recently publicized in the media due to many impending law suits. In embodiments of the inventions the hollow fiber drug releasing devices described in this disclosure can be used to provide protection and treatment of the applications listed above or the like. One skilled in the art can find other applications and it is not desired to limit the invention to the examples provided in the present disclosure.

In embodiments of the invention, in any such situation, a fabric or mesh could be provided in which some of the fibers are drug-containing fibers including the hollow fibers disclosed herein. Such drug-containing hollow fibers can be interwoven with other fibers. The other fibers can be conventional fibers, which can be solid fibers. Other fibers can have different properties, such as greater mechanical strength, compared to the drug-containing hollow fibers. The drug-containing hollow fibers can release their drug gradually as described elsewhere herein. The drug can be a drug that can protect against bacteria such as eradication biofilm or preventing biofilm from growing on or near the fiber or it can be agent such that to prevent fibrosis or formation of scar tissues. In other applications it can be desired to deliver drugs that promote scarring of the tissues involved. Other applications include hernia repair or hernia prophylaxis or preventing hernia from recurring or their combination. Such application can include other constructive or reconstructive surgeries or procedures. The hollow fibers can be either resorbable or non-resorbable or permanent or a combination of both.

Embodiments of the invention can be shaped like an organ of the body of the patient. For example, for breast reconstruction, an embodiment of the invention can be shaped like a portion of a breast. The hollow fiber constructs disclosed herein can be used as scaffolds for cell growth and in making different organs by provided support, nutrients, drugs, growth factor, genes and other factors and compounds by periodically or continuing filling the constructs with drugs. These constructs can thus be made in three dimensions and can be made by 3D printing or other 3D construction techniques, or 3D printing supplemented by other techniques.

A mesh of embodiments of the invention could be used for hernia repair or for repair of pelvic or vaginal abnormalities post surgery. Such a mesh can have one surface that is intended to face the viscera or internal organs, and an opposed surface having different properties. The surface facing the viscera or organs can have anti-adhesion properties such as a coating of gel or a material that is resorbable or it can deliver drugs to suppress or prevent adhesion to internal organs. As described elsewhere herein, the surgical repair meshes can be hybrid meshes made from conventional hernia meshes and at the same time include hollow fiber drug releasing constructs. This can be utilized to satisfy mechanical and drug releasing properties as desired.

Pouch

Fabric or mesh as described elsewhere herein can be used to form a pouch, enclosure or similar shapes. In an embodiment of the invention, the pouch can be used to partially enclose or completely enclose another implanted device. The pouch can be used for example to discourage the formation of biofilm around or on the other implanted device. Such a pouch could be used, for example, to enclose a pacemaker or a defibrillator or any other device that can become infected during implantation. Such a pouch could be used to surround or enclose an implantable pump, or an implanted artificial heart, or other artificial replacement body part, or generally any other implant. Pouches made of solid fiber with a drug-containing coating are known, but a pouch of an embodiment of the invention could contain a larger amount of drug than pouches such as a pouch made of drug-coated fiber and can deliver various drugs or biologics for long periods of time. Pouches or enclosures according to the invention are not to be limited by the type or structure of the drug to be delivered during implantation. Similar to other constructs disclosed elsewhere herein, the pouches or enclosures or related constructs can be made with filling ports so that they can be refilled with drugs as needed. The pouches can be employed to treat chronic disease especially when they are equipped with drug filling components as described elsewhere herein.

Placement of Device Near or Around a Transplanted Organ

Figure 19A:
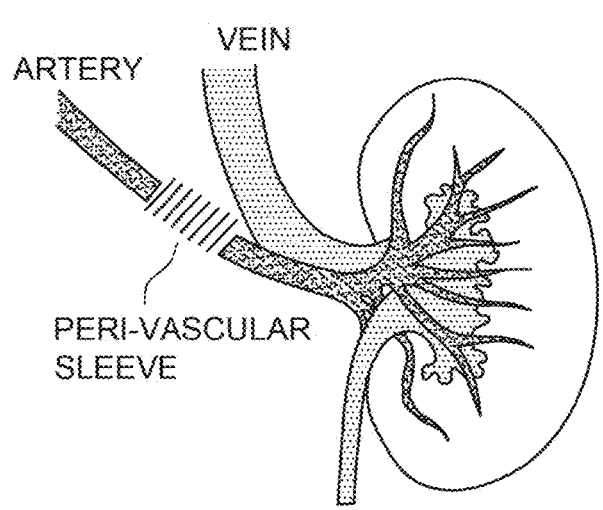
FIG. 19A shows a kidney with a perivascular sleeve around the artery.
Figure 19B:
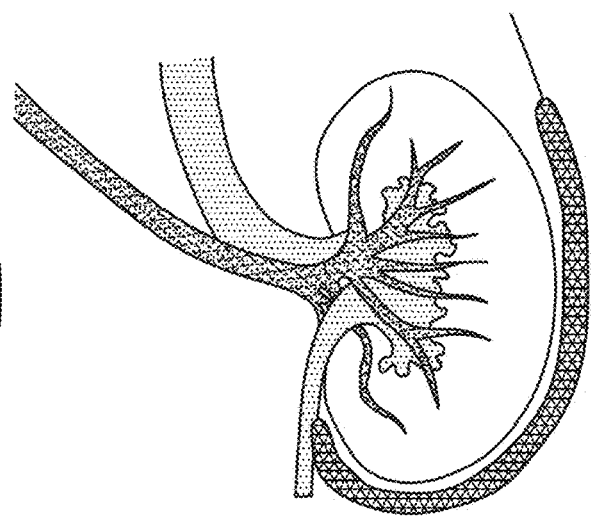
FIG. 19B shows a kidney partially surrounded by a pouch.

Rejection of transplanted organs is a significant issue in organ transplantation. Various drugs, such as tacrolimus, are effective in preventing rejection of transplanted organs. One of the most commonly transplanted organs is the kidney. A possible application of embodiments of the invention is to be implanted at or near the site of a transplanted organ so as to deliver an anti-rejection drug to the transplanted organ or to tissues near the transplanted organ. In many situations with prior art drug delivery technology, the drug must be administered systemically, which results in other parts of the body receiving more drug than necessary. Some anti-rejection drugs are toxic, so unnecessary exposure of other parts of the body to such drug is a disadvantageous. One form in which an embodiment of the invention could be implanted is as a piece of fabric near the transplanted organ. Another form is as a pouch that surrounds a large portion of the transplanted organ. Another form is as a sleeve that surrounds an artery carrying blood towards the organ, which would be penvascular drug delivery. In such a situation, the drug released from the device would have to pass through the wall of the blood vessel and then enter the blood, to be delivered to the organ. Any of these devices could be able to be re-filled or re-loaded with drug after implantation. FIG. 19A illustrates a sleeve surrounding an artery that carries blood into a kidney. FIG. 19B illustrates a pouch surrounding a portion of a kidney.

Stent for Nasal or Other Bodily Cavity, or Cardiovascular Stent

In an embodiment of the invention, the device could be a stent that is suitable to be placed in a nasal sinus after surgery or in some other bodily cavity. In such an instance, the fibers or the device overall can be designed to have some rigidity so as to provide physical separation of two portions or faces of tissues that have the propensity to adhere to each other for example after surgery. Such rigidity might be greater than what would be used for a device that is implanted under the skin or inside tissues as in hernia repair or other surgeries.

Example applications are to use the described hollow fiber constructs as nasal stents or stents for other body ducts such as the pancreas or gall bladder. In yet another embodiment of the invention, hollow drug-containing fibers could be used in cardiovascular stents. In embodiments of the invention the drug releasing hollow fibers or fabrics or constructs can be placed on the inside or outside of a conventional stent or can be interweaved within a conventional stent including vascular stents. In related embodiments, hollow fiber constructs can be used as cylindrical shaped stents to be placed on the exterior surface of the blood vessel to deliver drugs for preventing stenosis or related disease.

In an embodiment of the invention, provided is a cardiovascular stent that comprises a hollow fiber that contains drug in its lumen. The hollow fiber can be, for example, woven into a braid. The hollow fiber can be made of a resorable polymeric material such as poly-L-lactic acid. Such material can have a residence time in the human body of several years before complete resorption occurs. Other resorbable polymers also are identified elsewhere herein can be used, with resorption time tuned by monomer selection. The use a hollow fiber allows storage and release over time of a larger quantity of drug relative to drug incorporated into a solid. Such a stent could be used inside a blood vessel in the manner of conventional stents. In certain situations, a similar geometry of a sleeve could be placed around the outside of a blood vessel, nerve, or the like.

Suture

Referring now to FIGS. 19-22, in an embodiment of the invention, provided is a suture comprising a hollow fiber that contains drug, as described elsewhere herein. A suture can have an end that is somewhat rigid and sharp-pointed, for puncturing tissue or steering a path through tissue, while trailing portions of the suture can be more flexible. For example, the leading end can be curved and can have a sharp end that is useful for puncturing skin or tissue. Trailing portions of the same suture can be more flexible and can be multi-strand for flexibility. In an embodiment of the invention, trailing portions of the suture can comprise a plurality of individual hollow fibers that can be braided, or can be twisted, or might not be either braided or twisted.

In the trailing portion of the suture, there can be a plurality of hollow-fiber containing drug as disclosed herein, while a second type of strand or strands can be solid or of still other design. Materials of construction of some strands can be different from those of other strands. Some strands or fibers, such as the second type, can be structural, in that it or they can be mechanically stronger than the hollow fibers. Some or all of the hollow fiber strands can be pre-filled with drug. Some or all of the hollow fiber strands can be capable of being filled or re-filled during use. In embodiments, some hollow fibers can be pre-filled while other hollow fibers can be connectable to an external source or port allowing them to be filled or re-filled during use.

Figure 22:
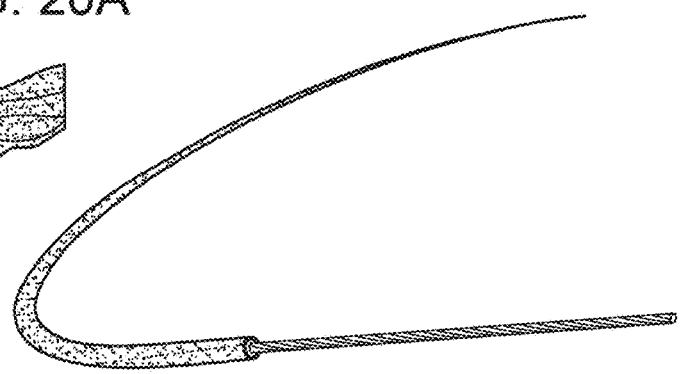
FIG. 22 shows a suture of FIG. 21 together with a suture needle.

A plurality of fibers can be twisted into a thread (FIG. 19; FIG. 22, shown much foreshortened) in a manner well known in the textiles field.

The fibers in the suture can be a mix of hollow and solid fibers, as shown in FIG. 19. For example, fibers that are not hollow and drug-containing can be made of a material that is different from the material of the hollow or drug-containing fibers, and can be structurally stronger than those fibers. For example, a suture configuration could have a structural fiber in the center and braided around it there could be a braid of hollow fibers that contain drug. This is illustrated in FIG. 19.

For such a suture, at the trailing end there can be left a trailing connection to the hollow fibers. Such a trailing connection can extend beyond the site of the suture in a patient's body, and can allow the hollow fibers to be refilled at any time at which the trailing connection is still connected to the hollow fibers. Such refilling can be accomplished by causing desired drug-containing fluid (solution, suspension, gel, etc.) to flow within the lumen generally along the longitudinal direction of the lumen toward the patient.

It is further possible that, in an embodiment of the invention, a suture could comprise a plurality of drug-containing hollow fibers, at least some of which can be braided with each other. The suture could further comprise a leading end that is stiff and sharp-pointed.

A suture can be used in an environment in which much of the suture is exposed to bodily fluids during use, but the suture as supplied can be in a dry condition. This means that in order to achieve release of the drug from the lumen of the fiber, with desired release kinetics, it can be useful to establish a liquid path connecting the outside of the fiber with the lumen of the fiber, through the pores. In order to help accomplish this, in embodiments the surface of the hollow fiber and the surface of the pores have hydrophilic characteristics.

Figure 20A:
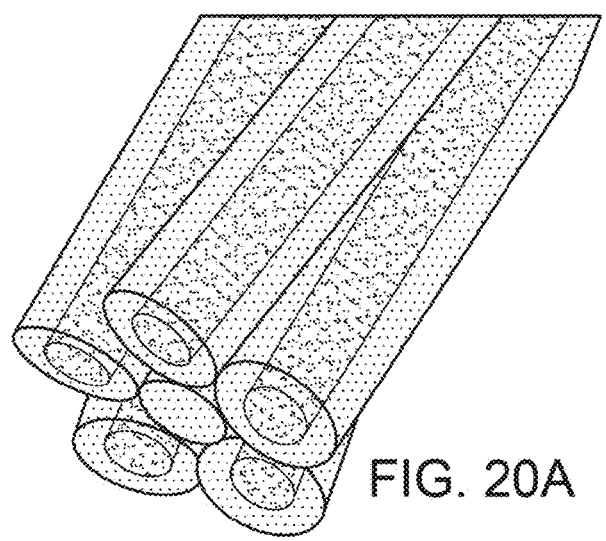
FIG. 20A shows a multi-fiber suture, in which outer fibers are hollow fibers and the inner fiber is a solid fiber.
Figure 20B:
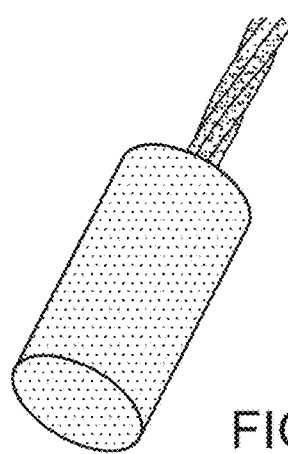
FIG. 20B shows a suture such as the suture of FIG. 19 potted in a potting material.

In order to form a connection suitable to transfer or flow liquid into the lumen of the hollow fiber at its trailing end, an end of the suture can be immersed in a liquid urethane potting material, which encapsulates the fiber ends. The urethane potting material may then be hardened into a solid material, as shown in FIG. 20.

Figure 21:
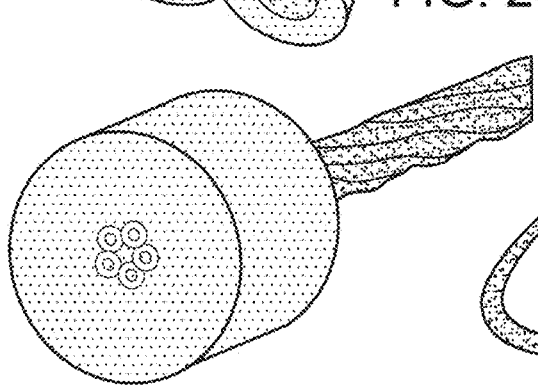
FIG. 21 shows the suture of FIG. 20 with some of the potting material removed to expose the lumens of the hollow fibers.

A portion of the hardened urethane can then be cut away, to re-expose the lumens or open fiber end of the hollow fibers, as shown in FIG. 21. The cut surface can be cleaned or polished if desired. Then the remaining urethane material can be clamped or joined to or placed in fluid communication with an appropriate filling manifold. A quantity of a filler material or formulation, containing a pharmaceutical or a biologic drug, can then be introduced through the filling manifold with sufficient pressure to cause it to flow into or through the fiber lumens, filling them. The release rate can depend on the drug formulation, on the driving force for release, which can be due to concentration gradient or to inclusion of osmogens or super-absorbents to making the construct so that it would function as an osmotic pump. Combinations of drug release mechanisms can be included in the formulation used to fill the lumens of hollow fibers.

After filling, the urethane potting material can be cut away and discarded. The distal ends of the fibers can be sealed, and the proximal end of the suture thread can be cemented or otherwise joined into the socket of a suture needle, as depicted in FIG. 22. The suture needle can be sharp-pointed at its end that is away from the fibers, so as to relatively easily puncture tissue. The suture needle can be more stiff, especially in bending, than the stiffness of the hollow-fiber portion of the trailing portion of the suture. The suture needle can be more stiff than the stiffness of the hollow fibers or even the stiffness of the solid-fiber portion of the suture. For example, the suture needle can be at least 5 times as stiff, or at least 10 times as stiff, or 100 times as stiff (with the possible exception of the very narrowest and sharpest portion of the suture needle nearest its tip). Alternatively, the device can be used with the fibers still assembled to the potting material that was used to help fill the fiber lumens. For example, this would permit the fibers to be filled or re-filled during use or during treatment for the desired period of time.

It is furthermore possible that the sutures or the fiber making the sutures can be segmented or compartmentalized after loading with drug, or alternatively before loading with drug, as described elsewhere herein. Such segmentation of compartmentalization would provide a larger number of individual drug-containing pockets or regions along the length of the suture, as opposed to having a single uninterrupted lumen in a given fiber.

Nerve Guide

Figure 23A:
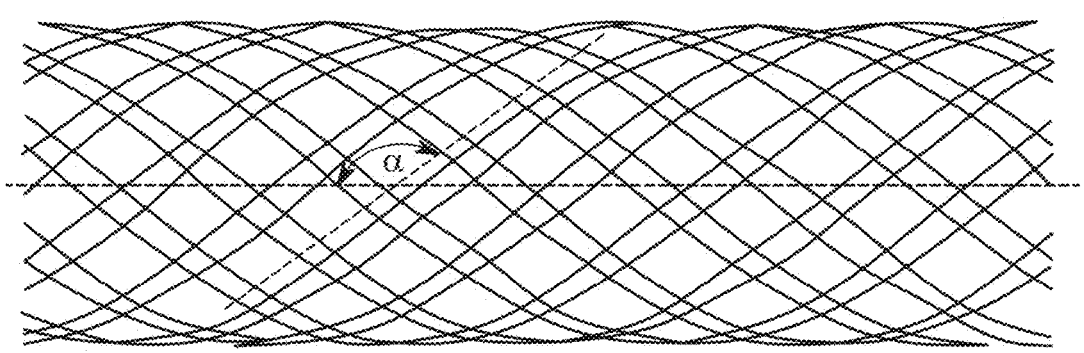
FIG. 23A shows a braid of hollow fibers.
Figure 23B:
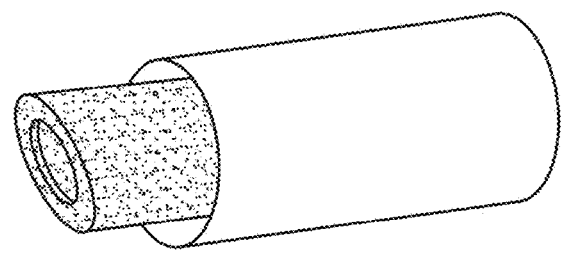
FIG. 23B shows a braid surrounded on the outside by a substantially impermeable layer (where drug does not permeate to provide an effective amount).

In an embodiment of the invention, it would be possible to make a nerve guide construct for use in re-growing, treating or repairing severed nerves. Referring now to FIG. 23A-23B, such a nerve guide could be of a generally tubular geometry and could be made by braiding fibers to form a tubular configuration. The fibers could be braided such that some individual fibers occupy a first generally helical path. Those fibers can cross over and under other fibers, and these other fibers can occupy a second generally helical path. The second generally helical path can be a helical path of opposite direction or handedness compared to the first helical path. FIG. 23A defines an angle alpha, which is the slope of the helix relative to the overall longitudinal direction of the braid. The angle alpha could be in the range of 15 degrees to 75 degrees, or more particularly, 30 degrees to 60 degrees. If there are two windings of opposite handedness or direction, the respective angles could be the same except for sign. What is illustrated in FIG. 23A shows fibers braided in pairs, but more generally any desired number of fibers could be braided together. At their ends, at least some of the fibers can have closed ends.

It is also possible that a nerve guide could have fibers that are helically wound just in one direction, without being braided. It is still further possible that there could be a layer that is wound helically in one direction, and is in turn surrounded by a layer that is wound helically in the opposite direction, with the layers being separate and unbraided.

In other embodiments, a mesh made from hollow fibers loaded with drugs can be rolled into a cylinder shape and used as a nerve guide construct. The cylindrical construct can be made such that it can be wrapped around the injured nerve. In this way it will be easy for the surgeon to wrap the hollow fiber mesh around the nerve and then suture the sides of the nerve guide mesh in place as desired. The nerve guide construct can be equipped with a filling catheter and port so that it can be loaded with drugs as described elsewhere herein. In related embodiments the hollow fibers used to make the nerve guide construct can comprise either permanent materials or resorbable materials as disclosed elsewhere herein. In the case when permanent fibers used, the nerve guide construct can be designed so that it can be removed after the completion of the therapy as describe elsewhere herein.

In such a nerve guide, at least some of the fibers could be hollow fibers of embodiments of the invention. Such hollow fibers could contain biologics, growth factors etc. that promote the regrowth or healing of nerve tissue. Referring now to FIG. 23B, it is further possible that the tubular construct could comprise, on its outside, a barrier that prevents or inhibits the outward passage of the biologic substances or molecular drugs that were originally contained in the hollow fibers. Such a barrier could be impermeable or only slightly permeable to such substances. Such a barrier could help to retain the useful biological substances or molecular drugs at or near the nerves that are to be regrown, repaired or treated.

Osmotic Pump

Figure 24A:
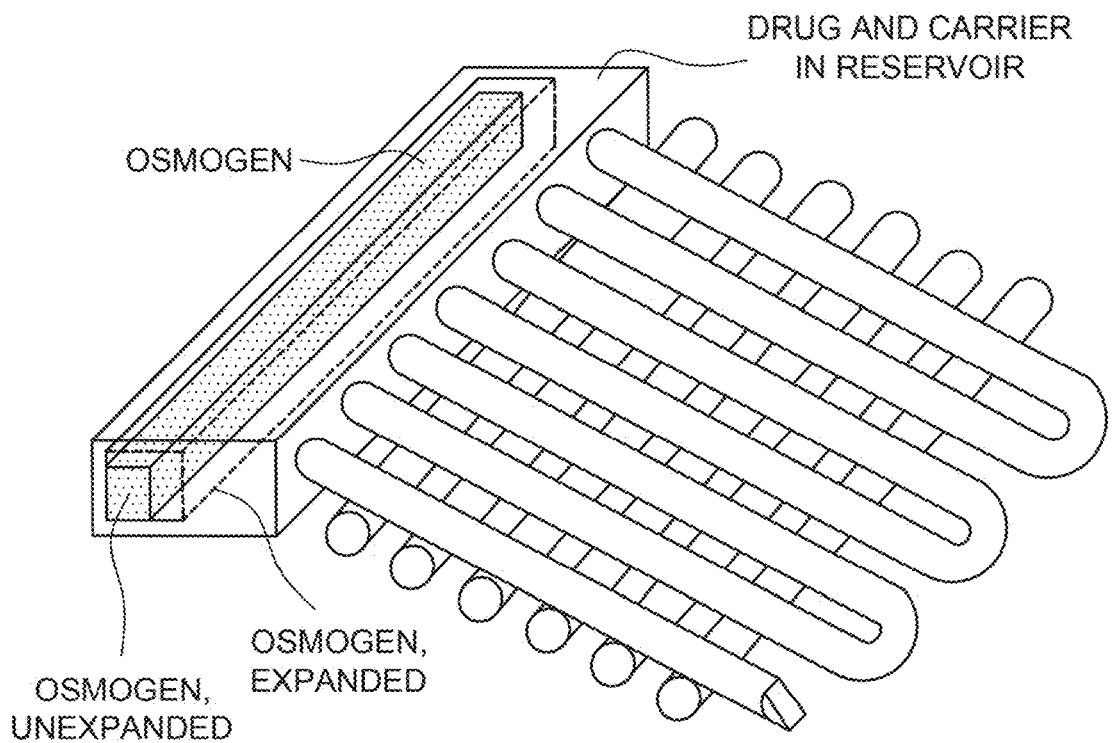
FIG. 24A shows an arrangement of hollow fibers connected to a manifold that is an osmotic pump.

Referring now to FIG. 24A, an osmotic pump, in general, is a device that comprises a chamber and a swellable material or an osmotic inducing agent referred to as an osmogen, and a fluid to be dispensed from the chamber. The osmogen can imbibe water or bodily fluids, and can swell (increase its volume) when it absorbs water or bodily fluids, and in so doing can expel or urge the fluid out of the chamber, often with drug, so as to be administered to the patient. In an embodiment of the invention, provided is porous-walled or semipermeable-walled hollow fibers in combination with an osmotic pump mechanism or assembly. Such a device can comprise a common reservoir and one or more hollow fibers in fluid communication with the common reservoir. The osmogen or osmotic pressure inducing agents can be located in the common reservoir such that when the osmogen expands, it expels drug-containing fluid from the common reservoir into the hollow fibers which can be loaded with drug or combination of drugs. The common reservoir can be made from semi-permeable membrane as it is known in the art of osmotic pumps. The hollow fibers according to embodiments of the invention will function as the drug reservoir of conventional osmotic pumps. The pores of the hollow fibers will function as the orifice or hole of a conventional osmotic pump. That drug-containing fluid can then exit to the surrounding tissue via the pores in hollow fiber walls or can expel other already-present fluid to exit to the surrounding tissue, or both.

The osmogene can comprise the drug, wherein the reservoir is configured with a membrane with a MW cutoff effective to retain the drug (e.g., drug with MW 2,500, MW cutoff 1,000).

In other embodiments of the invention, other designs of osmotic pumps are possible where one portion of hollow fiber contains an osmogen and the other portion is designed for drug delivery covering a spatial area of a bodily organ or tissues. The compartment that includes the osmotic agents can be made from semipermeable membrane to allow water to enter the pump. The hollow fibers in this pump construct will function to deliver drugs to the designated tissues as is known in the art of osmotic pumps. In embodiments of the invention the hollow fiber portion of the osmotic pump can cover a large surface area of tissues or organs to be treated.

Manifold or Reservoir, and Fluid Connection that is Releasable

Figure 24B:
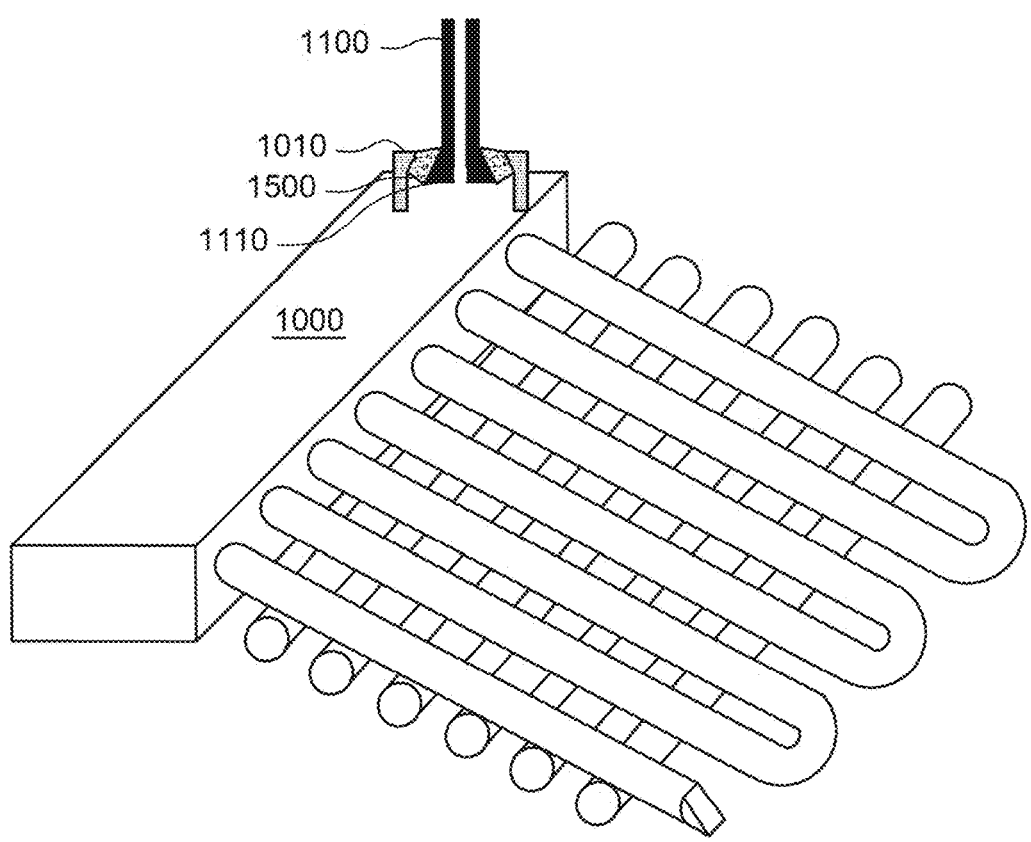
FIG. 24B shows an arrangement of hollow fibers connected to a manifold.
Figure 24F:
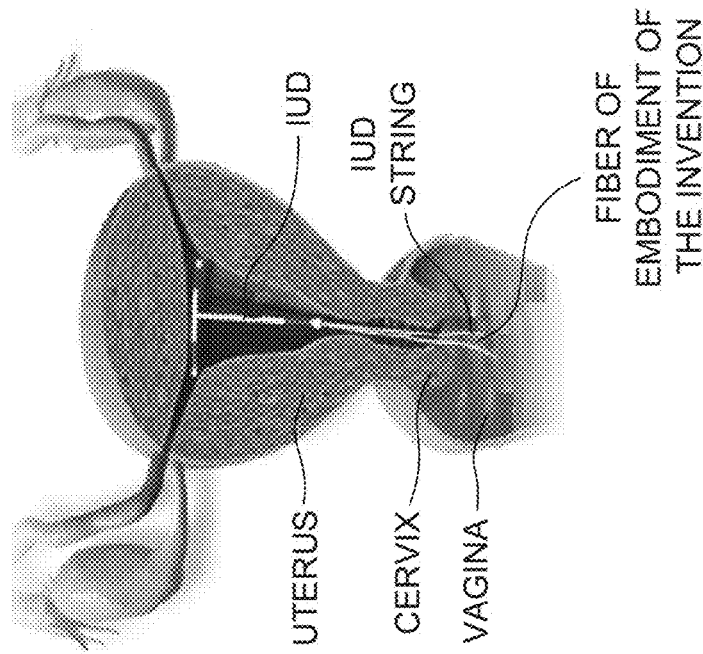
FIG. 24F shows an embodiment of the invention in use in the female reproductive tract.

Referring now to FIG. 24B, in an embodiment of the invention, provided is an implantable drug delivery device comprising hollow fibers, and a common space that is in fluid communication with the lumens of the hollow fibers. Furthermore, provided is a tube in communication with the common space such as to either introduce fluid to the common space, or remove fluid from the common space. It is of course also possible to provide two such tubes, one to introduce fluid and one to remove fluid. In related embodiments, the above tubes can be used to flush the device with a sterile solution or provide other treatments including irrigation, disinfection or to perform other functions such as draining, diagnostics or others.

As illustrated, at least some of the fibers can be straight in one direction or laid out in a U-shaped pattern such that each end of the fiber connects to the common space. It is also possible, and one such fiber is illustrated, that a hollow fiber can connect at one end to the common space and at the other end can be dead-ended. The dead end is illustrated as being crimped and possibly fused. It is possible to combine both U-shaped and dead-ended fibers.

There is further illustrated a tube that is in fluid communication with the common reservoir 1000. Such a tube 1100 can be used either to deliver fluid to the common reservoir or to remove fluid from the common reservoir 1000. Tube 1100 can be made of a non-resorbable material. A combination of features can be provided that allows tube 1100 to be separated from the rest of the device after a period of time. Tube 1100 can have at its end an enlarged feature 1110, which can comprise a taper and a maximum outside diameter. Also, common reservoir 1000 can have a receiving feature 1010 that comprises an inwardly-facing taper. Further, provided is a release component 1500, which can be shaped like a tapered collar, that is dimensioned to fit between tube enlarged feature 1110 and receiving feature 1010. Release component 1500 can be made of a material that is resorbable on a time scale comparable to a time at which it can be desired to disconnect tube 1100 from common reservoir 1000. Appropriate dimensions can be chosen such that when release component 1500 is in place and has not undergone resorption, it retains tube end 1110 within receiving feature 1010. However, when release component 1500 is no longer present, such as due to resorption, it can be possible for tube end to be withdrawn from receiving feature 1010. For example, various dimensions can be chosen such that the maximum outside diameter of tube enlarged feature 1110 can be smaller than the minimum inside diameter of receiving feature 1010. This allows the tube enlarged end 1110 to freely pass through receiving feature 1010 in the absence of release component 1500. Variations of the above designs are also possible depending on the therapy and on the site of implantation.

A related possibility would be to have the common reservoir 1000 be centrally located in the device, and to have hollow fibers extending out in various directions from the common reservoir. For example, the hollow fibers could extend out in an approximately radial pattern.

In an embodiment of the invention, the described construct could be used to deliver fluids into the patient's body. In an embodiment of the invention, a construct comprising hollow fibers connected to a manifold could be used to suction fluid out of the patient's body. For example, this could be used to relieve lymphedema.

Double Manifold or Reservoir

It is possible to have two fluid connections to the manifold, or fluid connections to both ends of the fibers, as illustrated in FIG. 24C. This would permit more options as far as filling, overflow, removing and flushing fluid to or from the lumens of the hollow fibers of the device or construct.

Embodiments of the invention could have two distinct ports. Such two ports could be located at and could be in fluid communication with opposite ends of hollow fibers. In such a way, one of the ports could be a supply port and the other could be a return port. This would make the channels or lumens flushable, i.e., instilled material could be removed from the device and from the patient's body, and could be replaced with other material such as a different drug or a different drug formulation. For example, it is possible that the needs for administered drug or dose could change during the course of treatment, in either the composition or the concentration or any other parameters can be adjusted or controlled as desired. As a further consideration, simply varying the solvent or other aspect of composition of a drug can also help in modulating its release profile. This would allow the delivered drug or drug formulation to be changed when desired. Such manipulation could also be accomplished to a lesser extent with a single manifold. With a single manifold, it would only be possible to introduce new material, not to remove old material. Thus, a drug or a drug formulation could be changed after or as the previously existing drug exited from the device by being administered to the patient.

Ports, Filling and Flushing

In embodiments of the invention, provided is a port or ports for establishing a fluid connection between a supply device outside the patient's body, such as a syringe, through the patient's skin, into a port. The port in turn can be in fluid communication with the lumens of the hollow fibers. The use of a port can provide a way of introducing drug or other substance to a device after the device has been implanted in a patient. The port can comprise a rubber or other polymeric septum, which can be able to be punctured by a hypodermic needle or similar device. When the hypodermic needle or similar device is absent, the septum can substantially maintain separation of its interior from its exterior and prevent leakage of the contents of the implant. The septum can be such that if it is punctured by a hypodermic needle and then the needle is removed, the material of the septum will close up sufficiently to prevent any significant leakage through the septum.

The use of a port can provide the ability to introduce additional drug into the device at some time after the implantation of the device, and thereby can make the device suitable for a longer period of use. As discussed elsewhere herein, it also becomes possible to change the substance that is delivered. With the use of two ports one of which can be used for removal of substances, it becomes possible to flush out the contents of the device, which can be useful for replacing the contents of the device with some other contents.

Figure 24E:
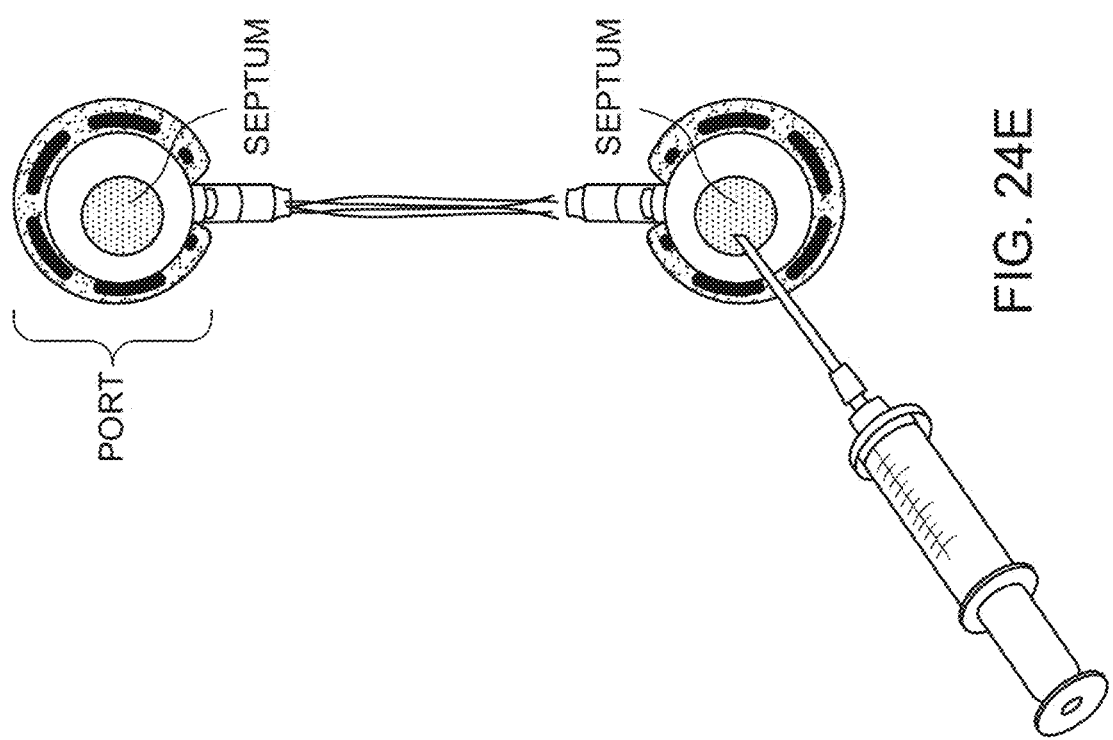
FIG. 24E shows a plurality of fibers that can be accessed through ports.

It is possible, as illustrated, to provide a port 1432 at each end of the hollow fibers 1430. The hollow fibers 1430 are shown in FIG. 24E as being in the form of a bundle of fibers, but they could also be in the form of an array of fibers such as a fabric or a braid. Of course, it would also be possible to provide such a device with only one port 1432 rather than two ports 1432 as illustrated. At the end that does not have a port 1432, the fibers could be dead-ended.

In yet another embodiment, it would be possible that the supply tube could also serve as a drain, such as a Penrose drain, to facilitate the drainage of fluid from a surgical site. Drainage of abscesses arising from internal infections is always necessary and in these cases, devices and constructs made with hollow fibers according to this invention can be used to facilitate such drainage. In related embodiments such devices or constructs can at the same time be used to deliver antibiotics or other drugs to the local sites. These procedures are common in cases of colon leakage in the abdominal cavity due to diverticulitis or related other causes such as appendicitis or the like. The tube could be a double-lumen tube, with one lumen serving to drain the surgical site and another lumen serving to supply drug to the hollow fibers. The drainage tube can be removed and the supply connection can be broken off of or disconnected from the hollow fiber network, by removing the tube at a desired time. This could be accomplished, as discussed elsewhere herein, by degradation of a connecting element.

In yet another embodiment of the invention, a triple-lumen construct could provide drainage of fluid from the surgical site, as well as fill to and overflow removal of drug from the hollow fibers.

Catheters and Tubes that Contain Fibers of Embodiments of the Invention

Referring now to FIG. 24D, sometimes tubes or catheters can be manufactured such that they contain, within their walls, fibers or strands of fibers. For example, such fibers can be provided for structural strength such reinforced tubing and hoses. Catheters can be manufactured to include braided fibers, or fibers in other configurations. An embodiment of the invention can be catheters or tubes that contain, in their walls, fibers that are drug-eluting. Such catheters or tubes can have, embedded within them, hollow fibers that contain drug. It is possible that the hollow fiber could be exposed at or near the surface of the catheter or tube. However, the hollow fiber does not have to be exposed at the surface of the catheter or tube. Rather, the drug-containing hollow fibers can be embedded in the wall of the catheter or tube. The surface of the catheter or tube can be a material that is chosen and manufactured for the properties that it presents to the tissue that it contacts. For example, such property can be smoothness, lubricity, hydrophilicity, chemical composition and other properties. In such tubing or catheter that contains hollow fibers, the hollow fibers can be pre-loaded with drug, or they can extend out of an end of the catheter or tube such that they can be filled or re-filled during use. In an embodiment such as a catheter or tube that contains hollow fibers, the path for the drug can be to pass out of the fiber lumen through the fiber wall, which can be porous, and then the drug can have to pass through that portion of the catheter wall or tube wall that exists between the hollow fiber and the surface of the catheter or tube. In such a situation, the wall of the catheter or tube might be a resistance to diffusion or passage of drug therethrough, but depending on the amount of surface area provided by the catheter or tube, and other factors, there can still be the ability to deliver a useful amount of drug to adjacent tissues.

In embodiments, the wall of the catheter or tube can contain more than one type of fiber. Different fibers within a wall of a catheter or tube can have different purposes. For example, again, some fibers can be structural while other fibers can be hollow fibers for drug delivery. Fibers that possess structural strength can be of use if the catheter or tube is intended to contain internal pressure during use. Multiple different kinds of drugs or drug-containing hollow fibers can be used within a construct. The catheter or tube material can be made from polymers or polymer blends that can allow or permit drug transport from the hollow fibers present in the catheter or tube wall to the adjacent tissues. Examples of such catheter materials can include polyurethane with different hydrophilicities such as those made by Lubrizol Company referred to as TPU, ethylene vinyl acetate copolymers (EVA) with high vinyl acetate content up 30 or 40% or more, silicone polymers known in drug delivery including Carbothane others, and other polymers dedicated for drug delivery. The catheter or tube material can include plasticizers diffusion enhancers or compounds that facilitate drug transport and diffusion such as polyethylene glycols (PEGs), polyvinyl pyrrolidone (PVP), polyvinyl alcohol, and the like. The catheter material can be made from sold polymer or can be made porous to facilitate drug transport from the hollow fibers to the surface of the catheter or tube in contact with tissues.

Two antibiotics that are currently approved by the US Food and Drug Administration for use with catheters are minocycline and rifampin. One of these is effective against gram-positive bacteria, while the other is effective against gram-negative bacteria. Of course, other antibiotics, antimicrobials and other drugs in general are also possible and could be used.

Use Near a Penetration Through the Skin

The fabrics, meshes, constructs or other embodiment of the invention can be used in or near a medical device that passes through the skin of a patient. For example, an embodiment of the invention could be used in connection with pin tract stabilizers such as for orthopedic pins that extend through the skin for stabilization of complex fractures or for distraction osteogenesis. The pin could be made of a plastic that includes hollow fibers of embodiments of the invention. Alternatively, a fabric of an embodiment of the invention could be used near a conventional pin for example in the form of a sleeve or a form of wrapping. Another related application is use of the fabrics of the invention to prevent catheter sites from being infected during use.

Of the fibers that make up the sleeve, some (or all) of those fibers could be hollow fibers that contain a pharmaceutical or biological substance in their lumens. It is also possible that some of the fibers could be solid fibers, which could be made of a different material.

An embodiment of the invention can be used near or around or in a feeding tube that extends through the skin of the abdomen of the patient. An embodiment of the invention can be used near or around or in a fistula for hemodialysis. An embodiment of the invention can be used near or around a catheter for peritoneal dialysis. An embodiment of the invention can be used near or around a post-surgical drainage tube.

Dental Applications

In an embodiment of the invention, a hollow fiber of an embodiment of the invention can be or can be part of dental floss. Dental floss can be either single-filament or multi-filament. Also in the dental field, in an embodiment of the invention, dental retraction cord, also referred to as gingival retraction cord, could be made containing hollow fiber(s) that contains drug prior to use or that is filled or re-filled with drug during use such as root canal or in the treatment of chronic gingivitis or the like. Such floss or cord could comprise features or chemistry that are described herein.

Rolled Up Geometry

Some of the description herein has been of embodiments in which fabric is implanted into a patient in a somewhat flat configuration. However, that is not the only possible configuration. It is further possible that an implant could comprise fabric or an assembly of fibers that is made in a generally flat configuration and is rolled up into a spiral configuration, and is implanted in the spiral configuration. The fabric or assembly of fibers could have any of the configurations described herein. Thus, the implant could have an overall external shape that is approximately cylindrical, yet the implant would also have the total fiber surface area and other properties associated with the fibers or fabric configuration. Such a device could be implanted in a location and manner similar to that in which known contraceptive rods are implanted, or it could be implanted in any other manner and location desired.

The fibers that are rolled up could be of any configuration. For example, the hollow fibers could extend longitudinally along the longitudinal axis of the rolled-up spiral. The cross-fibers could be solid fibers attached to the hollow fibers. The cross-fibers could be inter-woven with the hollow fibers. The cross-fibers could be randomly oriented. A bubble-wrap configuration as described in another embodiment herein could be rolled up.

It can also be appreciated that a device could comprise an assembly of fibers that is made in a generally flat configuration and is bunched together in any manner, such as a zig-zag configuration, and is implanted in the bunched-up configuration. The bunched-up configuration could, for example, be held together by stitches.

Applications associated with the female reproductive tract

Embodiments of the invention can use drug-containing hollow fibers in various products that are associated with the female reproductive tract.

One common device used in the female reproductive tract is a contraceptive in the form of an IntraUterine Device. Often such a device has the shape of a "T." Some such known devices comprise copper, which provides a contraceptive effect. Some such known devices release hormones such as levonorgestrel, which provide a contraceptive effect hormonally. In many such devices, one or more monofilament fibers called retrieval strings extend from the lower end of such a device, and can extend out through the cervix.

In an embodiment of the invention, such an IntraUterine Device can include fibers that are hollow and contain drug or other agent. For example, such fibers can extend from the stem of the "T" in an orientation similar to that of conventional retrieval strings. Such fibers can be of a length that is appropriate to remain within the uterus, or can be of a length that is appropriate to extend beyond the uterus through the cervix, or can be of a length that is appropriate to extend beyond the uterus through the cervix into the vagina. Such fibers could be provided instead of or in addition to conventional retrieval strings.

In an embodiment of the invention, such fibers can be included in a tampon or similar device. Such fibers could be included possibly in addition to other kinds of fibers that can also be present. The drug-containing hollow fibers can be placed in random relationship to other fibers that can also be present. Alternatively, the drug-containing hollow fibers can be attached to or woven among or otherwise placed in specific spatial relationship to other fibers that can also be present. Drug-containing hollow fibers can be placed throughout the space of a tampon, or they can be placed only in specific regions of a tampon, as desired.

In general, the substance to be released in any of these devices associated with the female reproductive tract can be an antibiotic such as to combat infection, or an anti-fungal substance, or a hormone associated with contraception, or a substance to inhibit or stop the spread of a sexually transmitted disease, or a chemotherapeutic substance, or generally any substance that has a desired clinical effect. It would be possible to provide more than one such substance in the device. Different substances or different concentrations can be placed in specific places within the device as may be desired. Different fibers can have different release substances as may be desired.

Substances could be delivered to only certain places in the female reproductive tract based on the substances being placed in only certain places along the length of the fiber. If desired, different substances could be provided in different places along the length of the fiber. These features could be provided, for example, if the fiber is subdivided into regions or compartments as discussed elsewhere herein, and appropriate drug is loaded into appropriate regions or compartments of the fiber.

Yet another device used in the female reproductive tract is a vaginal ring. Vaginal rings are made of a soft polymer and provide controlled release of drugs over extended periods of time. It is also possible that such a device could contain a substance that provides protection against sexually transmitted diseases. In an embodiment of the invention, fibers of an embodiment of the invention could be attached to or integral with a vaginal ring and could deliver drug. The fibers could extend along the perimeter of the ring, or could extend away from the ring, or both.

In yet another embodiment of the infection, the device could be used to treat urinary tract infections. A device comprising fibers of embodiments of the invention could be introduced into the urinary bladder and could deliver drugs as desired. The drugs could be antibiotics, anti-fungals, or any other desired substance. The device could be an array of fibers in a pattern, or it could be an un-patterned array. Provision could be made for the device to be pulled out or removed from the urinary bladder when desired.

Additional Uses

Fabric can be a material used in reconstructive surgery. Embodiments of the invention can be used in closure of a surgical site, for example the skull during brain surgery. A fabric or construct based on hollow fibers can be implanted in the brain to treat tumors or prevent metastasis or manage pain or perform other functions. Such devices can be equipped with filling ports to manage treatment or therapy as discussed elsewhere herein.

Embodiments of the invention can be used in surgery for joints such as the knee to deliver anticoagulant locally or manage pain or promote healing. The fabric or other form of the device can be left in place to deliver the anticoagulant or manage pain or promote growth of ligaments.

A device according to embodiments of the invention can be left in place after cancer surgery to deliver chemotherapeutic drugs, such as for the prevention of metastases. The place or position of the implanted device can be determined by the surgeon depending on type and location of surgery and on the known flow direction of fluids and cells that can cause metastasis.

Embodiments of the invention can be provided in the form of a fabric to be wrapped around or placed near a bone implant. Embodiments of the invention could be placed in or near a spinal fusion implant to deliver drug, growth factor etc. that might promote the growth of bone to achieve fusion or healing of bone. Other implants and constructs can be anticipated based on embodiments of the invention and hence other applications should not be limited to those mentioned in the present disclosure.

Use of Embodiments of the Invention for Diagnostic Purposes

The material contained inside a hollow fiber can be an absorbent or adsorbent for certain substances, whether those substances are solid or liquid or gas. The membrane can admit gases for adsorption onto a substance that is inside the lumen of the fiber. The membrane can admit liquids for adsorption onto a substance that is inside the lumen of the fiber. Such a fiber can be a way of obtaining a sample of a bodily material, and such sample can be used for diagnostic purposes or analysis such as to identify toxins or to diagnose diseases. This can be done either upon removal of the device from the body, or, if a connection to the fiber exists, perhaps material could be extracted from the fiber lumen while the device is still in place.

The fibers could be implanted under the skin or subcutaneous in such a way that it is possible to refill the fibers with the aid of catheters. An example application can be an implant in the lymph node basin to prevent or treat organ rejection or prevent cancer metastasis as in the case breast cancer or other forms of cancer including melanoma or similar skin disease.

EXAMPLES

Embodiments of the invention are further described, but are in no way limited by, the following non-limiting Examples.

Example 1. Antimicrobial Efficacy

To demonstrate proof of concept, we used microporous hydrophobic polypropylene fibers and hollow fiber fabrics and hollow fiber meshes with an internal diameter of 300 µm and with wall thickness about 30 microns. To assess the antimicrobial efficacy of drug loaded hollow fibers, we used a modified Kirby-Bauer assay where a zone of inhibition of bacterial growth was measured on a solid agar plate as is normally done in the field of microbiology. This model was used since it allowed us to capture the real time drug release from the hollow fibers and at the same time to represent a model of drug release into a soft tissue. The test antibiotics were vancomycin and ciprofloxacin and our challenge organisms were *Pseudomonas aeruginosa* PAO1 Xen41 and *Staphylococcus aureus* 16MRSA Xen30, both are bioluminescent strains. Vancomycin was chosen for proof of principle with the hollow fibers devices because this antibiotic has precedent in being commonly used to combat *S. aureus* infection in orthopedic joint arthroplasties, where locally high concentrations are delivered by elution from both non-absorbable (polymethyl methacrylate, PMMA) and absorbable mineral cements. Ciprofloxacin was used since it is a broad spectrum antibiotic used to target Gram negative pathogens such as *P. aeruginosa*. In addition, water soluble fluorescein sodium was used as a model drug to assess the release of a hydrophilic water-soluble agent from the hollow fiber drug delivery system. All reagents were purchased from Sigma-Aldrich. *P. aeruginosa* and *S. aureus* are biofilm-forming pathogens commonly isolated from infected meshes and sutures, and the strains we have selected have been transformed with bioluminescent genes so that live biofilm development and activity can be tracked in real time using a photon counting camera (Xenogen IVIS imaging system, Alameda, Calif.). The selection of methods and drugs was made to demonstrate the main embodiments of the invention regarding drug delivery and release from hollow fibers and hollow fiber based constructs and devices and in this sense the examples or methods are not be limited to antibiotics or antimicrobial drugs or applications.

Filling the Hollow Fibers

Figure 25:
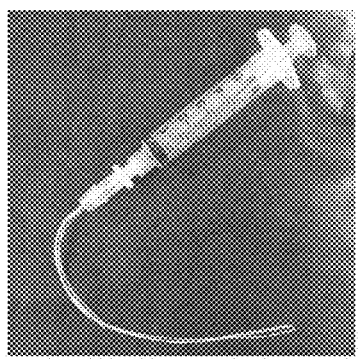
FIG. 25 shows a hollow fiber bundle attached to a syringe for filling the lumen of the fiber, for use in an experiment.

This example teaches one basic method to fabricate a hollow fiber construct for use in drug release per embodiments of the invention as provided in FIG. 25. The same fabrication principles can thus apply to more complex devices as described elsewhere herein. The drugs used in the Example are not intended to be limited to antibiotics. Other classes of small molecular weight drugs or biologics can be delivered from devices and constructs according to embodiments of the invention.

A small number of selected hollow fibers (300-micron internal diameter) were potted into a special Luer connector that fitted on a sterile syringe using a medical grade biocompatible polyurethane resin as used to make hemodialyzers. Once the resin was cross-linked or cured, fiber openings were exposed by cutting through the resin portion with a sharp tool. To fill the fibers, we filled a syringe barrel with a saturated solutions of either vancomycin (100 mg/mL), ciprofloxacin (30 mg/mL) or fluorescein (1000 mg/mL) in normal saline, then attached it to the fiber bundle potted into the Luer-lock fitting (FIG. 25). Pressure was applied on the syringe plunger until liquid drops were visibly seen to form at the open end of each of the hollow fibers. The open ends of the fibers were then closed or sealed either by tying a surgical knot or by the application of an adhesive resin. The Luer-lock ends of the fiber bundle were then tied off or sealed with an adhesive resin as described above. The hollow fibers made this way are filled with the saturated drug solution with both ends closed as it would be if they are used as implant according to embodiments of the invention.

Fluorescein Release

Figure 26C:
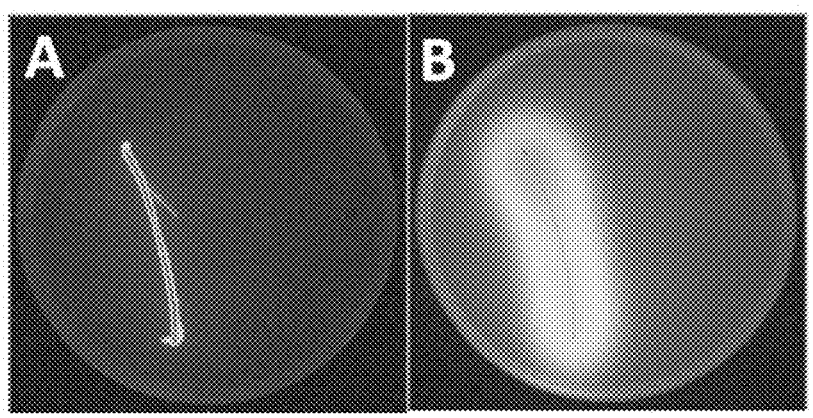
FIG. 26C is a three-dimensional intensity profile showing qualitatively how the fluorescein concentration varied spatially around the fiber.
Figure 26C:
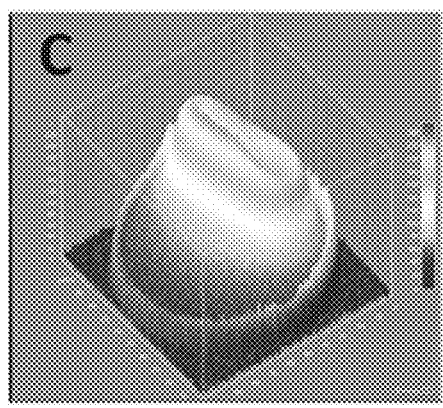
Figure 26D:
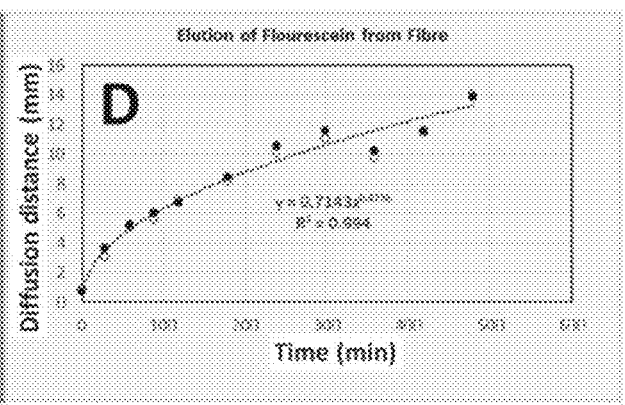
FIG. 26D is a plot showing release kinetics of the fluorescein.

To determine drug release properties from hollow fibers into an external medium or environment, we used a filter substrate or an agar plate method to simulate the drug release into a soft tissue with no convective flow. In this Example drug release takes place by diffusion only which is due to the concentration gradient between drug present in the fiber lumen and the external fluid in the agar. When untreated hydrophobic polypropylene fibers filled with drug were places on the agar surface there was no release as shown in FIG. 26A. However, after treating the drug-loaded hollow fibers with a small amount of 70% isopropanol, we obtained a significant release of the drug as shown in FIG. 26B. Treating the fibers with alcohol has rendered the pores in hollow fiber walls more hydrophilic as described elsewhere herein. The above treatment effected fluid communication between the drug present in the fiber lumen and the external fluid present in the agar gel or in the filter substrate. FIG. 26B shows significant Fluorescein release from the alcohol-treated polypropylene fibers at 8 hours after treatment with isopropanol. FIG. 26C is a 3D intensity profile showing qualitatively how the fluorescein concentration varied spatially around the fiber. FIG. 26D is a plot of release kinetics, release rate versus time, showing that the release was half order (exponent=0.47). These results are consistent with drug release from a reservoir by diffusion which follows the well-known Higuchi Equation.

The drug-loaded hollow fiber was placed on a lysogeny broth solid agar plate and the fluorescent signal was measured periodically using a gel imaging system. The images were imported into FIJI image analysis software (available at http://fiji.sc/Fiji) and were spatially calibrated using the diameter of the plate (100 mm). The automatic threshold function was used to determine the edge of the spreading fluorescein at the middle of the length of the fiber, i.e., the mid-point between fiber ends. Measurements were made in duplicate for each fiber. The elution distance from the edge of the fiber was measured and plotted as a function of time. The experiment was performed in triplicate. The "trendline" function was used to determine the power law function as shown in FIG. 26D.

This example demonstrates the general drug release from hollow fibers and provide methods that can be used to assess the release rates. The Example also shows the overall regularities of the release kinetics from the hollow fibers of the invention.

Based on these results, it is also possible to determine the duration of drug release if the initial amount of drug present in the fiber lumen is known. The latter quantity can be calculated from the volume and concentration of the solution used to fill the hollow fibers before sealing them. The above methods can be used to determine the amount of drug to be loaded in the construct or device according to the embodiments on the invention. Design parameters of the constructs including the fiber density in the fabric, number of fabric layers in the construct, dimension of the device, surface area of the fibers used in the device and other parameters useful to determine device requirements for different applications. Fluorescein is used here as a model hydrophilic drug only. Other drugs with different log p or other different properties can be used following the methods of the Examples to design constructs and control drug release properties as required.

Zone of Inhibition (ZOI)

Figure 27:
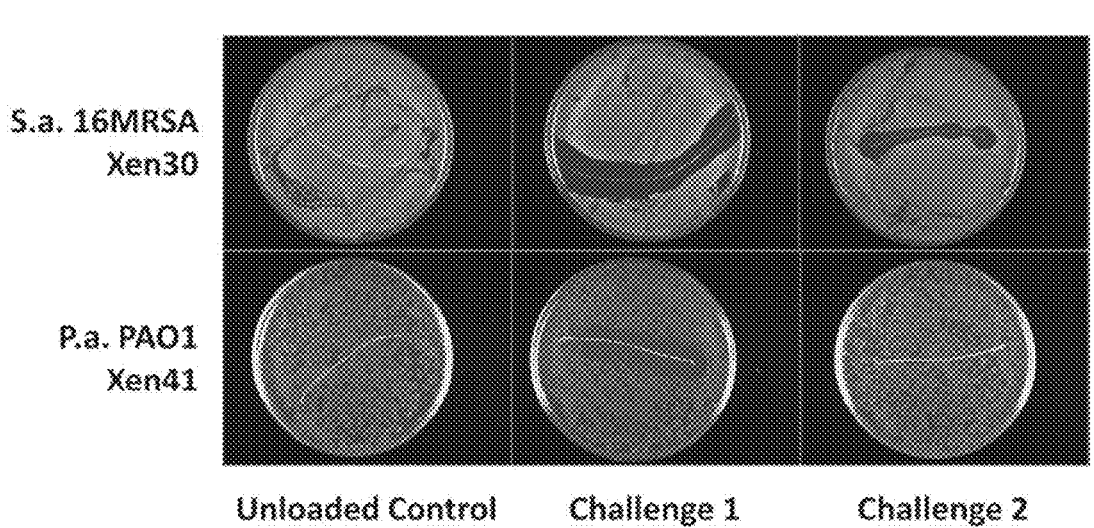
FIG. 27 shows that a zone of inhibition was achieved by the drug-loaded fibers challenged by bacteria.

In another set of experiments, we loaded hydrophobic polypropylene hollow fibers with either ciprofloxacin or vancomycin and challenged such fibers with *P. aeruginosa* or *S. aureus*, respectively (FIG. 17). A lawn of bacteria was spread out onto an LB (Luria broth) agar plate. A fiber was placed on top of the agar plate as shown in FIG. 27. The plate was incubated at 5% $CO_2$ at 37° C. for 18 hours for the first challenge. The fibers were then aseptically removed from the original plate and placed on a fresh lawn of bacteria on a new plate for the second challenge and incubated as before. Drug-free hollow fibers rinsed with isopropanol alone were used as controls. Experiments were repeated in triplicate. We were able to demonstrate drug release and achieve a zone of clearing after 24 hours in both cases. The fibers were then placed on a fresh plate and re-challenged. The vancomycin fiber showed activity on the second challenge (FIG. 27). FIG. 27 shows that a zone of inhibition was achieved by the vancomycin loaded fibers against our MRSA strain (top panel) for 2 days and by ciprofloxacin against *P. aeruginosa* for one challenge. The therapeutic release period can be predicted to increase by manipulating the amount of drug loaded in fiber lumens as well the wall surface hydrophobicity including the surface and pore structure of the fiber. The results of this example clearly demonstrate that the amount of drug included in the form of saturated drug solution can be sufficient for short duration therapies and that when long-term treatment is required loading the fibers with solid particles can be required as described elsewhere herein. Solid particles are known to include more drug amounts and can thus make up larger drug reservoir inside the lumens of the fibers. This example also demonstrates that adjusting the hydrophilic-hydrophobic properties of the fibers is required to allow drug release. The level of fiber treatment can be tailored to and controlled to further design the drug delivery characteristic of the devices and constructs of the invention.

Figure 28:
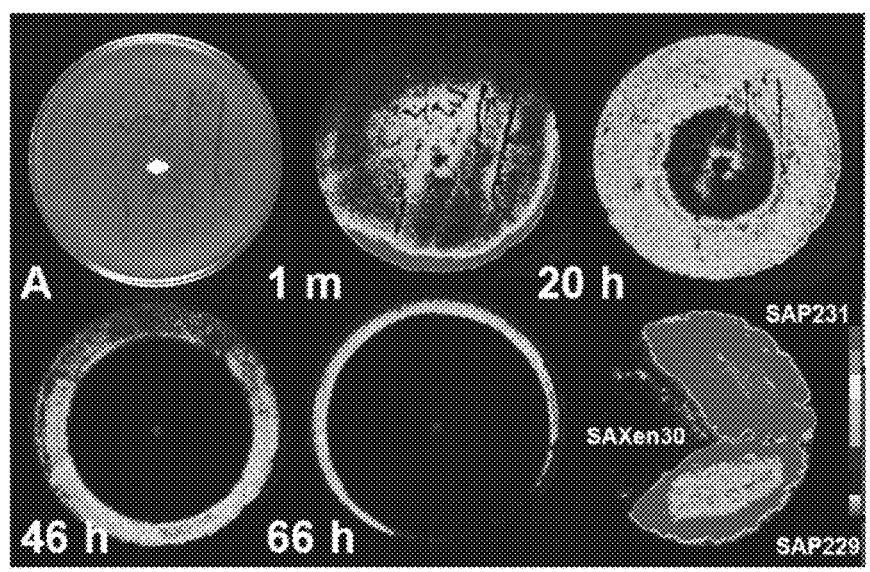
FIG. 28 shows results of a lawn biofilm killing assay technique.

Measuring bioluminescence allows the assessment of both biofilm activity and the zone of inhibition the the 24-hour biofilm lawn assay as shown in FIG. 28. The zone of inhibition (ZOI) method can be to be used to assess the antimicrobial activity of the released drug and at the same time to monitor for the development of resistant mutants within the ZOI. In this Example we have monitored the development of resistance by measuring the MIC before and after repeated exposure to the final mesh formulations using Etest®-strips (bioMerieux). To perform the lawn biofilm killing assay, a lawn of bacteria is allowed to grow for 24 hours before placing the drug loaded device over the surface of the lawn. In this assay, the biofilm activity was quantitated by measuring bioluminescence and the zone of killing was quantified as a function of time. The dark area in FIG. 28 indicate that the bacteris is dead bacteria. Panel A and time zones 1 minute to 66 hrs are PAO1 Xen41. The bottom right panel shows signal from three 24 hrs cultures from bioluminescent *S. aureus* strains (Xen41 and the SAP strains (SAP231 is a USA300 MRSA and SAP229 is a MSSA). The SAP strains are much brighter than the Xen41 strain.

Example 2: Release of Tacrolimus from Fiber Meshes In Vitro

Figure 29A:
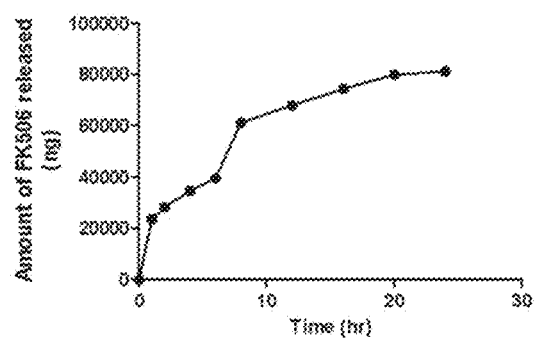
FIG. 29A shows a release profile of tacrolimus from a fiber bundle, in the form of a detailed curve of cumulative release over first 24 hrs.
Figure 29B:
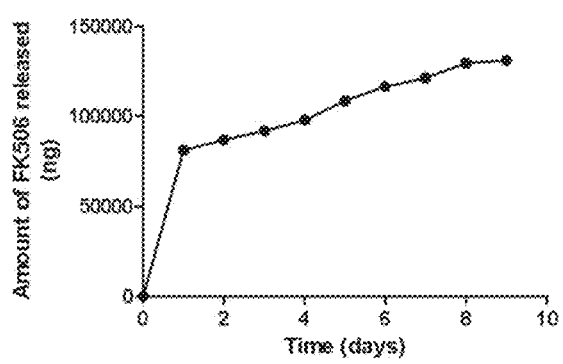
FIG. 29B shows a release profile of tacrolimus from a fiber bundle, in the form of cumulative release over 9 days.
Figure 29C:
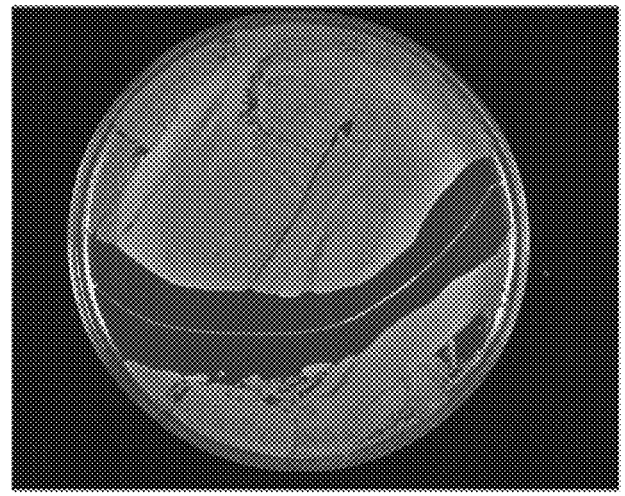
FIG. 29C is an image of a hollow fiber loaded with antibiotic showing evenly distributed release and a wide effective zone of inhibition of bacteria on an agar plate.

Initial experimentation has confirmed the suitability of the hollow fiber mesh technology as a platform for tacrolimus delivery. A small bundle of hollow fibers made from microporous polypropylene with a diameter of 300 μm and a pore size of 0.3-0.5 μm was loaded with tacrolimus dissolved in 100% ethanol (10 mg in 200 μl), and the two ends of fibers were tied or sealed as detailed in Example 1. The fibers were placed into 50 ml of phosphate buffered saline (PBS) with 0.5% Cremophor EL surfactant. At specified time intervals 1 ml of the PBS was removed for liquid chromatography-mass spectrometry (LS-MS) assay for tacrolimus; the removed volume was replaced with fresh PBS. Release kinetics of the tacrolimus is shown in FIG. 29A-FIG. 29B. FIG. 29A shows a release profile of tacrolimus from fiber bundle, in the form of a detailed curve of release over first 24 hrs. FIG. 29B shows a release profile of tacrolimus from fiber bundle, in the form of cumulative release (in ng) over 9 days.

These data indicates that after an initial burst of tacrolimus (lasting just 8 hours), a slow and steady release pattern persisted for 9 days (until the end of the experiment). Even this initial burst can be due in some part to artifact during loading the fibers with drug which can be mitigated (e.g. by post-filling rinsing). A total of some 130,000 ng of tacrolimus was released over 9 days from 6 fibers (5 cm in length); this is of more than adequate scale to achieve loco-regional immunosuppression even in a human context, and certainly in an experimental rat context. The quantity released represents just 1.3% of the amount of tacrolimus loaded into the fiber; in a clinical scenario, assuming the mesh construct depot were allowed to be proportionally reduced to 25% of its initial load before refill, a patient could achieve effective locoregional control for 519 days with just one treatment.

These results illustrate the potential of this technology to achieve a level of predictability and precision of drug delivery which has never before been possible.

FIG. 30A illustrates the possible placement of devices of an embodiment of the invention, for a possible human limb transplant or for treatment of cancer metastasis. Such devices could deliver anti-rejection drug to the lymphatic system or for treating other disease. FIG. 30B similarly illustrates possible device placement for a limb transplant in a rat.

This Example demonstrates drug delivery of a hydrophobic drug such as tacrolimus from the hollow fiber constructs of embodiments of the invention. The results also provide evidence that long-term treatment can be possible with the use devices based on hollow fibers. Limb rejection, organ rejection, treatments for preventing cancer metastasis and drug delivery to loco-regional and remote regions can be addressed by devices and implants according to embodiments of the present invention.

Example 3. Diffusion, Drug Release from Hollow Fibers and Constructs/Devices in Tissue and Considerations for Device Design Inflammation in Wound Enhances Drug Release During inflammation there is tissue swelling, and consequently the water volume fraction approaches 1, i.e., ε approaches 1. This leads to an increase of diffusivity up to the value $D_W$. If slow diffusion in the tissue controls the drug release, and as this diffusion is essentially enhanced during inflammation, then inflammation promotes the drug release. The situation corresponds to $$D_p R_f \sim D_{ti} \ell_p \quad (14)$$

during inflammation.

This means that the contributions of diffusion in the pores and diffusion in tissue are comparable, and so the more general Equation (9) has to be used when the inflammation is present.

Influence of the Local State of the Lymphatic System

The regional lymphatic system usually moves interstitial liquid with velocity in the range of about $5*10^{-4}$ to $5*10^{-3}$ cm/sec. In order to determine whether this convection affects diffusion transport, it is necessary to estimate the Peclet number (Pe):

$$Pe = \frac{R_f V}{D_{ti}} \quad (15)$$

Onset of Steady Diffusion Transport

When transport within membrane pores is slower, Equation (2) yields estimates, where $D_p$ is in the range of $10^{-7}$ to $10^{-8}$ cm²/sec. Table 1 provides $T_p$ (sec) as function of $1_p$ and $D_p$.

TABLE

| $D_p$ (cm²/sec) | $l_p$ (microns) | |
| --- | --- | --- |
| | 30 | 60 |
| $3 * 10^{-8}$ | 140 | 560 |
| $3 * 10^{-7}$ | 14.5 | 56 |

It is seen that the onset of steady state is very rapid. This will be true when interstitial flow is not weak and Pe>>1.

However, when there is stagnation of liquid within the wound, Equation (3) has to be used for estimating $T_p$. As long as steady state is not achieved within the wound, it is also impossible for porous layer of the membrane to achieve steady state. Table 2 is a table of $T_p$ (sec), when there is stagnation of interstitial liquid.

Values of Pe are presented in Table 2. Because Pe mainly is large, the convection provides rapid convective transport at some distance from the fiber surface, while the diffusion dominates at a smaller distance, smaller than δ, which is called the diffusion layer thickness. The calculated values for δ are given in Table 2 as well.

TABLE

| | $V_t$(cm/s) | | | |
| --- | --- | --- | --- | --- |
| | $5 * 10^{-4}$ | | $5 * 10^{-3}$ | |
| $D_{ti}$ (cm²/s) | Pe | δ(micron) | Pe | δ(micron) |
| $10^{-6}$ | 5 | 67 | 50 | 21 |
| $10^{-7}$ | 50 | 21 | 500 | 6.7 |

δ is calculated using the equation $$\delta = \frac{R_f}{Pe^{0.5}} \quad (16)$$

Consideration of the Table shows that convection can essentially enhance the transport within tissue. When this is true, Equation (10) has to be used. However, there is uncertainty, because information about lymph flow within a wound is scarce. In particular, the regional lymph system might be damaged within the wound, which might lead to stagnation of interstitial flow within the wound.

The drug release $T_p$ during the non-steady diffusion, in comparison to a steady state, is stronger than that during the steady state.

Estimate for Duration of Drug Release.

A crude estimate assumes that only a small portion of drug stored in the fiber lumen is released before the onset of steady release.

The total amount of drug stored in fiber lumen is about half of the volume of the fiber lumen, multiplied by the density of the drug. Assuming that the release rate is constant.

$$M_r = L 2\pi R_f L D_p \frac{C_s}{\ell_p} \quad (17)$$

$$\frac{\pi R_i^2 L \rho_p}{2} = 2\pi R_f L D_p \frac{C_s}{\ell_p} T_r \quad (18)$$

$$T_r = \frac{R_i^2 \ell_p \rho_p}{4 D_p R_f C_s} \quad (19)$$

$D_p \sim 0.3\, D_w$ for $\varepsilon_p \sim 0.5$. $R_i = 1.2 \times 10^{-2}$ cm, $\ell_p \sim 3 \times 10^{-2}$ cm, $R_f \sim 1.5 \times 10^{-2}$ cm where $\rho_p$ is the density of the powder particles.

Substituting these values for parameters yields equation $$T_r \sim \frac{1.5 \times 10^{-5}}{D_w} \frac{\rho_p}{C_s} \quad (20)$$

which is illustrated by Table 3, which gives $T_r$ in seconds.

TABLE

| $D_w$ | $\rho_p/C_s$ | | | | |
| --- | --- | --- | --- | --- | --- |
| (cm²/sec) | 1 | 10 | 100 | 1000 | 10000 |
| $3 * 10^{-8}$ | 500 | 5000 | $5 * 10^4$ | $5 * 10^5$ | $5 * 10^6$ |
| $3 * 10^{-7}$ | 50 | 500 | 5000 | $5 * 10^4$ | $5 * 10^5$ |

In this table, $\rho_p = C_s$ (i.e., the first column in the table) corresponds to filling the lumen with saturated solution. In this case, $T_r$ equals 8 to 80 sec. It can be seen that filling the lumen with saturated solution does not provide sufficient duration of drug release. This means that in order to provide sufficient duration of drug release, it is necessary to fill the lumen with powder particles of drug in solid form, rather than simply with saturated solution.

Correction to Estimation of Duration Time for Drug Release

It is also possible to consider how the drug powder changes due to dissolution of drug from the drug particles. This can be discussed assuming a vertical orientation of the fiber. The first powder particles to dissolve are a layer of powder particles adjacent to the porous layer of the membrane.

FIG. 31 illustrates that as dissolution of powder particles occurs, a very thin liquid region forms between the interior wall of the lumen and the remaining powder particles. This leaves the column of powder particles unsupported and unstable. As a result, the powder particles can rearrange themselves into a differently-configured column as shown in FIG. 32. In this rearranged configuration, the powder particles are again in contact with the interior wall of the lumen, and the column has become shorter in the vertical direction. As a result, an empty region forms at the top of the column.

This results in the appearance within the lumen of an upper zone that is free from powder. This is not favorable, because the drug release no longer occurs within the zone where powder particles are absent. Such a complication is inherent in fiber orientations that are different from horizontal orientation. However, there is an angle of inclination of fiber a, below which the column of particles remains, in spite of formation of liquid layer adjacent to wall force from particles (FIG. 33). For the slope shown in FIG. 33, the powder column does not collapse and rearrange itself, but rather the overall configuration of the powder column remains approximately the same as individual particles become smaller due to dissolution and a small portion of the perimeter of the lumen becomes particle-free. The situation corresponding to slope with angles smaller than a is not so harmful as the vertical situation because the empty upper zone without particles does not form. The presence of a liquid layer without particles along the entire length of fibers does not affect the release derivation, because drug remains stored in powder within any cross-section of the fiber. A decrease of the release rate in time is possible, because of decrease of drug concentration in solution near porous layer.

It is not realistic to provide permanent orientation of the wound surface with only a small slope relative to horizontal, because of patient movement and because of the unpredictability of the patient's position, with associated variation of fiber orientation.

Taking into account the influence of wound movement (movement of the patient's body accompanied with wound movement), a programmed movement can be proposed to prevent the formation of zone without particles near the tip of the fiber, namely the change of vertical orientation by 180 degrees (FIG. 34). After such a change of orientation, particles fall into zone that had previously been devoid of particles. A slow settling velocity of falling small particles has to be accounted for, when the program of movement is specified. The settling velocity of spherical particles at small Reynolds number is $$V_s = \frac{a_p^2(\rho_p - \rho_w)g}{18\,\mu} \quad (21)$$

$$V_s = \frac{2(\ell_p - s_w)a_p^2}{q2} \sim 20\frac{\ell_p - s_w}{s_w}a_p^2 \quad (22)$$

where $\mu$ is the viscosity of water (centipoises), $\rho_p$ and $\rho_w$, are the densities of the drug particles and the water, respectively, and $a_p$ is the diameter of the drug particle (in cm).

The velocity equals about $2*10^{-5}$ cm/sec when $\rho_p=2*\rho_w$, and equals about $2*10^{-6}$ cm/sec when $\rho_p=1.1*\rho_w$, for $a_p=10$ microns. The velocities remain very low even for larger particles such as $a_p=30$ microns. Correspondingly, the times required for settling a distance about 1 cm are too large, such as hours or days. The times decrease if the formation of zone larger than 1 mm of height is prevented. It means that the period of reorientation has to be short. While this can be arranged in daytime, the requirement is difficult for nighttime.

Another correction relates to the right hand side of (Equation 18), because the axial symmetry in diffusion flux is absent. The release occurs through the zone of contact between the fiber and the wound surface (FIG. 34). FIG. 34 illustrates, in cross-section, a parallel array of hollow fibers that forms contact zones, strips having width b, with adjacent tissue. This contact zone is the strip with length of about the fiber length and a width of b, which is much smaller than the fiber perimeter, i.e., $b<<2*\pi*R_f$. FIG. 34 illustrates, in cross-section, a parallel array of hollow fibers that forms somewhat narrow contact zones with adjacent tissue. FIG. 35 illustrates diffusion occurring through those narrow contact zones. FIG. 36 illustrates diffusion occurring both through the contact zone and through adjacent tissue.

Although the drug release through the b-strips only causes non-uniformity in treatment of the wound with drug, this non-uniformity is not large and can be not harmful. This statement accounts for the fact that diffusion from strips occurs not only in the radial direction (this occurs at axial symmetry) but in the lateral direction as well (FIG. 35). The wound area between strips is treated with drug due to the lateral component of the diffusion flux.

The assumed width, b, of the strip or zone of contact between the fiber and the tissue influences the transport of drug into the tissue. The smaller is b, the smaller is the release rate and correspondingly, the longer, can be drug release. Corrected times for release duration are given in Table 4 based on the assumption that the width of the b-strip is one-tenth of the perimeter of the fiber. Table 4 gives $T_r$ for $b=0.1*2*\pi*R_f$

TABLE

| | $\rho_r/C_s$ | | | |
|---|---|---|---|---|
| $D_w$ (cm²/sec) | 1 | 10 | 100 | 1000 |
| $3*10^{-7}$ | 500 | 5000 | $5*10^4$ | $5*10^5$ |
| $3*10^{-6}$ | 50 | 500 | 5000 | $5*10^4$ |

The previous tables considered only diffusion transport of drug in the tissue. However, there is also the possibility of interstitial flow of fluid. Interstitial flow contributes to the uniformity of treatment of the wound. The interstitial liquid flows parallel to the wound surface (parallel to fiber array) because the normal component of flow is absent (disregarding osmosis). When liquid flows near a certain strip, that liquid becomes enriched with drug. Afterwards, liquid flows near a part of the wound surface which does not contact with the membrane. Because of interstitial flow, this area is treated with drug that had been received near the b-strip. Naturally, this mechanism would not work when interstitial flow is parallel to strip areas, but such coincidence would be a rare case.

As the contact are between the fiber and the wound restricts release rate, the formation a cloth from fibers crossing each other in perpendicular direction might not be desirable from this point of view, because in this case fibers are not straight and strips do not form (FIG. 36). Instead, the contact between fiber and the wound occurs within patches, whose area is much smaller than that of the b-strips.

It seems that a parallel array of fibers can be useful; in which the fibers are almost pressed against each other in the lateral direction. Fibers can be attached to a flat plastic sheet.

Its rigidity or elasticity can be chosen so as to provide the fiber contact with the entire surface of the wound, which is not exactly flat.

From this analysis of b-bands, it can be concluded that the desirable value of fiber-to-fiber spacing in the device might be influenced by how much interstitial or lymphatic flow there is in a particular body location. For example, for a bodily location where interstitial fluid motion or lymphatic flow is substantial, redistribution of the drug would occur anyway due to convective motion of the interstitial fluid. In such a situation, the fiber-to-fiber spacing might be relatively unimportant and could perhaps be relatively large. For a bodily location having little or no such motion of interstitial fluid, it might be relatively more important for the fibers to be close together. An example of such a situation might be a bandage that is externally applied. In a wound near the external surface of the wound, it might be expected that the interstitial fluid might be relatively stagnant.

Example 4

Methodology of Filling Fiber Lumens with Disperse Drug Particles.

A methodology of filling fiber lumens with drug particles is described here. It turns out that there are some special considerations that relate to the particle size and the method of filling the lumen.

When the fiber lumens contain drug in the form of solid particles, the size of those particles can be chosen with consideration of both dissolution kinetics during drug release, and the process of loading the particles into the fiber lumens during manufacturing. It is believed that a suitable particle dimension is of the order of 10 microns. This value is chosen because larger particles are less suitable to provide a solute concentration about $C_s$ (the saturation concentration) near the porous layer (wall), while for purposes of loading the drug particles into the fiber, a formed packed bed of smaller particles causes an excessively high hydrodynamic resistance to the flow of liquid through it, as for purposes of initial filling of the lumen with particles from a suspension. A typical suspension used to load drug particles into the lumen might have a suspension volume fraction, for example, of 0.1. This corresponds to a suspension volume $V_s$ about $5V_l$ ($V_l$ is lumen volume) that is required to fill the packed bed of powder at a volume fraction about 0.5 within the lumen volume. (A packing fraction of about 0.5 is typical for beds of particles that are approximately spherical of somewhat uniform size.) While the measurement of such small volumes is not easy, it is sufficient to use a vertical hollow fiber with length 5L (L is the required length for parallel array of fibers). The detection of flowing suspension at the fiber outlet means, that the volume $5V_l$ was flowing through the entrance portion of fiber. This can be achieved by pre-treating the suspension with a hydrophilic polymer or a polyelectrolyte.

Particle deposition on wall from flowing suspension, even at vertical fiber orientation, could occurs due to its adhesion. The particle aggregation occurs due to radial coagulation. The deposition and aggregation might cause the lumen to clog before it is filled with suspension. Both deposition and aggregation can be prevented using suspension pretreatment by means of an adsorption hydrophilic polymer or poly electrolyte, which provides aggregate stability of suspension. Loading the fiber lumens with particles can be achieved if liquid flows out of an open tip, while it is impossible for the suspended particles to flow out of the tip because the flow of the particles is blocked by the surrounding particles in the packed bed. As a result the particles from the suspension can accumulate inside lumen and form a packed column inside the lumen. Formation of a packed bed of powder within Lumen The outlet of vertical fibers is submerged in stagnant coarser powder, as is shown in FIG. 27A. The particles in the bed are relatively larger, and the particles exiting from the tip of the fiber are relatively smaller. When the suspension used in the experiment flows downward through the lumen and into the powder bed, it is observed, that no particle is present in the effluent from the powder bed. This indicates complete capture of particles of flowing suspension in the stagnant packed bed of coarser particles. The moment of complete filling of lumens with powder can be identified by the formation of a conical deposit at fiber inlet above a completely filled lumen.

In an array of hollow fibers, one tip of every hollow fiber, which can be designated the inlet, is inserted in a header, which allows simultaneous filling of a group of fibers with drug suspension. The other tip of the fiber, which can be designated the outlet, can be open for liquid flow therethrough, because filling of the lumen occurs when particles are involved in axial liquid stream and its velocity is not too low. Although the lower ends of the fibers can be arranged to be sufficiently open to allow liquid to pass therethrough, there still can be provided some restriction at the outlet tip so that at least some drug particles are retained even as the liquid part of the suspension passes through the open tip of the fiber.

It might be thought that one might use a microfiltration membrane that is penetrable for liquid and not penetrable for the particles of drug. However, because of the small cross-sectional dimensions of the fiber lumens, it would not be realistic to install such a membrane within the cross-section of the lumen.

In order to provide water outflow from fibers and simultaneously to prevent outflow of the particles that are suspended in this flow, the fibers first of all can be installed in a vertical orientation with their open (outflow) tip submerged in a bed of powder. The powder can consist of approximately mono-disperse particles, whose average dimension exceeds the average dimension of suspended drug particles by a factor of about 2 to 3 times. Thus, the liquid can flow through the powder without meeting a substantial resistance, while suspended particles can penetrate into powder only during a short time at the very beginning of this process, because of phenomenon known as calmatation. The suspended particles will cause clogging within a local region of the powder bed within a small distance from the open tip. After this localized clogging has established itself, there will be little or no flux of suspended particles flowing out from the tip.

As a result, as soon as the penetration of suspended particles into the powder bed becomes impossible, those powder particles will be held back and will accumulate above the submerged tip of the fiber, which begins to fill the lumens with almost packed powder. The height of accumulated drug powder gradually grows up to complete filling of lumen, when this height equals to the fiber length. If it is assumed that a constant supply pressure is applied to the suspension entering the lumen inlets, it can be expected that the volumetric velocity of suspension entering lumens gradually decreases with time, because the hydrodynamic resistance of column of accumulated drug powder is proportional to its growing height h(t). The kinetics of the resistance growth and the kinetics of the associated decrease of suspension flow rate can be quantified using Darcy law and the equation for Darcy constant. The latter depends on particle diameter $d_p$ squared and on porosity, which is about 0.5 for high packing density and does depend on $d_p$. Hence, the larger $d_p$ is a consequently the larger Darcy constant is, the higher suspension velocity and shorter time, required for filling lumens with drug powder. On the other hand $d_p$ has to be sufficiently small in comparison with internal diameter of fiber $2R_i$. If the particle size $d_p$ approaches the fiber lumen diameter $2R_i$, there is an increasing probability for clogging of entrance lumen. This probability decreases with decreasing volume fraction of suspension because the clogging occurs when some particles enter a pore simultaneously. Although a larger particle dimension can be used with decreasing suspension volume fraction, which would reduce or eliminate the likelihood of clogging at the fiber entrance, this decrease will lead to longer time of lumens filling with the drug. This indicates that it can be desirable to use drug particles within the size range 20 micron<$d_p$<60 micron.

This process is further illustrated in FIGS. 37A-37C. In FIG. 37A, a hollow fiber is shown partially submerged into a bed of particles. The size of particles in this bed can be 2 to 4 times the size of particles in the eventual suspension that is supplied to the lumen of the fiber. FIG. 37B shows some suspension particles entering the powder bed. Upon entering the powder bed, they will form a clog near the lower end of the fiber. This clogging of pores by particles smaller than the particles that originally made up the powder bed or pores is called calmatation. Thus, the tip of the hollow fiber becomes impermeable for further passage of suspension particles, yet it remains permeable for passage of the liquid that is the carrier for the suspension. FIG. 37C shows the lumen of the fiber continuing to fill further with particles from the suspension. (In FIG. 37C, for simplicity of illustration, the particles in the powder bed are not shown.)

Fabrication of Parallel Array of Fibers, Loaded with Powder

A header as a collector chamber with one inlet for suspension and many outlets for attachment of fibers of their parallel array which outlets are submerged in packed bed of coarser powder. Completion of loading of fibers with particles can be detected as an onset of formation of a conical deposit above the inlet of the header. When the loading with powder particles is completed, the parallel array of fibers can be held together by sticking the fibers to one or two thin plastic films. Afterwards, both openings of each fiber can be closed with the use of resin or by any other desired means. Alternatively, if desired, one end could be connected to a supply means for introducing additional drug during treatment.

Existing technology of fabric formation, such as weaving, can be adjusted to accommodate the fabrication process of fabric formed from hollow fibers that are loaded with drug powder.

Quantification of the Time Required for Filling the Lumen of Hollow Fiber with Particles by Means of Filtration A filtration process occurs with the open tip of the fibers being submerged in packed bed of particles, in a particular situation such that the dimension of the powder bed particles exceeds the dimension of the suspension particles by a factor of several times. This situation provides straining of the suspension particles as a result of a local clogging of the powder bed pores near the fiber outlet by suspension particles, while the liquid part of the suspension continues to be able to flow through the particle bed. Naturally, the packed bed changes the hydrodynamic resistance for liquid flow, which increases, when suspended particles are deposited in pores between larger particles of the packed bed. But the cross-section for liquid stream increase as $2\pi l^2$, where $l > R_i$ and $l$ is the distance to the outlet pores. We will assume that the hydrodynamic resistance of the divergent flow within the powder bed near the lumen outlet is smaller than the hydrodynamic resistance of the stacked powder inside the lumen. Even if this is not valid initially, when the lumen is essentially empty of powder, this will be valid later, when the particle accumulation inside the lumen causes growth of the flow resistance of the stack of powder inside the lumen. Hence, we will focus on kinetics of growth of the hydrodynamic resistance of lumen, caused by the increasing of length of the powder-filled portion of the lumen, which is denoted by h(t). A differential equation for h(t) can be obtained, taking into account the fact that the suspension velocity decreases with time due to the growth of hydrodynamic resistance of the powder column at a given constant supply pressure p of the suspension, based on the fact that the rate of particle accumulation is proportional to the instantaneous velocity of suspension u(t).

Denote $n_o$ as the numerical concentration of suspension, $\alpha_s=4/3n_o\pi a_p^3$ which is the volume fraction of suspended particles, $\alpha_p$ is the volume fraction of powder inside the lumens.

Let us denote the increase in powder column height Δh for a time interval Δt, and let us denote the increase in amount of particles in accumulated powder as ΔN. ΔN is caused by convective transport with instantaneous velocity u(t)

$$\Delta N=n_o u(t)\pi R_i^2\Delta t \tag{4.1}$$

As ΔN causes the increase in powder column height Δh, the volume of particles within Δh can be presented through ΔN and Δh.

$$\alpha_p\pi R_i^2\Delta h=\Delta N^*V \tag{4.2}$$

Combining the above two Equations yields $$\frac{dh}{dt}=\frac{\alpha_s}{\alpha_p}u(h) \tag{4.3}$$

because $n_0V=\alpha_s$ u(h) can be expressed with the use of the Darcy Equation $$u(h)P_e=\frac{K\Delta p}{\mu h} \tag{4.4}$$

where K is the Darcy constant, μ is the viscosity of water and the Darcy constant K is given by $$K=\frac{\varepsilon^3 a_p^2}{(1-\varepsilon)^2 4k} \tag{4.5}$$

where $a_p$ is the particle radius, the coefficient k~5, and ε is the porosity of the packed powder which fills the lumens, having an approximate value of ε~0.5. As p is expressed in mmHg, while μ is expressed in centipoise, multiplying Equation(4.4) by the expression $$\frac{1330}{\text{mmHg}}\frac{\text{dyne}}{\text{cm}^2}=1$$

allows the substitution p=100 mmHg into Equation (4.4), giving $$h = \frac{0.5 * 1330 * 100 * \alpha_p^2}{4 * 5 * 10^{-2} * h} \quad (4.6)$$

$$u = \frac{3.3 * 10^5 * \alpha_p^2}{h}$$

Substituting u(h) into the right hand side of Equation (4.3) yields a simple differential equation for determining h(t), whose solution is $$h^2 = 2\frac{\alpha_s}{\alpha_p} 3.3 * 10^5 a_p^2 t \quad (4.7)$$

The equation for time required for filling with powder a fiber with length L follows from Equation (4.7)

$$T_p = 1.5 \cdot 10^{-6} \frac{\alpha_p}{\alpha_s}\left(\frac{L}{a_p}\right)^2 \sim 7.5 * 10^{-7}\left(\frac{L}{a_p}\right)^2 \alpha_s^{-1} \quad (4.8)$$

because $\alpha_p \sim 0.5$

This equation yields, for example, for $a_{p=10}$ micron, L=10 cm, $\alpha_s$=0.1, $T_p \sim 750$ sec~12.5 min. This time is not too long for production of an array or fabric of drug-containing fibers. This time can be further decreased with increasing $\alpha_p$ and $\alpha_s$. However, this is risky, because the larger $\alpha_p$ and $\alpha_s$ are, the larger is the probability of clogging the entrance of the hollow fiber.

Specification of particle dimension for powder used to prevent outflow of suspended particles from fiber After the value of $\alpha_p$ is specified, this can be used for specification for dimension of particle powder used to prevent the outflow of suspended particles, $2a_{str}$. If this dimension is too large, there is no straining and, consequently, no accumulation of suspended particles in lumens. If this dimension is too small, the pores remaining after filling the powder with dimension $2a_{str}$ with particles with dimension $2a_p$ are rather narrow. This means that hydrodynamic resistance for flow from lumens is high. This resistance will combine with the resistance of packed bed, formed inside lumens, so as to cause an increase in time $T_p$ in comparison with that according to equation (4.8).

The criterion below contains information about straining which has to be accounted for to select a value for $2a_{str}$.

Straining and Cake Formations

It has been demonstrated that under low-flow conditions and relatively high solids flux, the formulation of a mat of solids on top of the porous media can occur, even if the size of the particles are considerably smaller than the pore size opening.

As noted previously, mechanical straining is frequently the sole mechanism for removal of suspended particulate matter in a diatomite filter. If a mono-disperse filter aid is employed (i.e. single uniform diameter for all media grains) and sphericity is assumed for both the media and suspended particles in raw water, those suspended particles with diameter of 0.155 times the media diameter or larger would be removed at the media surface due to straining. Smaller suspended particles would pass through the filter. If media with a hetero-disperse size distribution is employed, or if conditions other than clean bed are examined, removal due to straining is improved somewhat.

Hence the condition for selection value for $a_{str}$ is $$\frac{a_p}{a_{str}} > 0.155 \quad (4.9)$$

Hence a proper choice can be $a_{str} \sim 50$ to 100 micron

The condition of particle sphericity and monosphericity is important. Violation of this condition may lead to uncontrollable straining. The particles in the powder bed can, for example, be latex particles. However, it can be undesirable for the particles to have an especially low density. It can be preferable to have powder bed spherical particles that are relatively heavy (dense), such as metal particles. In the situation of a vertical or inclined hollow fiber, the weight of the column of powder particles inside the fiber causes force to be applied to larger particles in the powder bed below the tip of the fiber. This force can displace powder under the fiber tip in the radial direction or perhaps even upward, similar to what occurs in a U-tube for a liquid in a solution. In order to avoid or counteract this possible effect, it can be desirable to provide a level of powder bed particles that extends a certain distance above the fiber tip, so as to prevent displacement of powder around the fiber tip, i.e., it can be desirable to "bury" the fiber tip some distance into the bed of coarse powder particles.

Feeding Hollow Fiber with Suspension

Stokes' Law gives the settling velocity of a sphere in a viscous fluid as $$V_s = \frac{d^2(\rho_1 - \rho_2)g}{18\mu} \quad (4.10)$$

where d is the diameter of a spherical particle, g is the acceleration of gravity, $\rho_1$ and $\rho_2$ are the densities of the particle and of the liquid respectively, and $\eta_0$ is the viscosity of the liquid.

It means that the settling time for a distance about 120 cm can take about $1*10^4$ seconds, or several hours. This means that there is no need for stirring the suspension to prevent suspended particles from settling during the typical time period of about $1*10^3$ seconds that would be required for filling the fiber with powder particles. Hence, a standard glass vertical tube with diameter about 20 cm can be used as a vessel for supplying the suspension. The diameter of such a tube does not have to be especially large; it would already be some factor larger than the fiber diameter because the fiber diameter is quite small. The lower opening of such a tube can be suitable for a cork to be inserted into the tube lower opening. In turn, the fiber can be inserted into and through the cork. In more detail, the fiber inlet end, which extends beyond the cork into the interior of the reservoir tube, can extend some distance above the cork so that if any deposit forms on the cork, it will not affect the flow of suspension into the fiber opening. This is illustrated in FIG. 38.

Because the fiber outlet is open for liquid flow, flow of suspension into and through the fiber occurs due to hydrostatic pressure, caused by the height of the liquid column. The hydrostatic pressure at the lower end of the fiber can be for example about 70 mmHg, if the height of the vertical tube reservoir is about 1 meter.

The amount of suspension required for filing the lumen with powder can be estimated as volume of liquid which is determined by its velocity u(h(t)) lumen cross-section and calculated time $T_{op}$ according to equation 4.8. However the calculation can be simplified taking into account Equation (4.3).

$$\pi R_i^2 \int_0^{T_D} U_p dt = \frac{\alpha_p}{\alpha_c} \pi R_i^2 \int_0^{T_D} \frac{dh}{dt} dt = \frac{\alpha_p}{\alpha_c} \pi R_i^2 \int_0^L dh = \frac{\alpha_p}{\alpha_c} \pi R_i^2 L \quad (4.11)$$

where $\pi R_i^2 L$ is the volume of the lumen. Although $\alpha_p/\alpha_c \gg 1$, this volume is very small in comparison with the volume of glass tube that serves as a reservoir for the suspension, because the cross-section of the glass tube is typically orders of magnitude larger than that of the lumens.

It is possible that, with time, a sediment can form at the top (inlet) of the fiber on the wall thickness of the fiber wall, as illustrated in FIG. 39. In a certain moment, this sediment can be involved in suspension flow towards fiber inlet. It is possible that if the volumetric concentration of sediment particles entering into the lumens at a certain moment is high, and clogging might occur. If this is observed to occur, stirring might be used to prevent the formation of sediment, but the arrangement for stirring in a narrow tube might sometimes be problematic. Alternatively, vibration of the tube might prevent sedimentation.

The problem caused by sediment formation around the opening of the inlet tip of the fiber might not arise if particles of sediment are continuously involved in flow toward lumens. If there is a monolayer of particles around the opening not involved in flow, a small pile of particles can form on the edge of the fiber wall, and that pile can have a certain slope. By the nature of the particles, the slope cannot exceed a certain angle because particles will tend to slide downward along that slope even without being driven by flow. Hence, perhaps, flow by itself is not sufficient to prevent the sediment formation with a certain slope. However, flow still provides a steady movement of sediment particles from the accumulated deposit into the lumen. This suggests that neither stirring nor vibration are required.

Detection of the Moment of Completion of Loading of Lumens with Powder

If a fiber is made of a material that is transparent, the color and visible appearance of the fiber will change due to filling with powder. When powder fills the lumens completely, particle accumulation above the opening of inlet tip will start to occur. A cone of visible sediment can be expected to form on the inlet tip as soon as the lumen is filled with powder.

Another manifestation of the onset of complete filling of lumens with powder is that the hydrodynamic resistance stops growing and the velocity of filtration along fibers stops decreasing. The detection of this moment for a single fiber is not easy. However, when an array of fibers is filling, detection is easier.

Closing the Fiber Tip

When the fibers are filled with particles, it can be desirable that both tips or ends of the fiber have to be closed so that particles are not able to fall out of the fiber. Closing (such as with epoxy resin) is not the problem. Attention has to be paid not to lose portions of drug adjacent to open tips before the closing of the open tips. First, the fiber can be disconnected from the cork, while the fiber remains in its vertical orientation. Afterwards, the fiber orientation can carefully be re-oriented to horizontal one with fiber tip remaining within the powder bed formed by the coarse powder particles. After horizontal or nearly horizontal orientation is achieved, the fiber tip can be disconnected from the coarse powder.

In this procedure, attention has to be paid to both tips. When the approach to horizontal orientation is required, for lower tip this may cause powder outflow from the upper tip. Therefore, in embodiments the upper tip is closed before performing the procedure focused on the lower tip.

When the fiber is in use, as both tips of the fiber are closed and as water is essentially incompressible, it might appear that the volume of the solution inside the fiber would decrease due to drug release, but that is not possible. The diffusion of drug into the surrounding tissues is accompanied with and simultaneous with another diffusion phenomenon in the opposite direction. The premise for this is not only the requirement of constant volume inside the lumen. In addition, the gradient in drug concentration is accompanied by a gradient of water concentration. The direction of the water concentration gradient is a driving force for diffusion of water into the interior of the lumen. This situation is described by the theory of mutual diffusion. However, it is not necessary to consider this topic here, because the relevant corrections are not large.

Visualization of Drug Release

The opportunity to visualize drug release, if the fiber is made of a transparent material, is a unique feature of this new method of drug release. Although numerous other drug delivery systems exist, only this system allows visualization of drug release. Of course, we do not consider and visualize the actual molecular diffusion of drug. However, we can detect and measure a process, which is in close connection to drug diffusion and can accomplish quantitative measurements based on visualization, based on the collective shrinkage of the drug particles as dissolution occurs, and the change in the height of the powder column due to rearrangement of the column of drug particles.

As it was described above, drug diffusion initiates the dissolution of particle adjacent to lumen wall, which leads to formation of gap between powder and wall. The particle foiling in this gap leads to sinking upper boundary of powder and formation zone of solution without powder near the upper tip. If the wall of hollow fiber is transparent it is possible to visualize this zone and to measure the rate of sinking for upper level of powder. The rate of sinking of this level can be easily recalculated in rate of drug release.

Stabilization of Vertical Distribution of Drug Particles in Lumens with the Use of Water Soluble Polymer Gel In some embodiments, the lumens can be filled with gel, with the drug particles being uniformly distributed in this gel. This can be a good way to prevent settling of drug particles into the gap that can ordinarily be formed near the lumen wall due to the gradual dissolution and shrinkage of drug particles. In this situation with a gel, even though the drug near the wall dissolves, there will not be any settling of particles near the wall with the resulting appearance of a drug-free void space near upper tip, because the high viscosity of the gel prevents settling of the drug particles. Naturally, in this gel situation, the rate of drug release will be reduced as a thicker gel layer without particles forms near the wall. While the initial concentration gradient is $C_s/l_p$, eventually this concentration gradient decreases to $C_s/(l_p + R_i)$ at the time when the drug is almost completely dissolved.

$(R_i + l_p)/l_p \sim 125/30 \sim 4$

This decrease in the drug release rate can in embodiments be acceptable.

When the flow of polymer/particle mixture is arranged, it can be stopped as soon as the mixture starts to flow from the outlet tip of the fiber. A complication may occur during preparation of the mixture of gel and particles. There is no guarantee of uniform particle distribution within the mixture. It is possible that particle aggregation during mixing can occur. The aggregate could possible clog the inlet tip of the fiber, preventing filling of lumens. If the aggregation during mixing is weak, the aggregation may occur during flow of the mixture through lumens, with resulting clogging of the fiber. If the aggregation occurs either during mixing or during fiber lumen filling, the decrease in particle volume fraction may be helpful. However, this is bad for the duration of drug release. Polydisperse particles can be used. A mixture of particles and polymer is called a colloid. Much literature is devoted to colloids, but visible particles are much larger than those in colloids.

Three Exemplary Approaches to Filling Lumens with Dispersed Drug

One possibility is filling by the gel particle composite discussed herein. But that possibility is uncertain because of possible particle aggregation during mixing or during filling. Experiments with polydisperse experimental particles rather than drug particles could provide information.

A second possibility is filling the lumens with suspension flow with the discharge end of the fiber being submerged into a powder bed of coarse powder particles (described herein).

A third possibility is, filling the lumen with suspension without submerging the fiber end into a bed of powder particles of coarse powder. In this situation, as soon as outflow from the outlet end of the fiber is detected, the flow is stopped and outlet closes. This procedure makes us of sedimentation that will occur inside the lumen in the vertical direction. At vertical fiber orientation, the sediment forms and the height of the column of sedimented powder increases with time, leaving the vertically upper portion of the fiber empty of particles. In order to obtain a settled sediment column having a height equal to desired length of fiber L, a fiber with larger length nL is used. If the initial volume fraction of suspension is α/n, where α is the maximum volume fraction of sediment, a will be achieved within the entire desired height (length L) when sedimentation occurs in fiber with height nL. After the completion of the sedimentation process, it is possible to cut off and discard the upper portion of the fiber, which no longer contains particles because the particles have all settled into the lower portion of the fiber. This process yields a fiber with length L that is filled with sediment of powder particles.

Perhaps, a level above fiber tip has to be provided (FIG. 38) to prevent powder around fiber displacement.

Feeding Hollow Fiber with Suspension

A calculation can be performed relating to any of the fiber filling procedures that involve the preparation and flowing of a suspension. The settling velocity of particles $a_p=10$ micron is about $$U_{sed} = \frac{4\pi a_p^3 (\rho_p - \rho_w)}{3 * 6\pi \mu a_p} = \frac{2}{9\mu} a_p^2 \frac{(\rho_p - \rho_w)}{\rho_w} \cong 20 a_p^2 \frac{(\rho_p - \rho_w)}{\rho_w}$$

This means that the vertically downward travel of particles through a settling distance of about 10 cm takes about $10^6$ sec, or approximately 10 days. This means that it is unnecessary to stir the suspension to prevent the particles from settling during a typical time period of about $10^3$ sec that would typically be required for filling the fiber with powder. Hence, a standard glass vertical tube with height about 20 cm can be used as vessel for suspension. Its diameter can be fairly small because the fiber diameter is much smaller. The tube lower opening can be suitable for insertion of a cork. The fiber can be inserted in the cork, and the fiber inlets can be located sufficiently high above the cork, because of the possibility that a deposit might form on the cork and might be involved in flow towards fiber opening.

When the fiber outlet is open for liquid flow, flow occurs as driven by the hydrostatic pressure caused by the height of the liquid column. This pressure is about 70 mmHg, if the length of vertical tube is about 1 meter.

The amount of suspension, required for filling of the lumens with powder can be estimated as volume of liquid which is determined by its velocity u(h(t)) lumens cross-section and calculated time $T_p$ according to Equation (4.8)

Reservoir devices with microporous hydrophilic membrane and in particular hollow fibers have an important advantage, in that they can be loaded with any other water soluble drug without the possibility of it degrading as in the case of hydrophilic non porous membrane. The hydrophilicity of porous layer promotes its spontaneous filling with water due to imbibitions, which is impossible in the case of a hydrophobic porous membrane. The drug transport thorough hydrophobic porous media is very slow because it occurs due to slow surface diffusion of adsorbed organic molecules. This complication may occur even in the case of hydrophilic membrane, if a dry zone near the external surface of membrane arises due to water evaporation. However, this cannot occur, when reservoir device is incorporated in a wound and wound afterwards if closed. In addition, there is no skin, which may be a barrier for drug transport into the wound tissue.

Large release rate and long release duration can be useful for wound treatment. The analysis revealed that fine hydrophilic microporous hollow fibers are in a unique drug delivery device for providing high release rate and also long duration of drug release.

If the fiber lumen is filled with the saturated concentration of drug, for typical drugs and conditions, the duration of drug release is too short, according to theory outlined below.

If the fiber lumen is filled with drug solution which concentration is near saturation, the amount of drug stored in the lumen can be increased by means of increasing solubility of by choice of a drug of greater solubility. However, this does not lead to an increase in drug release duration time T, because of simultaneously increases the drug loss due to release which is proportional to $C_s$. The drug release duration T equals the ratio of stored amount to amount released per unit time. $C_s$ cancels in this ratio. Hence, it is possible to enhance the release rate by increasing $C_s$, but the duration of release cannot be increased in this way.

Meantime, the solubility of typical drugs in water $C_s$ is usually rather low. At least, it is orders of magnitude lower than density of solid drug $\rho_p$ $$C_s \ll \rho_p \quad (1)$$

$\rho_p$ usually does not differ very much from 1 g/cm$^3$, So, the only possibility to achieve long term release is a decrease of $C_s$. As this leads to decrease of release rate, the characteristic length for diffusion has to be decreased, that will allow to achieve high gradient of drug concentration is spite not high $C_s$. With the decreasing $C_s$, a restriction arises that the drug concentration still has to exceed the minimum inhibition concentration (MIC), which depends of the kind of bacteria to be disinfected, or, more generally, the minimum effective concentration for any given substance and purpose. The selection of a proper drug usually allows one to attain a rather low MIC and corresponding rather low $C_s$, with associated long duration of drug release, if the reservoir is filled with powder of drug. The application of a membrane with a rather thin microporous layer having thickness $l_p$ makes it possible to achieve a rather high release rate in spite of the fact that $C_s \ll \rho_p$.

At first glance there is another possibility to provide long term release, namely by means increasing of ratio reservoir volume to its surface, because the stored amount is proportional to reservoir volume, while total release rate is proportional to reservoir surface. This statement if valid of the sink boundary condition is used, i.e. zero drug concentration on membrane external surface $C_m$. However, the sink boundary condition is an over-simplification, because of the coupling between drug transport within the Drug Delivery Device and drug transport in adjacent tissue. The release rate into surrounding tissue is proportional to drug concentration on the external surface of the membrane $C_m$. The disregard of this concentration inherent in sink boundary conditions can be justified only in conditions when drug transport through tissue does not affect the transport within the Drug Delivery Device. Meantime, the larger reservoir dimension (larger radius of single fiber $R_f$, which lumen is an example of drug reservoir and which can be rather large, such as 3 mm), the slower transport in tissue and, consequently, smaller the release rate.

The knowledge about transport processes within the wound is poor and we are forced to use knowledge about transport processes within tissue. This transport occurs not only due to diffusion. In at least some situations, a large role is played by convection, because interstitial fluid can be moving in the lymphatic flow involving regional lymph nodes, local venules and arterioles. The range of velocity V for interstitial fluid is $5*10^{-4}$ to $5*10^{-5}$ cm/sec. The question of whether convection affects diffusion transport can be addressed by estimation of the Peclet number Pe, which is an estimate for the ratio of convection flux to diffusion flux $$Pe = \frac{LV}{D},$$

where $L \approx R_f$ in our case, where L is the characteristic length for diffusion, and D is diffusivity. The diffusivity within tissue Du is in the range of $10^{-7}$ to $10^{-6}$ cm$^2$/sec. For $R_f$ 750 micron, Pe varies in the range of 5 to 500 for the mentioned ranges for V and $D_{ti}$.

Because Pe>>1, convection enhances transport within tissue, while in a thin-scale diffusion layer near membrane, the diffusion flux predominates. An equation for the thickness $\delta$ is known to be $$\delta \sim R_f / P_e^{0.5} \quad (2)$$

The larger $\delta$ is, i.e., the larger $R_f$, the smaller is the concentration gradient at the membrane surface $C_m/\delta$, and the slower is diffusion transport in tissue.

A rigorous modeling requires the separation of diffusion in pores within the Drug Delivery Device and diffusion in adjacent tissue.

For the assumption that steady state is achieved, the diffusion fluxes through the porous layer and through adjacent tissue have to be equal:

$$D_p \frac{C_s - C_m}{\ell_p} = D_{ti} \frac{C_m}{\delta} \quad (3)$$

where $D_p$ is drug diffusivity within the porous layer r. The equation (3) can be used for determination of the unknown $C_m$ and afterwards the release rate (per unit surface D)

$$M_r = D_{ti} cm/\delta = \frac{D_p C_s}{\ell_p}\left(1 + \frac{D_p}{D_{ti}} \frac{\delta}{\ell_p}\right) \quad (4)$$

The release is maximal, when transport within tissue is rapid, i.e. $\delta$ and consequently $R_f$ are small $$D_p \delta \sim D_p \frac{R_f}{P_e^{0.5}} \ll D_{ti} \ell_p \quad (5)$$

Although a Drug Delivery Device in the form of larger reservoir (hollow fiber of larger radius; slit like reservoir of large width between two parallel membranes) can provide long term release, this is not the best choice, because the release rate is determined by slow diffusion in tissue (large $\delta$), is uncontrollable, and varies over a broad range from one patient to another.

An array of fine hollow fibers ($R_f$~300 micron, $l_p$~30 micron) can be the optimal choice, because harmful influence of transport in tissue is eliminated (small $\delta$), high release rate can be provided due to small $l_p$ in spite of $C_s$ not being large, while long duration of release occurs due to the large value of lp/$C_s$.

After the fibers are filled with drug powder and sealed at both ends, a square piece of fabric can be produced from loaded hollow fibers. Another version of Drug Delivery Device based on loaded hollow fibers is the formation of a parallel array of fibers (FIG. 31) by means of their sticking to two thin plastic strips perpendicular to array and located near fiber tips.

In order to eliminate the retention of air bubbles between adjacent fibers, it can be desirable to fill the wound with saline during the procedure in which the Drug Delivery Device is inserted into the wound. Although zones of direct contact of the membrane with tissue (b strips in FIG. 32) cover only a small portion of the wound surface, the entire surface of tissue is treated, first, by means of lateral diffusion from b strip and second due to drug diffusion into porous layer into gaps between fibers. The delay in diffusion through porous case and afterwards thought he liquid gap between fibers is not large in comparison with diffusion through contact zone, because the diffusivity in water gap (diffusivity in water) is about 3 times higher than that within porous layer.

The assumed steady transport through porous layer assumes steady boundary condition at the boundary between the lumens and porous layer of the wall, namely $C=C_s$. (where $C_s$ is the saturation concentration of drug in the liquid inside the lumen). This is approximately valid, when the lumen is filled with powder but is not valid when the lumen is initially filled with saturated solution. In last case, a lower concentration forms in lumens on its boundary with porous layer because of diffusion into porous layer. As this layer extends the release rate decreases in time. This is an additional disadvantage of filling the lumens with a simple solution as opposed to filling the lumens with solid particles.

The loss of dissolved drug in the lumens near the porous layer, caused by diffusion into the porous layer also occurs when lumen is loaded with a solid drug. However, when solid particles of drug are present, restoration of solute concentration occurs due to dissolution of drug particles, which compensates for the loss of drug due to diffusion. Hence, the concentration on the boundary lumen porous layer continues to be approximately equal to $C_s$, which provides steady drug release approximately according to equation (4).

As more detailed analysis is found, that a not large decrease in concentration on the boundary occurs with decreasing powder amount associated with its dissolution, because, smallest distance of particles to porous layer (to wall) increases. However, this trend may be not strong, because in an actual patient, the orientation of fibers would alternate. This in turn would result in sedimentation of particles in a variety of directions, essentially randomly distributed with a distribution of the orientations of sediment deposit within various lumens. In any event, as a result particles generally approach some wall of the fiber; which prevents any substantial decrease in solute concentration.

Example 5

Experimental Results about Loading of Particles into Lumens of Hollow Fibers

Experiments have been performed regarding the loading of particles into the lumens of hollow fibers by flowing suspension into the lumen. For these experiments, the particles were particles of graphite as an inert model substance that would be easily visible because of its color. The carrier liquid used for these experiments was ethanol. Ethanol was used in part because of its low surface tension, i.e., its property of being able to easily wet the hollow fiber material. For these experiments, the average particle size of the graphite particles was less than approximately 20 microns, and the suspension of graphite particles in the isopropanol had a concentration of approximately 1 gram of graphite in 20 milliliters of 70% isopropanol. The hollow fibers used in these experiments were made of polypropylene, which was transparent, allowing easy visualization of the extent of deposition of black particles of graphite within the lumens of the fibers. The hollow fibers used in these experiments had an inside diameter of 250 microns, and a wall thickness of 28 microns. The walls of the fibers had a pore size substantially smaller than one micron, and a porosity (pore fraction) of about 40%.

As discussed elsewhere herein, there are two possible flow configurations for such a process of loading particles into a lumen using a suspension. The configurations are defined by how the carrier liquid exits the lumen, while at least some of the particles are retained inside the lumen. In one configuration, the carrier liquid exits through an end of the lumen. In the other configuration, the carrier liquid exits through the pores of the wall of the lumen. Of course, it is also possible for there to be mixed situations in which some portion of the carrier liquid exits through one of those paths and another portion of the carrier liquid exits through the other of those paths.

For both of these types of experiments, a suspension was created and was loaded into the barrel of a conventional syringe. Several hollow fibers were sealed into a luer-lock fitting using an adhesive material such as caulking material. The adhesive material hardened after a short time and anchored the fibers and created a seal defining a fluid communication with the lumens of the fibers. The luer-lock fitting was able to engage with a corresponding fitting on the discharge end of the syringe. The number of fibers used was typically six.

For a downstream-exit experiment, the downstream ends of the fibers were embedded in a fitting that ended in a filter just downstream of the downstream ends of the fibers. This filter, having a pore size of about 5 microns, was suitable to retain the particles of the graphite, but would allow the carrier liquid to pass through the filter. As suspension was ejected from the syringe into the fibers, a deposit of powder built up at the filter and gradually become a larger and larger deposit within the lumens of the fibers.

For a wall-exit experiment, the downstream ends of the fibers were embedded in caulking material so as to completely block the downstream ends of the fibers resulting in a dead-end flow situation. In this situation, carrier liquid of the suspension had to exit through the pores in the walls of the hollow fibers. It did so, leaving the particles within the lumen as a deposit that gradually became a larger and larger deposit as suspension was ejected from the syringe.

FIG. 40 shows fibers that received particles of graphite (black) deposited in the fiber lumens by the wall-exit method. As described above, these fibers were made of transparent polypropylene. They were manufactured by Celgard and were arranged as six parallel fibers with a slight separation between them. The spacing between the fibers was maintained by cross-fibers. It can be seen that most of the cross-section of the lumen is black indicating filling by the deposited particles. In a few places the filling is incompletely or imperfectly black, but it still is mostly black. The perfectness or imperfection is a function of details of the filling process.

Example 6

In this Example, we address mechanism of drug release from hollow fibers loaded with solid drug particles or drug powder. When the fibers are vertically oriented, and assuming that the drug particles settle and rearrange themselves as they shrink during use for drug release for some time, the rate of decrease of drug powder height caused by particle shrinkage due to dissolution provides information about dissolution rate and consequently about drug release rate. Transport of dissolved drug through the walls of the hollow fibers to adjacent tissue will occur. The release rate of the drug can be measured by measuring the decrease of the amount of powder, i.e., the height of the powder column, in the fiber lumen. This can be done most easily if the hollow fiber is transparent or when the drug particles possess color or can be imaged by light or other means Another possible approach to measuring the amount of powder remaining inside the fiber lumen would be to occasionally inflow additional suspension during release so as to observe the moment when added particles compensate particle loss that has been caused by dissolution of particles. The moment of compensation onset is identified due to appearance of a conical deposit above the fiber inlet. The amount of in-flowed suspension required to reach the point where the fiber lumen is again full, can inform about the amount of drug that was released since the last time the fiber lumen was full.

Unique Long Drug Release from Hollow Fiber Mesh (HFM) Enables New Significant Applications.

A unique and very important advantage of hollow fiber mesh (HFM) is the ability to provide or achieve long-term treatment and high concentration of drug in lymph nodes provided that the MIC is not too high.

Loading of lymphatics with drug or use of convective flow, originated by venule by HFM implantation can be useful at different locations of primary tumor because mainly everywhere in tissue lymphatics and/or venules are present. To this end, the locations of primary tumor have to be classified into 2 groups: that ones, when the distance between LN and primary tumor is not too large and that ones, when this distance is too large.

While modeling is focused on situation when the distance between a LB and skin is not large, the deeper implantation of HFM necessitated by deeper location of LB does not look impossible. This can lead to large extension of application area, it can be a claim.

Two conditions for targeting primary tumor, using HFM:
i) There is a critical molecular weight of drug. Drug molecules of supercritical molecular weight cannot penetrate through LN wall into surrounding drug tissue. This constraint exists even for much better penetrable wall of ILC.
ii) It seems there is no strong interstitial flow around LN, afferent and efferent capillaries. Hence, convection does not accelerate slow diffusion. On the other hand, rather long time for diffusion may be available (at least days) because cancer develops slowly. This makes unique long release from HFM very significant. During release time $T_{rel}^{fab}$, a zone loaded by drug around LN width $$W_{rel} \sim \sqrt{2DT_{rel}^{fab}}$$

forms, according to the Einstein equation. When the release stops, the zone width continues to grow due to diffusion. An essential increase of width $$W(t) \sim \sqrt{2DT} \; t > T_{rel}^{fab}$$

is possible if t essentially exceeds $T_{rel}^{fab}$.

Venules and Drug Transport to Tumor:

There is information that 90% of interstitial flow is directed to venules. If the distance between tumor and venule is not too long, the mesh placement between a venule and tumor leads to drug stream through tumor.

Preventing Metastasis with the Use of Hollow Fiber Membrane:

It can be assumed that metastasis appearance at long distance from primary tumor is possible only by carrier cell transport with blood or lymph. The HFM placement between primary tumor and LB (or venules) prevents the infection of lymph stream or blood stream with cancer cells.

Materials

Any of the described constructs such as hollow fibers could be made of material that is either resorbable or non-resorbable.

Sometimes, implants are made containing drug for purpose of controlled release drug delivery. For example, a form of contraceptive implant (sold by Merck as Nexplanon or Implanon) is a subdermal contraceptive implant. Such a device can be 4 cm long and 2 mm in diameter for implantation under the skin of the upper arm. An earlier device operating on the same principle was known as Norplant. Such device is non-resorbable and is removed after a period of some years of implantation. For example, the Nexplanon device can be made of ethylene vinyl acetate copolymer and can contain the hormone etonogestrel.

Drug delivery devices that are similar in principle to these just-described contraceptive devices could be made of materials that are resorbable. It can be understood that in general, when drug delivery implants are made of resorbable material, it is often true that the degradation rate of the resorbable implant is not what determines the release rate of the drug. Rather, the release rate is determined by diffusion. Typically the duration of release is shorter than the duration of existence of the resorbable implant inside the body of the patient.

Examples of polymers that are resorbable include the following: poly lactic acid; poly glycolic acid; poly lactic co-glycolic acid; aliphatic polyesters; polyanhydrides; polyphosphazenes; poly amino acids; poly orthoesters; natural biodegradable polymers such as albumin, collagen, dextran, gelatin, pectin, and starch. PLA and other resorbable polymers are capable of being melted and are capable of being attached by softening due to temperature or other parameters.

Porosity in a wall of a resorbable fiber could be created by manufacturing methods similar to those used in some fibers made of non-resorbable material. This can include making small holes in the wall of a fiber followed by stretching of the fiber in desired directions, which can make the holes or pores elongated.

Surfactants used in embodiments of the invention can include any of various surfactants, including anionic, cationic, nonionic and amphoteric types.

Suitable anionic surfactants include fatty acid soaps covering a range of alkyl chain length up to for example about 18 carbon atoms or more and can be straight or branched chain alkyl groups. These surfactants are normally used at a pH higher than the dissociation constant of their corresponding carboxylic acid. Another class of anionic surfactants that has been found to be effective with the present method is alkyl sulfates and sulfonates, such as sodium dodecyl sulfate (SDS). Yet another useful anionic surfactant can be based on alkylpolyoxyethylene sulfate. Another anionic surfactant that can be used is an alkylbenzene sulfonate. Linear and branched chain alkylbenzene sulfates with one or more sulfonate groups have been found to be useful. Suitable anionic surfactants also include alpha-olefin sulfonates, monoalkyl phosphates, acyl isothionates, acyl glutamates, N-acyl sarcosinates and alkenyl succinates and the like that have an anionic surface group and possess surface activity.

Suitable amphoteric surfactants include alkyldimethylamine oxides, alkylcarboxy betaines, alkylsulfobetaines, amide-amino acid type amphoterics and others that can exhibit amphoteric and surface activity. Amphoteric substances have characteristics of both acid and alkali groups.

Useful nonionic surfactants include polyoxyethylene alkyl ethers, polyethylene alkylphenyl ethers, polyethylene fatty acid esters, sorbitan fatty acid esters, polyethylene sorbitan fatty acid esters, sugar esters of fatty acids, alkyl polyglycosides, fatty acid diethanolamides, fatty acid monoglycerides, alkylmonoglyceral ethers, fatty acid polypropyleneglycol esters and the like.

Cationic surfactants useful herein include alkyltrimethylammonium salts and their phosphonium analogues, dialkyldimethyl ammonium salts, alkylammonium salts, alkylbenzyldimethylammonium salts, alkylpyridinium salts and the like which bear cationic functional groups and possess some surface activity.

Polymeric dispersants are also useful herein. Although they do not have the molecular structure of a typical surfactant, they have similar effects. These include formaldehyde condensates of naphthalene sulfonate, sodium acrylates or copolymers of other acrylic acids, copolymers of olefins and sodium maleate, lignin sulfonates, polyphosphates, silicates and polysilicates, carboxymethyl cellulose, cationic cellulose, cationic starches, polyvinyl alcohol, polyethylene glycol, polyacrylamides and the like. These compositions are also useful herein as surfactants. There are also detergent substances which are not strictly surfactants. Examples include trisodium phosphate, sodium carbonate and polymers. Such substances can also be used with the present invention.

Solubilizing agents can be any of the following types: (1) Agents that inhibit crystal formation of the drugs or otherwise act by complexation of the drug, such as polyvinylpyrrolidone, polyethyleneglycol and cyclodextrins; (2) a high Hydrophilic-Lipophilic-Balance micelle forming surfactant, particularly anionic surfactants such as Tween 20, Tween 60, Tween 80, polyoxyethylene or polyethylene containing surfactants and other long chain anionic surfactants such as sodium lauryl sulfate; (3) citrate esters and their combinations with anionic surfactants (e.g., alkyl esters particularly triethyl citrate.

Osmotic agents or osmogens can be any of the following types: inorganic water soluble osmogens, such as magnesium sulfate, sodium chloride, sodium sulfate, potassium chloride, sodium bicarbonate, etc.; organic polymeric osmogens such as sodium carboxymethyl cellulose, hydroxypropyl methylcellulose, hydroxyethylmethylcellulose, etc.; organic water soluble osmogens such as sorbitol, mannitol etc.

Substances that can be caused to flow through pores to coat the pores and thereby render them more hydrophilic include plasticizers, which would be a low molecular weight organic molecule that is compatible with the material of which the wall is made. An example is an alcohol. Another example is polyvinylpyrrolidone.

Membrane materials of which the walls could be made include liquid membranes, ceramic membranes, and polymeric membranes. Examples of polymeric membranes include cellulose acetate; nitrocellulose; cellulose esters (CA, CN, CE); polysulfone; polyethersulfone; polyacrylonitrile; polyamide; polyimide; polyethylene; polypropylene; polytetrafluoroethylene; polyvinylidene fluoride; polyvinylchloride. Examples of ceramic membranes include alumina; titania; zirconia; recrystallized silicon carbide; and some glassy materials.

For a coating material that might be forced through the pores for the purpose of hydrophilizing the pore surfaces, there are several possibilities: polyvinyl alcohol; polyvinylpyrrolidone; polyvinyl acetate partially hydrolyzed; polyethyleneglycol of various molecular weights; polyacrylamides and their derivatives; cellulose based polymers; other surface hydrophilizing polymers. These polymers either separately or as blends can be dissolved in appropriate solvents such as alcohols, esters, amines and amides.

Anti-flocculating agents can comprise surfactants of all types, poly electrolytes, hydrating agents such as polyvinyl alcohol, and organic liquids or solvents.

It can be appreciated that embodiments of the invention provide large surface area of fibers, and provide a wide range of ability to adjust drug loading contained in the device, drug release rate and other drug release characteristics. These adjustments can be achieved by appropriately choosing, among other factors, the amount of drug contained in the device, use of suspension of drug particles rather than drug in solution, pore size, surface properties, formulation of the contents inside the fiber lumens, and other parameters. It is furthermore possible to vary such properties from place to place within the device.

It can be appreciated that with embodiments of the invention, it is possible to deliver protein or drugs that are sensitive to steps of manufacturing process such as temperature, because it is possible to avoid exposure of such substances to excessive temperatures during manufacture.

It is also possible, as has been explained, for the device to serve a combination of structural and drug-delivery roles. It is possible for the device to have desired shape and to have mechanical properties that are directionally dependent, if desired.

It can be appreciated that embodiments of the invention offer various advantages over existing technologies.

Embodiments of the invention can be fabricated to any shape and size, and can be pliable and compatible with tissues and with tissue movement. A planar construct can be fashioned so as to emit drug equally from both of its opposing faces, or unequally from its two faces, or only from one of its faces. If there is a filling tube or port, it can be located at any position or orientation to facilitate its access.

Embodiments of the invention can be made so that the device is able to be re-filled or re-loaded after it has been implanted in the patient. This allows for long-term administration of quantities of drug that are not limited by what can be contained in the device at the time of its implantation. This allows for variable dosing and even for the drug to be changed over a period of time. This allows locoregional administration of drugs for purposes such as immunosuppression or chemotherapy without carry-over into the systemic circulation. The port for re-filling or re-loading the device can be situated away from the area of delivery of immunosuppressant or other drug, to lessen the chances of introduced infection with port access. Drug can, for example be administered to the lymphatic system to be carried by flow in a known direction of lymph flow.

Embodiments of the invention are capable of delivering multiple agents simultaneously. If different materials or pore sizes are required for delivery of different agents, different fibers of appropriate specifications can be incorporated into the device appropriately.

Embodiments of the invention can be flushable, in the sense that it can also be possible to remove fluid from the device if desired. In addition to a filling port/tube, the device can be equipped with an efflux channel or port, such that the instilled material can be removed from or flushed through the device if need arises (e.g. in the case of development of unwanted high concentrations of a drug such that less release than normal is desired). As a further consideration, simply varying the solvent composition of a drug can also help in modulating its release profile. If there is a connection outside the patient, different drugs or drug formulations can be delivered at different times.

In connection with discussion of different drugs at different times or places, different drugs could be located in two different layers. Different drugs could be same class of drugs, such as different antibiotics for different classes of bacteria, or alternatively one antibiotic and one other category of substance such as an analgesic or an anti-inflammatory. Anti-adhesion substances could be included anywhere where it would be beneficial to do so. It would also be possible to use embodiments of the invention in combination with conventional surgical mesh, such as with one device implanted next to the other device.

Embodiments of the invention offer the possibility of being removable such as in the event of a complication such as infection, perhaps removable by means of a fairly minor superficial surgical procedure. One embodiment of the invention even offers the possibility of removal by essentially being pulled out like a string, after resorption of certain elements of the device that maintain its shape and interconnection.

Embodiments of the invention offer the capability of prophylaxing their own possible complications. There are two largely foreseeable complication risks attendant to the use of implants such as mesh constructs of embodiments of the invention. The first such complication risk is fibrosis: any implanted foreign body might develop a fibrous capsule at its periphery. It is unclear whether such a capsule would impede the effective delivery of drug to the adjacent tissues, but in the event that it does, the mesh can itself be used to deliver a fibrolytic agent, such as the clostridial collagenase used to treat Dupuytren's contracture. It is possible to envision a regimen where every 3 months the mesh would be prophylactically so treated until an inconsequential fibrotic response obtained. The second major complication risk is infection. Here again, the mesh can serve as its own defense by instilling and elaborating an antimicrobial agent (perhaps an antimicrobial peptide) that would accumulate locally and prevent local colonization and propagation of bacteria without the need for widespread systematic antibiotic exposure. These are important advantages of embodiments of the invention.

Embodiments of the invention can make use of knowledge about lymphatic flow and circulation so as to track and kill micrometastases. Embodiments of the invention can make use of the manufacturing experience of hollow fibers for dialysis technology.

In embodiments of the invention, drug delivery devices and constructs can be made containing both the flat sheet membranes and also hollow fibers. For example, hollow fibers could be attached to membranes in appropriate places. Such a hybrid design is envisioned to be suitable to perform certain therapies or treatments.

It is possible that, in an embodiment of the invention, Hydrodynamically Driven drug release and Diffusion Driven drug release can be combined in a particular device or construct. For example, it is possible that a device or construct could contain two different drugs, and the desired release characteristic for one of the drugs is Hydrodynamically Driven drug release and the desired release characteristic for the other drug is Diffusion Driven drug release. Different places in the device or construct could contain membranes or fibers having different release characteristics. Even for a single drug, it would be possible to have some of the construct be Hydrodynamically Driven and some other of the construct be Diffusion Driven.

It also would be possible for part of the construct to be a flat-sheet membrane construct while some other part of the construct comprises hollow fibers. For example, the hollow fibers could be attached at certain places to the membrane.

NUMBERED EMBODIMENTS

The invention is further described below with reference to numbered embodiments. All numbered embodiments to a device can be used in a method of a numbered embodiment, unless a recitation is in conflict.

Embodiment A1: A medical device configured for implantation within a subject's body, comprising: one or more hollow, non-metallic fibers having native-permeable walls that define interior lumens, wherein a drug is located in at least some of said lumen, wherein the walls comprise pores, wherein said walls provide a drug release rate that after implantation provides a pharmaceutically effective amount of drug, and wherein: (a) the hollow, non-metallic fibers are comprised in a fiber-complex, which is a fabric construct or a yarn construct, or (b) at least some of said lumens further contains a polymeric substance, said polymeric substance having a molecular weight such that said polymeric substance is resistant to passing through said wall, said polymeric substance comprising (i) a polymeric substance that absorbs water when in the presence of aqueous bodily fluids, (ii) a viscosity-enhancing or gel-forming substance that produces a high viscosity liquid or a gel when in aqueous solution, or (iii) a swellable material that increases its volume upon absorption of bodily fluids, or (c) the permeable wall comprises a base material that is treated to render it more hydrophilic than in its untreated condition, or (d) different parts of said lumen(s) (this can be in different fibers) contain a distinct second drug or a formulation of the first drug that is different from a formulation of the drug compared to fibers in another part of said device, or (e) the hollow, non-metallic fiber or fibers are comprised in a suture and are attached to suture lead end that has a sharpness and stiffness selected for use as a suture lead, or (f) the medical device further comprises a reservoir of drug, the reservoir in fluid communication with the hollow, non-metallic fibers, or (g) one or more of the hollow, non-metallic fibers terminates in (i) a port configured to provide a fluid connection to a conduit for filing or draining that hollow fiber from outside the subject's body or (ii) a fluid connection to such a conduit, or (h) one or more of the hollow, non-metallic fibers is arrayed along a catheter, or (i) one or more of the hollow, non-metallic fibers having end(s) fixed in a potting material configured to provide a connector to a supply or drain line, or (j) a said hollow, non-metallic fiber has one or more deformations at selected place(s) along its length that obstruct fluid communication in the fiber interior, said the walls of hollow fiber exhibiting a molecular weight cutoff of about 500 Daltons or higher (e.g., about 1,000 Daltons or higher, or about 2,000 Daltons or higher); or (k) a device according to one of (a) through (j), wherein the device is resorbable; or (l) any combination of the foregoing.

Embodiment A2. The medical device of Embodiment A1, wherein the medical device is a fiber-complex pursuant to (a), wherein a plurality of the hollow, non-metallic fibers are present and are joined to form the fiber-complex.

Embodiment A3. The medical device of Embodiment A1, wherein the medical device comprises a first fabric construct pursuant to (a) and, laminated against the first fabric construct, (1) a barrier layer resistant to permeation of the drug through the barrier or (2) second fabric construct comprising second fibers.

Embodiment A4. The medical device of Embodiment A3, wherein the medical device is pursuant to (1).

Embodiment A5. The medical device of Embodiment A3, wherein the laminated barrier or fabric is resistant to adhering to tissue.

Embodiment A6. The medical device of Embodiment A4 that is a tissue guide, wherein the fabric construct is configured to substantially surround an area of tissue or an area where tissue growth is sought, and wherein the barrier layer is exterior to the fabric construct (relative to the tissue or area).

Embodiment A7. The medical device of Embodiment A1, wherein the medical device is pursuant to (d).

Embodiment A8. The medical device of Embodiment A7, wherein the distinctions of the drug compositions include distinctions in excipient (including surfactant).

Embodiment A9. The medical device of Embodiment A1, wherein the medical device is pursuant to (b).

Embodiment A10. The medical device of Embodiment A9, wherein the medical device is pursuant to (b)(ii), and wherein at least in portions of the device the drug is in a reservoir-providing amount comprising particles comprising drug, wherein the drug particles are suspended in a viscous fluid comprising the viscosity-enhancing or gel-forming substance—in embodiments the viscous fluid has a viscosity of about 500 centipoise or higher (e.g., 1,000 centipoise or higher).

Embodiment A11. The medical device of Embodiment A1, wherein the medical device is pursuant to (c).

Embodiment A12. The medical device of Embodiment A1 that is a suture, wherein the medical device is pursuant to (e).

Embodiment A13. The medical device of Embodiment A1, wherein the medical device is pursuant to (f).

Embodiment A14. The medical device of Embodiment A13, wherein the reservoir is a manifold in fluid communication with multiple said hollow, non-metallic fibers.

Embodiment A15. The medical device of Embodiment A13, wherein the reservoir is configured to be filled or re-filled or drained via tubing to the exterior of the subject while they are implanted in a subject.

Embodiment A16. The medical device of Embodiment A1, wherein the medical device is pursuant to (g).

Embodiment A17. The medical device of Embodiment A1, wherein the medical device is pursuant to (h).

Embodiment A18. The medical device of Embodiment A1, wherein the medical device is pursuant to (i).

Embodiment A19. The medical device of Embodiment A1, wherein the medical device is pursuant to (j).

Embodiment A20. A method for treating a subject, comprising: (A) implanting into a tissue location of the subject a medical device, wherein the tissue location has an initial interstitial flow (i.e., prior to implant), a real-time interstitial flow (e.g., after implant) and has a hydrodynamic permeability, the device comprising a permeable wall (which can be a native-permeable wall; which can be a device of the invention with hollow fibers) and a chamber comprising drug, wherein the hydrodynamic permeability of the wall is approximately equal to or greater than a hydrodynamic permeability of the tissue, (B) having the real-time interstitial flow penetrate the wall into the chamber with a penetrating velocity, wherein the penetrating velocity is greater than the initial interstitial velocity, and (C) providing hydrodynamic driven release of the drug into the local interstitial flow (wherein, in embodiments, the hydrodynamic driven release is comparable to or predominates over diffusion driven release). (In embodiments, the method treats an medical indication in the subject).

Embodiment A21. A method of implanting within the body of a subject a medical device comprising one or more hollow, non-metallic fibers having a native-permeable wall that defines an interior lumen, wherein a drug selected for effectiveness against a medical indication is located in at least some of said interior lumen, wherein said wall provides for release of the drug, the medical device placed so as to deliver an effective amount of the drug at a disease affected tissue while delivering less than such an amount at a tissue different from the affected tissue. (In embodiments, the method treats an medical indication in the subject).

Embodiment A22. The method of Embodiment A21, wherein the hollow, non-metallic fiber(s) are linearly cohesive with two ends, and wherein one or more resorbable second fibers or linking structures structurally restrain the linearly cohesive fibers to form a fabric construct, and wherein the method further comprises leaving the medical device in the subject for a period of time for the resorbable fibers or linking structures to be sufficiently degraded so that the linearly cohesive fibers are no longer structurally restrained, and pulling a portion of the linearly cohesive fibers (such as an end) to pull the linearly cohesive fibers from the body of the subject.

Embodiment A23. A method of filling with particles of a first average size one or more hollow, non-metallic fibers having native-permeable walls that define interior lumens, the hollow fibers having a first and second end, comprising: (A) restricting particle flow through the second ends (e.g., by placing the second ends in particles of a second, larger size, by placing the ends against a filter or membrane, or by closing the ends); (B) flowing the particles suspended in a liquid into the first ends; (C) allowing the suspending fluid to flow out through pores in the walls, or through the second ends, or both; and (D) maintaining the flowing and allowing until the particles pack in the lumens to a desired packing density.

Embodiment B1: A bilayer medical device configured for implantation, comprising: a first polymeric layer; a second polymeric layer; bondings between said first layer and said second layer, wherein said bondings define discrete regions enclosing individual volumes between said first layer and said second layer; and drug, wherein the amount of drug is a pharmaceutically effective amount when released from the medical device after implant, the drug contained in at least some of the discrete regions, wherein said first layer is permeable to said drug.

In method or device of a numbered bilayer embodiment:

Embodiment B2: wherein said second layer is less permeable (including substantially impermeable) to said drug or said drug formulation than said first layer.

Embodiment B3: wherein at said bondings, said first layer and said second layer are fused to each other.

Embodiment B4: wherein said bondings define closed perimeters around said discrete regions.

Embodiment B5: wherein said junctions define discrete regions that are interconnected with others of said regions.

Embodiment B6: wherein some of said discrete regions contain a second drug or a second drug formulation, different from said first drug or said first drug formulation.

Embodiment B7: wherein said first polymeric layer or said second polymeric layer are resorbable.

Embodiment B8: in combination with sub-device comprising one or more hollow, non-metallic fibers having native-permeable walls.

In a method or device of a numbered embodiment:

Embodiment C1: wherein at least in portions of the device (per the device or as utilized in the method) the drug is in a reservoir-providing amount comprising particles comprising drug (e.g., particle size about 20 to about 60 micrometers, or about 0.1 to about 10 micrometers).

Embodiment C2: embodiment of Embodiment C1, wherein the drug particles are suspended in a viscous fluid comprising the viscosity-enhancing or gel-forming substance.

Embodiment C3: wherein the device (which can be as utilized in the method) is configured to resiliently retain or support tissue.

Embodiment C4: wherein the lumens of the first hollow fibers have diameter of about 50 microns or more.

Embodiment C5: wherein the drug is formulated with one or more of a surfactant (e.g., anionic surfactant, cationic surfactant, nonionic surfactant, amphoteric surfactant, zwitterionic surfactant); a thickener; a suspending agent; a gel-forming agent; a buffer; a viscosity modifier or an osmotic agent.

Embodiment C6: wherein the drug is an antimicrobial; an antibiotic, an anti-biofilm drug; a chemotherapeutic drug; a growth factor, a substance to suppress fibrosis; an anesthetic; an analgesic; an anti-inflammatory; an immunosuppressant; an immune modulator; a chemotherapeutic agent; an anti-coagulant; an anti-adhesion drug; a muscle relaxant; a tissue relaxant; and a biologic.

Embodiment C7: wherein the hollow fibers first fiber(s) are joined to each other or to other segments thereof.

Embodiment C8: embodiment of Embodiment C7, wherein the fibers or segments are joined to each other by heat fusing, solvent fusing, ultrasonic fusing, or adhesive bonding.

Embodiment C9: wherein the hollow fibers first fibers are joined to each other by joining structures (which can be adhesive).

Embodiment C10: embodiment of Embodiment C9, where the joining structures are resorbable (and in embodiments wherein the first hollow fibers are not resorbable).

Embodiment C11: wherein the drug is effective to limit the formation of a biofilm on the medical device.

Embodiment C12: wherein the device comprises a second drug (which in embodiments can be in the same lumen as the first drug), and wherein the first drug is an antibiotic that is effective against a first class of pathogens and the second drug is an antibiotic that is effective against a second class of pathogens different from said first class.

Embodiment C13: wherein the device is a fiber-complex pursuant to (a), wherein a said hollow, non-metallic fiber has deformations at selected place(s) along its length that obstruct fluid communication in the fiber lumen such that the device uniformly releases drug (i.e., that drug does not settle within the lumen so that portions (areas of 5 mm or 25 mm$^2$ depending on being a linear device or a 3-D shaped device) are not devoid of an effective amount of drug).

Embodiment C14: embodiment of Embodiment C13, wherein the deformations are effected by heat sealing, exposing to a laser, ultrasonic welding, or exposure to a solvent (such as solvent welding).

Embodiment C15: embodiment of Embodiment C13 or Embodiment C14, wherein the drug in one or more of the hollow, non-metallic fibers with deformations is in a reservoir-providing amount comprising particles comprising drug.

Embodiment C16: wherein ends of at least some of the hollow fibers are closed by heat-sealing, ultrasonic welding, exposure to a laser, solvent welding, or being patched with a glue or an adhering polymer. (b), wherein prior to use the material in the lumen(s) is in dry form.

Embodiment C17: wherein the device is pursuant to (b)(ii), and wherein at least in portions of the device the drug is in a reservoir-providing amount comprising particles comprising drug.

Embodiment C18: embodiment of Embodiment C17, wherein the drug particles are suspended in a viscous fluid comprising the viscosity-enhancing or gel-forming substance.

Embodiment C19: embodiment of Embodiment C17 or Embodiment C18, wherein the drug particles have average diameter about 100 times an average diameter for the pores.

Embodiment C20: embodiment of Embodiment C19, wherein the viscosity in combination with the size of drug particles and the inside diameter of said hollow fiber is sufficient to produce a settling time of said drug particles that is about 1000 seconds or longer (or about 10,000 seconds or longer).

Embodiment C21: embodiment of Embodiment C18, wherein the viscosity is higher at a temperature from about 35° C. to about 39° C. than it is at 25° C. (e.g., a triblock copolymer).

Embodiment C22: wherein the native-permeable walls are treated to render them more hydrophilic than in their untreated condition, the native-permeable walls comprise polypropylene.

Embodiment C23: wherein the native-permeable walls are treated to render them more hydrophilic than in their untreated condition, wherein the treatment comprises exposure to ozone or to gamma radiation, to electron beam radiation, to an acid, to an alcohol, or to a non-alcohol organic solvent.

Embodiment C24: wherein the native-permeable walls are treated to render them more hydrophilic than in their untreated condition, wherein treatment comprises exposure to ozone on only one side of the device, or exposure to electron beam radiation from a particular direction relative to the device wherein the electron beam radiation has a penetrating distance that is less than a diameter of the fiber, or to a liquid on only one side of the device.

Embodiment C25: wherein the hydrophilic treatment pursuant to (c) wherein wall comprises a structural material that does not contain oxygen, and wherein at surfaces of the walls or surfaces of the pores, the walls comprise a second substance that can adhere to said first substance and but is more hydrophilic than the first substance (e.g., comprises one or more (1) oxygen-containing groups (e.g., hydroxyl group (e.g., alcohol of C5 or less), carboxyl group a peroxy group), or (2) polar groups comprising nitrogen, sulphur or phosphorus)(while the second substance is generally applied via the treatment, the device embodiment can be interpreted irrespective of the treatment).

Embodiment C26: wherein the hydrophilic treatment pursuant to (c) wherein wall comprises a structural material that does not contain oxygen, and wherein surfaces of the pores comprise a coating of second substance that is more hydrophilic than the first substance (e.g., where the coating formed by forcing the second substance (e.g., polymer) through the pores).

Embodiment C27: wherein for a hollow, non-metallic fibers having native-permeable walls the structural polymer of the walls is polypropylene, a polyethersulfone-polyvinyl pyrrolidone blend (PES-PVP), cellulose triacetate, polyacrylonitrile (AN 69), silicones, or polyethylene vinyl alcohol (PEVA)

Embodiment C28: wherein the surfaces of one or more of the hollow, non-metallic fibers have a contact angle with water of less than 90 degrees.

Embodiment C29 wherein the reservoir is connected to configured to connect to a supply or drain line configured to supply drug from or drain to outside the subject's body.

Embodiment C30: embodiment of Embodiment C29, wherein the reservoir is connected to configured to connect to the supply and the drain line.

Embodiment C31: wherein the reservoir is connected to the lumens of multiple said hollow, non-metallic fibers having native-permeable walls.

Embodiment C32: embodiment of Embodiment C31, wherein the hollow fibers are connected via a connection formed of potting material.

Embodiment C33: wherein the tissue guide is configured as a nerve guide (e.g., tublular).

Embodiment C34: wherein the pouch is configured to enclose a cardiac pacemaker or a defibrillator or an implantable pump or an artificial heart.

Embodiment C35: wherein one or more of the hollow, non-metallic fibers are filled with drug formulation comprising particles comprising drug, wherein the drug formulation comprises polymeric substance that absorbs water or surfactant.

Embodiment C36: wherein lumens of one or more hollow, non-metallic fibers are connected to configured to connect to a supply line configured to supply drug from outside the subject's body.

Embodiment C37: wherein the device is resorbable.

Embodiment C38: wherein the medical device comprises a fabric construct pursuant to (a), wherein the fabric construct is configured as a pouch configured to partially or completely enclose a second medical device.

Embodiment C39: wherein the Darcy permeability of the native-permeable wall is about 10E−19 m$^4$/Ns or higher.

Embodiment C40: wherein the Darcy permeability of the native-permeable wall is about 10E−17 m$^4$/NS or higher.

Embodiment C41: wherein at least some of said hollow, non-metallic fibers are configured to be filled or re-filled via tubing to the exterior of the subject while they are implanted in a subject.

Embodiment D1: In embodiments wherein the medical device has connection to or is configured to connect to a supply line or a drain line, wherein the connection, or piece configured to connect is resorbable.

Embodiment E1: In a method of a numbered embodiment or utilizing a device of a numbered embodiment, wherein said drug has a smallest hydrodynamic size dimension, and wherein the permeable wall has an average pore diameter that is about 2 times or more (or about 10 times or more, or about 100 times or more) as large as that size dimension.

In a Method or Device of a Numbered Embodiment Calling for Second Fibers, the Second Fibers:

Embodiment F1: can be solid or hollow.

Embodiment F2: can be stronger than the first, or weaker than the first.

Embodiment F2A: can have a different mechanical property from the first.

Embodiment F2B: can be resorbable, as can the in embodiments the first.

Embodiment F3: can contain drug or not.

Embodiment F4: can contain drug with a different drug, or formulated differently from the drug in the first fibers.

Embodiment F5: embodiment of Embodiment F4, wherein the differences in formulation include differences in the presence of surfactant, the type of surfactant or the concentration of surfactant.

Embodiment F6: can be oriented in a different direction that the first fibers, including perpendicular.

Embodiment F7: are hollow-non-metallic fibers have native-permeable walls, wherein the first native-permeable walls and the second native-permeable walls are differently treated to render them more hydrophilic than in their untreated condition.

Embodiment F8: are hollow-non-metallic fibers have native-permeable walls, wherein the first native-permeable walls and the second native-permeable walls are different in one or more of porosity, pore size, pore size distribution, hydrophobicity, surface treatment or composition of the respective native-permeable wall.

Embodiment F9: wherein the fiber-complex is a fabric construct, the first fibers are oriented in a first direction, and the second fibers are oriented in a second direction different from the first providing crossing points where the fibers cross—and in embodiments wherein the first fibers and second fibers being joined to each other at least some said crossing points.

Embodiment F10: wherein the second fibers are said hollow, non-metallic fibers having a second native-permeable wall, wherein the drug in said second fibers is (i) distinct from the first drug, or (ii) formulated differently from the first drug.

In a method or device of a numbered embodiment calling for a first fabric and a second fabric or a barrier:

Embodiment G1: wherein the second fabric construct is pursuant to (a) and the drug comprised in the second fibers is a second drug that is distinct from the first or formulated differently, wherein if the second drug is the same as the first, the release profile by diffusion is distinct from that for the first drug.

Embodiment G2: embodiment of Embodiment G1, wherein the second fibers are stronger than the first fibers Embodiment G3: where there is a barrier layer, and wherein at least portions of the barrier layer extend beyond the fabric construct and the devices comprises such portions coated with adhesive, the adhesive configured to adhere the device to a substrate.

In a Method or Device of a Numbered Embodiment Calling for Second Fibers and Optionally Third Fibers:

Embodiment H1: two or more of the first, second and third fibers are interwoven.

Embodiment H2: two or more of the first, second and third fibers are joined to each other.

Embodiment H3: embodiment of Embodiment H2, where the fibers are joined to each other by heat fusing, solvent fusing, ultrasonic fusing, or adhesive bonding.

Embodiment H4: two or more of the first, second and third fibers are joined to each other by joining structures (which can be adhesive).

Embodiment H5, where the joining structures are resorbable (and in embodiments wherein one or more of the first hollow fibers, second fibers or third fibers are not resorbable).

Embodiment H6: wherein the first hollow fiber is a single fiber dispersed within the device.

Embodiment H7: wherein the fiber-complex is a fabric construct, wherein the first fibers are oriented in a first direction, and the second fibers are oriented in a second direction different from the first, and the fabric construct further comprises third fibers oriented in a third direction different from the second, wherein the second and third fibers are stronger the first.

In a Numbered Embodiment that is Method or Device Calling for a Suture:

Embodiment I1: wherein the one or more hollow, non-metallic fibers having native-permeable walls is supported by one or more structural fibers that are stronger than said hollow fibers.

Embodiment I2: embodiment of Embodiment I1, wherein the one or more hollow, non-metallic fibers are braided or wound about the structural fibers.

Embodiment I3: wherein one or more hollow, non-metallic fibers are pre-filled with drug while one or more other hollow, non-metallic fibers are configured to be filled or re-filled while they are implanted in a subject.

Embodiment I4: wherein the hollow, non-metallic fibers are braided.

Embodiment I5: wherein the hollow, non-metallic fibers are braided with one or more second fibers that are stronger than the hollow, non-metallic fibers.

In a Hydrodynamic Driven Release Method (which can Use any Medial Device of a Numbered Embodiment, or any Treatment Method of a Numbered Embodiment):

Embodiment J1: wherein the velocity of the penetrating flow is less than about double the initial interstitial velocity.

Embodiment J2: wherein a permeability of wall Darcy Constant K is about one order of magnitude or more higher than a permeability of tissue Darcy Constant Kti, wherein a membrane porosity is about 0.2 to 0.5, and a mean diameter of membrane pores exceeds a mean diameter of tissue pores by a factor of about three or more times.

Embodiment J3: wherein a permeability of wall Darcy Constant K is at least one order of magnitude higher than a tissue Darcy Constant Kti, wherein a membrane porosity is about 0.2 to 0.5, wherein average pore diameters in the wall are about 0.1 micron or more.

Embodiment J4: wherein the medical device is configured to provide a shape of drug emitting surface, whereby the shape in conjunction with the local interstitial flow provides a shaped flux of drug, wherein the shaped flux is configured to provide more drug to a target tissue, and less to an adjacent, non-target tissue.

Embodiment J5: wherein the molecular weight of the drug is about 1,000 or higher.

Embodiment J6: wherein at least in portions of the device the drug is in a reservoir-providing amount comprising particles comprising drug of average diameter about 0.1 to about 10 micrometers.

Embodiment J7: embodiment of Embodiment J6, wherein drug solubility is about 4 times the minimum inhibitory concentration for the illness or infection to be treated.

Embodiment J8: wherein HDR is greater than DDR by about one order of magnitude or more (such as about two orders of magnitude or more).

Embodiment J9: wherein the device is positioned to provide a shaped flux configured to intercept two or more separated portions of a target tissue (which can be a tumor).

In a method of implantation or treatment (which can use any medial device of a numbered embodiment, or any treatment method of a numbered embodiment):

Embodiment K1: wherein the medical device is placed between a lymphatic bed and a tumor, wherein the device provides a anti-cancer drug flux that provides an effective amount of drug to most or all of fluid flow that would carry metastatic cancer cells.

Embodiment K2: wherein the device is positioned to provide drug flow into the lymphatic system.

Embodiment K3: wherein the device is positioned to provide drug flow to a target tissue (such as tumor).

Embodiment K3: wherein the device is periodically refilled while in situ.

Any combination of disclosed features, components and methods is possible.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

This invention described herein is of a medical implants, methods of forming the same, and methods of use. Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims. It is to be further understood that while the specification addresses in detail theoretical considerations, the constructs and methods of the invention are believed to be novel irrespective of the mechanism of action.

The invention claimed is:

1. An implantable device for administering a drug, the device comprising:
   a plurality of nonmetallic hollow fibers having native-permeable walls, the walls having characteristics such that molecules of the drug can pass through the walls while a larger osmogen or hydrating molecule cannot pass through the walls, the hollow fibers having respective fiber lumens, the hollow fibers having respective first ends and respective second ends opposite the first ends;
   a reservoir having a reservoir internal lumen, wherein at the first ends, the fiber lumens are in fluid communication with the reservoir internal lumen;
   a port connected to the reservoir internal lumen and comprising a septum that is configured to self-seal after puncture such that the drug can be fed into the reservoir internal lumen and thence into the fiber lumens, wherein the hollow fibers or the hollow fibers and further fibers are interwoven or adhered to form a fabric construct.

2. The device of claim 1, further comprising
   a draining reservoir having draining reservoir internal lumen, wherein the second ends of the hollow fibers are in fluid communication with the draining reservoir internal lumen; and
   a drain port connected to the draining reservoir internal lumen and comprising a draining septum that is configured to self-seal after puncture such that fluid can be drained from the draining reservoir internal lumen and hence from the fiber lumens.

3. The device of claim 1, wherein the fiber lumens contain dry particles of the drug.

4. The device of claim 1, wherein the fiber lumens contain particles of the drug that are suspended in a gel or in a liquid that has a viscosity greater than 500 centiPoise.

5. The device of claim 1, wherein the fiber lumens contain particles of the drug that have an average diameter of about 0.1 to about 10 micrometers.

6. The device of claim 1, wherein the fiber lumens contain as the drug at least one of a substance selected from the group consisting of: an antimicrobial; an antibiotic; an anti-biofilm drug; a chemotherapeutic drug; a growth factor, a substance to suppress fibrosis; an anesthetic; an analgesic; an anti-inflammatory; an immunosuppressant; an immune modulator; a chemotherapeutic agent; an anti-coagulant; an anti-adhesion drug; a muscle relaxant; a tissue relaxant; and a biologic, and peptides, proteins, enzymes, antibodies, DNA, RNA, growth factors or modulators, immunogens, immune-therapeutics, and any substance that can act on a cell, virus, tissue, organ or organism to create a change in functioning of the cell, virus, organ or organism to achieve a pharmaceutical or therapeutic effect.

7. The device of claim 1, wherein the fabric construct comprises solid fibers that are intertwined with or interspersed with or attached to the hollow fibers.

8. The device of claim 1, further comprising an osmogen contained inside the device, the osmogen being in a dry condition, the osmogen being capable of absorbing liquid and swelling and urging material to pass through the walls out of the device, wherein the material can pass through the wall and the osmogen has a molecular weight such that the osmogen is unable to pass through the wall.

9. The device of claim 1, wherein the device or a portion thereof is resorbable.

10. The device of claim 1, wherein the device comprises a resorbable connector joining the feeder member to a remainder of the device, and wherein when the resorbable connector is resorbed, the feeder member becomes disconnected from the remainder of the device.

11. The device of claim 1, wherein the fabric construct is configured to substantially surround an area of tissue to be treated, a nerve, a blood vessel, a lymph duct, a lymph node, organ or implant.

12. The device of claim 1, further comprising a second plurality of second nonmetallic hollow fibers having second native-permeable walls, the second native-permeable walls having characteristics such that molecules of a second drug, which can be the same as the first, can pass through the second native-permeable walls while larger molecules cannot pass through the second native-permeable walls, the second fibers having respective second fiber lumens containing the second drug.

13. The device of claim 1, wherein the fabric construct comprises connecting elements that are resorbable or wherein the further fibers interwoven among the hollow fibers or adhered to the hollow fibers are resorbable.

14. The implantable device of claim 1, comprising in the hollow fibers the drug and the osmogen or hydrating molecule.

15. A kit comprising the device of claim 2, further comprising a catheter comprising two lumens and configured to supply a first material to the fiber lumens via the first reservoir and also remove a second material from the fiber lumens via the draining reservoir, feeding and draining occurring through respective catheter lumens.

16. A method of treating a patient comprising: providing in the patient's body a device of claim 1; and further comprising, prior to the implanting the device, cutting an outer perimeter of the fabric construct to a desired shape and cauterizing cut ends of the hollow fibers formed by the cutting.

17. A method of treating a patient comprising: providing in the patient's body a device of claim 1; and penetrating the patient's skin and penetrating the feeder septum to introduce a first flowable substance into the device.

18. The method of claim 17, further comprising thereafter so introducing a second flowable substance in the device.

19. A method of non-systematically delivering the drug to a patient comprising: providing the fabric construct of claim 1 in a patient configured to deliver the drug to a tissue to be treated, a nerve, a blood vessel, a lymph duct, a lymph node, organ; and periodically delivering the drug to the device via the septum.

20. A method of treating or ameliorating a condition comprising applying the method of claim 19 by having the fabric construct configured to: for metastatic cancer, provide the device configured for drug delivery to one or more lymph nodes at or near the site of a primary cancer and periodically delivering one or more chemotherapy drugs to the device; or for pain, provide the device configured for drug delivery at or near a site of pain and periodically delivering one or more one or more anti-inflammatory agents, analgesics, or pain medications to the device; or of infection, provide the device configured for drug delivery at or near tissue identified as a reservoir of infection and periodically delivering one or more one or more antimicrobial agents, antiseptic agents, antibiotics or antivirals to the device.

21. A method of treating a patient comprising: providing in a patient's body a device of claim 2; and introducing a first flowable substance through the first septum and simultaneously withdrawing a second flowable substance through the draining septum.

22. A method of treating a patient comprising: residing in the patient's body a device of claim 12 for a period of time effective to deliver the drug and for the connecting elements or fibers to resorb at least in part; and further comprising pulling on the hollow fibers such that they are drawn as linear fiber from the patient's body.

\* \* \* \* \*